United States Patent
Li et al.

(10) Patent No.: US 7,923,004 B2
(45) Date of Patent: Apr. 12, 2011

(54) 4-ETHYNYL PYRAZOLE DERIVATIVE COMPOUNDS AND METHODS FOR TREATMENT OF HCV

(75) Inventors: Guolin Li, Montvale, NJ (US); Reza Fathi, HoHoKus, NJ (US); Zhen Yang, Ridgewood, NJ (US); Yun Liao, Glenrock, NJ (US); Qiang Zhu, Edson, NJ (US); Angela Lam, Fort Lee, NJ (US); Anthony Sandrasagra, Princeton, NJ (US); Kenneth Nawoschik, Spring Valley, NY (US); Hyun-Joon Cho, Spring Valley, NY (US); Jie Cao, White Plains, NY (US); Wu Ruoqiu, Garnerville, NY (US); C. Richard Wobbe, Lexington, MA (US); Yixin Liu, Rancho Cucamonga, CA (US)

(73) Assignee: XTL Biopharmaceuticals Ltd. (IL)

( * ) Notice: Subject to any disclaimer, the term of this patent is extended or adjusted under 35 U.S.C. 154(b) by 15 days.

(21) Appl. No.: 11/974,744

(22) Filed: Oct. 15, 2007

(65) Prior Publication Data

US 2009/0041723 A1    Feb. 12, 2009

Related U.S. Application Data

(60) Provisional application No. 60/933,565, filed on Jun. 6, 2007, provisional application No. 60/925,528, filed on Apr. 20, 2007, provisional application No. 60/851,643, filed on Oct. 13, 2006.

(51) Int. Cl.
*A61K 38/21* (2006.01)
(52) U.S. Cl. .............. 424/85.7; 544/140; 514/236.5; 514/237.5; 514/326; 548/365.1; 546/211
(58) Field of Classification Search ............... 548/356.1, 548/364.1
See application file for complete search history.

(56) References Cited

U.S. PATENT DOCUMENTS

| | | | |
|---|---|---|---|
| 5,091,386 | A | 2/1992 | Kesseler et al. |
| 5,300,521 | A | 4/1994 | Eberle et al. |
| 6,916,839 | B2 | 7/2005 | Ebenbeck et al. |
| 7,238,722 | B2 | 7/2007 | Ebenbeck et al. |
| 2002/0156115 | A1 | 10/2002 | Oda et al. |
| 2002/0183366 | A1 | 12/2002 | Garvey et al. |
| 2003/0191171 | A1 | 10/2003 | Oda et al. |
| 2006/0183751 | A1 | 8/2006 | Hu et al. |

FOREIGN PATENT DOCUMENTS

| | | |
|---|---|---|
| EP | 1 219 173 | 7/2002 |
| WO | WO 02/051810 A2 | 7/2002 |
| WO | WO 2005/033100 A1 | 4/2005 |
| WO | WO 2006/028524 A2 | 3/2006 |

OTHER PUBLICATIONS

Chen et al. Bioorg. Med. Chem. Lett. 19 (2009) 1105-1109.*
"Apath, LLC: HCV Replicon," 2003, [Online] [Retrieved on Nov. 15, 2007] Retrieved from the Internet<URL:http://www.apath.com/Directory/Licensing/Technology/HCV_Replicon.asp>.
Chawla, G. et al., "Challenges in Polymorphism of Pharmaceuticals," CRIPS, Jan.-Mar. 2004, pp. 9-12, vol. 5, No. 1.
"Hepatitis C: Treatment—MayClinic.com," Mayo Clinic Staff, Sep. 14, 2007 [Online] [Retrieved on Nov. 14, 2007] Retrieved from the Internet<URL:http://www.mayoclinic.com/health/hepatitis-c/DS00097/DSECTION=8>.
Newman, A.W. et al., "Solid-State Analysis of the Active Pharmaceutical Ingredient in Drug Products," DDT, Oct. 2003, pp. 898-905, vol. 8, No. 19.
PCT International Search Report, PCT/US2006/005236, Feb. 12, 2007, 1 page.
PCT International Search Report and Written Opinion, PCT/US07/22055, Sep. 12, 2008, 7 pages.

* cited by examiner

*Primary Examiner* — Kamal A Saeed
*Assistant Examiner* — Valerie Rodriguez-Garcia
(74) *Attorney, Agent, or Firm* — Fenwick & West LLP

(57) ABSTRACT

Aryl substituted pyrazole derivatives are provided, as well as processes for their preparation. The invention also provides compositions and methods for the treatment of HCV by administering a compound of the present invention, alone or in combination with additional antiviral agents, in a therapeutically effective amount.

13 Claims, No Drawings

4-ETHYNYL PYRAZOLE DERIVATIVE COMPOUNDS AND METHODS FOR TREATMENT OF HCV

RELATED APPLICATIONS

This applications claims priority to U.S. provisional application Ser. No. 60/851,643, filed Oct. 13, 2006; U.S. provisional application Ser. No. 60/925,528 filed Apr. 20, 2007; and U.S. provisional application Ser. No. 60/933,565, filed Jun. 6, 2007.

BACKGROUND OF THE INVENTION

Infection with the Hepatitis C virus (HCV) represents a serious world-wide health crisis. In more than 70% of infected individuals, the virus evades clearance by the immune system leading to a persistent HCV infection. The long term effects of persistent HCV infection range from an apparently healthy carrier state to chronic hepatitis, liver fibrosis, cirrhosis, and eventually hepatocellular carcinoma. HCV is a leading cause of chronic liver disease. A leading therapy currently available for treatment of HCV infection uses a combination of pegylated α-interferon and ribavirin. However, many of the patients treated with this therapy fail to show a sufficient antiviral response. Additionally, interferon treatment also induces severe side-effects (i.e. retinopathy, thyroiditis, acute pancreatitis, depression) that diminish the quality of life of treated patients. Thus, it is important that more effective treatments be identified.

The identification of inhibitors of HCV replication and/or proliferation has been facilitated by the development of a cell-based system to study HCV replication. Inhibition of HCV replication may be performed using the HCV Replicon Assay developed in the laboratories of Bartenschlager (Lohman et al, Science 285, 110-113, 1999), Rice (Blight et al, Science 290, 1972-1974, 2000) and Lemon (Yi and Lemon, J. Virol. 78(15), 7904-7915, 2004). The assay is performed using the either the Huh-Luc-Neo cell line (HCV genotype 1b replicon; Lohman et al, Science 285, 110-113, 1999) or the En5-3/Htat2ANeo cell line (HCV genotype 1a replicon; Yi and Lemon, J. Virol. 78(15), 7904-7915, 2004) Huh-Luc-Neo cells are a human hepatoma cell line (Huh-7) stably expressing a bi-cistronic subgenomic HCV genotype 1b replicon (luc-neo/ET) containing the HCV IRES in which the structural protein sequences of HCV have been deleted and replaced by a construct containing sequences coding for the firefly luciferase reporter gene, the neomycin selectable marker and the EMCV IRES to direct expression of a truncated HCV genome expressing the genotype 1b non-structural proteins NS3, NS4A, NS4B, NS5A, and NS5B. The En5-3/Htat2ANeo cells are a Huh-7 cell line stably expressing the pLTR-SEAP (HIV LTR driven secreted alkaline phosphatase reporter) and a bi-cistronic subgenomic HCV genotype 1a replicon (Htat2ANeo) and is similar to the genotype 1b luc-neo/ET replicon except that the HCV structural proteins sequences have been replaced by the HIV tat gene, the FMDV 2A proteinase sequences, the neomycin selectable marker and the EMCV IRES which directs expression of the genotype 1a non-structural proteins (NS3-NS5B; Yi et al, Virology, 304(2), 97-210, 2002).

Strategies in new drug discovery often look to natural products for leads in finding new chemical compounds with therapeutic properties. One of the recurring problems in drug discovery is the availability of organic compounds derived from natural sources. Techniques employing combinatorial chemistry attempt to overcome this problem by allowing the high throughput synthesis and testing of hundreds or thousands of related synthetic compounds, called a chemical library. In designing the synthesis of a prospective therapeutic compound or a chemical library, one often looks to natural chemical motifs which are known to have broad biological activity.

Pyrazole has a long history of application in pharmaceutical and agrochemical industry, and posses a widespread occurrence as sub-structures in a large variety of compounds, which exhibit important biological activities and pharmacological properties. Elguero, J. In Comprehensive Heterocyclic Chemistry II; Katritzky, A. R.; Rees, C. W.; Scriven, E. F. V.; Pergamon-Elsevier Science: Oxiford, 1996; Vol. 6, pp. 1-75; (b) Sutharchanadevi, M.; Murugan, R. In Comprehensive Heterocyclic Chemistry II; Katritzky, A. R.; Rees, C. W.; Scriven, E. F. V.; Pergamon-Elsevier Science: Oxiford, 1996; Vol. 6, pp. 221-260.

SUMMARY OF THE INVENTION

The present invention provides pyrazole derivatives of the formula I:

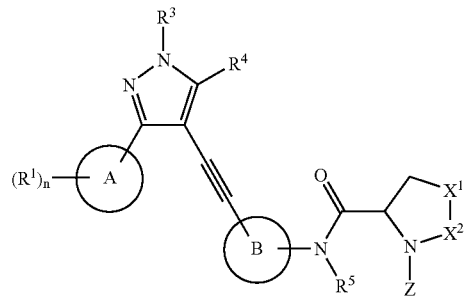

or a pharmaceutically acceptable salt or hydrate thereof, wherein:

ring A is selected from a 5- or 6-membered aromatic rings which may optionally contain 0 to 3 ring heteroatoms;

each $R^1$ is independently selected from alkyl, alkenyl, alkynyl, aralkyl, $-(CH_2)_a-O-R^{11}$, $-(CH_2)_a-N(R^{12})(R^{13})$, $-(CH_2)_a-N(R^{11})-(CH_2)_bC(O)R^{14}$, $-(CH_2)_a-N(R^{11})SO_2R^{11}$, $-(CH_2)_a-SR^{11}$, $-(CH_2)_a-C(O)R^{14}$, $-(CH_2)_a-C(O)-(CH_2)_bOR^{11}$, $-(CH_2)_a-C(O)-(CH_2)_bN(R^{12})(R^{13})$, $-(CH_2)_aO-(CH_2)_b-C(O)R^{14}$, $-(CH_2)_aOC(O)-(CH_2)_bN(R^{12})(R^{13})$, CN, $CF_3$, $NO_2$, $SO_2$, $-SOR^{11}$, $-SO_3R^{11}$, $-SO_2N(R^{12})(R^{13})$, cycloalkyl, cycloalkenyl, halo, phosphate, phosphonate, aryl and a heterocyclic group;

additionally or alternatively two $R^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{11}$;

each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

a is 0 to 6;

b is 0 to 6;

$R^3$ is selected from H, alkyl, alkenyl, alkynyl, aralkyl, —$(CH_2)_z$—O—$R^{31}$, —$(CH_2)_z$—$N(R^{32})(R^{33})$, —$(CH_2)_w$—$C(O)R^{34}$, —$(CH_2)_wC(O)$—$N(R^{32})(R^{33})$, —$(CH_2)_w$—$SO_2$—$R^{31}$ cycloalkyl, cycloalkenyl, aryl and a heterocyclic group;

$R^{31}$ is selected from H, alkyl, alkenyl, alkynyl, cycloalkyl, cycloalkenyl, aralkyl, aryl and a heterocyclic group;

$R^{32}$ and $R^{33}$ are independently selected from H, alkyl, alkenyl, alkynyl, cycloalkyl, cycloalkenyl, aralkyl, aryl and a heterocyclic group; or $R^{32}$ and $R^{33}$ may be taken together with the nitrogen to which they are attached form a 5- to 7-membered ring which may optionally contain a further heteroatom;

$R^{34}$ is selected from H, alkyl, —OH, —O-alkyl, —O-aryl, —O-aralkyl, alkenyl, alkynyl, cycloalkyl, cycloalkenyl, aralkyl, aryl and a heterocyclic group;

w is 0 to 6;

z is 1 to 6;

$R^4$ is independently selected from H, CN, $CF_3$, alkyl, alkenyl, alkynyl, aralkyl, cycloalkyl, cycloalkenyl, aryl and a heterocyclic group;

ring B is selected from a 5- or 6-membered aromatic rings which may optionally contain 0 to 3 ring heteroatoms;

$R^5$ is independently selected from H, alkyl, alkenyl, alkynyl, aralkyl, cycloalkyl, cycloalkenyl, aryl and a heterocyclic group;

$X^1$ is selected from $CH_2$, O, S, $SO_2$, and —$N(R^{101})$—;

$R^{101}$ is selected from H, alkyl, alkenyl, alkynyl, aralkyl, —C(=O)—$R^{102}$, cycloalkyl, cycloalkenyl, aryl and a heterocyclic group;

$R^{102}$ is selected from H, alkyl, alkenyl, alkynyl, aralkyl, —$N(R^{103})(R^{104})$, cycloalkyl, cycloalkenyl, aryl and a heterocyclic group;

$R^{103}$ and $R^{104}$ are independently selected from H, alkyl, alkenyl, alkynyl, aralkyl, cycloalkyl, cycloalkenyl, aryl and a heterocyclic group, or $R^{103}$ and $R^{104}$ may be taken together with the nitrogen to which they are attached form a 5- to 7-membered ring which may optionally contain a further heteroatom;

$X^2$ is selected from —$CH_2$—, —$CH_2CH_2$—, —C(=O)$CH_2$—, and —C(=O)—;

Z is selected from H, alkyl, alkenyl, alkynyl, aralkyl, cycloalkyl, cycloalkenyl, —$(CH_2)_c$—O—$R^{15}$, —$(CH_2)_c$—$N(R^{16})(R^{17})$, —$(CH_2)_c$—$N(R^{15})$—$(CH_2)_eC(O)R^{18}$, —$(CH_2)_c$—$SR^{15}$, —$(CH_2)_d$—$C(O)R^{18}$, —$(CH_2)_d$—C(O)—$(CH_2)_eOR^{15}$, —$(CH_2)_d$—C(O)—$(CH_2)_eN(R^{16})(R^{17})$, —$(CH_2)_eO$—$(CH_2)_e$—C(O)$R^{18}$, —$(CH_2)_cOC(O)$—$(CH_2)_eN(R^{16})(R^{17})$, —$SO_2R^{15}$, —$SO_3R^{15}$, cycloalkyl, cycloalkenyl, aryl and a heterocyclic group;

each $R^{15}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{16}$ and $R^{17}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{16}$ and $R^{17}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{18}$ is independently selected from H, alkyl, —OH, —O-alkyl, —O-aryl, —O-aralkyl, alkenyl, alkynyl, cycloalkyl, cycloalkenyl, aralkyl, aryl and a heterocyclic group;

c is 1 to 6;

d is 0 to 6;

e is 0 to 6;

or Z is a group having the formula -A-B—C—$R^8$, wherein

A is selected from —C(=O)—, and —$SO_2$—;

B is selected from —$(CH_2)_x$—$CH(R^6)$—$(CH_2)_y$—, and

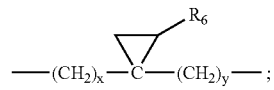

x is 0 to 4;

y is 0 to 4;

$R^6$ is independently selected from H, alkyl, alkenyl, alkynyl, aralkyl, —$(CH_2)_f$—Y—$(CH_2)_g$—$R^{61}$, —$(CH_2)_f$—$N(R^{62})(R^{63})$, —$(CH_2)_f$—$N(R^{61})$—$(CH_2)_gC(O)R^{64}$, —$(CH_2)_f$—$N(R^{61})SO_2R^{61}$, —$(CH_2)_f$—$SR^{61}$, —$(CH_2)_f$—$C(O)R^{64}$, —$(CH_2)_f$—C(O)—$(CH_2)_gOR^{61}$, —$(CH_2)_f$—C(O)—$(CH_2)_gN(R^{62})(R^{63})$, —$(CH_2)_f$—Y—$(CH_2)_g$—$C(O)R^{64}$, —$(CH_2)_f$—Y—C(O)—$(CH_2)_gN(R^{62})(R^{63})$, —$(CH_2)_f$—Y—$(CH_2)_g$—C(=$NOR^{61}$)—$R^{61}$, cycloalkyl, cycloalkenyl, aryl and a heterocyclic group;

each $R^{61}$ is independently selected from H, alkyl, alkenyl, alkynyl, cycloalkyl, cycloalkenyl, aralkyl, aryl and a heterocyclic group;

each $R^{62}$ and $R^{63}$ are independently selected from H, alkyl, cycloalkyl, cycloalkenyl, alkenyl, alkynyl, aralkyl, aryl and a heterocyclic group; or $R^{62}$ and $R^{63}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{64}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

Y is selected from a chemical bond, —O—, and aryl;

f is 1 to 6;

g is 0 to 6;

C is selected from —$N(R^7)$—C(=O)—, —$N(R^7)$—S(=O)$_2$—, and —$CH_2$—;

$R^7$ is independently selected from H, alkyl, alkenyl, alkynyl, aralkyl, cycloalkyl, cycloalkenyl, aryl and a heterocyclic group;

$R^8$ is independently selected from H, alkyl, alkenyl, alkynyl, aralkyl, —$(CH_2)_r$—O—$(CH_2)_s$—$R^{81}$, —$(CH_2)_r$—$N(R^{82})(R^{83})$, —$(CH_2)_r$—$N(R^{81})$—$(CH_2)_sC(O)R^{84}$, —$(CH_2)_r$—$N(R^{81})SO_2R^{81}$, —$(CH_2)_r$—$SR^{81}$, —$(CH_2)_r$—$C(O)R^{84}$, —$(CH_2)_r$—C(O)—$(CH_2)_sOR^{81}$, —$(CH_2)_r$—$R^{81}$, —$(CH_2)_r$—$C(O)(CH_2)_sN(R^{82})(R^{83})$, —$(CH_2)_rO$—$(CH_2)_s$—$C(O)R^{84}$, —$(CH_2)_rOC(O)$—$(CH_2)_sN(R^{82})(R^{83})$, cycloalkyl, cycloalkenyl, aryl and a heterocyclic group;

each $R^{81}$ is independently selected from H, alkyl, alkenyl, alkynyl, cycloalkyl, cycloalkenyl, aralkyl, aryl and a heterocyclic group;

each $R^{82}$ and $R^{83}$ are independently selected from H, alkyl, cycloalkyl, cycloalkenyl, alkenyl, alkynyl, aralkyl, aryl and a heterocyclic group; or $R^{82}$ and $R^{83}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

each $R^{84}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;

s is 0 to 6; and n is 0 to 5.

The invention also provides a synthetic process for the preparation of compounds of the invention. The process uses mild reaction conditions, which provides a high substituent tolerance. Thus, the process is applicable to the preparation of a wide variety of pyrazole derivatives with diverse substitution patterns. Additionally, the process is appropriate for use with combinatorial synthesis techniques. Thus, the process provides a method for producing a library of pyrazole derivatives for biological screening.

The invention also provides compositions and methods for the treatment of HCV by administering a compound of the present invention in a therapeutically effective amount.

The invention also provides methods of inhibiting HCV replication by contacting the HCV virus with a compound of the present invention. The invention further provides methods for inhibiting the functions of HCV NS3, NS4A, NS4B and/or NS5A indirectly and/or by contacting the NS3, NS4A, NS4B and/or NS5A with a compound according to the present invention.

DETAILED DESCRIPTION OF THE INVENTION

The term "halo" or "halogen" as used herein includes fluorine, chlorine, bromine and iodine.

The term "alkyl" as used herein contemplates substituted or unsubstituted, straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl, and the like. The alkyl group may be optionally substituted with one or more substituents selected from halo, CN, $NO_2$, $CO_2R$, C(O)R, —O—R, —N(R')(R''), —N(R)C(O)R, —N(R)$SO_2$R, —SR, —C(O)N(R')(R''), —OC(O)R, —OC(O)N(R')(R''), $SO_2$, —SOR, —$SO_3$R, —$SO_2$N(R')(R''), phosphate, phosphonate, substituted and unsubstituted cycloalkyl, and substituted and unsubstituted cycloalkenyl, wherein the substituted cycloalkyl and the substituted cycloalkenyl may be substituted with one or more of halo, CN, $CF_3$, $CO_2R$, C(O)R, C(O)$NR_2$, $NR_2$, $NO_2$, and OR.

The term "alkenyl" as used herein contemplates substituted or unsubstituted, straight and branched chain alkene radicals containing from two to 8 carbon atoms. An alkenyl group may be optionally substituted with one or more substituents selected from halo, CN, $NO_2$, $CO_2R$, C(O)R, —O—R, —N(R')(R''), —N(R)C(O)R, —N(R)$SO_2$R, —SR, —C(O)N(R')(R''), —OC(O)R, —OC(O)N(R')(R''), $SO_2$, —SOR, —$SO_3$R, —$SO_2$N(R')(R''), phosphate, phosphonate, substituted and unsubstituted cycloalkyl, substituted and unsubstituted cycloalkenyl, substituted and unsubstituted aryl and a substituted and unsubstituted heterocyclic group, wherein the substituted cycloalkyl, substituted cycloalkenyl, substituted aryl and substituted heterocyclic group may be substituted with one or more of halo, CN, $CF_3$, $CO_2R$, C(O)R, C(O)$NR_2$, $NR_2$, $NO_2$, and OR.

The term "alkynyl" as used herein contemplates substituted or unsubstituted, straight and branched carbon chain containing from two to 8 carbon atoms and having at least one carbon-carbon triple bond. The term alkynyl includes, for example ethynyl, 1-propynyl, 2-propynyl, 1-butynyl, 3-methyl-1-butynyl, and the like. An alkynyl group may be optionally substituted with one or more substituents selected from halo, CN, $NO_2$, $CO_2R$, C(O)R, —O—R, —N(R')(R''), —N(R)C(O)R, —N(R)$SO_2$R, —SR, —C(O)N(R')(R''), —OC(O)R, —OC(O)N(R')(R''), $SO_2$, —SOR, —$SO_3$R, —$SO_2$N(R')(R''), phosphate, phosphonate, substituted and unsubstituted cycloalkyl, substituted and unsubstituted cycloalkenyl, substituted and unsubstituted aryl and substituted and a unsubstituted heterocyclic group, wherein the substituted cycloalkyl, substituted cycloalkenyl, substituted aryl and substituted heterocyclic group, may be substituted with one or more of halo, CN, $CF_3$, $CO_2R$, C(O)R, C(O)$NR_2$, $NR_2$, $NO_2$, and OR.

The term "cycloalkyl" as used herein contemplates substituted or unsubstituted cyclic alkyl radicals containing form 3 to 7 carbon atoms and includes cyclopropyl, cyclopentyl, cyclohexyl, and the like. A cycloalkyl group may be optionally substituted with one or more substituents selected from halo, CN, $NO_2$, $CO_2R$, C(O)R, —O—R, —N(R')(R''), —N(R)C(O)R, —N(R)$SO_2$R, —SR, —C(O)N(R')(R''), —OC(O)R, —OC(O)N(R')(R''), $SO_2$, —SOR, —$SO_3$R, —$SO_2$N(R')(R''), phosphate, phosphonate, substituted and unsubstituted alkyl, substituted and unsubstituted cycloalkenyl, substituted and unsubstituted aryl and a substituted and unsubstituted heterocyclic group, wherein the substituted alkyl, substituted cycloalkenyl, substituted aryl and substituted heterocyclic group may be substituted with one or more of halo, CN, $CF_3$, $CO_2R$, C(O)R, C(O)$NR_2$, $NR_2$, $NO_2$, and OR.

The term "cycloalkenyl" as used herein contemplates substituted or unsubstituted cyclic alkenyl radicals containing form 5 to 7 carbon atoms in which has a double bond between two of the ring carbons and includes cyclopentenyl, cyclohexenyl, and the like. A cycloalkenyl group may be optionally substituted with one or more substituents selected from halo, CN, $NO_2$, $CO_2R$, C(O)R, —O—R, —N(R')(R''), —N(R)C(O)R, —N(R)$SO_2$R, —SR, —C(O)N(R')(R''), —OC(O)R, —OC(O)N(R')(R''), $SO_2$, —SOR, —$SO_3$R, —$SO_2$N(R')(R''), phosphate, phosphonate, substituted and unsubstituted alkyl, substituted and unsubstituted alkenyl, substituted and unsubstituted aryl and a substituted and unsubstituted heterocyclic group, wherein the substituted alkyl, substituted alkenyl, substituted aryl and substituted heterocyclic group may be substituted with one or more of halo, CN, $CF_3$, $CO_2R$, C(O)R, C(O)$NR_2$, $NR_2$, $NO_2$, and OR.

The term "aralkyl" as used herein contemplates a lower alkyl group which has as a substituent an aromatic group, which aromatic group may be substituted or unsubstituted. An aralkyl group may be optionally substituted with one or more substituents selected from halo, CN, $NO_2$, $CO_2R$, C(O)R, —O—R, —N(R')(R''), —N(R)C(O)R, —N(R)$SO_2$R, —SR, —C(O)N(R')(R''), —OC(O)R, —OC(O)N(R')(R''), $SO_2$, —SOR, —$SO_3$R, —$SO_2$N(R')(R''), phosphate, phosphonate, substituted and unsubstituted alkyl, substituted and unsubstituted alkenyl, substituted and unsubstituted cycloalkyl, substituted and unsubstituted cycloalkenyl, substituted and unsubstituted aryl and a substituted and unsubstituted heterocyclic group, wherein the substituted alkyl, substituted alkenyl, substituted cycloalkyl, substituted cycloalkenyl, substituted aryl and substituted heterocyclic group may be substituted with one or more of halo, CN, $CF_3$, $CO_2R$, C(O)R, $C(O)NR_2$, $NR_2$, $NO_2$, and OR.

The terms phosphate and phosphonate as used herein refer to the moieties having the following structures, respectively:

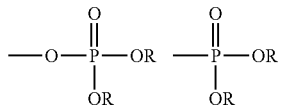

The term "heterocyclic group" or "heterocyclic ring" as used herein contemplates substituted or unsubstituted aromatic and non-aromatic cyclic radicals having at least one heteroatom as a ring member. Preferred heterocyclic groups are those containing 5 or 6 ring atoms which includes at least one hetero atom, and includes cyclic amines such as morpholino, piperidino, pyrrolidino, and the like, and cyclic ethers, such as tetrahydrofuran, tetrahydropyran, and the like. Aromatic heterocyclic groups, also termed "heteroaryl" groups contemplates single-ring hetero-aromatic groups that may include from one to three heteroatoms, for example, pyrrole, furan, thiophene, imidazole, oxazole, thiazole, triazole, pyrazole, pyridine, pyrazine, pyridazine, pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, tetrahydroisoquinoline, quinoxaline, quinoxoline, benzimidazole, benzofuran, purine, imidazopyridine, benzotriazole, and the like. A heterocyclic group may be optionally substituted with one or more substituents selected from halo, alkyl, CN, $NO_2$, $CO_2R$, C(O)R, —O—R, —N(R')(R''), —N(R)C(O)R, —N(R)$SO_2R$, —SR, —C(O)N(R')(R''), —OC(O)R, —OC(O)N(R')(R''), $SO_2$, —SOR, —$SO_3R$, —$SO_2N(R')(R'')$, phosphate, phosphonate, substituted and unsubstituted alkyl, substituted and unsubstituted alkenyl, substituted and unsubstituted cycloalkyl, substituted and unsubstituted cycloalkenyl, substituted and unsubstituted aryl and a substituted and unsubstituted heterocyclic group, wherein the substituted alkyl, substituted alkenyl, substituted cycloalkyl, substituted cycloalkenyl, substituted aryl and substituted heterocyclic group may be substituted with one or more of halo, CN, $CF_3$, $CO_2R$, C(O)R, $C(O)NR_2$, $NR_2$, $NO_2$, and OR.

The terms "aryl", "aromatic group", or "aromatic ring" as used herein contemplates substituted or unsubstituted single-ring aromatic groups (for example, phenyl, pyridyl, pyrazole, etc.) and polycyclic ring systems (naphthyl, quinoline, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halo, alkyl, CN, $NO_2$, $CO_2R$, C(O)R, —O—R, —N(R')(R''), —N(R)C(O)R, —N(R)$SO_2R$, —SR, —C(O)N(R')(R''), —OC(O)R, —OC(O)N(R')(R''), $SO_2$, —SOR, —$SO_3R$, —$SO_2N(R')(R'')$, phosphate, phosphonate, substituted and unsubstituted alkyl, substituted and unsubstituted alkenyl, substituted and unsubstituted cycloalkyl, substituted and unsubstituted cycloalkenyl, substituted and unsubstituted aryl and a substituted and unsubstituted heterocyclic group, wherein the substituted alkyl, substituted alkenyl, substituted cycloalkyl, substituted cycloalkenyl, substituted aryl and substituted heterocyclic group may be substituted with one or more of halo, CN, $CF_3$, $CO_2R$, C(O)R, $C(O)NR_2$, $NR_2$, $NO_2$, and OR.

With respect to the above definitions, each R is independently selected from H, substituted and unsubstituted alkyl, substituted and unsubstituted cycloalkyl, substituted and unsubstituted cycloalkenyl, substituted and unsubstituted alkenyl, substituted and unsubstituted alkynyl, substituted and unsubstituted aralkyl, substituted and unsubstituted aryl and a substituted and unsubstituted heterocyclic group. Each R' and R'' are independently selected from H, substituted and unsubstituted alkyl, substituted and unsubstituted cycloalkyl, substituted and unsubstituted cycloalkenyl, substituted and unsubstituted alkenyl, substituted and unsubstituted alkynyl, substituted and unsubstituted aralkyl, substituted and unsubstituted aryl and substituted and unsubstituted heterocyclic group; or R' and R'' may be taken together with the nitrogen to which they are attached to form a 5- to 7-membered ring which may optionally contain a further heteroatom. The substituted alkyl, substituted cycloalkyl, substituted cycloalkenyl, substituted alkenyl, substituted alkynyl, substituted aralkyl, substituted aryl and substituted heterocyclic group may be substituted with one or more of halo, CN, $CF_3$, OH, $CO_2H$, $NO_2$, $C_{1-6}$alkyl, —O—($C_{1-6}$alkyl), —$NH_2$, —NH($C_{1-6}$alkyl) and —N($C_{1-6}$alkyl)$_2$.

The term "heteroatom", particularly as a ring heteroatom, refers to N, O, and S.

All value ranges, for example those given for n and m, are inclusive over the entire range. Thus, a range of 0 to 4 would include the values 0, 1, 2, 3 and 4.

The present invention pyrazole derivatives having the formula I:

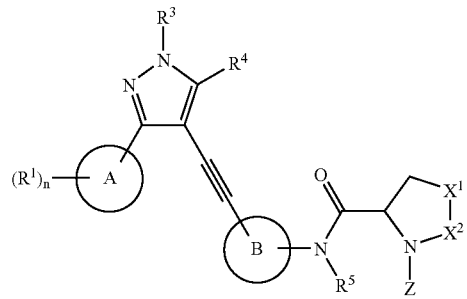

or a pharmaceutically acceptable salt or hydrate thereof, wherein:

ring A is selected from a 5- or 6-membered aromatic rings which may optionally contain 0 to 3 ring heteroatoms;

each $R^1$ is independently selected from alkyl, alkenyl, alkynyl, aralkyl, —$(CH_2)_a$—O—$R^{11}$, —$(CH_2)_a$—N($R^{12}$)($R^{13}$), —$(CH_2)_a$—N($R^{11}$)—$(CH_2)_b$C(O)$R^{14}$, —$(CH_2)_a$—N($R^{11}$)$SO_2R^{11}$, —$(CH_2)_a$—$SR^{11}$, —$(CH_2)_a$—C(O)$R^{14}$, —$(CH_2)_a$—C(O)—$(CH_2)_b$O$R^{11}$, —$(CH_2)_a$—C(O)—$(CH_2)_b$N($R^{12}$)($R^{13}$), —$(CH_2)_a$O—$(CH_2)_b$—C(O)$R^{14}$, —$(CH_2)_a$OC(O)—$(CH_2)_b$N($R^{12}$)($R^{13}$), CN, $CF_3$, $NO_2$, $SO_2$, —$SOR^{11}$, —$SO_3R^{11}$, —$SO_2N(R^{12})(R^{13})$, cycloalkyl, cycloalkenyl, halo, phosphate, phosphonate, aryl and a heterocyclic group;

additionally or alternatively two $R^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{11}$;

each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

a is 0 to 6;

b is 0 to 6;

$R^3$ is selected from H, alkyl, alkenyl, alkynyl, aralkyl, —$(CH_2)_z$—O—$R^{31}$, —$(CH_2)_z$—$N(R^{32})(R^{33})$, —$(CH_2)_w$—$C(O)R^{34}$, —$(CH_2)_w C(O)$—$N(R^{32})(R^{33})$, —$(CH_2)_w$—$SO_2$—$R^{31}$ cycloalkyl, cycloalkenyl, aryl and a heterocyclic group;

$R^{31}$ is selected from H, alkyl, alkenyl, alkynyl, cycloalkyl, cycloalkenyl, aralkyl, aryl and a heterocyclic group;

$R^{32}$ and $R^{33}$ are independently selected from H, alkyl, alkenyl, alkynyl, cycloalkyl, cycloalkenyl, aralkyl, aryl and a heterocyclic group; or $R^{32}$ and $R^{33}$ may be taken together with the nitrogen to which they are attached form a 5- to 7-membered ring which may optionally contain a further heteroatom;

$R^{34}$ is selected from H, alkyl, —OH, —O-alkyl, —O-aryl, —O-aralkyl, alkenyl, alkynyl, cycloalkyl, cycloalkenyl, aralkyl, aryl and a heterocyclic group;

w is 0 to 6;

z is 1 to 6;

$R^4$ is independently selected from H, CN, $CF_3$, alkyl, alkenyl, alkynyl, aralkyl, cycloalkyl, cycloalkenyl, aryl and a heterocyclic group;

ring B is selected from a 5- or 6-membered aromatic rings which may optionally contain 0 to 3 ring heteroatoms;

$R^5$ is independently selected from H, alkyl, alkenyl, alkynyl, aralkyl, cycloalkyl, cycloalkenyl, aryl and a heterocyclic group;

$X^1$ is selected from $CH_2$, O, S, $SO_2$, and —$N(R^{101})$—;

$R^{101}$ is selected from H, alkyl, alkenyl, alkynyl, aralkyl, —$C(=O)$—$R^{102}$, cycloalkyl, cycloalkenyl, aryl and a heterocyclic group;

$R^{102}$ is selected from H, alkyl, alkenyl, alkynyl, aralkyl, —$N(R^{103})(R^{104})$, cycloalkyl, cycloalkenyl, aryl and a heterocyclic group;

$R^{103}$ and $R^{104}$ are independently selected from H, alkyl, alkenyl, alkynyl, aralkyl, cycloalkyl, cycloalkenyl, aryl and a heterocyclic group, or $R^{103}$ and $R^{104}$ may be taken together with the nitrogen to which they are attached form a 5- to 7-membered ring which may optionally contain a further heteroatom;

$X^2$ is selected from —$CH_2$—, —$CH_2CH_2$—, —$C(=O)CH_2$—, and —$C(=O)$—;

Z is selected from H, alkyl, alkenyl, alkynyl, aralkyl, cycloalkyl, cycloalkenyl, —$(CH_2)_c$—O—$R^{15}$, —$(CH_2)_c$—$N(R^{16})(R^{17})$, —$(CH_2)_c$—$N(R^{15})$—$(CH_2)_e C(O)R^{18}$, —$(CH_2)_c$—$SR^{15}$, —$(CH_2)_d$—$C(O)R^{18}$, —$(CH_2)_d$—$C(O)$—$(CH_2)_c OR^{15}$, —$(CH_2)_d$—$C(O)$—$(CH_2)_e N(R^{16})(R^{17})$, —$(CH_2)_c$—O—$(CH_2)_e$—$C(O)R$, —$(CH_2)_c OC(O)$—$(CH_2)_e N(R^{16})(R^{17})$, —$SO_2 R^{15}$, —$SO_3 R^{15}$, cycloalkyl, cycloalkenyl, aryl and a heterocyclic group;

each $R^{15}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{16}$ and $R^{17}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{16}$ and $R^{17}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{18}$ is independently selected from H, alkyl, —OH, —O-alkyl, —O-aryl, —O-aralkyl, alkenyl, alkynyl, cycloalkyl, cycloalkenyl, aralkyl, aryl and a heterocyclic group;

c is 1 to 6;

d is 0 to 6;

e is 0 to 6;

or Z is a group having the formula -A-B—C—$R^8$, wherein

A is selected from —$C(=O)$—, and —$SO_2$—;

B is selected from —$(CH_2)_x$—$CH(R^6)$—$(CH_2)_y$—, and

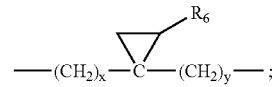

x is 0 to 4;

y is 0 to 4;

$R^6$ is independently selected from H, alkyl, alkenyl, alkynyl, aralkyl, —$(CH_2)_f$—Y—$(CH_2)_g$—$R^{61}$, —$(CH_2)_f$—$N(R^{62})(R^{63})$, —$(CH_2)_f$—$N(R^{61})$—$(CH_2)_g C(O)R^{64}$, —$(CH_2)_f$—$N(R^{61})SO_2 R^{61}$, —$(CH_2)_f$—$SR^{61}$, —$(CH_2)_f$—$C(O)R^{64}$, —$(CH_2)_f$—$C(O)$—$(CH_2)_g OR^{61}$, —$(CH_2)_f$—$C(O)$—$(CH_2)_g N(R^{62})(R^{63})$, —$(CH_2)_f$—Y—$(CH_2)_g$—$C(O)R^{64}$, —$(CH_2)_f$—Y—$C(O)$—$(CH_2)_g N(R^{62})(R^{63})$, —$(CH_2)_f$—Y—$(CH_2)_g$—$C(=NOR^{61})$—$R^{61}$, cycloalkyl, cycloalkenyl, aryl and a heterocyclic group;

each $R^{61}$ is independently selected from H, alkyl, alkenyl, alkynyl, cycloalkyl, cycloalkenyl, aralkyl, aryl and a heterocyclic group;

each $R^{62}$ and $R^{63}$ are independently selected from H, alkyl, cycloalkyl, cycloalkenyl, alkenyl, alkynyl, aralkyl, aryl and a heterocyclic group; or $R^{62}$ and $R^{63}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{64}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

Y is selected from a chemical bond, —O—, and aryl;

f is 1 to 6;

g is 0 to 6;

C is selected from —$N(R^7)$—$C(=O)$—, —$N(R^7)$—$S(=O)_2$—, and —$CH_2$—;

R$^7$ is independently selected from H, alkyl, alkenyl, alkynyl, aralkyl, cycloalkyl, cycloalkenyl, aryl and a heterocyclic group;

R$^8$ is independently selected from H, alkyl, alkenyl, alkynyl, aralkyl, —(CH$_2$)$_r$—O—(CH$_2$)$_s$—R$^{81}$, —(CH$_2$)$_r$—N(R$^{82}$)(R$^{83}$), —(CH$_2$)$_r$—N(R$^{81}$)—(CH$_2$)$_s$C(O)R$^{84}$, —(CH$_2$)$_r$—N(R$^{81}$)SO$_2$R$^{81}$, —(CH$_2$)$_r$—SR$^{81}$, —(CH$_2$)$_r$—C(O)R$^{84}$, —(CH$_2$)$_r$—C(O)—(CH$_2$)$_s$OR$^{81}$, —(CH$_2$)$_r$—R$^{81}$, —(CH$_2$)$_r$—C(O)(CH$_2$)$_s$N(R$^{82}$)(R$^{83}$), —(CH$_2$)$_r$O—(CH$_2$)$_s$—C(O)R$^{84}$, —(CH$_2$)$_r$OC(O)—(CH$_2$)$_s$N(R$^{82}$)(R$^{83}$), cycloalkyl, cycloalkenyl, aryl and a heterocyclic group;

each R$^{81}$ is independently selected from H, alkyl, alkenyl, alkynyl, cycloalkyl, cycloalkenyl, aralkyl, aryl and a heterocyclic group;

each R$^{82}$ and R$^{83}$ are independently selected from H, alkyl, cycloalkyl, cycloalkenyl, alkenyl, alkynyl, aralkyl, aryl and a heterocyclic group; or R$^{82}$ and R$^{83}$ may be taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group;

each R$^{84}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;
  s is 0 to 6; and
n is 0 to 5.

In preferred embodiments of the invention, one or more of the following selections is made: Ring A is phenyl or pyridyl, and more preferably is phenyl; Ring B is phenyl or pyridyl, and more preferably is phenyl; R$^1$ is selected from halo, CF$_3$, NO$_2$, alkyl, OH, and NH$_2$; R$^3$ is an alkyl group and preferably is methyl, ethyl, isopropyl, 2-hydroxyethyl (—CH$_2$CH$_2$—OH), 2-cyanoethyl (—CH$_2$CH$_2$—CN), and N,N-dimethylaminoethyl (—CH$_2$CH$_2$—N(CH$_3$)$_2$), and more preferably R$^3$ is methyl; R$^4$ is H; R$^5$ is H or alkyl; and/or R$^7$ is H or alkyl.

In one embodiment, the invention provides a compound of the formula II

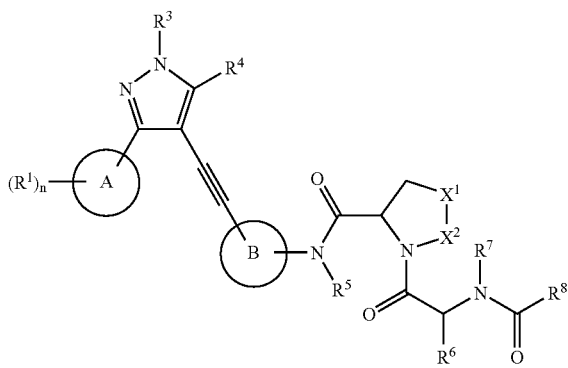

(II)

or a pharmaceutically acceptable salt or hydrate thereof, wherein:

ring A is selected from a 5- or 6-membered aromatic rings which may optionally contain 0 to 3 ring heteroatoms;

each R$^1$ is independently selected from alkyl, alkenyl, alkynyl, aralkyl, —(CH$_2$)$_a$—O—R$^{11}$, —(CH$_2$)$_a$—N(R$^{12}$)(R$^{13}$), —(CH$_2$)$_a$—N(R$^{11}$)—(CH$_2$)$_b$C(O)R$^{14}$, —(CH$_2$)$_a$—N(R$^{11}$)SO$_2$R$^{11}$, —(CH$_2$)$_a$—SR$^{11}$, —(CH$_2$)$_a$—C(O)R$^{14}$, —(CH$_2$)$_a$—C(O)—(CH$_2$)$_b$OR$^{11}$, —(CH$_2$)$_a$—C(O)—(CH$_2$)$_b$N(R$^{12}$)(R$^{13}$), —(CH$_2$)$_a$O—(CH$_2$)$_b$—C(O)R$^{14}$, —(CH$_2$)$_a$OC(O)—(CH$_2$)$_b$N(R$^{12}$)(R$^{13}$), CN, CF$_3$, NO$_2$, SO$_2$, —SOR$^{11}$, —SO$_3$R$^{11}$, —SO$_2$N(R$^{12}$)(R$^{13}$), cycloalkyl, cycloalkenyl, halo, phosphate, phosphonate, aryl and a heterocyclic group;

additionally or alternatively two R$^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from R$^{11}$;

each R$^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each R$^{12}$ and R$^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or R$^{12}$ and R$^{13}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;

each R$^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

a is 0 to 6;
  b is 0 to 6;

R$^3$ is selected from H, alkyl, alkenyl, alkynyl, aralkyl, —(CH$_2$)$_z$—O—R$^{31}$, —(CH$_2$)$_z$—N(R$^{32}$)(R$^{33}$), —(CH$_2$)$_w$—C(O)R$^{34}$, —(CH$_2$)$_w$C(O)—N(R$^{32}$)(R$^{33}$), —(CH$_2$)$_w$—SO$_2$—R$^{31}$ cycloalkyl, cycloalkenyl, aryl and a heterocyclic group;

R$^{31}$ is selected from H, alkyl, alkenyl, alkynyl, cycloalkyl, cycloalkenyl, aralkyl, aryl and a heterocyclic group;

R$^{32}$ and R$^{33}$ are independently selected from H, alkyl, alkenyl, alkynyl, cycloalkyl, cycloalkenyl, aralkyl, aryl and a heterocyclic group; or R$^{32}$ and R$^{33}$ may be taken together with the nitrogen to which they are attached form a 5- to 7-membered ring which may optionally contain a further heteroatom;

R$^{34}$ is selected from H, alkyl, —OH, —O-alkyl, —O-aryl, —O-aralkyl, alkenyl, alkynyl, cycloalkyl, cycloalkenyl, aralkyl, aryl and a heterocyclic group;

w is 0 to 6;
z is 1 to 6;

R$^4$ is independently selected from H, CN, CF$_3$, alkyl, alkenyl, alkynyl, aralkyl, cycloalkyl, cycloalkenyl, aryl and a heterocyclic group;

ring B is selected from a 5- or 6-membered aromatic rings which may optionally contain 0 to 3 ring heteroatoms;

R$^5$ is independently selected from H, alkyl, alkenyl, alkynyl, aralkyl, cycloalkyl, cycloalkenyl, aryl and a heterocyclic group;

X$^1$ is selected from CH$_2$, O, S, SO$_2$, and —N(R$^{101}$)—;

R$^{101}$ is selected from H, alkyl, alkenyl, alkynyl, aralkyl, —C(=O)—R$^{102}$, cycloalkyl, cycloalkenyl, aryl and a heterocyclic group;

R$^{102}$ is selected from H, alkyl, alkenyl, alkynyl, aralkyl, —N(R$^{103}$)(R$^{104}$), cycloalkyl, cycloalkenyl, aryl and a heterocyclic group;

$R^{103}$ and $R^{104}$ are independently selected from H, alkyl, alkenyl, alkynyl, aralkyl, cycloalkyl, cycloalkenyl, aryl and a heterocyclic group, or $R^{103}$ and $R^{104}$ may be taken together with the nitrogen to which they are attached form a 5- to 7-membered ring which may optionally contain a further heteroatom;

$X^2$ is selected from —$CH_2$—, —$CH_2CH_2$—, —C(=O)$CH_2$—, and —C(=O)—;

$R^6$ is independently selected from H, alkyl, alkenyl, alkynyl, aralkyl, —$(CH_2)_f$—Y—$(CH_2)_g$—$R^{61}$, —$(CH_2)_f$—N($R^{62}$)($R^{63}$), —$(CH_2)_f$—N($R^{61}$)—$(CH_2)_g$C(O)$R^{64}$, —$(CH_2)_f$—N($R^{61}$)SO$_2R^{61}$, —$(CH_2)_f$—S$R^{61}$, —$(CH_2)_f$—C(O)$R^{64}$, —$(CH_2)_f$—C(O)—$(CH_2)_g$O$R^{61}$, —$(CH_2)_f$—C(O)—$(CH_2)_g$N($R^{62}$)($R^{63}$), —$(CH_2)_f$—Y—$(CH_2)_g$—C(O)$R^{64}$, —$(CH_2)_f$—Y—C(O)—$(CH_2)_g$N($R^{62}$)($R^{63}$), —$(CH_2)_f$—Y—$(CH_2)_g$—C(=NO$R^{61}$)—$R^{61}$, cycloalkyl, cycloalkenyl, aryl and a heterocyclic group;

each $R^{61}$ is independently selected from H, alkyl, alkenyl, alkynyl, cycloalkyl, cycloalkenyl, aralkyl, aryl and a heterocyclic group;

each $R^{62}$ and $R^{63}$ are independently selected from H, alkyl, cycloalkyl, cycloalkenyl, alkenyl, alkynyl, aralkyl, aryl and a heterocyclic group; or $R^{62}$ and $R^{63}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;

each $R^{64}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

Y is selected from a chemical bond, —O—, and aryl;

f is 1 to 6;

g is 0 to 6;

$R^7$ is independently selected from H, alkyl, alkenyl, alkynyl, aralkyl, cycloalkyl, cycloalkenyl, aryl and a heterocyclic group;

$R^8$ is independently selected from H, alkyl, alkenyl, alkynyl, aralkyl, —$(CH_2)_r$—O—$(CH_2)_s$—$R^{81}$, —$(CH_2)_r$—N($R^{82}$)($R^{83}$), —$(CH_2)_r$—N($R^{81}$)—$(CH_2)_s$C(O)$R^{84}$, —$(CH_2)_r$—N($R^{81}$)SO$_2R^{81}$, —$(CH_2)_r$—S$R^{81}$, —$(CH_2)_r$—C(O)$R^{84}$, —$(CH_2)_r$—C(O)—$(CH_2)_s$O$R^{81}$, —$(CH_2)_r$—$R^{81}$, —$(CH_2)_r$—C(O)—$(CH_2)_s$N($R^{82}$)($R^{83}$), —$(CH_2)_r$O—$(CH_2)_s$—C(O)$R^{84}$, —$(CH_2)_r$OC(O)—$(CH_2)_s$N($R^{82}$)($R^{83}$), cycloalkyl, cycloalkenyl, aryl and a heterocyclic group;

each $R^{81}$ is independently selected from H, alkyl, alkenyl, alkynyl, cycloalkyl, cycloalkenyl, aralkyl, aryl and a heterocyclic group;

each $R^{82}$ and $R^{83}$ are independently selected from H, alkyl, cycloalkyl, cycloalkenyl, alkenyl, alkynyl, aralkyl, aryl and a heterocyclic group; or $R^{82}$ and $R^{83}$ may be taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group;

each $R^{84}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;

s is 0 to 6; and n is 0 to 5.

In another embodiment, the invention provides a compound of the formula III:

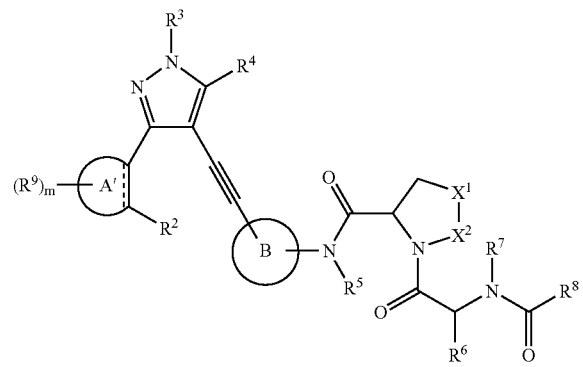

(III)

or a pharmaceutically acceptable salt or hydrate thereof, wherein:

ring A is selected from a 5- or 6-membered aromatic rings which may optionally contain 0 to 3 ring heteroatoms;

each $R^9$ is independently selected from alkyl, alkenyl, alkynyl, aralkyl, —$(CH_2)_a$—O—$R^{91}$, —$(CH_2)_a$—N($R^{92}$)($R^{93}$), —$(CH_2)_a$—N($R^{91}$)—$(CH_2)_b$C(O)$R^{94}$, —$(CH_2)_a$—N($R^{91}$)SO$_2R^{91}$, —$(CH_2)_a$—S$R^{91}$, —$(CH_2)_a$—C(O)$R^{94}$, —$(CH_2)_a$—C(O)—$(CH_2)_b$O$R^{91}$, —$(CH_2)_a$—C(O)—$(CH_2)_b$N($R^{92}$)($R^{93}$), —$(CH_2)_a$O—$(CH_2)_b$—C(O)$R^{94}$, —$(CH_2)_a$OC(O)—$(CH_2)_b$N($R^{92}$)($R^{93}$), CN, CF$_3$, NO$_2$, SO$_2$, —SO$R^{91}$, —SO$_3R^{91}$, —SO$_2$N($R^{92}$)($R^{93}$), cycloalkyl, cycloalkenyl, halo, phosphate, phosphonate, aryl and a heterocyclic group;

additionally or alternatively two $R^9$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{91}$;

each $R^{91}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{92}$ and $R^{93}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{92}$ and $R^{93}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;

each $R^{94}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

a is 0 to 6;

b is 0 to 6;

$R^2$ is selected from OH, SH, and NH$_2$;

$R^3$ is selected from H, alkyl, alkenyl, alkynyl, aralkyl, —$(CH_2)_z$—O—$R^{31}$, —$(CH_2)_z$—N($R^{32}$)($R^{33}$), —$(CH_2)_w$—C(O)$R^{34}$, —$(CH_2)_w$C(O)—N($R^{32}$)($R^{33}$), —$(CH_2)_w$—SO$_2$—$R^{31}$ cycloalkyl, cycloalkenyl, aryl and a heterocyclic group;

$R^{31}$ is selected from H, alkyl, alkenyl, alkynyl, cycloalkyl, cycloalkenyl, aralkyl, aryl and a heterocyclic group;

$R^{32}$ and $R^{33}$ are independently selected from H, alkyl, alkenyl, alkynyl, cycloalkyl, cycloalkenyl, aralkyl, aryl and a heterocyclic group; or $R^{32}$ and $R^{33}$ may be taken together with the nitrogen to which they are attached form a 5- to 7-membered ring which may optionally contain a further heteroatom;

$R^{34}$ is selected from H, alkyl, —OH, —O-alkyl, —O-aryl, —O-aralkyl, alkenyl, alkynyl, cycloalkyl, cycloalkenyl, aralkyl, aryl and a heterocyclic group;

w is 0 to 6;

z is 1 to 6;

$R^4$ is independently selected from H, CN, $CF_3$, alkyl, alkenyl, alkynyl, aralkyl, cycloalkyl, cycloalkenyl, aryl and a heterocyclic group;

ring B is selected from a 5- or 6-membered aromatic rings which may optionally contain 0 to 3 ring heteroatoms;

$R^5$ is independently selected from H, alkyl, alkenyl, alkynyl, aralkyl, cycloalkyl, cycloalkenyl, aryl and a heterocyclic group;

$X^1$ is selected from $CH_2$, O, S, $SO_2$, and —N($R^{101}$)—;

$R^{101}$ is selected from H, alkyl, alkenyl, alkynyl, aralkyl, —C(=O)—$R^{102}$, cycloalkyl, cycloalkenyl, aryl and a heterocyclic group;

$R^{102}$ is selected from H, alkyl, alkenyl, alkynyl, aralkyl, —N($R^{103}$)($R^{104}$), cycloalkyl, cycloalkenyl, aryl and a heterocyclic group;

$R^{103}$ and $R^{104}$ are independently selected from H, alkyl, alkenyl, alkynyl, aralkyl, cycloalkyl, cycloalkenyl, aryl and a heterocyclic group, or $R^{103}$ and $R^{104}$ may be taken together with the nitrogen to which they are attached form a 5- to 7-membered ring which may optionally contain a further heteroatom;

$X^2$ is selected from —$CH_2$—, —$CH_2CH_2$—, —C(=O)$CH_2$—, and —C(=O)—;

$R^6$ is independently selected from H, alkyl, alkenyl, alkynyl, aralkyl, —$(CH_2)_f$—Y—$(CH_2)_g$—$R^{61}$, —$(CH_2)_f$—N($R^{62}$)($R^{63}$), —$(CH_2)_f$—N($R^{61}$)—$(CH_2)_g$C(O)$R^{64}$, —$(CH_2)_f$—N($R^{61}$)$SO_2R^{61}$, —$(CH_2)_f$—$SR^{61}$, —$(CH_2)_f$—C(O)$R^{64}$, —$(CH_2)_f$—C(O)—$(CH_2)_g OR^{61}$, —$(CH_2)_f$—C(O)—$(CH_2)_g N(R^{62})(R^{63})$, —$(CH_2)_f$—Y—$(CH_2)_g$—C(O)$R^{64}$, —$(CH_2)_f$—Y—C(O)—$(CH_2)_g N(R^{62})(R^{63})$, —$(CH_2)_f$—Y—$(CH_2)_g$—C(=NOR$^{61}$)—$R^{61}$, cycloalkyl, cycloalkenyl, aryl and a heterocyclic group;

each $R^{61}$ is independently selected from H, alkyl, alkenyl, alkynyl, cycloalkyl, cycloalkenyl, aralkyl, aryl and a heterocyclic group;

each $R^{62}$ and $R^{63}$ are independently selected from H, alkyl, cycloalkyl, cycloalkenyl, alkenyl, alkynyl, aralkyl, aryl and a heterocyclic group; or $R^{62}$ and $R^{63}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{64}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

Y is selected from a chemical bond, —O—, and aryl;

f is 1 to 6;

g is 0 to 6;

$R^7$ is independently selected from H, alkyl, alkenyl, alkynyl, aralkyl, cycloalkyl, cycloalkenyl, aryl and a heterocyclic group;

$R^8$ is independently selected from H, alkyl, alkenyl, alkynyl, aralkyl, —$(CH_2)_r$—O—$(CH_2)_s$—$R^{81}$, —$(CH_2)_r$—N($R^{82}$)($R^{83}$), —$(CH_2)_r$—N($R^{81}$)—$(CH_2)_s C(O)R^{84}$, —$(CH_2)_r$—N($R^{81}$)$SO_2R^{81}$, —$(CH_2)_r$—$SR^{81}$, —$(CH_2)_r$—C(O)$R^{84}$, —$(CH_2)_r$—C(O)—$(CH_2)_s OR^{81}$, —$(CH_2)_r$—$R^{81}$, —$(CH_2)_r$—C(O)—$(CH_2)_s N(R^{82})(R^{83})$, —$(CH_2)_r O$—$(CH_2)_s$—C(O)$R^{84}$, —$(CH_2)_r OC(O)$—$(CH_2)_s N(R^{82})(R^{83})$, cycloalkyl, cycloalkenyl, aryl and a heterocyclic group;

each $R^{81}$ is independently selected from H, alkyl, alkenyl, alkynyl, cycloalkyl, cycloalkenyl, aralkyl, aryl and a heterocyclic group;

each $R^{82}$ and $R^{83}$ are independently selected from H, alkyl, cycloalkyl, cycloalkenyl, alkenyl, alkynyl, aralkyl, aryl and a heterocyclic group; or $R^{82}$ and $R^{83}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

each $R^{84}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;

s is 0 to 6; and m is 0 to 4.

In a preferred embodiment, the invention provides a compound of the formula IV:

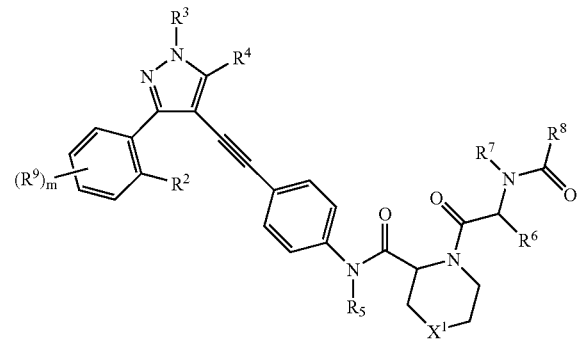

(IV)

or a pharmaceutically acceptable salt or hydrate thereof, wherein:

each $R^9$ is independently selected from alkyl, alkenyl, alkynyl, aralkyl, —$(CH_2)_a$—O—$R^{91}$, —$(CH_2)_a$—N($R^{92}$)($R^{93}$), —$(CH_2)_a$—N($R^{91}$)—$(CH_2)_b C(O)R^{94}$, —$(CH_2)_a$—N($R^{91}$)$SO_2R^{91}$, —$(CH_2)_a$—$SR^{91}$, —$(CH_2)_a$—C(O)$R^{94}$, —$(CH_2)_a$—C(O)—$(CH_2)_b OR^{91}$, —$(CH_2)_a$—C(O)—$(CH_2)_b N(R^{92})(R^{93})$, —$(CH_2)_a O$—$(CH_2)_b$—C(O)$R^{94}$, —$(CH_2)_a OC(O)$—$(CH_2)_b N(R^{92})(R^{93})$, CN, $CF_3$, $NO_2$, $SO_2$, —$SOR^{91}$, —$SO_3R^{91}$, —$SO_2N(R^{92})(R^{93})$, cycloalkyl, cycloalkenyl, halo, phosphate, phosphonate, aryl and a heterocyclic group;

additionally or alternatively two $R^9$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{91}$;

each R$^{91}$ is independently selected from H, alkyl, alkyl-O-alkyl, alkyl-O-aryl, alkenyl, alkynyl, cycloalkyl, cycloalkenyl, aralkyl, aryl and a heterocyclic group;

each R$^{92}$ and R$^{93}$ are independently selected from H, alkyl, cycloalkyl, cycloalkenyl, alkyl-O-alkyl, alkyl-O-aryl, alkenyl, alkynyl, aralkyl, aryl and a heterocyclic group; or R$^{92}$ and R$^{93}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;

each R$^{94}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

a is 0 to 6;
b is 0 to 6;

R$^2$ is selected from OH, SH, and NH$_2$;

R$^3$ is selected from H, alkyl, alkenyl, alkynyl, aralkyl, —(CH$_2$)$_z$—O—R$^{31}$, —(CH$_2$)$_z$—N(R$^{32}$)(R$^{33}$), —(CH$_2$)$_w$—C(O)R$^{34}$, —(CH$_2$)$_w$C(O)—N(R$^{32}$)(R$^{33}$), —(CH$_2$)$_w$—SO$_2$—R$^{31}$ cycloalkyl, cycloalkenyl, aryl and a heterocyclic group;

R$^{31}$ is selected from H, alkyl, alkenyl, alkynyl, cycloalkyl, cycloalkenyl, aralkyl, aryl and a heterocyclic group;

R$^{32}$ and R$^{33}$ are independently selected from H, alkyl, alkenyl, alkynyl, cycloalkyl, cycloalkenyl, aralkyl, aryl and a heterocyclic group; or R$^{32}$ and R$^{33}$ may be taken together with the nitrogen to which they are attached form a 5- to 7-membered ring which may optionally contain a further heteroatom;

R$^{34}$ is selected from H, alkyl, —OH, —O-alkyl, —O-aryl, —O-aralkyl, alkenyl, alkynyl, cycloalkyl, cycloalkenyl, aralkyl, aryl and a heterocyclic group;

w is 0 to 6;
z is 1 to 6;

R$^4$ is independently selected from H, CN, CF$_3$, alkyl, alkenyl, alkynyl, aralkyl, cycloalkyl, cycloalkenyl, aryl and a heterocyclic group;

R$^5$ is independently selected from H, alkyl, alkenyl, alkynyl, aralkyl, cycloalkyl, cycloalkenyl, aryl and a heterocyclic group;

X$^1$ is selected from CH$_2$, O, S, SO$_2$, and —N(R$^{101}$)—;

R$^{101}$ is selected from H, alkyl, alkenyl, alkynyl, aralkyl, —C(=O)—R$^{102}$, cycloalkyl, cycloalkenyl, aryl and a heterocyclic group;

R$^{102}$ is selected from H, alkyl, alkenyl, alkynyl, aralkyl, —N(R$^{103}$)(R$^{104}$), cycloalkyl, cycloalkenyl, aryl and a heterocyclic group;

R$^{103}$ and R$^{14}$ are independently selected from H, alkyl, alkenyl, alkynyl, aralkyl, cycloalkyl, cycloalkenyl, aryl and a heterocyclic group, or R$^{103}$ and R$^{104}$ may be taken together with the nitrogen to which they are attached form a 5- to 7-membered ring which may optionally contain a further heteroatom;

R$^6$ is independently selected from H, alkyl, alkenyl, alkynyl, aralkyl, —(CH$_2$)$_f$—Y—(CH$_2$)$_g$—R$^{61}$, —(CH$_2$)$_f$—N(R$^{62}$)(R$^{63}$), —(CH$_2$)$_f$—N(R$^{61}$)—(CH$_2$)$_g$C(O)R$^{64}$, —(CH$_2$)$_f$—N(R$^{61}$)SO$_2$R$^{61}$, —(CH$_2$)$_f$—SR$^{61}$, —(CH$_2$)$_f$—C(O)R$^{64}$, —(CH$_2$)$_f$—C(O)—(CH$_2$)$_g$OR$^{61}$, —(CH$_2$)$_f$—C(O)—(CH$_2$)$_g$N(R$^{62}$)(R$^{63}$), —(CH$_2$)$_f$—Y—(CH$_2$)$_g$—C(O)R$^{64}$, —(CH$_2$)$_f$—Y—C(O)—(CH$_2$)$_g$N(R$^{62}$)(R$^{63}$), —(CH$_2$)$_f$—Y—(CH$_2$)$_g$—C(=NOR$^{61}$)—R$^{61}$, cycloalkyl, cycloalkenyl, aryl and a heterocyclic group;

each R$^{61}$ is independently selected from H, alkyl, alkenyl, alkynyl, cycloalkyl, cycloalkenyl, aralkyl, aryl and a heterocyclic group;

each R$^{62}$ and R$^{63}$ are independently selected from H, alkyl, cycloalkyl, cycloalkenyl, alkenyl, alkynyl, aralkyl, aryl and a heterocyclic group; or R$^{62}$ and R$^{63}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;

each R$^{64}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

Y is selected from a chemical bond, —O—, and aryl;

f is 1 to 6;
g is 0 to 6;

R$^7$ is independently selected from H, alkyl, alkenyl, alkynyl, aralkyl, cycloalkyl, cycloalkenyl, aryl and a heterocyclic group;

R$^8$ is independently selected from H, alkyl, alkenyl, alkynyl, aralkyl, —(CH$_2$)$_r$—O—(CH$_2$)$_s$—R$^{81}$, —(CH$_2$)$_r$—N(R$^{82}$)(R$^{83}$), —(CH$_2$)$_r$—N(R$^{81}$)—(CH$_2$)$_s$C(O)R$^{84}$, —(CH$_2$)$_r$—N(R$^{81}$)SO$_2$R$^{81}$, —(CH$_2$)$_r$—SR$^{81}$, —(CH$_2$)$_r$—C(O)R$^{84}$, —(CH$_2$)$_r$—C(O)—(CH$_2$)$_s$OR$^{81}$, —(CH$_2$)$_r$—R$^{81}$, —(CH$_2$)$_r$—C(O)—(CH$_2$)$_s$N(R$^{82}$)(R$^{83}$), —(CH$_2$)$_s$—O—(CH$_2$)$_s$—C(O)R$^{84}$, —(CH$_2$)$_r$OC(O)—(CH$_2$)$_s$N(R$^{82}$)(R$^{83}$), cycloalkyl, cycloalkenyl, aryl and a heterocyclic group;

each R$^{81}$ is independently selected from H, alkyl, alkenyl, alkynyl, cycloalkyl, cycloalkenyl, aralkyl, aryl and a heterocyclic group;

each R$^{82}$ and R$^{83}$ are independently selected from H, alkyl, cycloalkyl, cycloalkenyl, alkenyl, alkynyl, aralkyl, aryl and a heterocyclic group; or R$^{82}$ and R$^{83}$ may be taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group;

each R$^{84}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;
s is 0 to 6; and
m is 0 to 4.

In a further preferred embodiment, the invention provides a compound of the formula V:

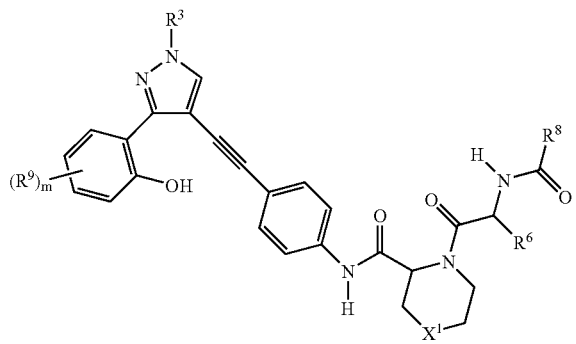

(V)

or a pharmaceutically acceptable salt or hydrate thereof, wherein:

each R$^9$ is independently selected from alkyl, alkenyl, alkynyl, aralkyl, —(CH$_2$)$_a$—O—R$^{91}$, —(CH$_2$)$_a$—N(R$^{92}$)(R$^{93}$), —(CH$_2$)$_a$—N(R$^{91}$)—(CH$_2$)$_b$C(O)R$^{94}$, —(CH$_2$)$_a$—

N(R$^{91}$)SO$_2$R$^{91}$, —(CH$_2$)$_a$—SR$^{91}$, —(CH$_2$)$_a$—C(O)R$^{94}$, —(CH$_2$)$_a$—C(O)—(CH$_2$)$_b$OR$^{91}$, —(CH$_2$)$_a$—C(O)—(CH$_2$)$_b$N(R$^{92}$)(R$^{93}$), —(CH$_2$)$_a$—(CH$_2$)$_b$—C(O)R$^{94}$, —(CH$_2$)$_a$OC(O)—(CH$_2$)$_b$N(R$^{92}$)(R$^{91}$), CN, CF$_3$, NO$_2$, SO$_2$, —SOR$^{91}$, —SO$_3$R$^{91}$, —SO$_2$N(R$^{92}$)(R$^{93}$), cycloalkyl, cycloalkenyl, halo, phosphate, phosphonate, aryl and a heterocyclic group;

additionally or alternatively two R$^9$ substituents on adjacent ring atoms may be combined to form a fused 5 or 6-membered ring, wherein the fused 5- or 6-membered ring may contain from 0 to 3 ring heteroatoms and may be further substituted with one or more substituents selected from R$^{91}$;

each R$^{91}$ is independently selected from H, alkyl, alkyl-O-alkyl, alkyl-O-aryl, alkenyl, alkynyl, cycloalkyl, cycloalkenyl, aralkyl, aryl and a heterocyclic group;

each R$^{92}$ and R$^{93}$ are independently selected from H, alkyl, cycloalkyl, cycloalkenyl, alkyl-O-alkyl, alkyl-O-aryl, alkenyl, alkynyl, aralkyl, aryl and a heterocyclic group; or R$^{92}$ and R$^{93}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;

each R$^{94}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

a is 0 to 6;
b is 0 to 6;

R$^3$ is selected from H, alkyl, alkenyl, alkynyl, aralkyl, —(CH$_2$)$_z$—O—R$^{31}$, —(CH$_2$)$_z$—N(R$^{32}$)(R$^{33}$), —(CH$_2$)$_w$—C(O)R$^{34}$, —(CH$_2$)$_w$C(O)—N(R$^{32}$)(R$^{33}$), —(CH$_2$)$_w$—SO$_2$—R$^{31}$ cycloalkyl, cycloalkenyl, aryl and a heterocyclic group;

R$^{31}$ is selected from H, alkyl, alkenyl, alkynyl, cycloalkyl, cycloalkenyl, aralkyl, aryl and a heterocyclic group;

R$^{32}$ and R$^{33}$ are independently selected from H, alkyl, alkenyl, alkynyl, cycloalkyl, cycloalkenyl, aralkyl, aryl and a heterocyclic group; or R$^{32}$ and R$^{33}$ may be taken together with the nitrogen to which they are attached form a 5- to 7-membered ring which may optionally contain a further heteroatom;

R$^{34}$ is selected from H, alkyl, —OH, —O-alkyl, —O-aryl, —O-aralkyl, alkenyl, alkynyl, cycloalkyl, cycloalkenyl, aralkyl, aryl and a heterocyclic group;

w is 0 to 6;
z is 1 to 6;

R$^6$ is independently selected from H, alkyl, alkenyl, alkynyl, aralkyl, —(CH$_2$)$_f$—Y—(CH$_2$)$_g$—R$^{61}$, —(CH$_2$)$_f$—N(R$^{62}$)(R$^{63}$), —(CH$_2$)$_f$—N(R$^{61}$)—(CH$_2$)$_g$C(O)R$^{64}$, —(CH$_2$)$_f$—N(R$^{61}$)SO$_2$R$^{61}$, —(CH$_2$)$_f$—SR$^{61}$, —(CH$_2$)$_f$—C(O)R$^{64}$, —(CH$_2$)$_f$—C(O)—(CH$_2$)$_g$OR$^{61}$, —(CH$_2$)$_f$—C(O)—(CH$_2$)$_g$N(R$^{62}$)(R$^{63}$), —(CH$_2$)$_f$—Y—(CH$_2$)$_g$—C(O)R$^{64}$, —(CH$_2$)$_f$—Y—C(O)—(CH$_2$)$_g$N(R$^{62}$)(R$^{63}$), —(CH$_2$)$_f$—Y—(CH$_2$)$_g$—C(=NOR$^{61}$)—R$^{61}$, cycloalkyl, cycloalkenyl, aryl and a heterocyclic group;

each R$^{61}$ is independently selected from H, alkyl, alkenyl, alkynyl, cycloalkyl, cycloalkenyl, aralkyl, aryl and a heterocyclic group;

each R$^{62}$ and R$^{63}$ are independently selected from H, alkyl, cycloalkyl, cycloalkenyl, alkenyl, alkynyl, aralkyl, aryl and a heterocyclic group; or R$^{62}$ and R$^{63}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;

each R$^{64}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

Y is selected from a chemical bond, —O—, and aryl;
f is 1 to 6;
g is 0 to 6;
X$^1$ is selected from CH$_2$, O, S, SO$_2$, and —N(R$^{101}$)—;

R$^{101}$ is selected from H, alkyl, alkenyl, alkynyl, aralkyl, —C(=O)—R$^{102}$, cycloalkyl, cycloalkenyl, aryl and a heterocyclic group;

R$^{102}$ is selected from H, alkyl, alkenyl, alkynyl, aralkyl, —N(R$^{103}$)(R$^{104}$), cycloalkyl, cycloalkenyl, aryl and a heterocyclic group;

R$^{103}$ and R$^{104}$ are independently selected from H, alkyl, alkenyl, alkynyl, aralkyl, cycloalkyl, cycloalkenyl, aryl and a heterocyclic group, or R$^{103}$ and R$^{104}$ may be taken together with the nitrogen to which they are attached form a 5- to 7-membered ring which may optionally contain a further heteroatom;

R$^8$ is independently selected from H, alkyl, alkenyl, alkynyl, aralkyl, —(CH$_2$)$_r$—O—(CH$_2$)$_s$—R$^{81}$, —(CH$_2$)$_r$—N(R$^{82}$)(R$^{83}$), —(CH$_2$)$_r$—N(R$^{81}$)—(CH$_2$)$_s$C(O)R$^{84}$, —(CH$_2$)$_r$—N(R$^{81}$)SO$_2$R$^{81}$, —(CH$_2$)$_r$—SR$^{81}$, —(CH$_2$)$_r$—C(O)R$^{84}$, —(CH$_2$)$_r$—C(O)—(CH$_2$)$_s$OR$^{81}$, —(CH$_2$)$_r$—R$^{81}$, —(CH$_2$)$_r$—C(O)—(CH$_2$)$_s$N(R$^{82}$)(R$^{83}$), —(CH$_2$)$_r$O—(CH$_2$)$_s$—C(O)R$^{84}$, —(CH$_2$)$_r$OC(O)—(CH$_2$)$_s$N(R$^{82}$)(R$^{83}$), cycloalkyl, cycloalkenyl, aryl and a heterocyclic group;

each R$^{81}$ is independently selected from H, alkyl, alkenyl, alkynyl, cycloalkyl, cycloalkenyl, aralkyl, aryl and a heterocyclic group;

each R$^{82}$ and R$^{83}$ are independently selected from H, alkyl, cycloalkyl, cycloalkenyl, alkenyl, alkynyl, aralkyl, aryl and a heterocyclic group; or R$^{82}$ and R$^{83}$ may be taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group;

each R$^{84}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;
s is 0 to 6; and
m is 0 to 4.

In a further preferred embodiment, the invention provides a compound of the formula VI:

(VI)

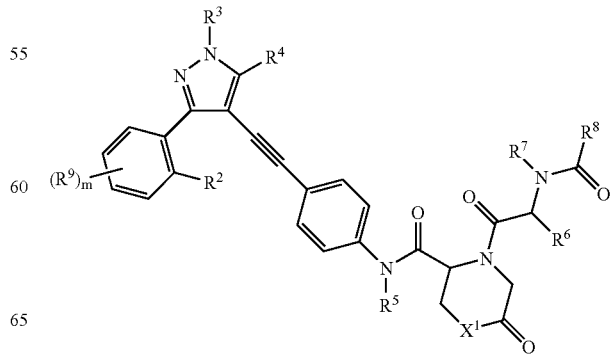

or a pharmaceutically acceptable salt or hydrate thereof, wherein:

each $R^9$ is independently selected from alkyl, alkenyl, alkynyl, aralkyl, —$(CH_2)_a$—O—$R^{91}$, —$(CH_2)_a$—$N(R^{92})(R^{93})$, —$(CH_2)_a$—$N(R^{91})$—$(CH_2)_b C(O)R^{94}$, —$(CH_2)_a$—$N(R^{91})SO_2R^{91}$, —$(CH_2)_a$—$SR^{91}$, —$(CH_2)_a$—$C(O)R^{94}$, —$(CH_2)_a$—$C(O)$—$(CH_2)_b OR^{91}$, —$(CH_2)_a$—$C(O)$—$(CH_2)_b N(R^{92})(R^{93})$, —$(CH_2)_a O$—$(CH_2)_b$—$C(O)R^{94}$, —$(CH_2)_a OC(O)$—$(CH_2)_b N(R^{92})(R^{93})$, CN, $CF_3$, $NO_2$, $SO_2$, —$SOR^{91}$, —$SO_3R^{91}$, —$SO_2N(R^{92})(R^{93})$, cycloalkyl, cycloalkenyl, halo, phosphate, phosphonate, aryl and a heterocyclic group;

additionally or alternatively two $R^9$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{91}$;

each $R^{91}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{92}$ and $R^{93}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{92}$ and $R^{93}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{94}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

a is 0 to 6;
b is 0 to 6;

$R^2$ is selected from OH, SH, and $NH_2$;

$R^3$ is selected from H, alkyl, alkenyl, alkynyl, aralkyl, —$(CH_2)_z$—O—$R^{31}$, —$(CH_2)_z$—$N(R^{32})(R^{33})$, —$(CH_2)_w$—$C(O)R^{34}$, —$(CH_2)_w C(O)$—$N(R^{32})(R^{33})$, —$(CH_2)_w$—$SO_2$—$R^{31}$ cycloalkyl, cycloalkenyl, aryl and a heterocyclic group;

$R^{31}$ is selected from H, alkyl, alkenyl, alkynyl, cycloalkyl, cycloalkenyl, aralkyl, aryl and a heterocyclic group;

$R^{32}$ and $R^{33}$ are independently selected from H, alkyl, alkenyl, alkynyl, cycloalkyl, cycloalkenyl, aralkyl, aryl and a heterocyclic group; or $R^{32}$ and $R^{33}$ may be taken together with the nitrogen to which they are attached form a 5- to 7-membered ring which may optionally contain a further heteroatom;

$R^{34}$ is selected from H, alkyl, —OH, —O-alkyl, —O-aryl, —O-aralkyl, alkenyl, alkynyl, cycloalkyl, cycloalkenyl, aralkyl, aryl and a heterocyclic group;

w is 0 to 6;
z is 1 to 6;

$R^4$ is independently selected from H, CN, $CF_3$, alkyl, alkenyl, alkynyl, aralkyl, cycloalkyl, cycloalkenyl, aryl and a heterocyclic group;

$R^5$ is independently selected from H, alkyl, alkenyl, alkynyl, aralkyl, cycloalkyl, cycloalkenyl, aryl and a heterocyclic group;

$X^1$ is selected from $CH_2$, O, S, $SO_2$, and —$N(R^{101})$—;

$R^{101}$ is selected from H, alkyl, alkenyl, alkynyl, aralkyl, —$C(=O)$—$R^{102}$, cycloalkyl, cycloalkenyl, aryl and a heterocyclic group;

$R^{102}$ is selected from H, alkyl, alkenyl, alkynyl, aralkyl, —$N(R^{103})(R^{104})$, cycloalkyl, cycloalkenyl, aryl and a heterocyclic group;

$R^{103}$ and $R^{104}$ are independently selected from H, alkyl, alkenyl, alkynyl, aralkyl, cycloalkyl, cycloalkenyl, aryl and a heterocyclic group, or $R^{103}$ and $R^{104}$ may be taken together with the nitrogen to which they are attached form a 5- to 7-membered ring which may optionally contain a further heteroatom;

$R^6$ is independently selected from H, alkyl, alkenyl, alkynyl, aralkyl, —$(CH_2)_f$—Y—$(CH_2)_g$—$R^{61}$, —$(CH_2)_f$—$N(R^{62})(R^{63})$, —$(CH_2)_f$—$N(R^{61})$—$(CH_2)_g C(O)R^{64}$, —$(CH_2)_f$—$N(R^{61})SO_2R^{61}$, —$(CH_2)_f$—$SR^{61}$, —$(CH_2)_f$—$C(O)R^{64}$, —$(CH_2)_f$—$C(O)$—$(CH_2)_g OR^{61}$, —$(CH_2)_f$—$C(O)$—$(CH_2)_g N(R^{62})(R^{63})$, —$(CH_2)_f$—Y—$(CH_2)_g$—$C(O)R^{64}$, —$(CH_2)_f$—Y—$C(O)$—$(CH_2)_g N(R^{62})(R^{63})$, —$(CH_2)_f$—Y—$(CH_2)_g$—$C(=NOR^{61})$—$R^{61}$, cycloalkyl, cycloalkenyl, aryl and a heterocyclic group;

each $R^{61}$ is independently selected from H, alkyl, alkenyl, alkynyl, cycloalkyl, cycloalkenyl, aralkyl, aryl and a heterocyclic group;

each $R^{62}$ and $R^{63}$ are independently selected from H, alkyl, cycloalkyl, cycloalkenyl, alkenyl, alkynyl, aralkyl, aryl and a heterocyclic group; or $R^{62}$ and $R^{63}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{64}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

Y is selected from a chemical bond, —O—, and aryl;
f is 1 to 6;
g is 0 to 6;

$R^7$ is independently selected from H, alkyl, alkenyl, alkynyl, aralkyl, cycloalkyl, cycloalkenyl, aryl and a heterocyclic group;

$R^8$ is independently selected from H, alkyl, alkenyl, alkynyl, aralkyl, —$(CH_2)_r$—O—$(CH_2)_s$—$R^{81}$, —$(CH_2)_r$—$N(R^{82})(R^{83})$, —$(CH_2)_r$—$N(R^{81})$—$(CH_2)_s C(O)R^{84}$, —$(CH_2)_r$—$N(R^{81})SO_2R^{81}$, —$(CH_2)_r$—$SR^{81}$, —$(CH_2)_r$—$C(O)R^{84}$, —$(CH_2)_r$—$C(O)$—$(CH_2)_s OR^{81}$, —$(CH_2)_r$—$R^{81}$, —$(CH_2)_r$—$C(O)$—$(CH_2)_s N(R^{82})(R^{83})$, —$(CH_2)_r O$—$(CH_2)_s$—$C(O)R^{84}$, —$(CH_2)_r OC(O)$—$(CH_2)_s N(R^{82})(R^{83})$, cycloalkyl, cycloalkenyl, aryl and a heterocyclic group;

each $R^{81}$ is independently selected from H, alkyl, alkenyl, alkynyl, cycloalkyl, cycloalkenyl, aralkyl, aryl and a heterocyclic group;

each $R^{82}$ and $R^{83}$ are independently selected from H, alkyl, cycloalkyl, cycloalkenyl, alkenyl, alkynyl, aralkyl, aryl and a heterocyclic group; or $R^{82}$ and $R^{83}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

each $R^{84}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;
s is 0 to 6; and
m is 0 to 4.

In a further preferred embodiment, the invention provides a compound of the formula VII:

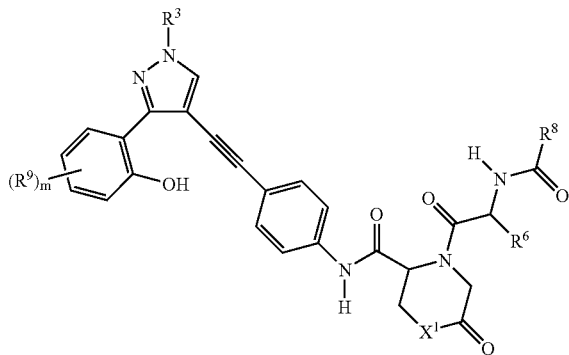

(VII)

or a pharmaceutically acceptable salt or hydrate thereof, wherein:

each $R^9$ is independently selected from alkyl, alkenyl, alkynyl, aralkyl, —$(CH_2)_a$—O—$R^{91}$, —$(CH_2)_a$—$N(R^{92})(R^{93})$, —$(CH_2)_a$—$N(R^{91})$—$(CH_2)_b C(O)R^{94}$, —$(CH_2)_a$—$N(R^{91})SO_2R^{91}$, —$(CH_2)_a$—$SR^{91}$, —$(CH_2)_a$—$C(O)R^{94}$, —$(CH_2)_a$—C(O)—$(CH_2)_b OR^{91}$, —$(CH_2)_a$—C(O)—$(CH_2)_b N(R^{92})(R^{93})$, —$(CH_2)_a O$—$(CH_2)_b$—$C(O)R^{94}$, —$(CH_2)_a OC(O)$—$(CH_2)_b N(R^{92})(R^{93})$, CN, $CF_3$, $NO_2$, $SO_2$, —$SOR^{91}$, —$SO_3R^{91}$, —$SO_2N(R^{92})(R^{93})$, cycloalkyl, cycloalkenyl, halo, phosphate, phosphonate, aryl and a heterocyclic group;

additionally or alternatively two $R^9$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{91}$;

each $R^{91}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{92}$ and $R^{93}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{92}$ and $R^{93}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{94}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

a is 0 to 6;
b is 0 to 6;

$R^3$ is selected from H, alkyl, alkenyl, alkynyl, aralkyl, —$(CH_2)_z$—O—$R^{31}$, —$(CH_2)_z$—$N(R^{32})(R^{33})$, —$(CH_2)_w$—$C(O)R^{34}$, —$(CH_2)_w C(O)$—$N(R^{32})(R^{33})$, —$(CH_2)_w$—$SO_2$—$R^{31}$ cycloalkyl, cycloalkenyl, aryl and a heterocyclic group;

$R^{31}$ is selected from H, alkyl, alkenyl, alkynyl, cycloalkyl, cycloalkenyl, aralkyl, aryl and a heterocyclic group;

$R^{32}$ and $R^{33}$ are independently selected from H, alkyl, alkenyl, alkynyl, cycloalkyl, cycloalkenyl, aralkyl, aryl and a heterocyclic group; or $R^{32}$ and $R^{33}$ may be taken together with the nitrogen to which they are attached form a 5- to 7-membered ring which may optionally contain a further heteroatom;

$R^{34}$ is selected from H, alkyl, —OH, —O-alkyl, —O-aryl, —O-aralkyl, alkenyl, alkynyl, cycloalkyl, cycloalkenyl, aralkyl, aryl and a heterocyclic group;

w is 0 to 6;
z is 1 to 6;

$R^6$ is independently selected from H, alkyl, alkenyl, alkynyl, aralkyl, —$(CH_2)_f$—Y—$(CH_2)_g$—$R^{61}$, —$(CH_2)_f$—$N(R^{62})(R^{63})$, —$(CH_2)_f$—$N(R^{61})$—$(CH_2)_g C(O)R^{64}$, —$(CH_2)_f$—$N(R^{61})SO_2R^{61}$, —$(CH_2)_f$—$SR^{61}$, —$(CH_2)_f$—$C(O)R^{64}$, —$(CH_2)_f$—C(O)—$(CH_2)_g OR^{61}$, —$(CH_2)_f$—C(O)—$(CH_2)_g N(R^{62})(R^{63})$, —$(CH_2)_f$—Y—$(CH_2)_g$—$C(O)R^{64}$, —$(CH_2)_f$—Y—C(O)—$(CH_2)_g N(R^{62})(R^{63})$, —$(CH_2)_f$—Y—$(CH_2)_g$—$C(=NOR^{61})$—$R^{61}$, cycloalkyl, cycloalkenyl, aryl and a heterocyclic group;

each $R^{61}$ is independently selected from H, alkyl, alkenyl, alkynyl, cycloalkyl, cycloalkenyl, aralkyl, aryl and a heterocyclic group;

each $R^{62}$ and $R^{63}$ are independently selected from H, alkyl, cycloalkyl, cycloalkenyl, alkenyl, alkynyl, aralkyl, aryl and a heterocyclic group; or $R^{62}$ and $R^{63}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{64}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

Y is selected from a chemical bond, —O—, and aryl;
f is 1 to 6;
g is 0 to 6;

$X^1$ is selected from $CH_2$, O, S, $SO_2$, and —$N(R^{101})$—;

$R^{101}$ is selected from H, alkyl, alkenyl, alkynyl, aralkyl, —C(=O)—$R^{102}$, cycloalkyl, cycloalkenyl, aryl and a heterocyclic group;

$R^{102}$ is selected from H, alkyl, alkenyl, alkynyl, aralkyl, —$N(R^{103})(R^{104})$, cycloalkyl, cycloalkenyl, aryl and a heterocyclic group;

$R^{103}$ and $R^{104}$ are independently selected from H, alkyl, alkenyl, alkynyl, aralkyl, cycloalkyl, cycloalkenyl, aryl and a heterocyclic group, or $R^{103}$ and $R^{104}$ may be taken together with the nitrogen to which they are attached form a 5- to 7-membered ring which may optionally contain a further heteroatom;

$R^8$ is independently selected from H, alkyl, alkenyl, alkynyl, aralkyl, —$(CH_2)_r$—O—$(CH_2)_s$—$R^{81}$, —$(CH_2)_r$—$N(R^{82})(R^{83})$, —$(CH_2)_r$—$N(R^{81})$—$(CH_2)_s C(O)R^{84}$, —$(CH_2)_r$—$N(R^{81})SO_2R^{81}$, —$(CH_2)_r$—$SR^{81}$, —$(CH_2)_r$—$C(O)R^{84}$, —$(CH_2)_r$—C(O)—$(CH_2)_s OR^{81}$, —$(CH_2)_r$—$R^{81}$, —$(CH_2)_r$—C(O)—$(CH_2)_s N(R^{82})(R^{83})$, —$(CH_2)_r O$—$(CH_2)_s$—$C(O)R^{84}$, —$(CH_2)_r OC(O)$—$(CH_2)_s N(R^{82})(R^{83})$, cycloalkyl, cycloalkenyl, aryl and a heterocyclic group;

each $R^{81}$ is independently selected from H, alkyl, alkenyl, alkynyl, cycloalkyl, cycloalkenyl, aralkyl, aryl and a heterocyclic group;

each $R^{82}$ and $R^{83}$ are independently selected from H, alkyl, cycloalkyl, cycloalkenyl, alkenyl, alkynyl, aralkyl, aryl and a heterocyclic group; or $R^{82}$ and $R^{83}$ may be taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group;

each $R^{84}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;
s is 0 to 6; and
m is 0 to 4.

The substances according to the invention may also be present as salts. In the context of the invention, preference is given to pharmaceutically acceptable salts. Pharmaceutically acceptable salts refers to an acid addition salt or a basic addition salt of a compound of the invention in which the resulting counter ion is understood in the art to be generally acceptable for pharmaceutical uses. Pharmaceutically acceptable salts can be salts of the compounds according to the invention with inorganic or organic acids. Preference is given to salts with inorganic acids, such as, for example, hydrochloric acid, hydrobromic acid, phosphoric acid or sulfuric acid, or to salts with organic carboxylic or sulfonic acids, such as, for example, acetic acid, maleic acid, fumaric acid, malic acid, citric acid, tartaric acid, lactic acid, benzoic acid, or methanesulfonic acid, ethanesulfonic acid, phenylsulfonic acid, toluenesulfonic acid or naphthalenedisulfonic acid. Pharmaceutically acceptable salts can also be metal or ammonium salts of the compounds according to the invention. Particular preference is given to, for example, sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine. (see, Berge et al. *J. Pharm. Sci.* 1977, 66, 1-19).

When one or more chiral centers are present in the compounds of the present invention, the individual isomers and mixtures thereof (e.g., racemates, etc.) are intended to be encompassed by the formulae depicted herein. Thus, for example, the exemplified compounds disclosed herein are depicted as specific stereoisomers. It should be understood that the present invention includes such compounds but having alternate stereochemistry at one or more of the chiral centers.

In certain embodiments, compounds of the invention may exist in several tautomeric forms. Accordingly, the chemical structures depicted herein encompass all possible tautomeric forms of the illustrated compounds. Compounds of the invention may exist in various hydrated forms.

It is understood that when n is a value greater than 1, each $R^1$ group may be selected independently. Thus, when more than one $R^1$ group is present, the $R^1$ groups may be selected from any of the stated groups so as to be the same or different. This also holds true for any other group or substituent which may be selected independently from among various groups or values.

In another aspect of the invention, a synthetic process for the preparation of the pyrazole derivatives is provided. The process uses mild reaction conditions, which provides a high substituent tolerance. The product is obtained in high yield and high purity. A process of the present invention is illustrated by Scheme I:

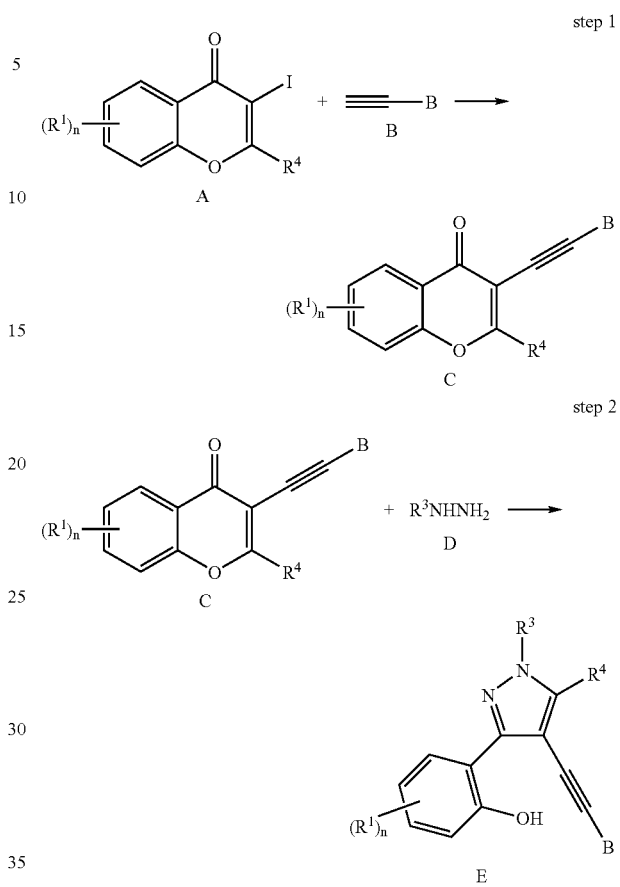

Step 1 of Scheme 1 preferably involves using a Sonogashira reaction in which a compound of the formula C is prepared by reacting a compound of the formula A with a terminal alkyne represented by the formula B in the presence of base and a transition metal catalyst, wherein $R^1$, $R^2$, $R^3$, $R^{15}$ and n are as described above for the compound of the formula I. A suitable base may be, for example, an organic base such as a primary, secondary or tertiary amine. Non-limiting examples include triethylamine, diisopropylamine, 1,8-diazabicyclo-[5.4.0]-undec-7-ene (DBU), 1,5-diazabicyclo-[4,3,0]-non-5-ene (DBN), or 1,4-diazabicyclo-[2.2.2]-octane (DABCO). Alternatively, an inorganic base may be used, such as an alkali metal or alkaline earth metal salt, such as a carbonate, bicarbonate or acetate salt.

The metal catalyst may be in the form of a salt or a complex with organic ligands. Particularly suitable metal catalysts are, for example, the Group VIII metals, preferably Pd(0) complexes or a Pd(II) salt. The ligands may be selected from, for example, phosphorus-containing ligands, such as triphenylphosphine (PPh₃) and 1,2-bis(diphenyl-phosphino) ethane (dppe). Preferred palladium catalysts include Pd(PPh₃)₂Cl₂, Pd(PPh₃)₄ and Pd(OAc)₂. The reaction is performed in the presence of a Cu(I) salt, such as a Cu(I) halide, Cu₂O, and CuCN, preferably CuI or CuCl. Suitable organic solvents include, but are not limited to, dioxane, tetrahydrofuran (THF) dimethylformamide (DMF), acetonitrile, dimethylsulfoxide, and other polar aprotic solvents or mixtures thereof. For further discussion of the Sonogashira reaction, see Sonogashira, K.; Tohda, Y; Hagihara, N. *Tetrahedron Lett.*

1975, 4467-4470; Sonogashira, K. In *Comprehensive Organic Synthesis*, Trost, B. M.; Fleming, L., Eds., Pergamon Press: New York, 1991, Vol. 3, chapter 2.4; Liao, Y.; Fathi, R.; Reitman, M.; Zhang, Y.; Yang, Z. *Tetrahedron Lett.* 2001, 42, 1815-1818; Nicolaou, K. C.; Smith, A. L. *Acc. Chem. Res.* 1992, 25, 497-503; Porco, J. A., Jr.; Schoenen, F. J.; Stout, T. J.; Clardy, J.; Schreiber, S. L. *J. Am. Chem. Soc.* 1990, 112, 7410-7411; Hundertmark, T.; Littke, A. F.; Buchwald, S. L.; Fu, G. C. *Org. Lett.* 2000, 2, 1729-1731, and references therein; Takeuchi, R.; Tanabe, K.; Tanaka, S. *J. Org. Chem.* 2000, 65, 1558-1561; Arterburn, J. B.; Rao, K. V.; Perry, M. C. *Tetrahedron Lett.* 2000, 41, 839-842; Gan, Z.; Roy, R. *Tetrahedron Lett.* 2000, 41, 1155-1159; Godt, A.; Unsal, O.; Roos, M. *J. Org. Chem.* 2000, 65, 2837-2842; Wu, M. J.; Lin, C. F.; Chen, S. H. *Org. Lett.* 1999, 1, 767-768; Yoshimura, F.; Kawata, S.; Hirama, M. *Tetrahedron Lett.* 1999, 40, 8281-8286; Ma, S.; Shi, Z.; Yu, Z. *Tetrahedron Lett.* 1999, 40, 2393-2396; Tretyakov, E. V.; Knight, D. W.; Vasilevsky, S. F. *J. Chem. Soc., Perkin Trans.* 1, 1999, 3713-3720; Thorand, S.; Krause, N. *J. Org. Chem.* 1998, 63, 8551-8553; and Sonogashira, K. in *Metal-Catalyzed Cross-Coupling Reactions*; Diederich, F., Stang, P. J., Wiley-VCH: New York, 1998; Chapter 5, each of which is incorporated by reference.

Step 2 of Scheme 1 involves a reaction in which a compound of the formula E is prepared by reacting a compound of the formula C with a hydrazine represented by the formula D. In a preferred embodiment, the hydrazine D is added directly to the pot containing the crude intermediate C.

It may be advantageous to employ a temporary protecting group in achieving the final product. The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

Further guidance for the synthesis of pyrazoles may be found in, for example, J. Elguero, Comprehensive Heterocyclic Chemistry II, Pergamon Press, Oxford, 1996, v. 3, p. 1. Starting materials useful for preparing compounds of the invention and intermediates thereof may be commercially available or can be prepared by well-known synthetic methods. Other methods for synthesis of the compounds described herein and/or starting materials are either described in the art or will be readily apparent to the skilled artisan. (see, e.g., Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Alternatives to the reagents and conditions may be found in the references provided above and in other compendiums well known to the skilled artisan. Accordingly, the synthetic methods and strategies presented herein are illustrative rather than comprehensive.

The compounds and processes disclosed herein are useful in the production of a library of pyrazole derivatives for biological screening. Derivatives of pyrazole posses a range of biological activities. Pyrazole-based compounds have shown efficacy, for example, as antivirals. Particularly, the compounds of the present invention may be used to prevent or treat infection with HCV.

The identification of inhibitors of HCV replication and/or proliferation has been facilitated by the development of a cell-based system to study HCV replication. Inhibition of HCV replication may be performed using the HCV Replicon Assay developed in the laboratories of Bartenschlager (Lohman et al, *Science* 285, 110-113, 1999), Rice (Blight et al, *Science* 290, 1972-1974, 2000) and Lemon (Yi and Lemon, *J. Virol.* 78(15), 7904-7915, 2004). The assay is performed using the either the Huh-Luc-Neo cell line (HCV genotype 1b replicon; Lohman et al, *Science* 285, 110-113, 1999) or the En5-3/Htat2ANeo cell line (HCV genotype 1a replicon; Yi and Lemon, *J. Virol.* 78(15), 7904-7915, 2004) Huh-Luc-Neo cells are a human hepatoma cell line (Huh-7) stably expressing a bi-cistronic subgenomic HCV genotype 1b replicon (luc-neo/ET) containing the HCV IRES in which the structural protein sequences of HCV have been deleted and replaced by a construct containing sequences coding for the firefly luciferase reporter gene, the neomycin selectable marker and the EMCV IRES to direct expression of a truncated HCV genome expressing the genotype 1b non-structural proteins NS3, NS4A, NS4B, NS5A, and NS5B. The En5-3/Htat2ANeo cells are a Huh-7 cell line stably expressing the pLTR-SEAP (HIV LTR driven secreted alkaline phosphatase reporter) and a bi-cistronic subgenomic HCV genotype 1a replicon (Htat2ANeo) and is similar to the genotype 1b luc-neo/ET replicon except that the HCV structural proteins sequences have been replaced by the HIV tat gene, the FMDV 2A proteinase sequence, the neomycin selectable marker and the EMCV IRES which directs expression of the genotype 1a non-structural proteins (NS3-NS5B; Yi et al, *Virology*, 304(2), 97-210, 2002). HCV targets through which inhibitors could act to inhibit replication in these assay systems include the NS3 protease, the helicase/ATPase, NS5A, the NS5B-RNA dependent RNA polymerase, and the HCV IRES.

Expression of HCV IRES driven luciferase reporter activity and HCV RNA is measured to obtain indirect and direct measures of replication of HCV RNA respectively. Inhibitors of HCV replication and/or proliferation are determined by initially identifying molecules that inhibit expression of the HCV IRES driven luciferase reporter in this HCV Replicon Luciferase Assay. Cell viability assays and control cell based luciferase assays are then run on hits identified in the HCV Replicon Luciferase Assay to eliminate cytoxic compounds and non-specific compounds which act by inhibiting the luciferase enzyme. Validated inhibitors of HCV replication and/or proliferation are identified by evaluating HCV Replicon Luciferase hits that are specific and non-cytoxic and demonstrating that these compounds inhibit replication of HCV RNA using a quantitative PCR based approach (Taqman) using primers and probes specific for HCV RNA (HCV Replicon RNA Assay with genotype 1a and 1b replicons).

The HCV Replicon Assay may be used to predict compound efficacy in treatment and/or prevention of HCV infection as well as inhibition of HCV replication and/or proliferation. The HCV Replicon encompasses a multiplicity of viral and host targets through which an inhibitor could work to inhibit HCV Replication. Viral targets expressed in the HCV Replicon include the HCV IRES (for translation), NS3 Protease, the HCV Helicase/ATPase, NS5A, and the NS5B polymerase. Without being limited to theory, it is believed that the compounds of the present invention inhibit HCV replication. The compounds of the invention may inhibit replication as by acting on the IRES, NS3 protease, NS5B polymerase, Helicase/ATPase, and/or NS5A.

The emergence of mutations in NS3, NS4A, NS4B and NS5A under selection with compounds of the present invention, indicates that the compounds exert their inhibitory capacity on HCV replication at least in part via NS3, NS4A, NS4B and NS5A either alone or in some combination. The compounds of the invention may inhibit HCV replication by mechanisms other than by targeting NS3, NS4A, NS4B, and NS5A either alone or in some combination. However, preferably the compounds of the invention inhibit HCV replication and more preferably they inhibit NS3, NS4A, NS4B, and NS5A either alone or in some combination. Most preferably, the compounds of the invention inhibit HCV replication by their interaction with NS5A. In addition, these compounds preferably inhibit multiple genotypes of HCV as evidenced by data presented here which indicate that these compounds are active in genotype 1a and 1b replicons.

Thus, in another embodiment, the present invention provides pharmaceutical compositions comprising an anti-HCV effective amount of a compound of the present invention, or a pharmaceutically acceptable salt or hydrate thereof, in combination with a pharmaceutically acceptable carrier or auxiliary agent. As used herein, the terms "pharmaceutically acceptable salts" and "hydrates" refer to those salts and hydrated forms of the compound that would favorably affect the physical or pharmacokinetic properties of the compound, such as solubility, palatability, absorption, distribution, metabolism and excretion. Other factors, more practical in nature, which those skilled in the art may take into account in the selection include the cost of the raw materials, ease of crystallization, yield, stability, solubility, hygroscopicity and flowability of the resulting bulk drug.

The invention also provides a method of treating HCV infection in a mammal, preferable a human, by administering to the mammal an effective amount of a compound of the present invention, a pharmaceutically acceptable salt or hydrate thereof, or a composition as described above. The compounds of the invention may be administered alone or may be administered in combination with other approved therapeutics, such as: an interferon (pegylated or not), preferably α-interferon, ribavirin, or interferon and ribavirin, or one or more other anti-HCV agent, such as an HCV protease inhibitor, HCV polymerase inhibitor, HCV IRES inhibitor, HCV Helicase and/or ATPase inhibitor, NS5A modulator, HCV NS2 inhibitor, or other HCV life cycle inhibitor. Combination therapies may include a compound of the invention with multiple different inhibitors of HCV life cycle (immunomodulatory agents, Toll Like Receptor modulators, antisense therapeutics etc.). The agents that comprise a combination therapy may be administered together or separately, e.g., prior to, concurrently with or following the administration of the compound of the invention or pharmaceutically acceptable salt thereof. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of wherein a compound of present invention, or a pharmaceutically acceptable salt thereof.

The compounds of the invention show additive effects, or even syngerstic effects, on replicon inhibition by interferon or other small-molecule HCV compounds. Thus, in certain preferred embodiments, the compounds of the present invention are administered in combination with interferon or other small-molecule HCV compounds. In particularly preferred embodiments, the compounds of the present invention are administered in combination with interferon, or a derivative thereof. Derivatives of interferon include interferons that have been modified by the addition of polyethylene glycol polymers.

The compounds of the present invention may be employed in solid or liquid form including, for example, amorphous powder or crystalline form, in solution or in suspension. They may be administered in numerous different ways, such as orally, parenterally, topically, transdermally or by inhalation. Oral administration or administration by injection is preferred. The choice of carrier and the content of active compound in the carrier are generally determined in accordance with the solubility and chemical properties of the desired product, the particular mode of administration and well established pharmaceutical practice. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

Examples of liquid carriers include syrups, peanut oil, olive oil, water, saline and the like. For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, may be used. Injectable forms must be fluid to the extent they can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. Compounds of the invention may be enclosed in hard or soft shell gelatin capsules, or compressed into tablets. Examples of oral liquid dosage forms include solutions, suspensions, syrups, emulsions, soft gelatin capsules and the like. Carriers for oral use (solid or liquid) may include time delay materials known in the art, such as glyceryl monostearate or glyceryl distearate alone or with a wax. To prepare a capsule, it may be advantageous to use lactose and a liquid carrier, such as high molecular weight polyethylene glycols.

Compositions and dosage forms prepared in accordance with the present invention optionally may contain lactose, sodium citrate, calcium carbonate, dicalcium phosphate and disintegrating agents such as starch, alginic acids and certain complex silica gels combined with lubricants such as magnesium stearate, sodium lauryl sulfate and talc may be used for preparing tablets, capsules and the like. Various other materials may be present as coatings or to otherwise modify the physical form of the dosage unit. For instance, tablets, and capsules may be coated with shellac, sugar or both. When aqueous suspensions are used they may contain emulsifying agents or agents which facilitate suspension. Diluents such as sucrose, ethanol, polyols such as polyethylene glycol, propylene glycol and glycerol, and mixtures thereof also may be used. In addition, the active compound may be incorporated into sustained-release preparations and formulations. If desired, certain sweetening and/or flavoring and/or coloring agents may be added. Other suitable vehicles or carriers for the above noted formulations and compositions can be found in standard pharmaceutical texts, e.g. in "Remington's Pharmaceutical Sciences", The Science and Practice of Pharmacy, 19.sup.th Ed. Mack Publishing Company, Easton, Pa., (1995).

When these compounds or their pharmaceutically acceptable salts are formulated together with a pharmaceutically acceptable carrier, the resulting composition may be administered in vivo to mammals, such as man, to treat or prevent HCV virus infection. Such treatment may also be achieved using a compound of this invention in combination with other anti-viral agents which include, but are not limited to a-interferon and ribavirin. The additional agents may be combined with compounds of this invention to create a single dosage form. Alternatively these additional agents may be separately administered to a mammal as part of a multiple dosage form.

EXAMPLES

General Methods

Reaction solvents were purchased from Aldrich or Acros without further purification and reagents were used as received. NMR spectra were recorded on an INOVA plus Varian 500 MHz spectrometer and TMS was used as internal reference ($\delta$=0.00 ppm). LC-MS spectra were obtained on a Micromass ZQ mass spectrometer in electrospray positive ionization (ES+) mode in line with a Waters 2795 HPLC system (Separations Module, Alliance™). LC-MS chromatography was performed on a Waters Symmetry C18 Column (3.5 μm, 2.1×50 mm, W93491F 26) using a flow rate of 0.4 mL/min in a gradient of 15-100% $CH_3CN$ in $H_2O$ in 9 min.

Example 1

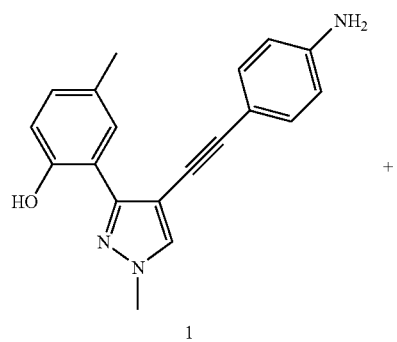

1

+

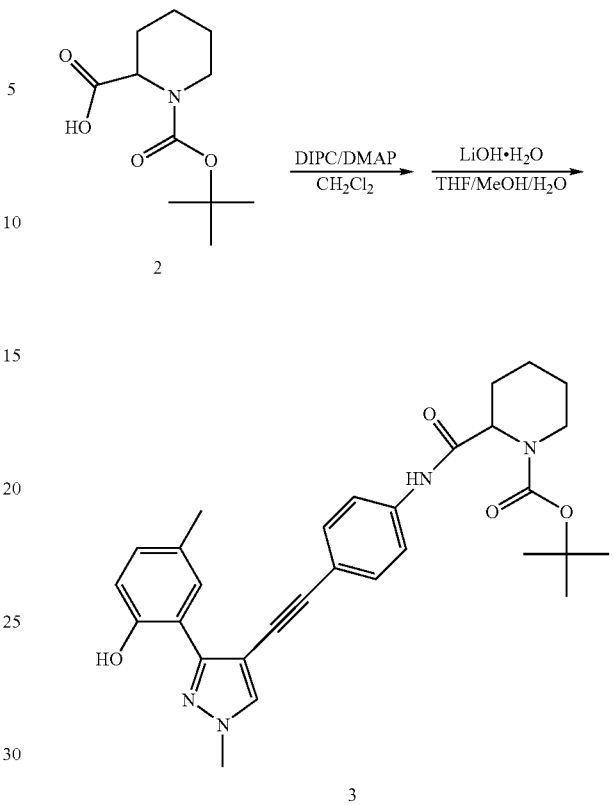

2-{4-[3-(2-Hydroxy-5-methyl-phenyl)-1-methyl-1H-pyrazol-4-ylethynyl]-phenylcarbamoyl}-piperidine-1-carboxylic acid tert-butyl ester (3)

To a solution of 2-[4-(4-amino-phenylethynyl)-1-methyl-1H-pyrazol-3-yl]-4-methyl-phenol (1) (15.2 g, 50 mmol) and N-Boc-2-piperidinecarboxylic acid (2) (34.4 g, 150 mmol) and 4-dimethylaminopyridine (DMAP, 0.6 g, 5 mmol) in dry dichloromethane (600 mL) was added N,N'-diisopropylcarbodiimide (DIPC, 23.3 mL, 150 mmol) slowly. The reaction mixture was stirred at rt overnight. Water (~100 mL) was added, and the mixture was stirred at rt for one hour. The organic layer was collected, filtered and concentrated. To the resultant residua was added THF (200 mL) and methanol (200 mL). A solution of lithium hydroxide monohydrate (21 g, 500 mmol) in water (100 mL) was slowly added above solution. The mixture was stirred at rt for 2 hours. It was then neutralized with acetic acid (29 mL, 500 mmol). The mixture was diluted with ethyl acetate (~300 mL), and washed with brine, and dried over sodium sulfate. It was filtered, concentrated and purified with silica column chromatography eluting with dichloromethane-ethyl acetate (v/v 9/1). After crystallizing with hexanes/ethyl acetate, the title compound (3, 20.09 g) was obtained as white powder in 78% yield. $^1$H NMR ($CDCl_3$, 500 MHz) $\delta$ 10.48 (s, 1H), 8.41 (s, 1H), 7.60 (s, 1H), 7.54 (d, 2H, J=8.0 Hz), 7.48 (d, 2H, J=8.0 Hz), 7.06 (d, 1H, J=8.0 Hz), 6.94 (d, 1H, J=8.0 Hz), 4.88 (br s, 1H), 4.08 (br s, 1H), 3.94 (s, 3H), 2.87 (t, 1H, J=6.1 Hz), 2.34 (s, 3H), 1.76-

1.55 (m, 4H), 1.53 (s, 9H), 1.47 (m, 1H), 1.27 (m, 1H). LCMS (ESI) m/z 515.16 (MH+, 100), 415.15; HPLC: $t_R$=6.88 min.
Example 2
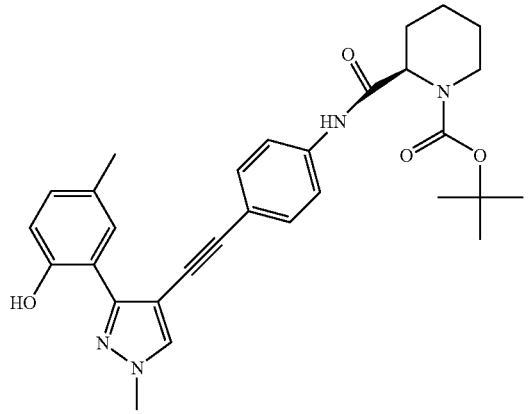
-continued
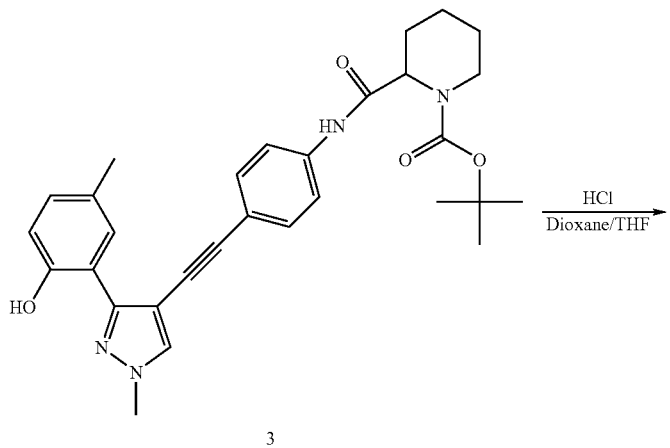
Using the same procedure for the preparation of 3, reaction of compound 1 and enantiomeric pure isomers (R and S) of N-Boc-2-piperidinecarboxylic acid (2) afforded R-3 and S-3. Their $^1$H NMR and LCMS data are identical with those of compound 3.
Example 3
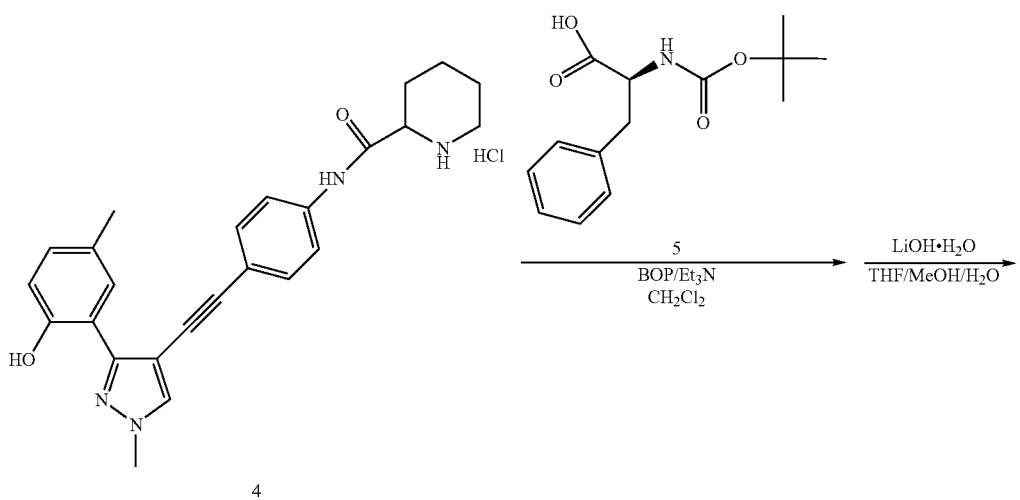

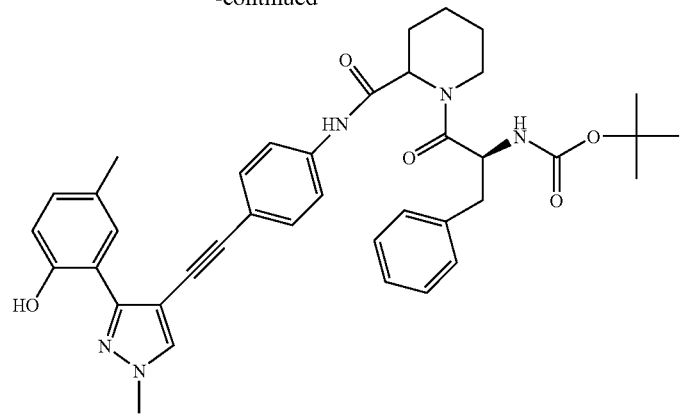

6

[1(S)-Benzyl-2-(2-{4-[3-(2-hydroxy-5-methyl-phenyl)-1-methyl-1H-pyrazol-4-ylethynyl]-phenylcarbamoyl}-piperidin-1-yl)-2-oxo-ethyl]-carbamic acid tert-butyl ester (6)

To a solution of compound 3 (7.3 g, 14.18 mmol) in THF (100 mL) was added a solution of 4 M HCl in dioxane (200 mL). The reaction mixture was stirred at rt and monitored with TLC and LC-MS. When all the starting material 3 was reacted, the reaction mixture was concentrated to dryness. Boc-L-phenylalanine (5, 11.3 g, 42.59 mmol) and dry dichloromethane (200 mL) and triethylamine (8.0 mL, 57.4 mmol) were added to above residua successively. The resultant solution was stirred at rt for 10 min. (benzotriazol-1-yloxy)tris (dimethylamino) phosphonium hexafluorophosphate (BOP, 18.8 g, 42.51 mmol) was added into above solution in portions. The final mixture was stirred at rt overnight. Solvent was then removed with rotavapor. To the resultant residua was added THF (200 mL) and methanol (200 mL). A solution of lithium hydroxide monohydrate (6 g, 143 mmol) in water (100 mL) was slowly added above solution. The mixture was stirred at rt for 2 hours. It was then neutralized with acetic acid (8.1 mL, 143 mmol). The mixture was diluted with ethyl acetate (~300 mL), and washed with brine, and dried over sodium sulfate. It was filtered, concentrated and purified with silica column chromatography eluting with dichloromethane-ethyl acetate (v/v 9/1). After crystallizing with hexanes/ethyl acetate, the title compound (6, 8.52 g) was obtained as white solid in 91% yield. The title compound was obtained as a mixture of two isomers. $^1$H NMR (CDCl$_3$, 500 MHz) δ 10.49 and 10.48 (both s, total 1H), 9.61 (s, 0.5H), 9.67 (s, 0.5H), 8.42 (s, 1H), 7.77 (m, 2H), 7.592 and 7.586 (both s, total 1H), 7.46 (m, 2H), 7.40-7.20 (m, 5H), 7.16-7.00 (m, 1H), 6.93 (d, 1H, J=8.0 Hz), 5.65-5.15 (m, 1.5H), 4.90 and 4.75 and 4.70 (all m, total 1H), 4.64 (m, 0.5H), 4.38 (br s, 0.5H), 3.93 (s, 3H), 3.70 (m, 0.5H), 3.02 (m, 3H), 2.64 and 2.43 and 2.23 and 1.99 (all m, total 1H), 2.35 and 2.31 (both s, total 3H), 1.85 and 1.70-1.48 and 1.35-1.10 (all m, total 4H), 1.46 and 1.44 and 1.38 (all s, total 9H). LCMS (ESI) m/z 662.05 (MH$^+$), 605.98, 359.06 (100), 303.04; HPLC: $t_R$=7.22 min.

Using the same procedure for synthesis of compound 6, compounds 7-12 were prepared in similar yields.

Example 4

7

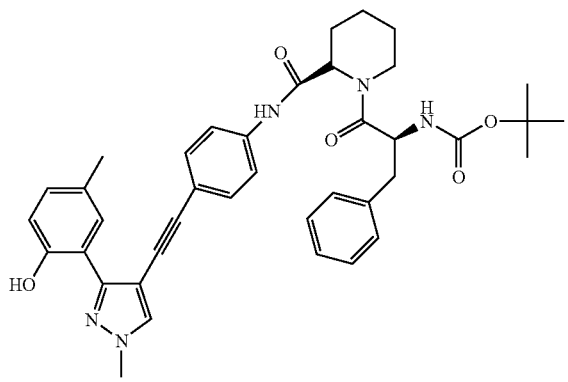

[1(S)-Benzyl-2-(2(R)-{4-[3-(2-hydroxy-5-methyl-phenyl)-1-methyl-1H-pyrazol-4-ylethynyl]-phenylcarbamoyl}-piperidin-1-yl)-2-oxo-ethyl]-carbamic acid tert-butyl ester (7)

$^1$H NMR (CDCl$_3$, 500 MHz) δ 10.48 (s, 1H), 8.68 (s, 1H), 8.42 (s, 1H), 7.75 (m, 2H), 7.59 (s, 1H), 7.45 (d, 2H, J=8.0 Hz), 7.38-7.20 (m, 5H), 7.05 (d, 1H, J=8.0 Hz), 6.93 (d, 1H, J=8.0 Hz), 5.44 (br s, 1H), 5.32 (d, 1H, J=3.0 Hz), 4.74 (m, 1H), 3.91 (s, 3H), 3.68 (m, 1H), 3.01 (m, 3H), 2.42 (m, 1H), 2.31 (s, 3H), 1.43 and 1.24 (both m, total 4H), 1.38 (s, 9H). LCMS (ESI) m/z 662.13 (MH$^+$), 606.08, 359.08 (100), 303.09; HPLC: $t_R$=7.22 min.

Example 5

8

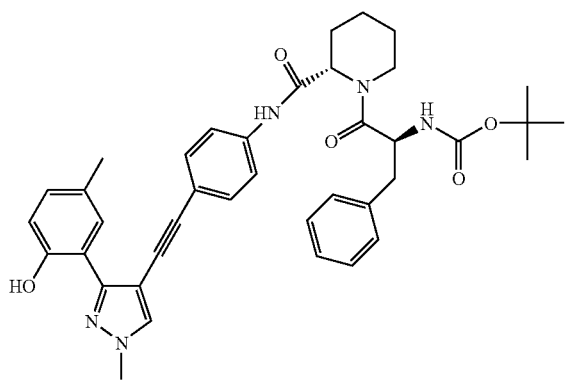

[1(S)-Benzyl-2-(2(S)-{4-[3-(2-hydroxy-5-methyl-phenyl)-1-methyl-1H-pyrazol-4-ylethynyl]-phenyl-carbamoyl}-piperidin-1-yl)-2-oxo-ethyl]-carbamic acid tert-butyl ester (8)

$^1$H NMR (CDCl$_3$, 500 MHz) δ 10.481 and 10.475 (both s, total 1H), 9.61 (s, 1H), 8.42 (s, 1H), 7.78 (m, 2H), 7.57 (s, 1H), 7.46 (m, 2H), 7.37-7.20 (m, 4H), 7.15-7.00 (m, 2H), 6.93 (d, 1H, J=8.0 Hz), 5.55-5.15 (m, 1.5H), 4.90 and 4.75 and 4.70 (all m, total 1H), 4.63 (m, 0.5H), 4.38 (br s, 0.5H), 3.91 and 3.89 (both s, total 3H), 3.70 (m, 0.5H), 3.03 (m, 3H), 2.74 and 2.46 and 2.22 and 1.99 (all m, total 1H), 2.34 and 2.31 (both s, total 3H), 1.85 and 1.70-1.48 and 1.35-1.10 (all m, total 4H), 1.45 and 1.43 and 1.37 (all s, total 9H). LCMS (ESI) m/z 662.14 (MH$^+$), 606.05, 359.08 (100), 303.10; HPLC: t$_R$=7.17 min.

Example 6

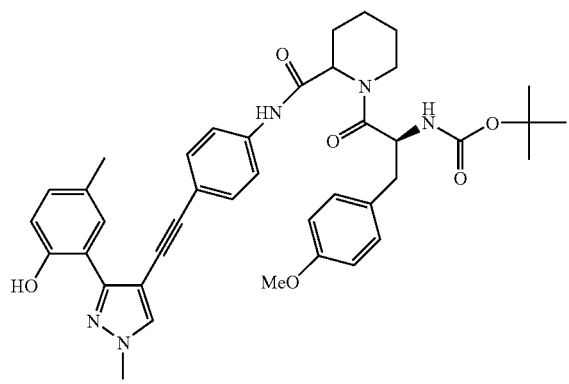

9

[2-(2-{4-[3-(2-Hydroxy-5-methyl-phenyl)-1-methyl-1H-pyrazol-4-ylethynyl]-phenylcarbamoyl}-piperidin-1-yl)-1(S)-(4-methoxy-benzyl)-2-oxo-ethyl]-carbamic acid tert-butyl ester (9)

The title compound was obtained as a mixture of two isomers. $^1$H NMR (CDCl$_3$, 500 MHz) δ 10.473 and 10.466 (both s, total 1H), 9.60 (s, 0.5H), 8.67 (s, 0.5H), 8.42 (s, 1H), 7.79 (d, 1H, J=8.0 Hz), 7.76 (d, 1H, J=8.0 Hz), 7.59 (m, 1H), 7.48 (d, 1H, J=8.0 Hz), 7.45 (d, 1H, J=7.0 Hz), 7.16 (d, 1H, J=8.0 Hz), 7.15 (d, 1H, J=8.0 Hz), 7.05 (d, 1H, J=7.5 Hz), 7.01 (d, 0.5H, J=8.5 Hz), 6.94 and 6.93 (both d, total 1H, J=8.0 Hz), 6.87 (d, 2H, J=9.0 Hz), 6.57 (d, 0.5H, J=8.5 Hz), 5.50-5.15 (m, 1.5H), 4.92 and 4.73 and 4.65 (all m, total 1.5H), 4.40 (m, 0.5H), 3.94 (s, 3H), 3.79 (s, 3H), 3.74 (m, 0.5H), 3.15-2.85 (m, 3H), 2.45 and 2.24 and 2.08 (all m, total 1H), 2.34 and 2.31 (both s, total 3H), 1.80-1.10 (m, 13H). LCMS (ESI) m/z 714.08 (MNa$^+$), 692.05 (MH$^+$), 636.05, 389.06 (100), 333.05; HPLC: t$_R$=7.05 min.

Example 7

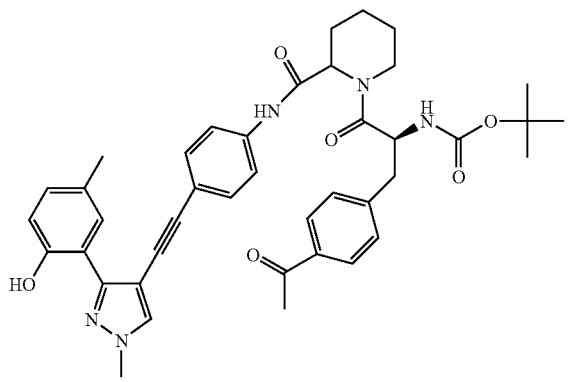

10

[1(S)-(4-Acetyl-benzyl)-2-(2-{4-[3-(2-hydroxy-5-methyl-phenyl)-1-methyl-1H-pyrazol-4-ylethynyl]-phenylcarbamoyl}-piperidin-1-yl)-2-oxo-ethyl]-carbamic acid tert-butyl ester (10)

The title compound was obtained as a mixture of two isomers. $^1$H NMR (CDCl$_3$, 500 MHz) δ 10.472 and 10.467 (both s, total 1H), 9.49 (s, 0.5H), 8.41 (s, 1H), 8.02 (s, 0.5H), 7.95 (d, 1H, J=8.0 Hz), 7.77 (d, 1H, J=8.5 Hz), 7.66 (d, 1H, J=7.5 Hz), 7.59 (m, 1H), 7.45 (m, 3H), 7.36 (d, 1H, J=7.5 Hz), 7.21 (d, 1H, J=8.0 Hz), 7.06 (m, 1H), 6.94 and 6.93 (both d, total 1H, J=8.0 Hz), 5.48-5.17 (m, 1.5H), 4.99 and 4.80 and 4.74 (all m, total 1H), 4.64 (m, 0.5H), 4.42 (m, 0.5H), 3.94 (s, 3H), 3.77 (m, 0.5H), 3.20-2.80 (m, 3H), 2.62 and 2.61 and 2.60 and 2.45 (all s, total 3H), 2.50 and 2.23 and 2.10 (all m, total 1H), 2.34 and 2.31 (both s, total 3H), 1.89 and 1.76-1.46 and 1.34-1.10 (all m, total 4H), 1.45 and 1.45 and 1.41 and 1.38 (all s, total 9H). LCMS (ESI) m/z 704.38 (MH$^+$), 648.31, 401.25 (100), 345.21; HPLC: t$_R$=5.87 min.

Example 8

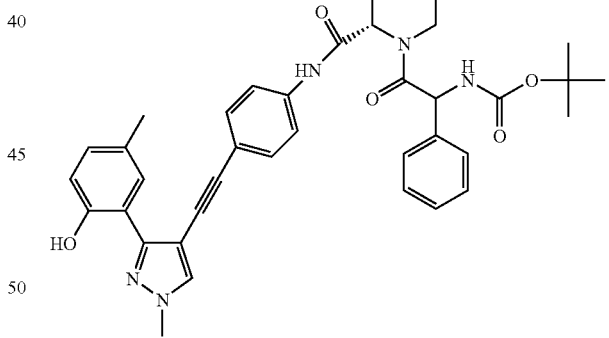

11

[2-(2(S)-{4-[3-(2-Hydroxy-5-methyl-phenyl)-1-methyl-1H-pyrazol-4-ylethynyl]-phenylcarbamoyl}-piperidin-1-yl)-2-oxo-1-phenyl-ethyl]-carbamic acid tert-butyl ester (11)

The title compound was obtained as a mixture of two isomers. $^1$H NMR (CDCl$_3$, 500 MHz) δ 10.48 and 10.46 (both s, total 1H), 9.29 (s, 0.3H), 8.48 and 8.44 and 8.40 (all s, total 1.3H), 7.89 (d, 0.4H, J=9.0 Hz), 7.80 (d, 1H, J=9.0 Hz), 7.61 (s, 1H), 7.57-7.20 (m, 8H), 7.07 (d, 1H, J=7.5 Hz), 6.94 (d, 1H, J=8.0 Hz), 6.02 and 5.72 and 5.58 and 5.51 and 5.45 and 5.39 (all m, total 2.5H), 4.92-4.60 (m, 0.5H), 3.95 (s, 3H), 3.86 (m, 1H), 3.25-2.36 (m, 2H), 2.34 and 2.33 (both s, total 3H), 1.85-1.30 (m, 13H). LCMS (ESI) m/z 670.16 (MNa$^+$), 648.16 (MH$^+$), 592.14, 548.11, 345.15 (100), 289.12; HPLC: t$_R$=7.65 min.

Example 9

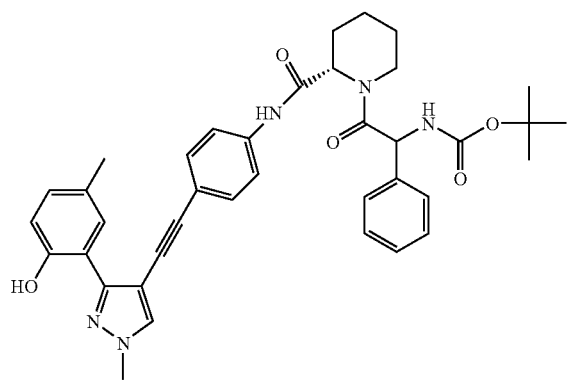

[2-(2(S)-{4-[3-(2-Hydroxy-5-methyl-phenyl)-1-methyl-1H-pyrazol-4-ylethynyl]-phenylcarbamoyl}-piperidin-1-yl)-2-oxo-1-phenyl-ethyl]-carbamic acid tert-butyl ester (12)

The title compound was obtained as a mixture of two isomers. $^1$H NMR (CDCl$_3$, 500 MHz) δ 10.48 and 10.46 (both s, total 1H), 9.29 (s, 0.3H), 8.48 and 8.44 and 8.40 (all s, total 1.3H), 7.89 (d, 0.4H, J=9.0 Hz), 7.80 (d, 1H, J=9.0 Hz), 7.61 (s, 1H), 7.57-7.20 (m, 8H), 7.07 (d, 1H, J=8.0 Hz), 6.94 (d, 1H, J=8.0 Hz), 6.02 and 5.72 and 5.58 and 5.51 and 5.45 and 5.39 (all m, total 2.5H), 4.92-4.60 (m, 0.5H), 3.95 (s, 3H), 3.86 (m, 1H), 3.25-2.36 (m, 2H), 2.34 and 2.33 (both s, total 3H), 1.85-1.30 (m, 13H). LCMS (ESI) m/z 670.18 (MNa$^+$), 648.19 (MH$^+$), 592.15, 548.17, 345.15, 289.15 (100); HPLC: t$_R$=7.65 min.

Example 10

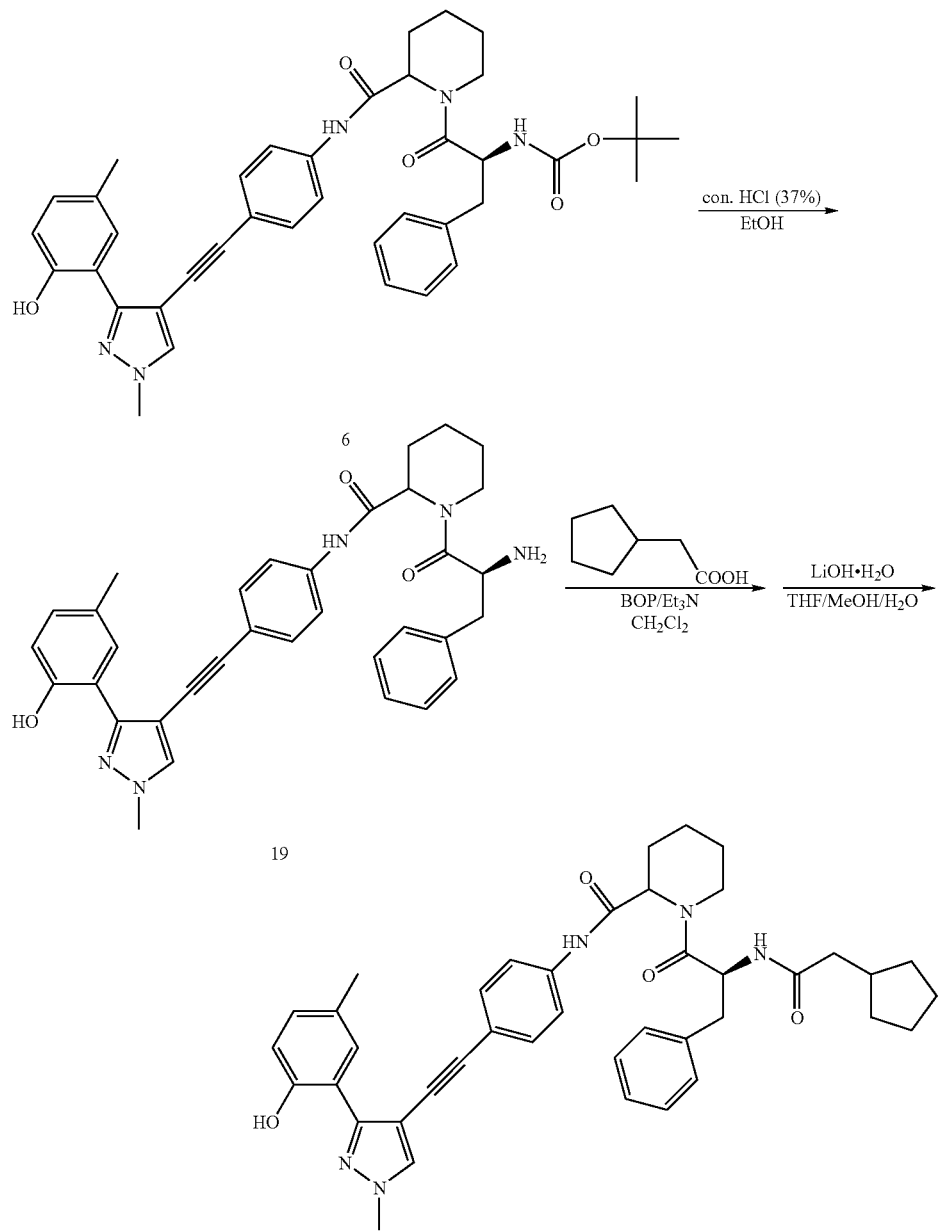

1-(2(S)-Amino-3-phenyl-propionyl)-piperidine-2-carboxylic acid {4-[3-(2-hydroxy-5-methyl-phenyl)-1-methyl-1H-pyrazol-4-ylethynyl]-phenyl}-amide (19)

A solution of compound 6 (9.9 g) in EtOH (80 mL) was cooled to 0° C. with ice-water bath. Concentrated hydrochloric acid (37%, 40 mL) was added into the above solution slowly at 0° C. The ice-bath was removed and the mixture was stirred at rt until the reaction was complete as indicated by LCMS (ca. 5 h). A solution of NaHCO$_3$ (40 g) in water (200 mL) was added slowly with stirring. The final mixture was extracted with EtOAc (~200 mL), and the organic layer was washed with brine and dried over sodium sulfate. It was filtered, and the solvent was removed with rotavapor. The residua was dried under high vacuum to provide the title compound as pale yellow gum-like powder (6.5 g, 77.4%) and was used for next step without further purification. LCMS (ESI) m/z 562.39 (MH$^+$), 259.26 (100); HPLC: $t_R$=5.05 min.

Example 11

1-[2(S)-(2-Cyclopentyl-acetylamino)-3-phenyl-propionyl]-piperidine-2-carboxylic acid {4-[3-(2-hydroxy-5-methyl-phenyl)-1-methyl-1H-pyrazol-4-ylethynyl]-phenyl}-amide (20)

To a solution of compound 19 (6.5 g, 11.57 mmol) in dry dichloromethane (100 mL) was added triethylamine (9.68 mL, 69.42 mmol) and cyclopentylacetic acid (4.35 mL, 34.71 mmol). The resultant solution was stirred at rt for 5 min. (benzotriazol-1-yloxy)tris(dimethylamino)phosphonium hexafluorophosphate (BOP, 15.36 g, 34.71 mmol) was added into the above solution in portions. The final mixture was stirred at rt overnight. The solvent was removed with rotavapor. To the residua was added THF (60 mL) and methanol (60 mL). A suspension of lithium hydroxide monohydrate (5.0 g, 119.2 mmol) in water (30 mL) was slowly added to the above solution. The mixture was stirred at rt for 1.5 hours and then neutralized with acetic acid (7.0 mL, 122.3 mmol). The mixture was diluted with ethyl acetate (~300 mL), and washed with brine, and dried over sodium sulfate. It was filtered, concentrated and purified with silica column chromatography eluting with dichloromethane-ethyl acetate (v/v 9/1). After crystallizing with hexanes/ethyl acetate, the title compound (20, 5.1 g) was obtained as white solid in 65.6% yield.

The title compound was obtained as a mixture of two isomers. $^1$H NMR (CDCl$_3$, 500 MHz) δ 10.49 and 10.46 (both s, total 1H), 9.96 (s, 0.5H), 8.71 (s, 0.5H), 8.43 and 8.37 (both s, total 1H), 7.86 (m, 2H), 7.57 (m, 1H), 7.46 (m, 2H), 7.40-7.19 (m, 4H), 7.17-6.99 (m, 2H), 6.92 (m, 1H), 6.42 and 6.30 (both m, total 1H), 5.50-5.20 (m, 1H), 4.91 (m, 1H), 4.59 (m, 0.5H), 4.44 (br s, 0.5H), 3.93 and 3.90 (both s, total 3H), 3.71 (m, 1H), 3.07 (m, 3H), 2.77 and 2.47 (both m, total 1H), 2.40-2.10 (m, 5H), 2.02-1.00 (m, 13H). LCMS (ESI) m/z 672.16 (MH$^+$), 369.10 (100); HPLC: $t_R$=7.20 min.

Using the same procedure for synthesis of compound 20, compounds 21 and 22 were prepared in similar yields.

Example 12

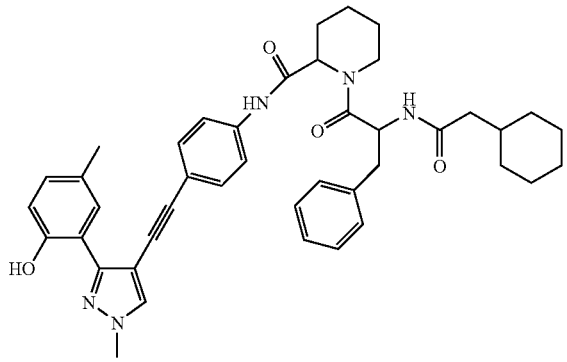

1-[2(S)-(2-Cyclohexyl-acetylamino)-3-phenyl-propionyl]-piperidine-2-carboxylic acid {4-[3-(2-hydroxy-5-methyl-phenyl)-1-methyl-1H-pyrazol-4-ylethynyl]-phenyl}-amide (21)

The title compound was obtained as a mixture of two isomers. $^1$H NMR (CDCl$_3$, 500 MHz) δ 10.53 and 10.49 and 10.47 (all s, total 1H), 9.99 (s, 0.5H), 8.71 (s, 0.5H), 8.43 and 8.37 (both s, total 1H), 7.86 (m, 2H), 7.59 (m, 1H), 7.47 (m, 2H), 7.40-7.19 (m, 4H), 7.17-6.99 (m, 2H), 6.93 (m, 1H), 6.42 and 6.30 (both m, total 1H), 5.50-5.20 (m, 1H), 4.91 (m, 1H), 4.59 (m, 0.5H), 4.44 (br s, 0.5H), 3.94 and 3.90 (both s, total 3H), 3.70 (m, 1H), 3.07 (m, 3H), 2.77 and 2.48 (both m, total 1H), 2.40-2.00 (m, 5H), 2.00-0.75 (m, 15H). LCMS (ESI) m/z 686.13 (MH$^+$), 383.07 (100); HPLC: $t_R$=7.38 min.

Example 13

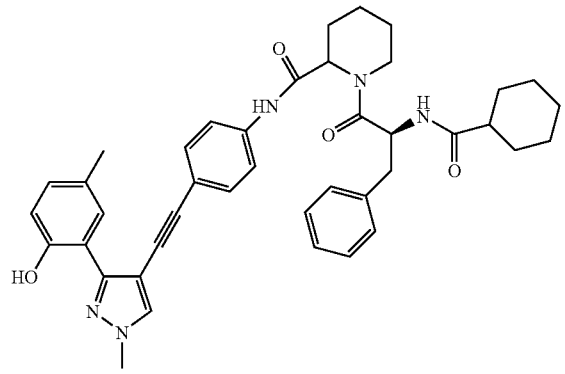

1-[2-(Cyclohexanecarbonyl-amino)-3-phenyl-propionyl]-piperidine-2-carboxylic acid {4-[3-(2-hydroxy-5-methyl-phenyl)-1-methyl-1H-pyrazol-4-ylethynyl]-phenyl}-amide (22)

The title compound was obtained as a mixture of two isomers. $^1$H NMR (CDCl$_3$, 500 MHz) δ 10.53 and 10.49 and 10.47 (all s, total 1H), 9.99 (s, 0.5H), 8.69 (s, 0.5H), 8.45 and 8.43 and 8.35 (all s, total 1H), 7.91 (d, 1H, J=8.5 Hz), 7.86 (d, 1H, J=8.5 Hz), 7.58 (s, 1H), 7.46 (m, 2H), 7.40-7.19 (m, 4H), 7.17-6.99 (m, 2H), 6.92 (m, 1H), 6.37 and 6.30 (both m, total 1H), 5.50-5.20 (m, 1H), 4.90 (m, 1H), 4.58 (m, 0.5H), 4.43 (br s, 0.5H), 3.94 and 3.91 (both s, total 3H), 3.69 (m, 1H), 3.06 (m, 3H), 2.76 and 2.47 (both m, total 1H), 2.40-2.05 (m, 4H), 2.00-1.00 (m, 14H). LCMS (ESI) m/z 672.10 (MH+), 369.08 (100); HPLC: $t_R$=7.17 min.

Example 14

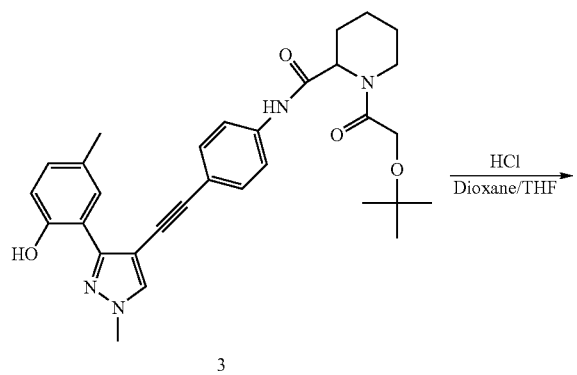

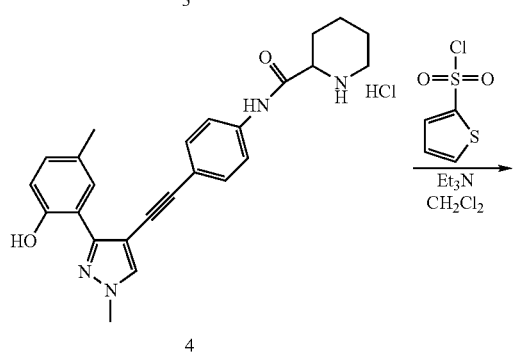

1-(Thiophene-2-sulfonyl)-piperidine-2-carboxylic acid {4-[3-(2-hydroxy-5-methyl-phenyl)-1-methyl-1H-pyrazol-4-ylethynyl]-phenyl}-amide (23)

To a solution of compound 3 (8.72 g, 16.95 mmol) in THF (100 mL) was added a solution of 4 M HCl in dioxane (200 mL). The reaction mixture was stirred at rt and monitored with TLC and LC-MS. When all the starting material 3 was reacted, the reaction mixture was concentrated to dryness. 2-Thiophenesulfonyl chloride (3.10 g, 16.95 mmol) and dry dichloromethane (~200 mL) were added to above residua. Triethylamine (12.0 mL, 86.1 mmol) was then slowly added to above mixture while cooling with an ice-water bath. The final mixture was stirred at rt overnight. It was then washed with brine, and dried over sodium sulfate. After filtration, the filtrate was concentrated and purified with silica column chromatography eluting with dichloromethane-ethyl acetate (v/v 9/1), then hexanes-ethyl acetate (v/v 1/1). The product was recrystallized from hot methanol to give the title compound (23, 5.93 g) as light yellow solid in 62.4% yield. $^1$H NMR (CDCl$_3$, 500 MHz) δ 10.48 (s, 1H), 8.45 (s, 1H), 8.41 (s, 1H), 7.67 (m, 2H), 7.61 (s, 1H), 7.58 (d, 2H, J=8.0 Hz), 7.50 (d, 2H, J=8.5 Hz), 7.14 (t, 1H, J=4.0 Hz), 7.07 (d, 1H, J=8.0 Hz), 6.94 (d, 1H, J=8.0 Hz), 4.66 (d, 1H, J=5.0 Hz), 4.07 (br d, 1H, J=13.5 Hz), 3.93 (s, 3H), 3.17 (t, 1H, J=13.0 Hz), 2.36 (m, 1H), 2.34 (s, 3H), 1.67-1.45 (m, 3H), 1.29 (m, 2H). LCMS (ESI) m/z 561.14 (MH+, 100); HPLC: $t_R$=5.82 min.

Example 15

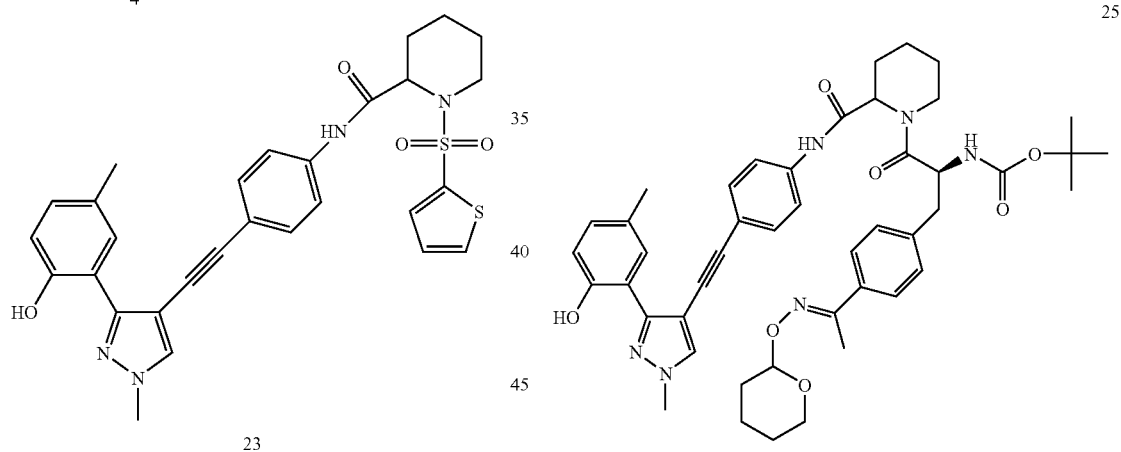

Synthetic Route:

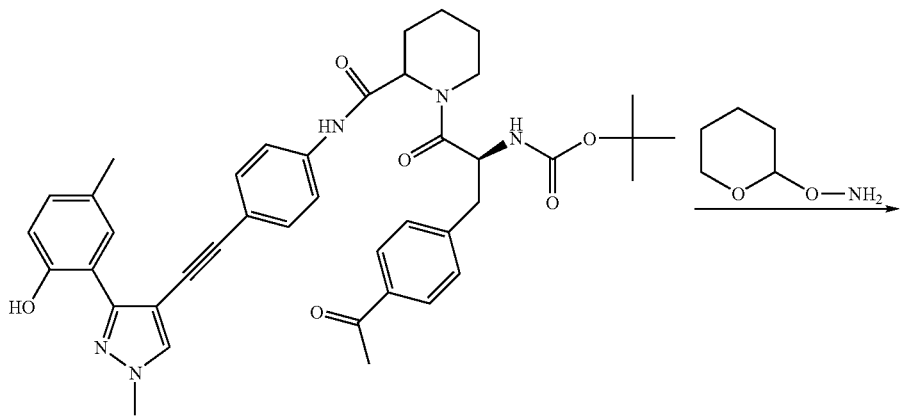

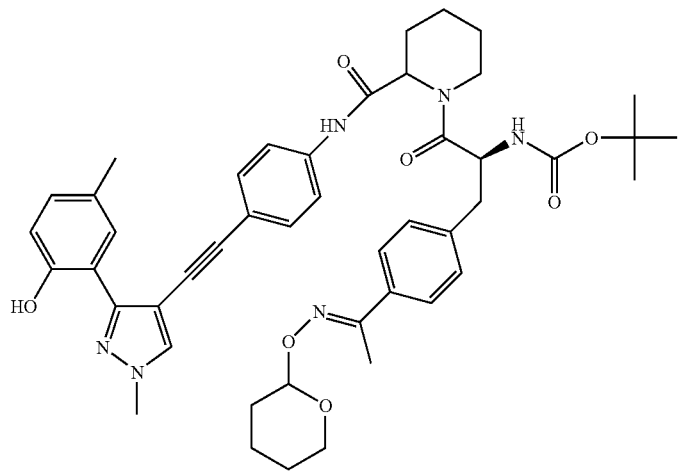
25
24 (20 mg) was mixed with O-(Tetrahydro-2H-pyran-2-yl) hydroxylamine Hydrochloride (20 mg), CsOAc (30 mg), molecular sieves (4A, 50 mg) and MeOH (anhydrous, 1 mL), and was shaken at r.t. for 5 days until all 24 was consumed. TLC purification with Ethyl acetate/hexane (1:1) led to pure 25 (90% yield). LCMS (6.26 min, [M+1]$^+$·803). $^1$H NMR (500 MHz, d6-DMSO): δ 10.32 (s, 1H), 6.8-8.3 (m, 13H), 4.2-5.4 (m, 3H), 3.94 (s, 3H), 3.6-3.8 (m, 2H), 3.4-3.6 (m, 2H), 2.7-2.9 (m, 2H), 2.25 (s, 3H), 2.20 (m, 3H), 1.2-1.8 (m, 21H).
Example 16
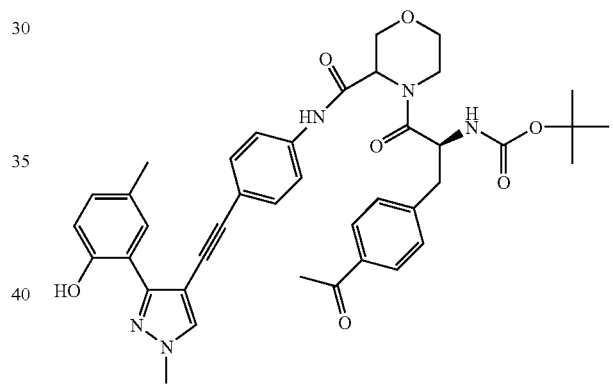
28
Synthetic Route:
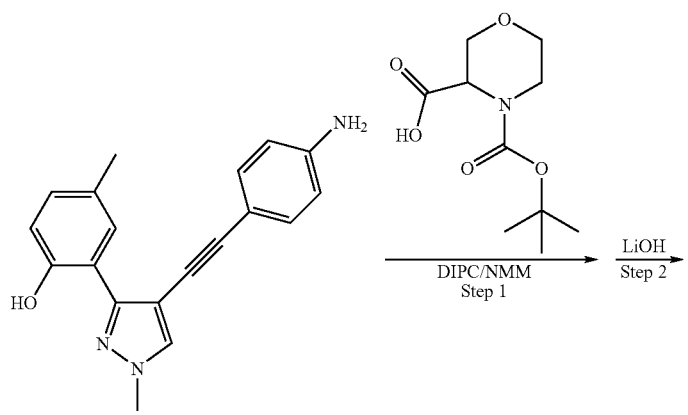
1

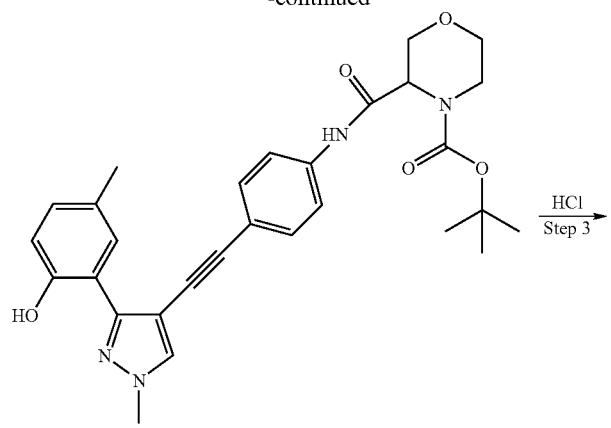

26

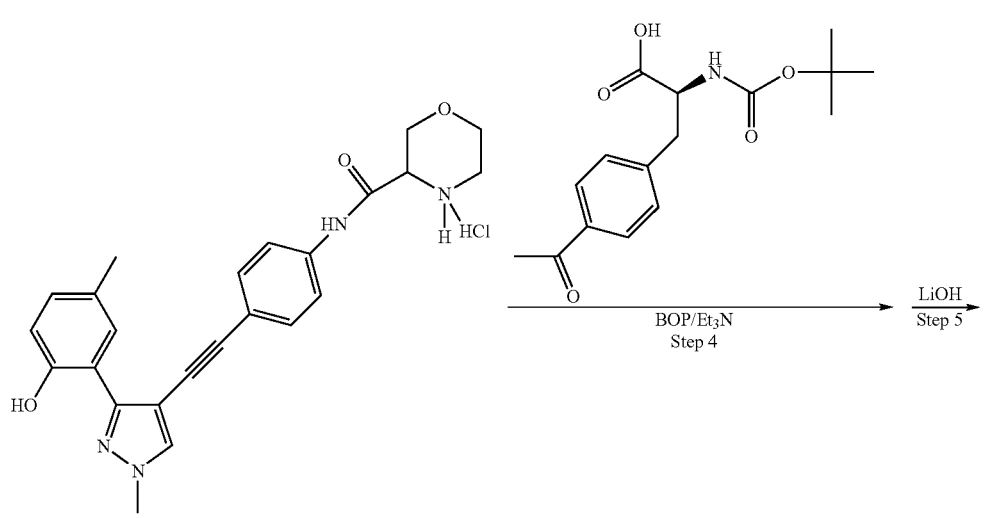

27

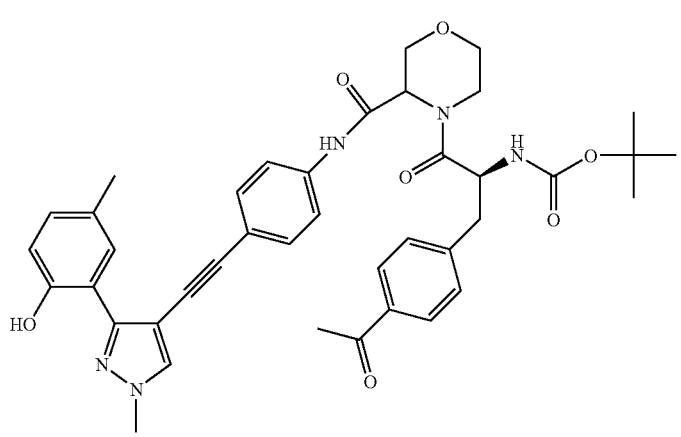

28

Steps 1-2: 1 (100 mg) was mixed with 4-(t-butoxycarbonyl)-morpholine-3-carboxylic acid (150 mg), diisopropyl carbonate (0.4 mL), 4-methylmorpholine (0.4 mL) and CH$_2$Cl$_2$ (anhydrous, 5 mL), and was shaken overnight until all 1 was consumed. Remove the solvent by rotavaporation. Then LiOH aq. (2 mL, 100 mg/mL), THF (2 mL) and MeOH (2 mL) were added. The mixture was shaken for 3 hrs. Remove THF and Methanol by rotavaporation. The remaining mixture was extracted with CH$_2$Cl$_2$. The combined CH$_2$Cl$_2$ layer was rotavaporated. TLC purification with Ethyl acetate/hexane (1:1) led to pure 26 (89% yield).

Steps 3-5: 26 (100 mg) was mixed with THF (3 mL), HCl in dioxane (4M, 1 mL) and Et$_3$SiH (0.2 mL), and was shaken for 6 hrs until all 26 was consumed. Remove the solvent completely by rotavaporation followed by high vacuum drying to give 27. 27 (10 mg) was mixed with (S)-3-(4-acetylphenyl)-2-(t-butoxycarbonyl)propanoic acid (20 mg), BOP (25 mg), Et$_3$N (0.5 mL) and CH$_2$Cl$_2$ (anhydrous, 2 mL), and shaken at r.t. overnight until all 27 was consumed. Remove CH$_2$Cl$_2$ by rotavaporation. Then LiOH aq. (0.5 mL, 100 mg/mL), THF (0.5 mL) and MeOH (0.5 mL) were added. The mixture was shaken for 3 hrs. Remove THF and Methanol by rotavaporation. The remaining mixture was extracted with CH$_2$Cl$_2$. The combined CH$_2$Cl$_2$ layer was rotavaporated. TLC purification with Ethyl acetate/hexane (1:1) led to pure 28 (81% yield from 26). LCMS (5.52 min, [M+1]$^+$·706). $^1$H NMR (500 MHz, d6-DMSO): δ 10.31 (s, 1H), 6.8-8.3 (m, 12H), 4.2-5.4 (m, 4H), 3.94 (s, 3H), 3.6-3.8 (m, 2H), 3.0-3.3 (m, 2H), 2.75 (s, 3H), 2.25 (s, 3H), 1.29 (s, 9H).

Example 17

29

The synthetic route is the same as for 28. LCMS (5.68 min, [M+Na+1]$^+$·717). $^1$H NMR (500 MHz, d6-DMSO): δ 10.31 (s, 1H), 6.7-8.3 (m, 12H), 4.2-5.4 (m, 4H), 3.94 (s, 3H), 3.70 (s, 3H), 3.6-3.8 (m, 2H), 3.0-3.3 (m, 2H), 2.25 (s, 3H), 1.29 (s, 9H).

Example 18

30

Synthetic route and procedure are the same as those of 28. LCMS (5.72 min, [M+Na]$^+$·686). $^1$H NMR (500 MHz, d6-DMSO): δ 10.31 (s, 1H), 6.7-8.3 (m, 13H), 4.2-5.4 (m, 4H), 3.94 (s, 3H), 3.6-3.8 (m, 2H), 3.0-3.3 (m, 2H), 2.25 (s, 3H), 1.29 (s, 9H).

Example 19

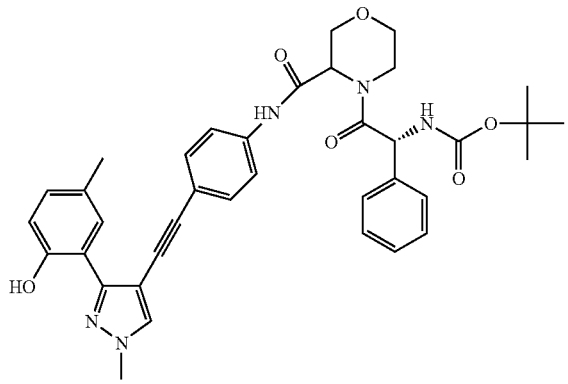

31

Synthetic route and procedure are the same as those of 28. LCMS (5.72 min, [M+Na]$^+$·672). $^1$H NMR (500 MHz, d6-DMSO): δ 10.31 (s, 1H), 6.7-8.3 (m, 13H), 4.2-5.4 (m, 4H), 3.94 (s, 3H), 3.6-3.8 (m, 2H), 3.0-3.3 (m, 2H), 2.26 (s, 3H), 1.29 (s, 9H).

Example 20

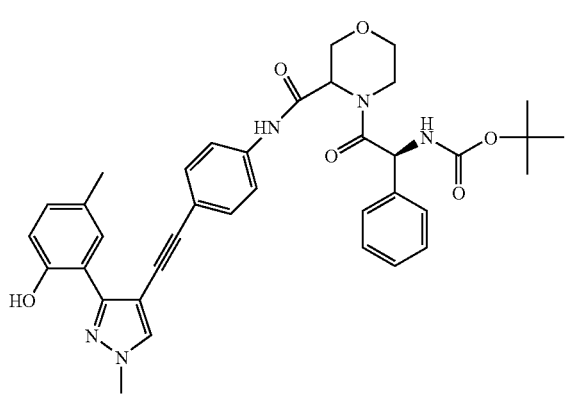

32

Synthetic route and procedure are the same as those of 28. LCMS (5.68 min, [M+Na]$^+$·672). $^1$H NMR (500 MHz, d6-DMSO): δ 10.31 (s, 1H), 6.7-8.3 (m, 13H), 4.2-5.4 (m, 4H), 3.94 (s, 3H), 3.6-3.8 (m, 2H), 3.0-3.3 (m, 2H), 2.26 (s, 3H), 1.29 (s, 9H).

Example 21

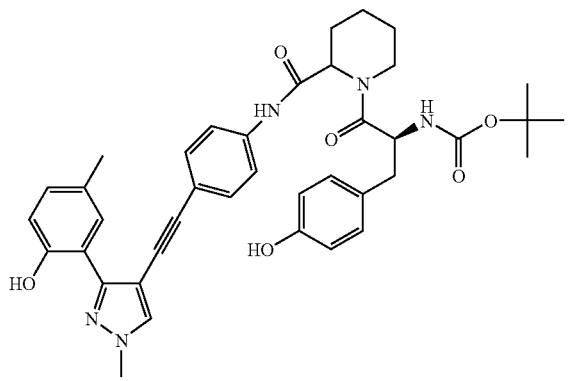

34

Synthetic Route:
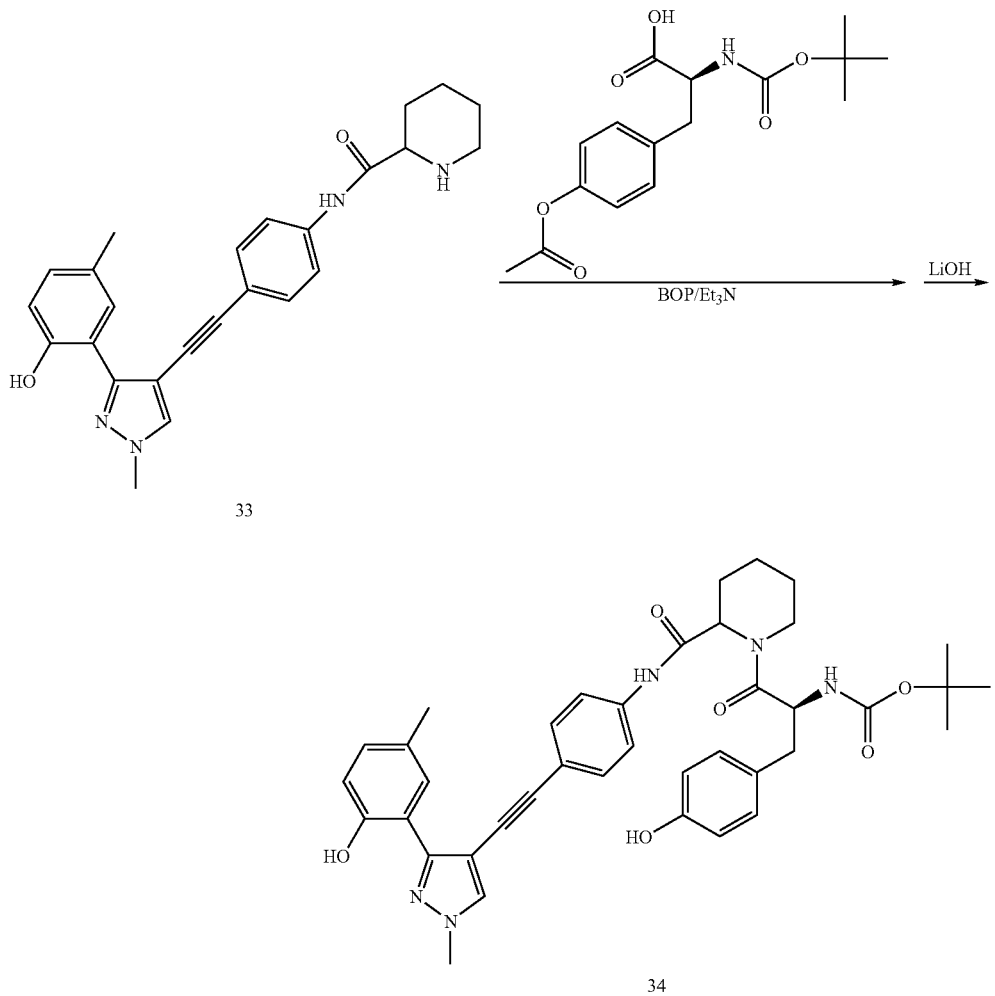
The synthetic procedure is the same as that of 28 from Step 4 to 5. LCMS (5.55 min, [M+1]$^+$ 678). $^1$H NMR (500 MHz, d6-DMSO): δ 10.33 (s, 1H), 9.15-9.25 (s, br, 1H), 6.7-8.3 (m, 13H), 4.2-5.2 (m, 2H), 3.93 (s, 3H), 3.6-3.8 (m, 2H), 3.0-3.3 (m, 2H), 2.25 (s, 3H), 1.5-2.0 (m, 6H), 1.29 (s, 9H).
Example 22
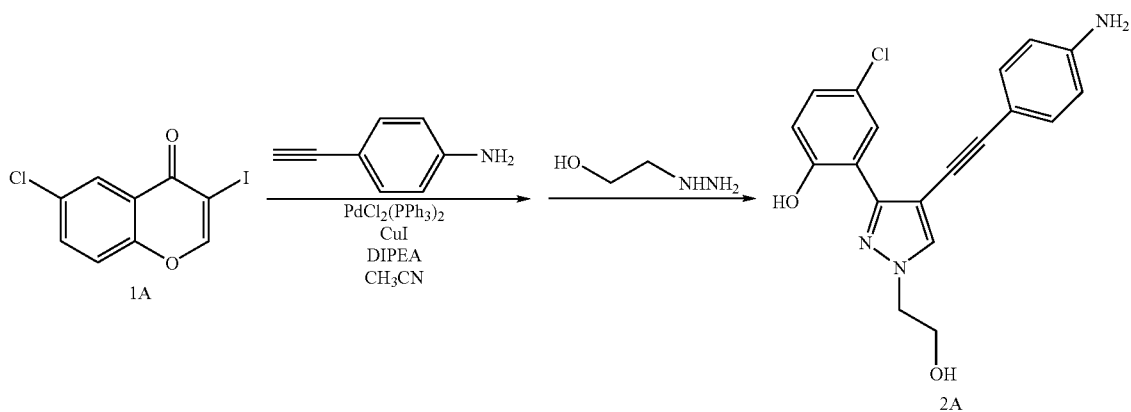

2-[4-(4-Amino-phenylethynyl)-1-(2-hydroxy-ethyl)-1H-pyrazol-3-yl]-4-chloro-phenol (2A)

To a mixture of 6-chloro-3-iodo-chromone (1A, 30.65 g, 0.1 mol), 4-ethynylaniline (14.05 g, 0.12 mol), PdCl$_2$(PPh$_3$)$_2$ (1.404 g, 2.0 mmol) and CuI (190 mg, 1.0 mmol) was added anhydrous CH$_3$CN (500 mL). Upon stirring, diisopropylethylamine (DIPEA, 69.7 mL, 0.4 mol) was added slowly to the above mixture. The reaction mixture was stirred at rt for 5 h. LCMS indicated all of 1A was consumed. 2-Hydroxyethylhydrazine (22 mL, 0.325 mol) was then added. The mixture was stirred at rt overnight. The mixture was filtered and the solid was washed with small amount of CH$_3$CN, and dried under high vacuum to give 2A (8.1 g). Silica (~100 mL) was added to the filtrate, and the solvent was removed with rotavapor. The resultant powder was load on a silica column and eluted with hexanes-ethyl acetate (v/v 2/1, 2/3, 1/1, 1/2) and then pure ethyl acetate. The fractions containing 2A were combined and solvent was removed. The residua were recrystallized from hexanes-ethyl acetate to give 2A (16.5 g). Total 24.6 g of the title compound 2A was obtained, and the yield is 69.5%. $^1$H NMR (CDCl$_3$/CD$_3$OD=5/1, 500 MHz) δ 8.71 (d, 1H, J=1.5 Hz), 7.80 (s, 1H), 7.39 (d, 2H, J=7.5 Hz), 7.19 (dd, 1H, J=8.0, 1.5 Hz), 6.95 (d, 1H, J=8.5 Hz), 6.70 (d, 2H, J=7.5 Hz), 4.28 (t, 2H, J=5.0 Hz), 3.98 (t, 2H, J=5.0 Hz). LCMS (ESI) m/z 354.17 (MH$^+$, 100); HPLC: t$_R$=4.05 min.

Example 23

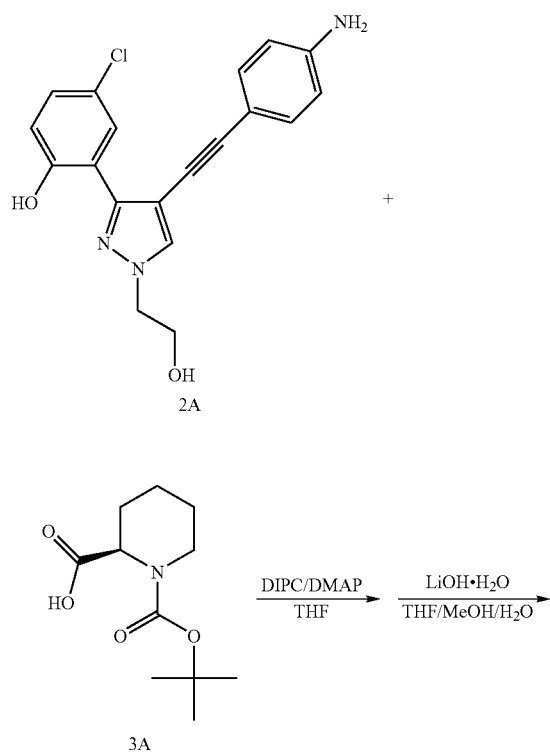

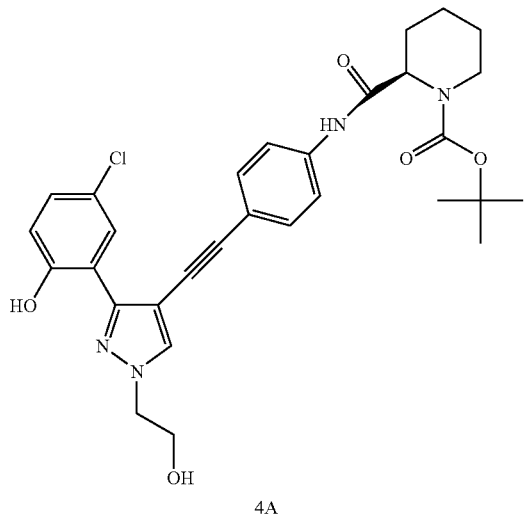

2(R)-{4-[3-(5-Chloro-2-hydroxy-phenyl)-1-(2-hydroxy-ethyl)-1H-pyrazol-4-ylethynyl]-phenylcarbamoyl}-piperidine-1-carboxylic acid tert-butyl ester (4A)

A solution of 2-[4-(4-Amino-phenylethynyl)-1-(2-hydroxy-ethyl)-1H-pyrazol-3-yl]-4-chloro-phenol (2A) (7.08 g, 20.0 mmol), N-Boc-2(R)-piperidinecarboxylic acid (3A) (18.35 g, 80.0 mmol) and 4-dimethylaminopyridine (DMAP, 0.978 g, 8.0 mmol) in anhydrous THF (100 mL) was cooled to 0° C. with and ice-water bath. N,N'-Diisopropylcarbodiimide (DIPC, 12.39 mL, 80.0 mmol) was added slowly to the above solution. The ice-water bath was removed and the reaction mixture was stirred at rt overnight. Water (~5 mL) and methanol (100 mL) were added. The mixture was cooled to 0° C. A solution of LiOH.H$_2$O (17.0 g, 405 mmol) in water (60 mL) were added slowly. The mixture was stirred at 0° C. for 2 h. It was then neutralized with acetic acid (23 mL, 402 mmol). The mixture was diluted with ethyl acetate (~200 mL), and washed with brine, and dried over sodium sulfate. It was filtered, concentrated and filtered again to remove diisopropylurea. The filtrate was purified with silica column chromatography eluting with hexanes-ethyl acetate (v/v 1/1, 2/3) to provide the title compound (4A, 8.2 g) as a yellowish solid in 72.6% yield. $^1$H NMR (CDCl$_3$, 500 MHz) δ 10.59 (s, 1H), 8.67 (d, 1H, J=1.5 Hz), 8.40 (br s, 1H), 7.77 (s, 1H), 7.54 (s, 4H), 7.20 (dd, 1H, J=9.0, 1.5 Hz), 6.96 (d, 1H, J=9.0 Hz), 4.88 (s, 1H), 4.31 (t, 2H, J=4.5 Hz), 4.06 (t, 3H, J=4.5 Hz), 3.75 (br s, 1H), 2.87 (t, 1H, J=12.0 Hz), 2.34 (m, 3H), 1.90-1.20 (m, 15H). LCMS (ESI) m/z 587.15 (MNa$^+$), 565.16 (MH$^+$), 465.19 (100), 354.09; HPLC: t$_R$=5.22 min.

Example 24

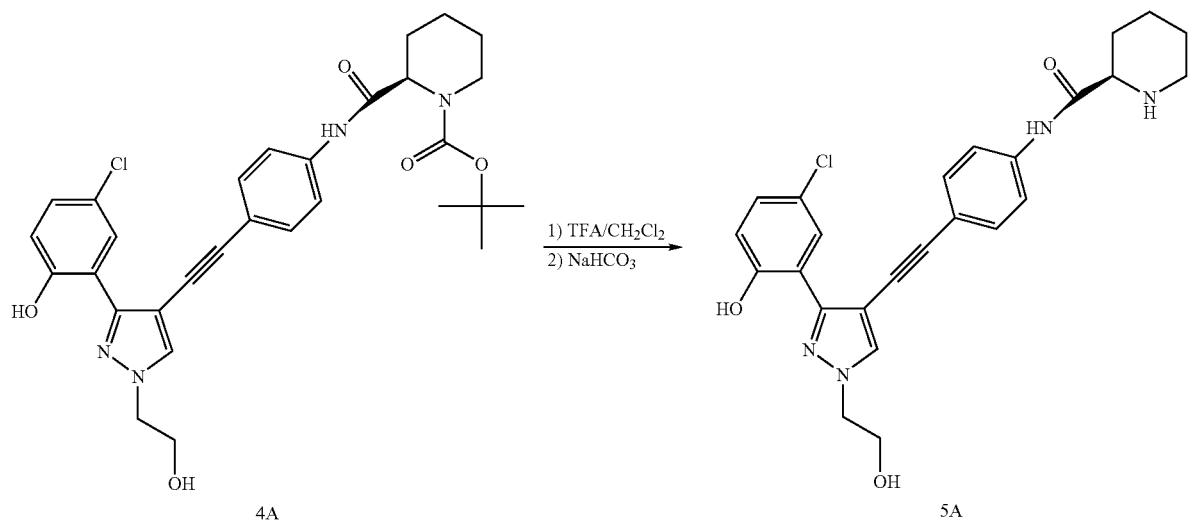

Piperidine-2(R)-carboxylic acid {4-[3-(5-chloro-2-hydroxy-phenyl)-1-(2-hydroxy-ethyl)-1H-pyrazol-4-ylethynyl]-phenyl}-amide (5A)

Compound 4A (8.2 g) was dissolved in dichloromethane (50 mL) and cooled to 0° C. with ice-water bath. TFA (50 mL) was added slowly to the above solution at 0° C. The mixture was stirred at 0° C. for 1.5 hour. LC-MS indicated the reaction was complete. Dichloromethane and TFA were removed with a rotavapor at rt. Dichloromethane (~100 mL) was added to the residua and removed again. The process was repeated twice more. The resultant residua were suspended in ethyl acetate (~50 mL). 5% Aqueous NaHCO₃ and solid NaHCO₃ were added slowly to neutralize any residual TFA. The mixture was filtered and the solid was washed with water and ethyl acetate. The solid was collected and dried under high vacuum in the presence of Drierite. The filtrate was collected and the organic layer was separated and dried over sodium sulfate. It was then filtered and the solvent was removed to give yellowish solid. The solid from filtration and the solid from filtrate were combined and the title compound 5A was obtained in quantitative yield. Using the same procedure for the preparation of 5A, the treatment of compound 16A (870 mg) with TFA (10 mL) in methylene chloride (10 mL) gives compound 17A in 74.0% yield. $^1$H NMR (DMSO-$d_6$, 500 MHz) δ 10.68 (s, 1H), 9.95 (br s, 1H), 8.36 (s, 1H), 8.28 (s, 1H), 7.73 (d, 2H, J=8.5 Hz), 7.46 (d, 2H, J=8.5 Hz), 7.29 (d, 1H, J=9.0 Hz), 6.99 (d, 1H, J=9.0 Hz), 5.01 (s, 1H), 4.26 (s, 2H), 3.78 (d, 2H, J=4.0 Hz), 2.99 (d, 1H, J=12.0 Hz), 2.60 (t, 1H, J=11.0 Hz), 1.84 (s, 1H), 1.77 (s, 1H), 1.51 (d, 1H, J=11.0 Hz), 1.41 (m, 3H). LCMS (ESI) m/z 465.06 (MH$^+$, 100); HPLC: $t_R$=4.02 min.

Example 25

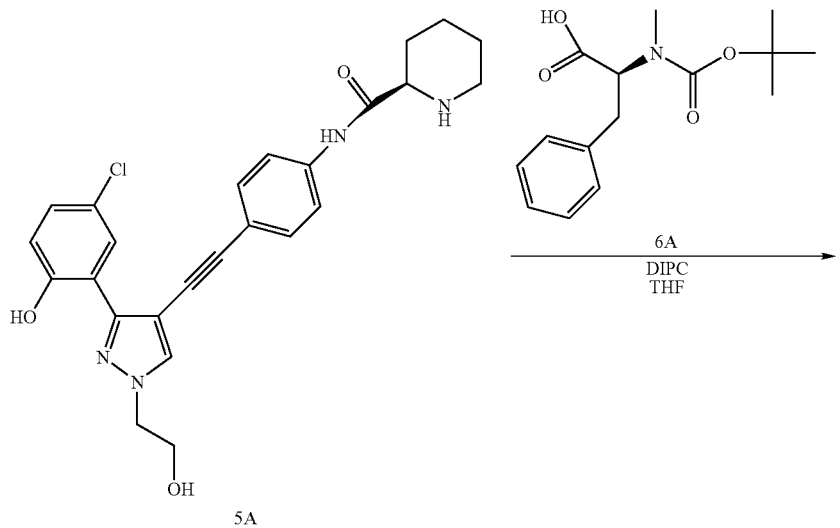

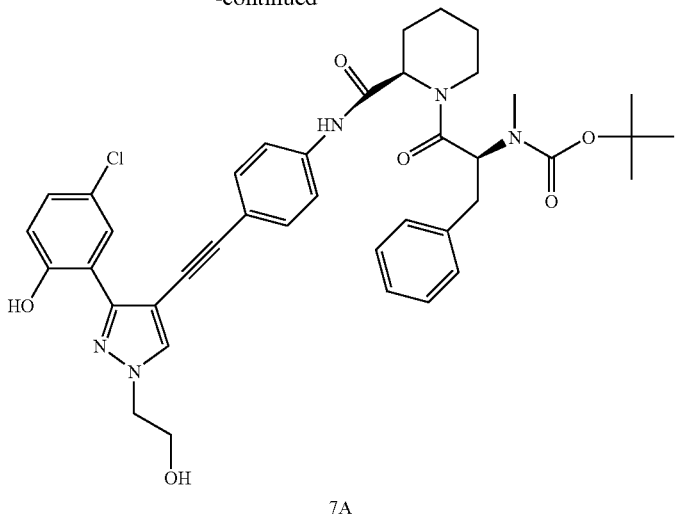

7A

[1(S)-Benzyl-2-(2(R)-{4-[3-(5-chloro-2-hydroxy-phenyl)-1-(2-hydroxy-ethyl)-1H-pyrazol-4-ylethynyl]-phenylcarbamoyl}-piperidin-1-yl)-2-oxo-ethyl]-methyl-carbamic acid tert-butyl ester (7A)

To a mixture of compound 5A (6.50 g, 13.98 mmol) and BOC-N-Me-Phe-OH (6A, 9.76 g, 34.94 mmol) was added anhydrous THF (350 mL) and the resultant mixture was stirred at rt for 10 min. Diisopropylcarbodiimide (DIPC, 5.41 mL, 34.94 mmol) was added slowly at rt. The reaction mixture was stirred at rt overnight. Water (~10 mL) was added to the above mixture and the reaction mixture was stirred at rt for 3 hour. Solvent was removed and the residua were dissolved in ethyl acetate. It was filtered to remove solid (diisopropylurea). The filtrate was purified by silica column chromatography eluting with hexanes-ethyl acetate (v/v 1/1, 2/3, 1/2) to provide the title compound (7A, 4.3 g) as foam-like powder in 42.3% yield. $^1$H NMR (CDCl$_3$, 500 MHz) δ 10.63 (s, 1H), 8.67 (s, 1H), 8.62 (s, 1H), 7.76 (s, 1H), 7.63 (m, 1H), 7.52 (d, 2H, J=7.5 Hz), 7.40-7.10 (m, 7H), 6.96 (d, 1H, J=8.0 Hz), 5.35 (br s, 1H), 5.13 (m, 1H), 4.29 (s, 2H), 4.05 (s, 2H), 3.81 (m, 1H), 3.20 (t, 1H, J=8.0 Hz), 3.09 (m, 2H), 2.94 (s, 3H), 2.87 (m, 1H), 2.35 (m, 1H), 1.75-1.10 (m, 12H), 0.74 (m, 1H). LCMS (ESI) m/z 748.26 (MNa$^+$), 726.27 (MH$^+$), 670.21, 626.20, 465.10, 373.18, 317.14 (100). HPLC: t$_R$=5.70 min.

Example 26

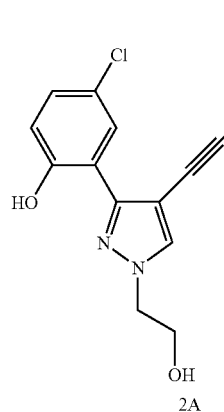

2A

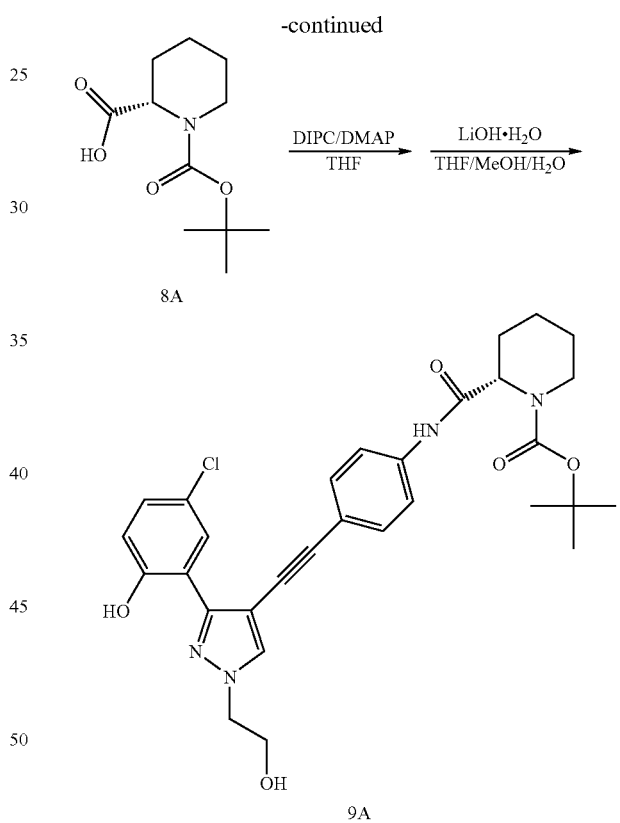

2(S)-{4-[3-(5-Chloro-2-hydroxy-phenyl)-1-(2-hydroxy-ethyl)-1H-pyrazol-4-ylethynyl]-phenylcarbamoyl}-piperidine-1-carboxylic acid tert-butyl ester (9A)

Using the same procedure for the preparation of compound 4A, reaction of compound 2A (2.17 g, 6.13 mmol) and N-Boc-2(S)-piperidinecarboxylic acid (3A) (5.63 g, 24.55 mmol) in the presence of DMAP (0.30 g, 2.46 mmol) and (DIPC, 3.80 mL, 24.54 mmol) in anhydrous THF (40 mL) provided the title compound (9A, 3.30 g) as a foam-like powder in 95.2% yield. The $^1$H NMR and LCMS data are exactly same with those of compound 4A.

Example 27
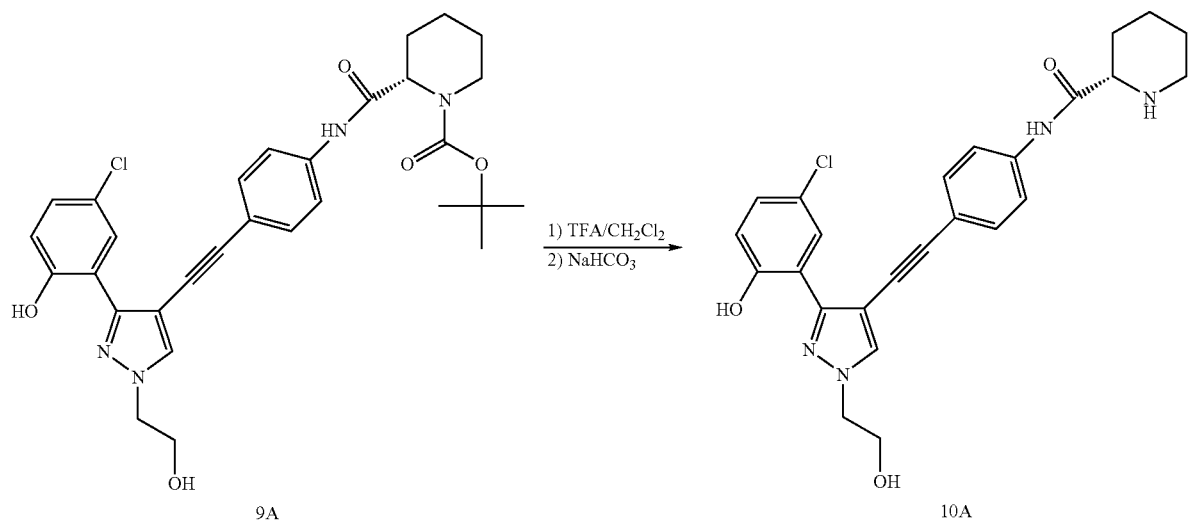
Piperidine-2(S)-carboxylic acid {4-[3-(5-chloro-2-hydroxy-phenyl)-1-(2-hydroxy-ethyl)-1H-pyrazol-4-ylethynyl]-phenyl}-amide (10A)
Using the same procedure for the preparation of 5A, treatment compound 9A with TFA in methylene chloride to give compound 10A in quantitative yield. Its $^1$H NMR and LCMS data are identical with those of compound 5A.
Example 28
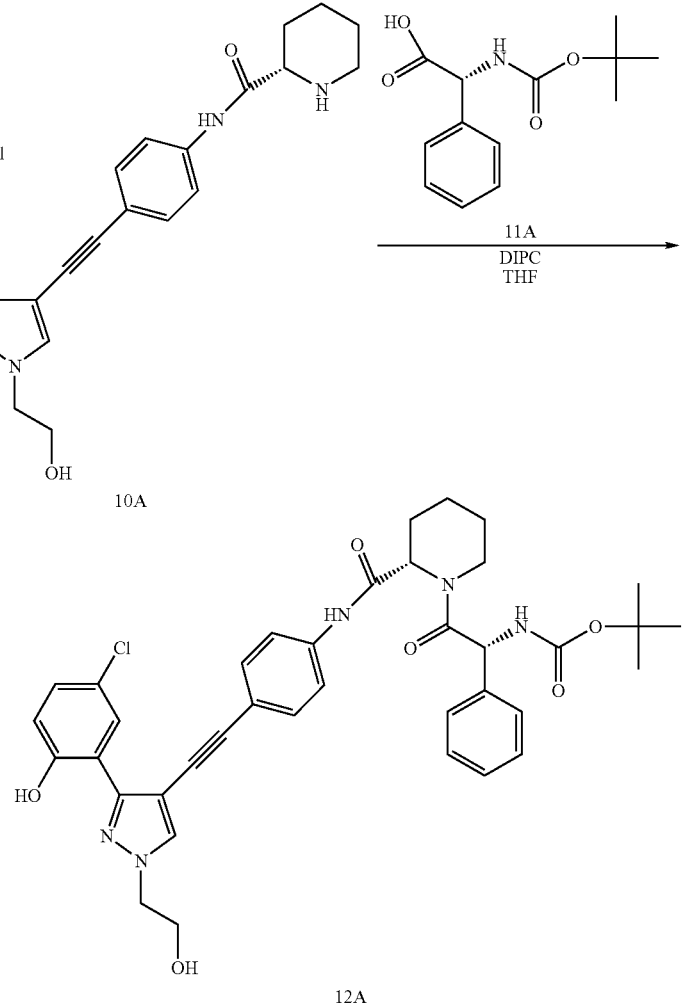

[2-(2(S)-{4-[3-(5-Chloro-2-hydroxy-phenyl)-1-(2-hydroxy-ethyl)-1H-pyrazol-4-ylethynyl]-phenylcarbamoyl}-piperidin-1-yl)-2-oxo-1(R)-phenyl-ethyl]-carbamic acid tert-butyl ester (12A)

To a mixture of compound 10A (1.0 g, 2.15 mmol) and BOC-D-Phg-OH (11A, 0.65 g, 2.58 mmol) was added anhydrous THF (30 mL) and the resultant mixture was stirred at rt for 5 min. DIPC (0.40 mL, 2.58 mmol) was added slowly at rt. The final reaction mixture was stirred at rt overnight. The solvent was removed and the residua were dissolved in small amount of ethyl acetate. Solid was removed by filtration. The filtrate was purified by silica column chromatography eluting with hexanes-ethyl acetate (v/v 3/1, 2/1, 1/1 and 2/3). The product was recrystallized from hexanes-ethyl acetate gave the title compound (12A, 0.81 g) as white crystals in 54% yield. ¹H NMR (CDCl₃, 500 MHz) δ 10.60 (s, 1H), 8.70 (s, 1H), 8.49 (s, 1H), 7.81 (d, 2H, J=8.0 Hz), 7.77 (s, 1H), 7.55 (d, 2H, J=8.0 Hz), 7.41 (m, 5H), 7.20 (d, 1H, J=8.5 Hz), 6.96 (d, 1H, J=9.0 Hz), 5.58 (d, 1H, J=3.5 Hz), 5.53 (d, 2H, J=3.5 Hz), 4.31 (s, 2H), 4.06 (d, 2H, J=3.5 Hz), 3.86 (d, 1H, J=13.0 Hz), 3.16 (t, 1H, J=13.0 Hz), 2.48 (d, 1H, J=13.5 Hz), 2.00 (s, 1H), 1.61 (br s, 2H), 1.56-1.30 (m, 11H), 0.88 (m, 1H). LCMS (ESI) m/z 720.27 (MNa⁺), 698.22 (MH⁺), 642.10, 598.15, 345.16 (100), 289.14. HPLC: t_R=5.25 min.

Example 29

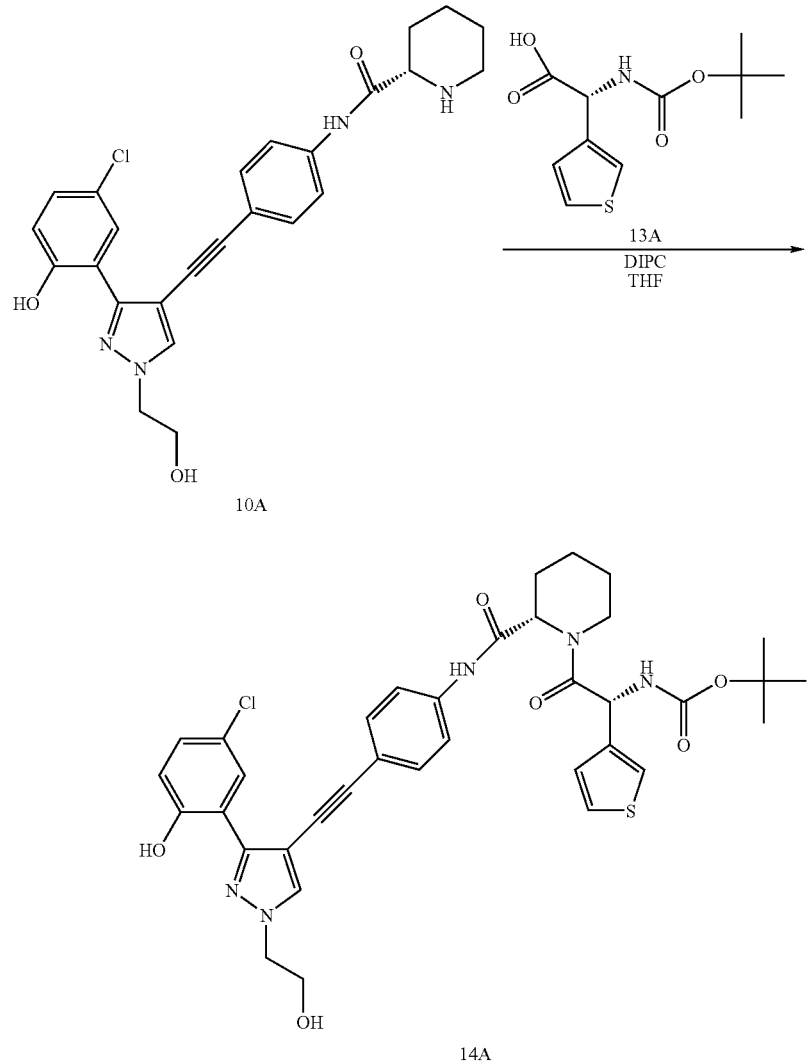

[2-(2(S)-{4-[3-(5-Chloro-2-hydroxy-phenyl)-1-(2-hydroxy-ethyl)-1H-pyrazol-4-ylethynyl]-phenylcarbamoyl}-piperidin-1-yl)-2-oxo-1(R)-thiophen-3-yl-ethyl]-carbamic acid tert-butyl ester (14A)

Using the same procedure for the preparation of 12A, reaction of compound 10A with BOC-R-thienylglycine (13A) afforded the title compound 14A in similar yield. ¹H NMR (CDCl₃, 500 MHz) δ 10.61 (s, 1H), 8.70 (s, 1H), 8.51 (s, 1H), 7.81 (d, 2H, J=8.5 Hz), 7.79 (s, 1H), 7.55 (d, 2H, J=8.0 Hz), 7.37 (d, 2H, J=14.0 Hz), 7.20 (d, 1H, J=8.0 Hz), 7.14 (d, 1H, J=4.0 Hz), 6.96 (d, 1H, J=8.0 Hz), 5.65 (d, 1H, J=3.5 Hz), 5.53 (br s, 1H), 5.47 (d, 2H, J=3.5 Hz), 4.31 (t, 2H, J=4.5 Hz), 4.06 (br s, 2H), 3.86 (d, 1H, J=13.0 Hz), 3.17 (t, 1H, J=13.0 Hz), 2.48 (d, 1H, J=13.5 Hz), 2.24 (s, 1H), 1.61 (m, 2H), 1.56-1.30 (m, 11H), 0.85 (m, 1H). LCMS (ESI) m/z 726.22 (MNa+), 704.17 (MH+), 648.11, 604.10, 351.10 (100), 295.08. HPLC: $t_R$=5.38 min.

Example 30

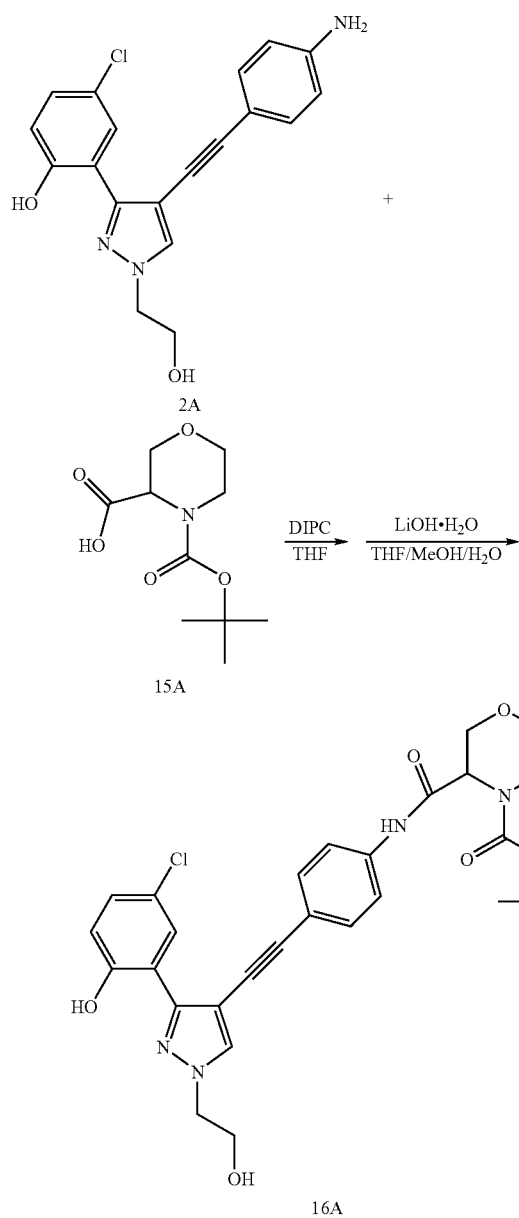

3(R,S)-{4-[3-(5-Chloro-2-hydroxy-phenyl)-1-(2-hydroxy-ethyl)-1H-pyrazol-4-ylethynyl]-phenylcarbamoyl}-morpholine-4-carboxylic acid tert-butyl ester (16A)

To a solution of 2-[4-(4-amino-phenylethynyl)-1-(2-hydroxy-ethyl)-1H-pyrazol-3-yl]-4-chloro-phenol (2A) (1.06 g, 3.0 mmol) and morpholine-3,4-dicarboxylic acid 4-tert-butyl ester (15A) (2.09 g, 9.0 mmol) in anhydrous THF (30 mL) was added N,N'-diisopropylcarbodiimide (DIPC, 1.68 mL, 10.8 mmol). The reaction mixture was stirred at rt overnight. Methanol (30 mL) and a solution of LiOH.H₂O (3.0 g, 69.85 mmol) in water (20 mL) were added slowly. The mixture was stirred rt for 4 h. It was then neutralized with acetic acid (4.0 mL, 69.87 mmol). The mixture was diluted with ethyl acetate (~100 mL), and washed with brine, and dried over sodium sulfate. It was filtered, concentrated and filtered again to remove diisopropylurea. The filtrate was purified with silica column chromatography eluting with dichloromethane/acetone (v/v 10/1, 4/1, 3/1) to provide the crude title compound (16A, 1.47 g), which was then recrystallized from hexanes/acetone to give pure compound 16 (1.22 g) as white powder in 71.7% yield. ¹H NMR (CDCl₃, 500 MHz) δ 10.60 (s, 1H), 8.67 (s, 1H), 8.33 (br s, 1H), 7.74 (s, 1H), 7.53 (s, 4H), 7.21 (dd, 1H, J=8.0, 2.0 Hz), 6.96 (d, 1H, J=8.5 Hz), 4.64 (s, 1H), 4.56 (d, 1H, J=11.5 Hz), 4.29 (d, 2H, J=4.5 Hz), 4.06 (d, 2H, J=4.5 Hz), 3.92 (d, 2H, J=11.0 Hz), 3.64 (dd, 1H, J=12.0, 3.5 Hz), 3.53 (t, 1H, J=11.5 Hz), 3.31 (br s, 1H), 2.08 (s, 1H), 1.54 (s, 9H). LCMS (ESI) m/z 567.12 (MH+), 511.04 (100), 467.06; HPLC: $t_R$=4.88 min.

Example 31

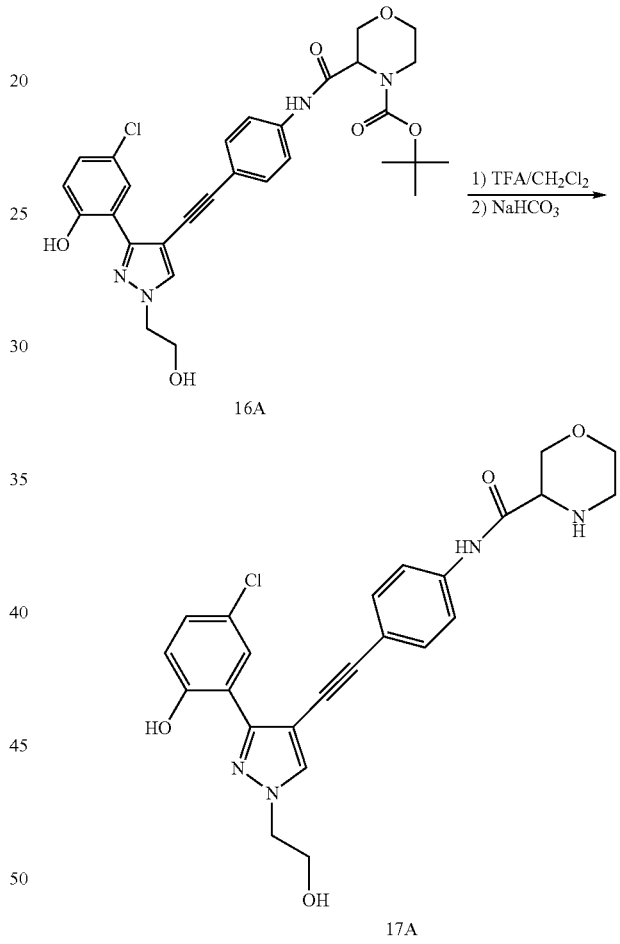

Morpholine-3(R,S)-carboxylic acid {4-[3-(5-chloro-2-hydroxy-phenyl)-1-(2-hydroxy-ethyl)-1H-pyrazol-4-ylethynyl]-phenyl}-amide (17A)

Using the same procedure for the preparation of 5A, treatment of compound 16A (870 mg) with TFA (10 mL) in methylene chloride (10 mL) gives compound 17A in 74.0% yield. ¹H NMR (DMSO-d₆, 500 MHz) δ 10.67 (s, 1H), 10.02 (s, 1H), 8.35 (s, 1H), 8.28 (s, 1H), 7.73 (d, 2H, J=8.0 Hz), 7.47 (d, 2H, J=8.5 Hz), 7.30 (d, 1H, J=9.0 Hz), 6.99 (d, 1H, J=8.5 Hz), 5.01 (br s, 1H), 4.26 (br s, 2H), 3.83 (d, 1H, J=7.5 Hz), 3.78 (d, 2H, J=2.5 Hz), 3.61 (m, 3H), 3.52 (m, 2H), 3.43 (t, 1H, J=10.0 Hz), 2.85 (d, 1H, J=13.0 Hz), 2.75 (t, 1H, J=11.0 Hz). LCMS (ESI) m/z 467.09 (MH+, 100); HPLC: $t_R$=3.92 min.

Example 32

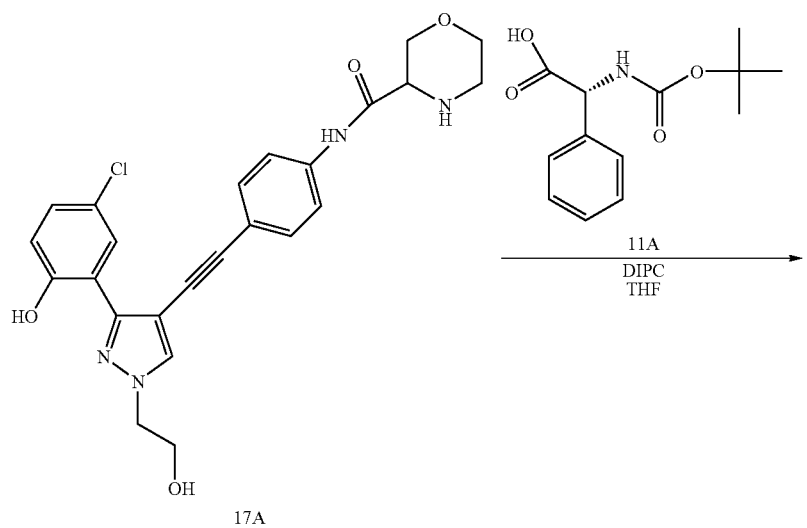

[2-(3(R,S)-{4-[3-(5-Chloro-2-hydroxy-phenyl)-1-(2-hydroxy-ethyl)-1H-pyrazol-4-ylethynyl]-phenylcarbamoyl}-morpholin-4-yl)-2-oxo-1(R)-phenyl-ethyl]-carbamic acid tert-butyl ester (18A)

Using the same procedure for the preparation of 12A, reaction of compound 17A with BOC-D-Phg-OH (11A) afforded the title compound 18A, which was purified by silica column chromatography eluting with dichloromethane/acetone (5/1, 4/1, 3/1) to give pure 18A as white powder in similar yield. $^1$H NMR (CDCl$_3$, 500 MHz) δ 10.677 and 10.668 (both s, total 1H), 9.39 and 8.70 and 8.64 (all s, total 2H), 7.88 (m, 2H), 7.79 and 7.77 (both s, total 1H), 7.56 (m, 2H), 7.43 (m, 5H), 7.19 (d, 1H, J=8.5 Hz), 6.95 (d, 1H, J=8.0 Hz), 5.98 and 5.72 and 5.48 and 5.41 (all d, total 2H, J=6.5-7.5 Hz), 5.28 and 5.13 (both s, total 1H), 4.78 (d, 0.5H, J=12.0 Hz), 4.63 (m, 0.5H), 4.29 (m, 2H), 4.03 (m, 2H), 3.83 and 3.63 and 3.42 and 3.17 and 3.04 (all m, total 5H), 1.94 (s, 1H, 1.51 and 1.45 (both s, total 9H). LCMS (ESI) m/z 722.20 (MNa$^+$), 700.21 (MH$^+$), 644.13 (100), 600.14, 354.07. HPLC: t$_R$=5.18 min.

Example 33

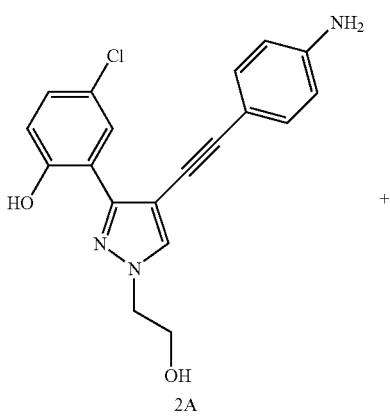

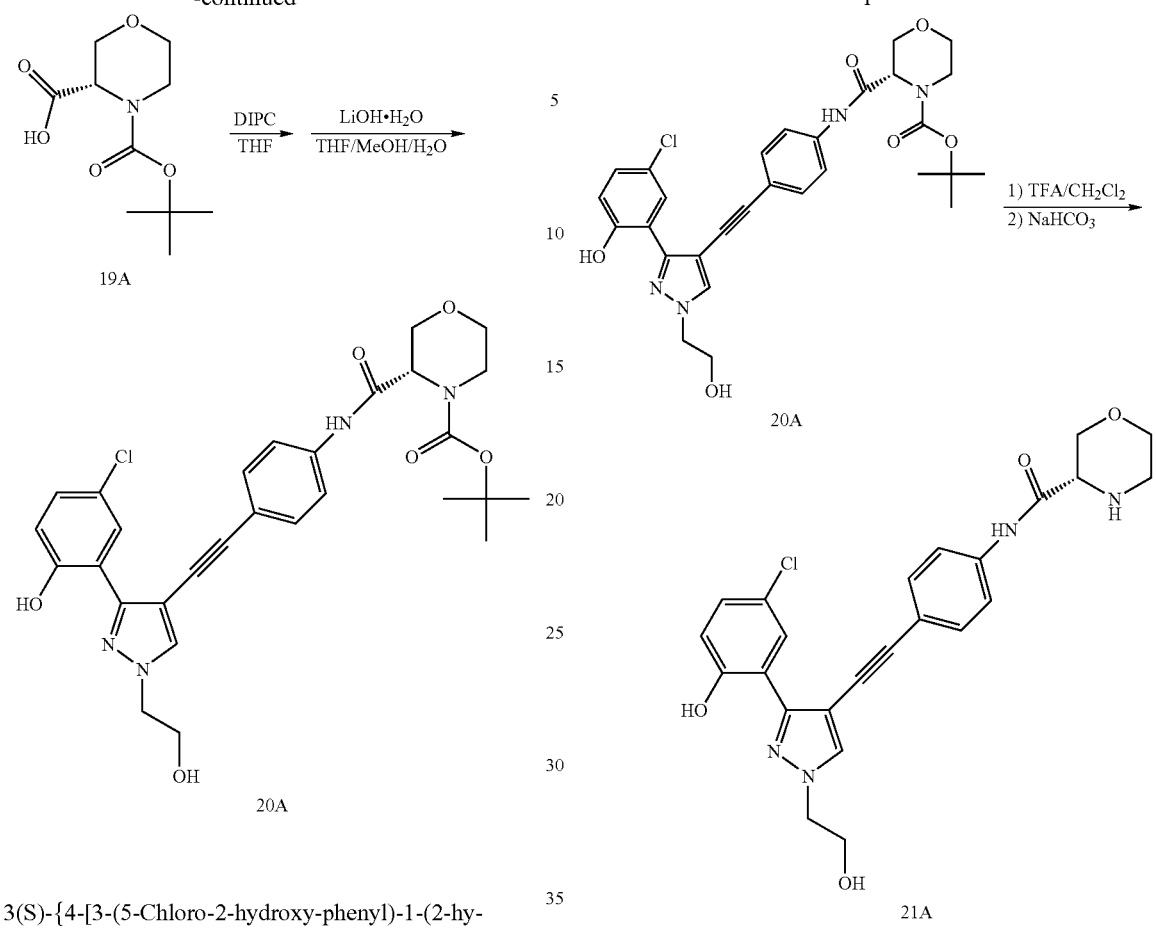

3(S)-{4-[3-(5-Chloro-2-hydroxy-phenyl)-1-(2-hydroxy-ethyl)-1H-pyrazol-4-ylethynyl]-phenylcarbamoyl}-morpholine-4-carboxylic acid tert-butyl ester (20A)

Using the same procedure for the preparation of 16A, reaction of compound 2A with (S)-morpholine-3,4-dicarboxylic acid 4-tert-butyl ester (19A) afforded the title compound 20A as a white powder in similar yield. Its $^1$H NMR and LCMS data are identical with those of compound 16A.

Example 34

Morpholine-3(S)-carboxylic acid {4-[3-(5-chloro-2-hydroxy-phenyl)-1-(2-hydroxy-ethyl)-1H-pyrazol-4-ylethynyl]-phenyl}-amide (21A)

Using the same procedure for the preparation of 17A, treatment of compound 20A with TFA in methylene chloride to give the title compound 21A as white powder in similar yield. Its $^1$H NMR and LCMS data are identical with those of compound 17A.

Example 35

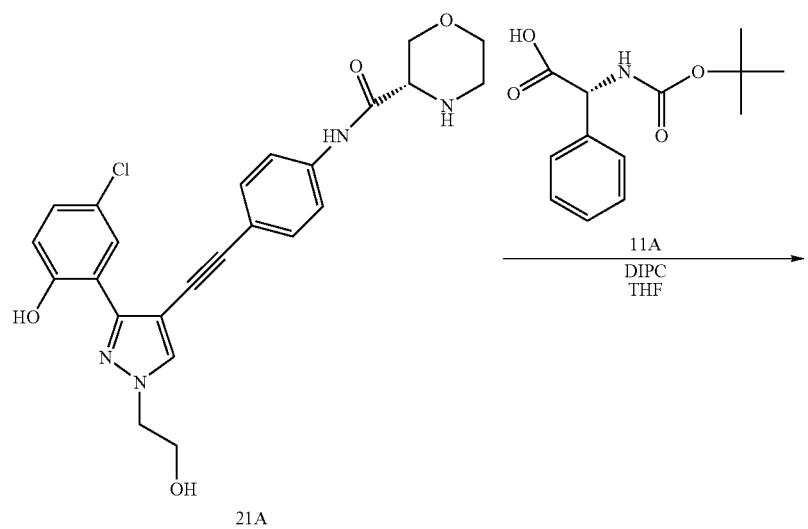

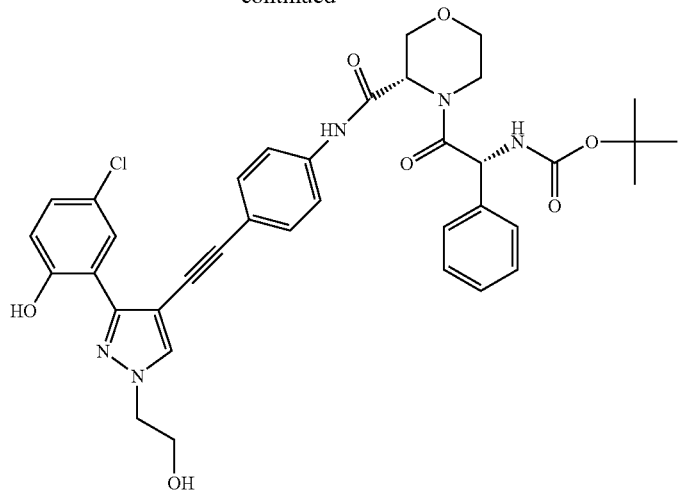

22A

[2-(3(S)-{4-[3-(5-Chloro-2-hydroxy-phenyl)-1-(2-hydroxy-ethyl)-1H-pyrazol-4-ylethynyl]-phenylcarbamoyl}-morpholin-4-yl)-2-oxo-1(R)-phenyl-ethyl]-carbamic acid tert-butyl ester (22A)

Using the same procedure for the preparation of 18A, reaction of compound 21A with BOC-D-Phg-OH (11A) afforded the title compound 22A as a white powder in similar yield. $^1$H NMR (CDCl$_3$, 500 MHz) δ 10.60 (s, 1H), 8.71 (s, 1H), 8.62 (s, 1H), 7.90 (d, 2H, J=8.5 Hz), 7.78 (s, 1H), 7.56 (d, 2H, J=8.5 Hz), 7.43 (m, 5H), 7.20 (dd, 1H, J=8.5, 1.5 Hz), 6.97 (d, 1H, J=9.0 Hz), 5.48 (d, 1H, J=6.5 Hz), 5.40 (d, 1H, J=6.0 Hz), 5.29 (s, 1H), 4.81 (d, 1H, J=12.0 Hz), 4.31 (t, 2H, J=5.0 Hz), 4.06 (m, 2H), 3.78 (d, 1H, J=10.5 Hz), 3.64 (t, 1H, J=12.5 Hz), 3.59 (t, 1H, J=1.0 Hz), 3.43 (dd, 1H, J=11.0, 2.5 Hz), 3.06 (t, 1H, J=10.5 Hz), 1.93 (t, 1H, J=5.0 Hz), 1.45 (s, 9H). LCMS (ESI) m/z 722.16 (MNa$^+$), 700.18 (MH$^+$), 644.13 (100), 600.11, 354.11. HPLC: t$_R$=4.48 min.

Example 36

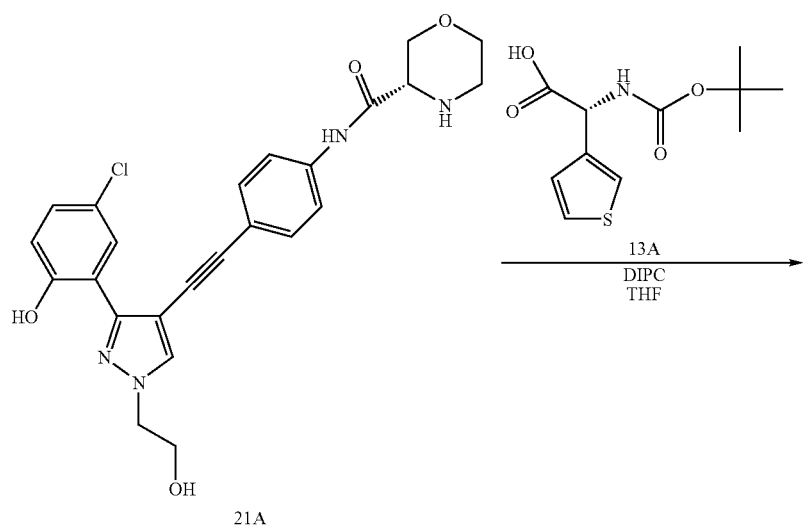

21A

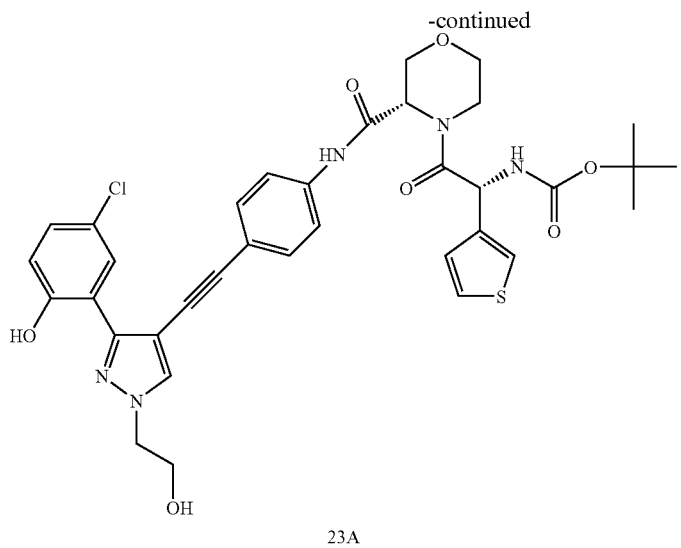

[2-(3(S)-{4-[3-(5-Chloro-2-hydroxy-phenyl)-1-(2-hydroxy-ethyl)-1H-pyrazol-4-ylethynyl]-phenylcarbamoyl}-morpholin-4-yl)-2-oxo-1(R)-thiophen-3-yl-ethyl]-carbamic acid tert-butyl ester (23A)

Using the same procedure for the preparation of 18A, reaction of compound 21A with BOC-R-thienylglycine (13A) afforded the title compound 23A as a white powder in similar yield. $^1$H NMR (CDCl$_3$, 500 MHz) δ 10.63 (s, 1H), 8.69 (s, 1H), 8.64 (s, 1H), 7.88 (d, 2H, J=8.0 Hz), 7.77 (s, 1H), 7.55 (d, 2H, J=9.0 Hz), 7.41 (m, 1H), 7.38 (s, 1H), 7.19 (d, 1H, J=8.5 Hz), 7.15 (d, 1H, J=4.5 Hz), 6.95 (d, 1H, J=9.0 Hz), 5.57 (d, 1H, J=5.5 Hz), 5.44 (d, 1H, J=6.0 Hz), 5.28 (s, 1H), 4.82 (d, 1H, J=12.0 Hz), 4.30 (t, 2H, J=5.0 Hz), 4.04 (m, 2H), 3.82 (m, 2H), 3.63 (m, 1H), 3.46 (dd, 1H, J=12.0, 2.5 Hz), 3.15 (m, 1H), 1.44 (s, 9H). LCMS (ESI) m/z 728.18 (MNa$^+$), 706.13 (MH$^+$), 650.07 (100), 605.99, 354.11. HPLC: t$_R$=5.12 min.

Example 37

2-[4-(4-Amino-phenylethynyl)-1H-pyrazol-3-yl]-4-chloro-phenol (24A)

To a mixture of 6-chloro-3-iodo-chromone (1A, 6.12 g, 20 mmol) and 4-ethynylaniline (2.32 g, 24 mmol) and PdCl$_2$(PPh$_3$)$_2$ (0.28 g, 0.4 mmol) and CuI (38 mg, 0.2 mmol) was added anhydrous CH$_3$CN (200 mL). Upon stirring, diisopropylethylamine (DIPEA, 14 mL, 80 mmol) was added slowly to the above mixture. The reaction mixture was stirred at rt for 7 h. LCMS indicated all of 1A was consumed. Anhydrous hydrazine (5.3 mL, 80 mmol) was then added. The mixture was stirred at rt overnight. Solvent was removed. The residua was dissolved in dichloromethane and loaded onto a silica column eluting with dichloromethane/ethyl acetate (v/v 6/1, 2/1, 1/1, 1/2, 1/5) to afford the title compound 24A (3.02 g) as a yellowish solid in 48.7% yield. $^1$H NMR (CDCl$_3$, 500 MHz) δ 10.05 (br s, 1H), 8.75 (d, 1H, J=2.0 Hz), 7.84 (s, 1H), 7.42 (d, 2H, J=8.5 Hz), 7.20 (dd, 1H, J=9.0, 2.0 Hz), 6.98 (d, 1H, J=8.5 Hz), 6.68 (d, 2H, J=8.0 Hz), 3.86 (s, 2H). LCMS (ESI) m/z 310.07 (MH$^+$, 100); HPLC: t$_R$=3.78 min.

Example 38

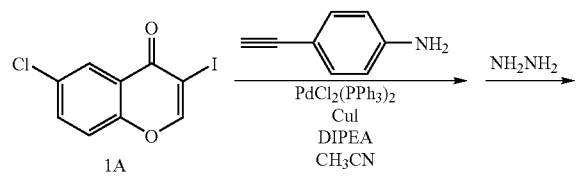

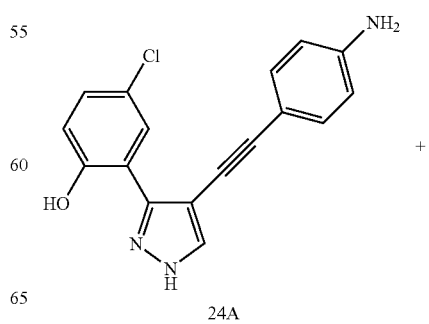

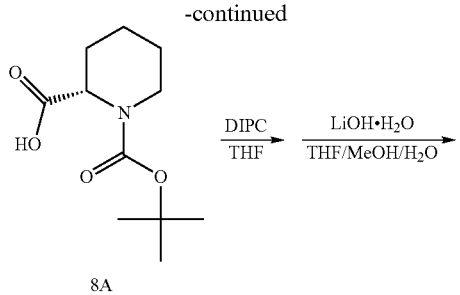

8A

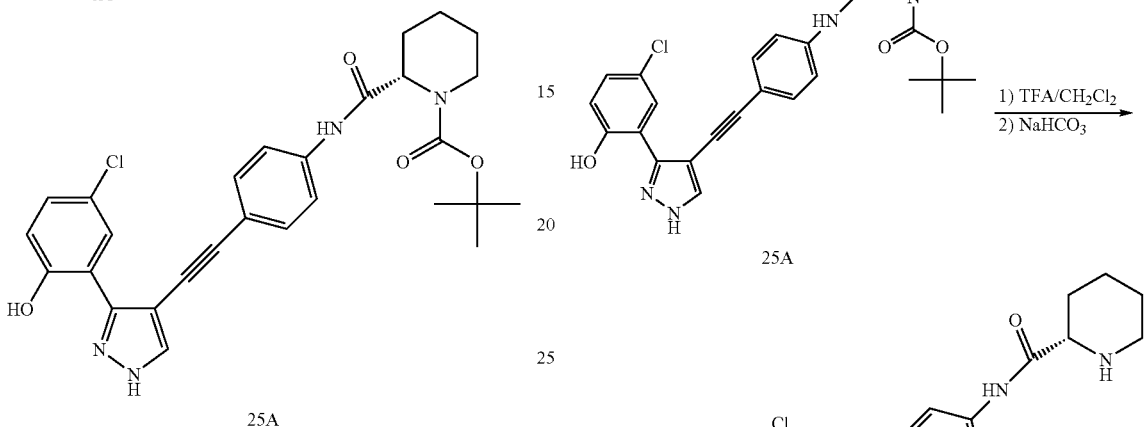

25A

2(S)-{4-[3-(5-Chloro-2-hydroxy-phenyl)-1H-pyrazol-4-ylethynyl]-phenylcarbamoyl}-piperidine-1-carboxylic acid tert-butyl ester (25A)

To a solution of compound 24A (520 mg, 1.7 mmol) and N-Boc-2(S)-piperidinecarboxylic acid (8A) (584 mg, 2.55 mmol) in anhydrous dichloromethane (30 mL) was added N,N'-diisopropylcarbodiimide (DIPC, 0.4 mL, 2.55 mmol). The reaction mixture was stirred at rt overnight. The solvent was removed. To the residua were added THF (40 mL) and methanol (40 mL) and a solution of LiOH.H$_2$O (2.0 g, 47.68 mmol) in water (20 mL). The mixture was stirred at rt for 3 h. It was then neutralized with acetic acid (3 mL, 52.41 mmol). The mixture was diluted with ethyl acetate (~100 mL), washed with brine, and dried over sodium sulfate. It was filtered, concentrated and filtered again to remove diisopropylurea. The filtrate was purified with silica column chromatography eluting with hexanes/ethyl acetate (v/v 2/1, 3/2, 1/1) to provide the title compound (25A, 500 mg) as a yellowish solid in 57.2% yield. $^1$H NMR (CDCl$_3$, 500 MHz) δ 10.62 (br s, 1H), 8.71 (d, 1H, J=2.0 Hz), 8.35 (br s, 1H), 7.84 (s, 1H), 7.55 (s, 4H), 7.22 (dd, 1H, J=9.0, 2.0 Hz), 6.99 (d, 1H, J=9.0 Hz), 4.90 (s, 1H), 4.05 (m, 1H), 2.90 (t, 1H, J=11.5 Hz), 2.35 (m, 1H), 1.80-1.30 (m, 16H). LCMS (ESI) m/z 587.15 (MNa$^+$), 521.05 (MH$^+$), 421.06; HPLC: t$_R$=5.32 min.

Example 39

Piperidine-2(S)-carboxylic acid {4-[3-(5-chloro-2-hydroxy-phenyl)-1H-pyrazol-4-ylethynyl]-phenyl}-amide (26A)

Using the same procedure for the preparation of compound 5A, treatment of compound 25A with TFA in methylene chloride gives the title compound 26A as a white powder in similar yield. LCMS (ESI) m/z 421.03 (MH$^+$, 100); HPLC: t$_R$=4.08 min.

Example 40

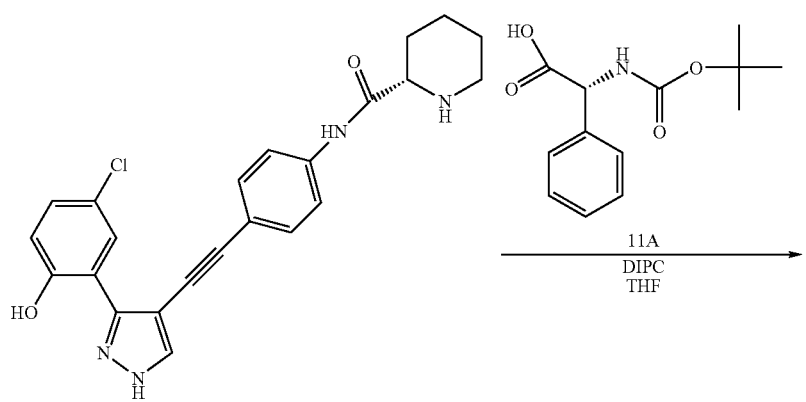

26A

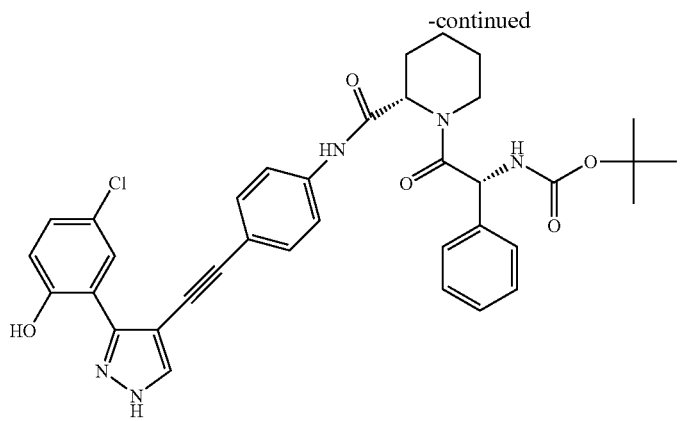

27A

[2(S)-(2-{4-[3-(5-Chloro-2-hydroxy-phenyl)-1H-pyrazol-4-ylethynyl]-phenylcarbamoyl}-piperidin-1-yl)-2-oxo-1(R)-phenyl-ethyl]-carbamic acid tert-butyl ester (27A)

To a mixture of compound 26A (468 mg, 1.11 mmol) and BOC-D-Phg-OH (11A, 280 mg, 1.11 mmol) was added anhydrous THF (10 mL) and the resultant mixture was stirred at rt for 5 min. DIPC (0.258 mL, 1.67 mmol) was added slowly at rt. The reaction mixture was stirred at rt overnight. Solvent was removed. The residua were dissolved in a small amount of ethyl acetate. Solid was removed by filtration. The filtrate was purified by silica column chromatography eluting with hexanes-ethyl acetate (v/v 3/1, 2/1, 1/1) to provide the title compound (27A, 275 mg) as an off-color foam-like powder in 37.8% yield. $^1$H NMR (CDCl$_3$, 500 MHz) δ 10.74 (br s, 2H), 8.75 (s, 1H), 8.52 (s, 1H), 7.82 (d, 2H, J=8.0 Hz), 7.79 (s, 1H), 7.58 (d, 2H, J=8.5 Hz), 7.43 (m, 5H), 7.21 (dd, 1H, J=8.0, 2.0 Hz), 6.98 (d, 1H, J=9.0 Hz), 5.61 (d, 1H, J=6.5 Hz), 5.56 (s, 2H), 3.90 (d, 1H, J=12.5 Hz), 3.20 (t, 1H, J=12.0 Hz), 2.51 (m, 1H), 1.62 (m, 2H), 1.55-1.30 (m, 11H), 0.91 (m, 1H). LCMS (ESI) m/z 720.27 (MNa$^+$), 676.17 (MNa$^+$), 654.22 (MH$^+$), 554.11, 345.17, 289.12 (100). HPLC: $t_R$=5.55 min.

Example 41

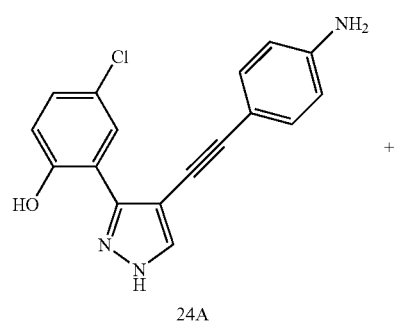

24A

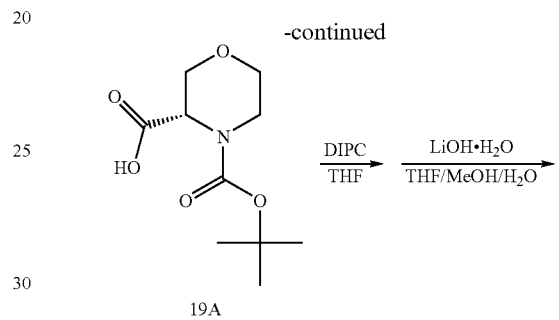

19A

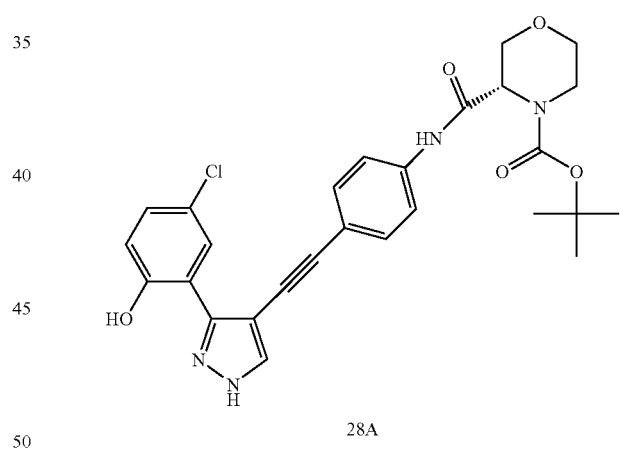

28A

3(S)-{4-[3-(5-Chloro-2-hydroxy-phenyl)-1H-pyrazol-4-ylethynyl]-phenylcarbamoyl}-morpholine-4-carboxylic acid tert-butyl ester (28A)

To a solution of compound 24A (930 mg, 3.0 mmol) and (S)-morpholine-3,4-dicarboxylic acid 4-tert-butyl ester (19A, 2.09 g, 9.0 mmol) in anhydrous dichloromethane (20 mL) was added N,N'-diisopropylcarbodiimide (DIPC, 1.4 mL, 9.0 mmol). The reaction mixture was stirred at rt overnight. Solvent was removed. To the residua were added THF (20 mL) and methanol (20 mL) and a solution of LiOH.H$_2$O (1.0 g, 23.84 mmol) in water (10 mL). The mixture was stirred at rt for 2 h. It was then neutralized with acetic acid (1.36 mL, 23.84 mmol). The mixture was diluted with ethyl acetate (~100 mL), washed with brine, and dried over sodium sulfate. It was filtered, concentrated and filtered again to remove diisopropylurea. The filtrate was purified with silica column chromatography eluting with dichloromethane/ethyl acetate (v/v 5/1, 3/1, 2/1, 1/1) to provide the title compound (28A, 1.12 g) as a yellowish solid in 71.3% yield. LCMS (ESI) m/z 587.15 (MNa$^+$), 521.05 (MH$^+$), 421.06; HPLC: $t_R$=5.32 min.

Example 42

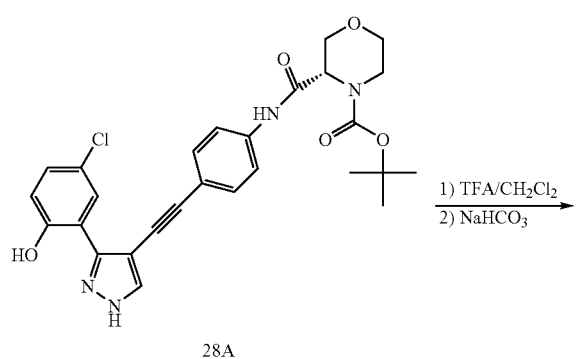

28A

1) TFA/CH$_2$Cl$_2$
2) NaHCO$_3$

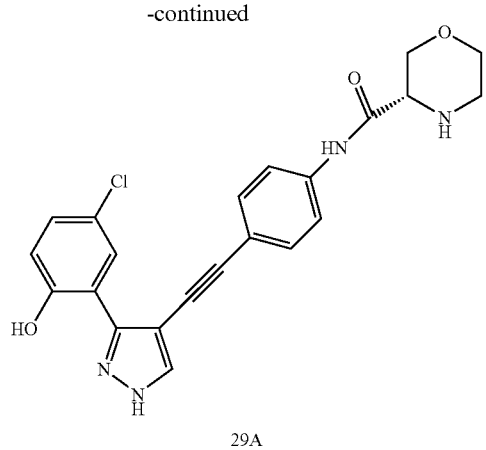

29A

Using the same procedure for the preparation of compound 5A, treatment of compound 28A with TFA in methylene chloride gives the title compound 29A as a white powder in similar yield. $^1$H NMR (DMSO-d$_6$, 500 MHz) δ 12.10 (br s, 1H), 9.98 (s, 1H), 8.29 (s, 1H), 8.14 (s, 1H), 7.72 (d, 2H, J=9.0 Hz), 7.44 (d, 2H, J=9.5 Hz), 7.29 (dd, 1H, J=8.5, 2.5 Hz), 6.99 (d, 1H, J=9.0 Hz), 3.82 (dd, 1H, J=10.0, 1.5 Hz), 3.61 (d, 1H, J=11.0 Hz), 3.49 (m, 2H), 3.41 (t, 1H, J=9.0 Hz), 2.83 (d, 1H, J=12.5 Hz), 2.74 (dt, 1H, J=12.0, 2.5 Hz). LCMS (ESI) m/z 423.01 (MH$^+$, 100); HPLC: $t_R$=3.78 min.

Example 43

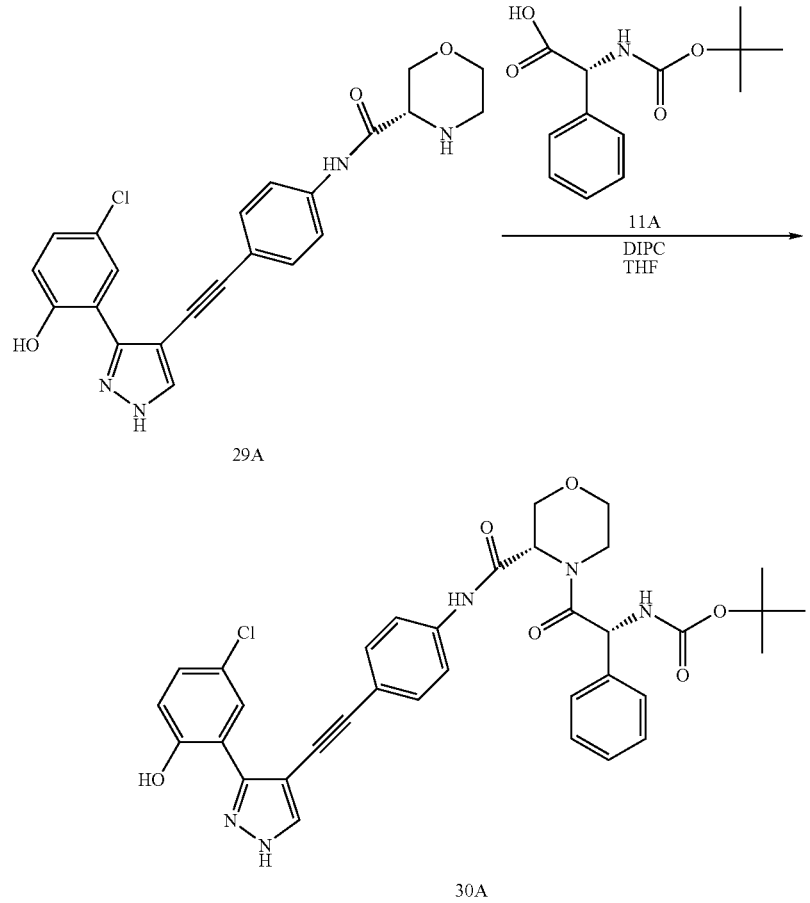

[2-(3(S)-{4-[3-(5-Chloro-2-hydroxy-phenyl)-1H-pyrazol-4-ylethynyl]-phenylcarbamoyl}-morpholin-4-yl)-2-oxo-1(R)-phenyl-ethyl]-carbamic acid tert-butyl ester (30A)

Using the same procedure for the preparation of 27A, reaction of compound 29A with BOC-D-Phg-OH (11A) afforded the title compound 30A, which was purified by silica column chromatography eluting with dichloromethane/ethyl acetate (10/1, 4/1, 3/1) to give pure 30A as a white powder in similar yield. $^1$H NMR (CDCl$_3$, 500 MHz) δ 10.73 (br s, 1H), 8.75 (s, 1H), 8.63 (s, 1H), 7.91 (d, 2H, J=8.5 Hz), 7.84 (s, 1H), 7.58 (d, 2H, J=7.5 Hz), 7.44 (m, 5H), 7.21 (d, 1H, J=9.0 Hz), 6.98 (d, 1H, J=8.0 Hz), 5.48 (d, 1H, J=6.0 Hz), 5.40 (d, 1H, J=5.0 Hz), 5.30 (s, 1H), 4.83 (d, 1H, J=12.0 Hz), 3.79 (d, 1H, J=13.0 Hz), 3.66 (t, 1H, J=13.0 Hz), 3.60 (t, 1H, J=1.0 Hz), 3.44 (dd, 1H, J=11.0, 1.5 Hz), 3.08 (t, 1H, J=10.5 Hz), 1.45 (s, 9H). LCMS (ESI) m/z 678.24 (MNa$^+$), 656.25 (MH$^+$), 600.16, 556.17. HPLC: t$_R$=5.12 min.

Example 44

[2-(3(S)-{4-[3-(5-Chloro-2-hydroxy-phenyl)-1H-pyrazol-4-ylethynyl]-phenylcarbamoyl}-morpholin-4-yl)-2-oxo-1(R)-thiophen-3-yl-ethyl]-carbamic acid tert-butyl ester (31A)

Using the same procedure for the preparation of 30A, reaction of compound 29A with BOC-R-thienylglycine (13A) afforded the title compound 31A as a white powder in similar yield. $^1$H NMR (CDCl$_3$, 500 MHz) δ 12.23 (br s, 1H), 10.96 (s, 1H), 8.74 (s, 1H), 8.69 (s, 1H), 7.87 (d, 2H, J=8.0 Hz), 7.81 (s, 1H), 7.57 (d, 2H, J=8.5 Hz), 7.41 (m, 1H), 7.39 (s, 1H), 7.17 (m, 2H), 6.96 (d, 1H, J=8.5 Hz), 5.59 (d, 1H, J=6.0 Hz), 5.46 (d, 1H, J=5.5 Hz), 5.29 (s, 1H), 4.83 (d, 1H, J=11.5 Hz), 3.85 (m, 2H), 3.65 (m, 1H), 3.47 (dd, 1H, J=13.0, 3.0 Hz), 3.17 (t, 1H, J=7.5 Hz), 1.43 (s, 9H). LCMS (ESI) m/z 684.24 (MNa$^+$), 662.26 (MH$^+$), 606.17, 562.17. HPLC: t$_R$=5.05 min.

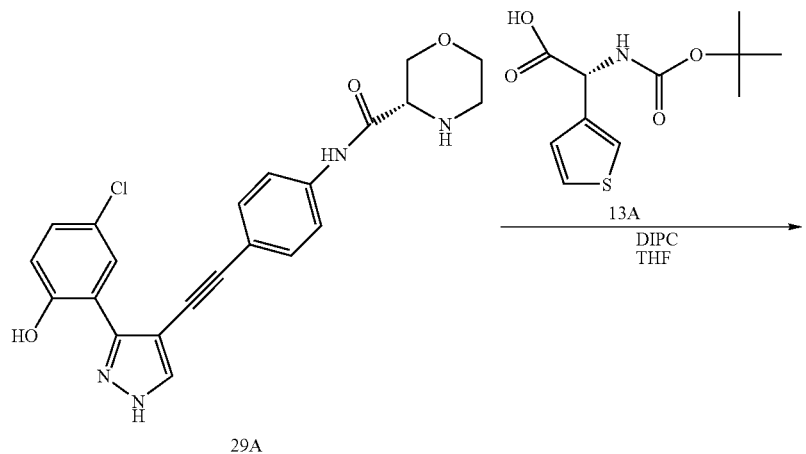

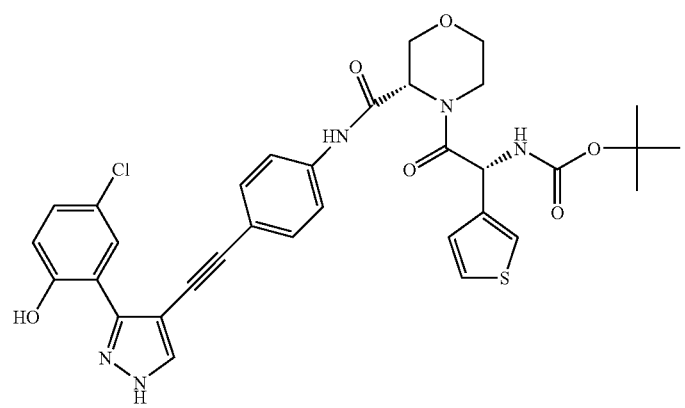

Example 45
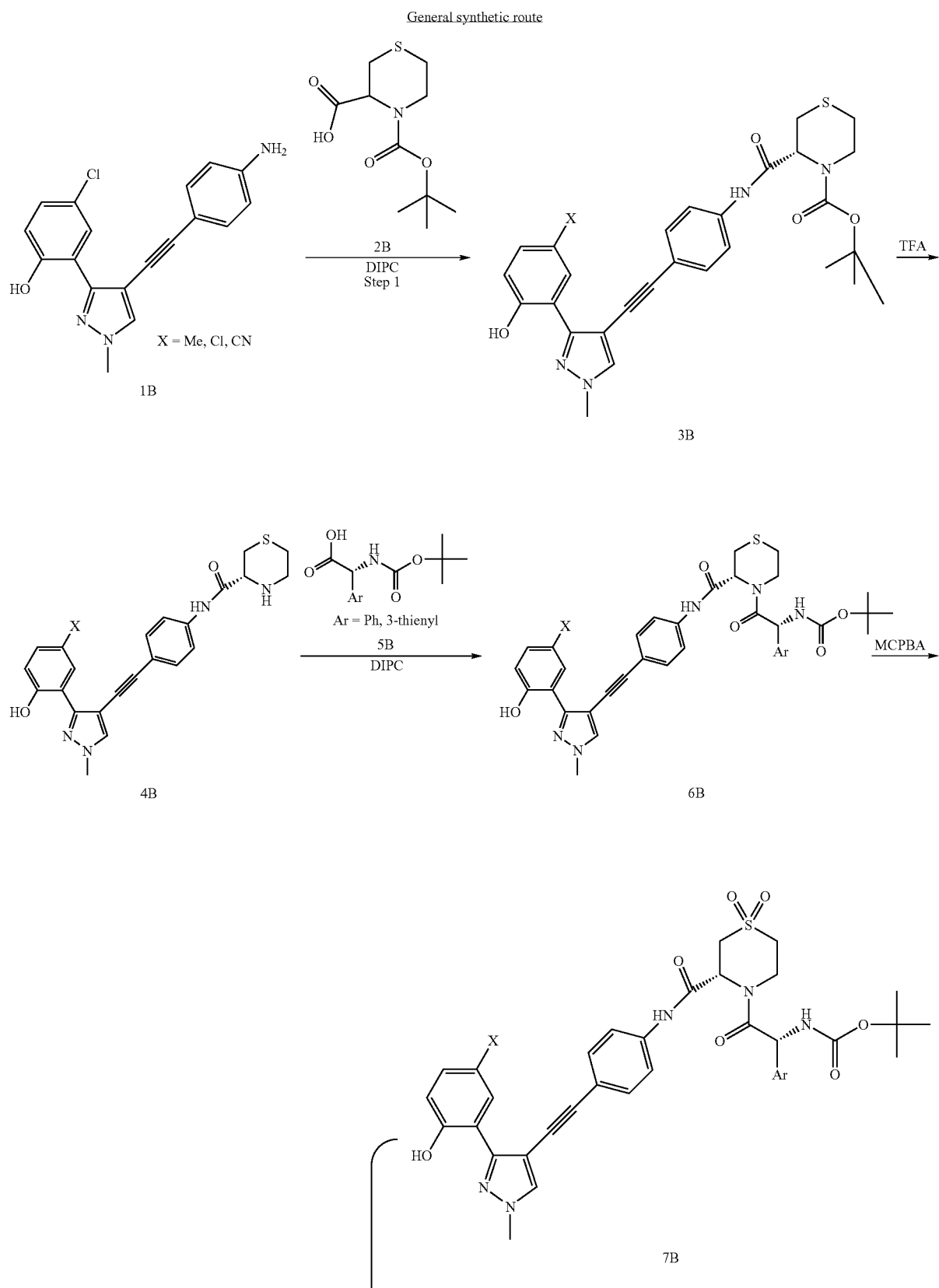
General synthetic route

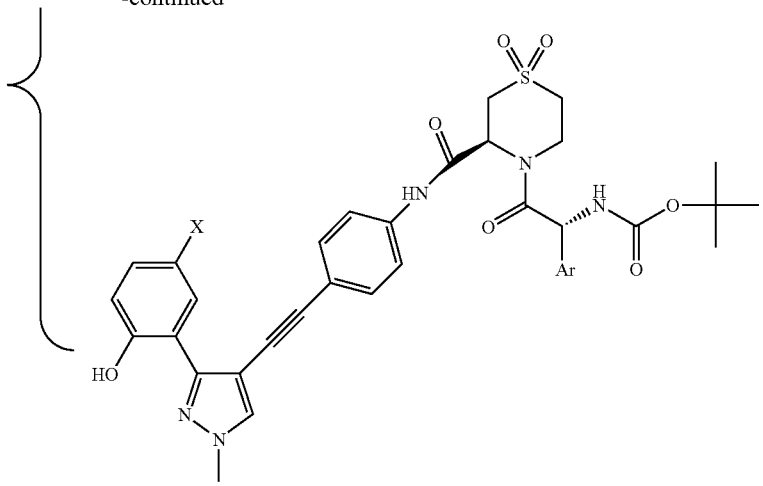

8B

General Synthetic Procedure:

Intermediate 3: Intermediate 1B (500 mg) was mixed with 4-(t-Butoxycarbonyl) thiomorpholine-3-carboxylic acid (2B, 1.1 equiv.), diisopropyl carbodiimide (DIPC) (0.5 mL), and CH$_2$Cl$_2$ (anhydrous, 10 mL), and was shaken overnight until all 1B was consumed according to LCMS. The solvent was removed by rotavaporation. Silica gel column chromatography purification with Dichloromethane/Ethyl Acetate (9:1) led to pure 3B (>90% yield).

Intermediate 4B: 3B (1 g) was mixed with CH$_2$Cl$_2$ (5 mL) and Et$_3$SiH (1 mL) and cooled to 0° C. before TFA (2 mL) was added slowly. The solution was shaken at r.t. for 1 hr until all 3B was consumed. A saturated aqueous solution of NaHCO$_3$ was added slowly at 0° C. until no gas generated. CH$_2$Cl$_2$ (200 mL) was added and the mixture was washed with saturated NaCl (aq) (25 mL, 3 times). The remaining CH$_2$Cl$_2$ layer was dried over molecular sieves (4 A) and filtered. The solvent was removed completely by rotavaporation followed by high vacuum drying to give 4B.

Intermediate 6B: 4B (100 mg) was mixed with (R)-2-(tert-butoxycarbonyl)-2-arylacetic acid (1.1 equiv.) and CH$_2$Cl$_2$/THF (anhydrous, 1/1, 5 mL) and cooled to 0° C. before DIPC (0.15 mL) was added slowly. The solution was stirred at 0° C. for about 3 hrs until all 4B was consumed. The solution was washed with saturated NaCl (aq) (25 mL, 3 times). The remaining CH$_2$Cl$_2$ layer was rotavaporated. Silica gel column chromatography purification with Dichloromethane/Ethyl Acetate (9:1) led to pure 6B (~80-90% yield).

Final products 7B and 8B: 6B (100 mg) was mixed with meta-chloroperoxybenzoic acid (mCPBA) (2.2 equiv.) and CH$_2$Cl$_2$/THF (anhydrous, 1/1, 5 mL) and was shaken overnight until all 6B was consumed. The solution was washed with saturated NaCl (aq) (25 mL, 3 times). The remaining CH$_2$Cl$_2$ layer was rotavaporated. Silica gel column chromatography purification with Dichloromethane/Ethyl Acetate (9:1) led to pure 7B (less polar) and 8B (more polar) (~80-90% yield).

Example 26

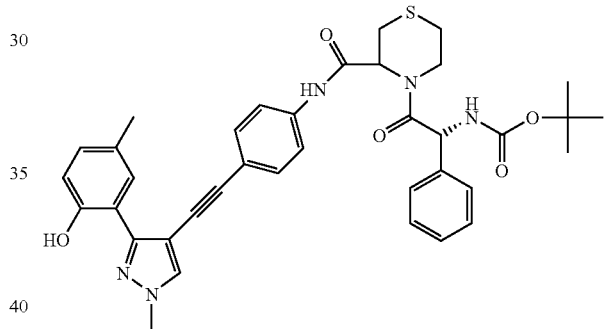

6B-1

LCMS (5.68 min, [M+1]$^+$·666). $^1$H NMR (500 MHz, d6-DMSO): δ 10.3 (s, 1H), 9.8-10.2 (m, 1H), 6.7-8.3 (m, 13H), 5.4-5.7 (m, 2H), 4.0-4.4 (m, 1H), 3.9 (s, 3H), 3.4-3.8 (m, 1H), 3.0-3.2 (m, 2H), 2.5-2.8 (m, 1H), 2.3 (s, 3H), 1.4 (s, 9H).

Example 46

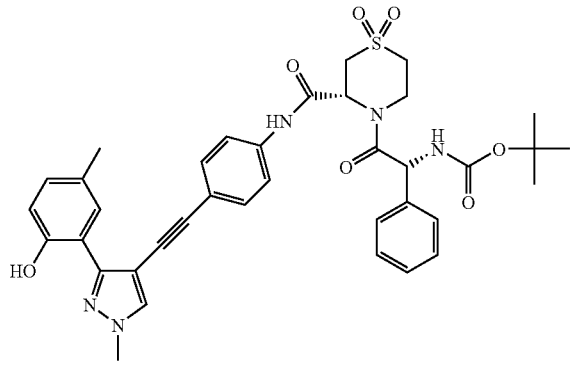

7B-1

LCMS (5.28 min, [M+1]+ 698). ¹H NMR (500 MHz, d6-DMSO): δ 10.3 (s, 1H), 10.0 (s, 1H), 6.8-8.3 (m, 13H), 5.5-5.8 (m, 2H), 4.9 (m, 1H), 4.0-4.3 (m, 2H), 3.9 (s, 3H), 3.4-3.8 (m, 3H), 2.9-3.2 (m, 2H), 2.3 (s, 3H), 1.4 (s, 9H).

Example 47

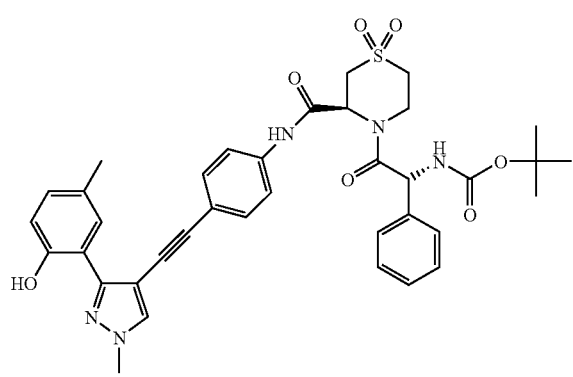

LCMS (5.28 min, [M+1]+ 698). ¹H NMR (500 MHz, d6-DMSO): δ 10.3 (s, 1H), 10.2 (s, 1H), 6.8-8.3 (m, 13H), 5.5-5.8 (m, 2H), 4.9 (m, 1H), 4.0-4.3 (m, 2H), 3.9 (s, 3H), 3.4-3.8 (m, 3H), 2.9-3.2 (m, 2H), 2.3 (s, 3H), 1.4 (s, 9H).

Example 48

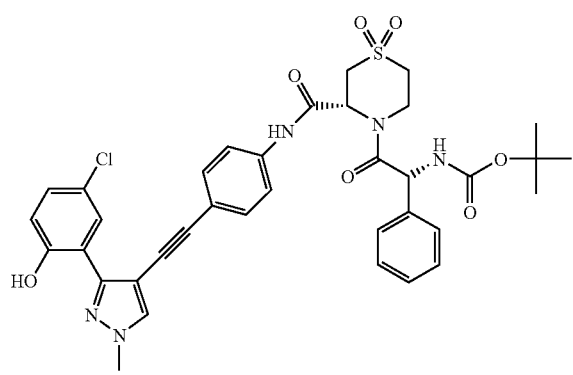

LCMS (5.32 min, [M+1]+ 718). ¹H NMR (500 MHz, d6-DMSO): δ 10.6 (s, 1H), 10.0 (s, 1H), 7.0-8.4 (m, 13H), 5.5-5.8 (m, 2H), 4.9 (m, 1H), 4.0-4.3 (m, 2H), 3.9 (s, 3H), 3.6-3.9 (m, 2H), 2.9-3.5 (m, 4H), 1.4 (s, 9H).

Example 49

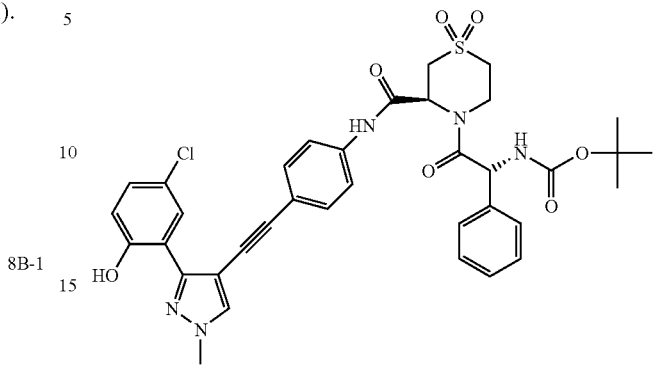

LCMS (5.38 min, [M+1]+ 718). ¹H NMR (500 MHz, d6-DMSO): δ 10.6 (s, 1H), 10.1 (s, 1H), 7.0-8.4 (m, 13H), 5.5-5.8 (m, 2H), 4.9 (m, 1H), 4.0-4.3 (m, 2H), 4.0 (s, 3H), 3.7-3.9 (m, 2H), 2.9-3.2 (m, 3H), 1.4 (s, 9H).

Example 50

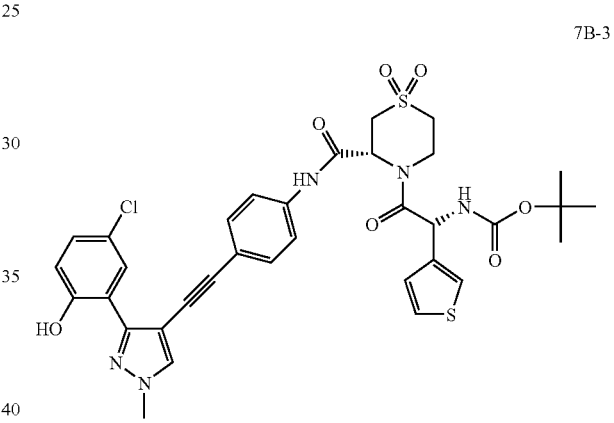

LCMS (5.28 min, [M+1]+ 724). ¹H NMR (500 MHz, d6-DMSO): δ 10.6 (s, 1H), 10.0 (s, 1H), 7.0-8.4 (m, 11H), 5.5-5.8 (m, 2H), 4.9 (m, 1H), 4.0-4.3 (m, 2H), 4.0 (s, 3H), 3.6-3.9 (m, 2H), 3.0-3.5 (m, 4H), 1.4 (s, 9H).

Example 51

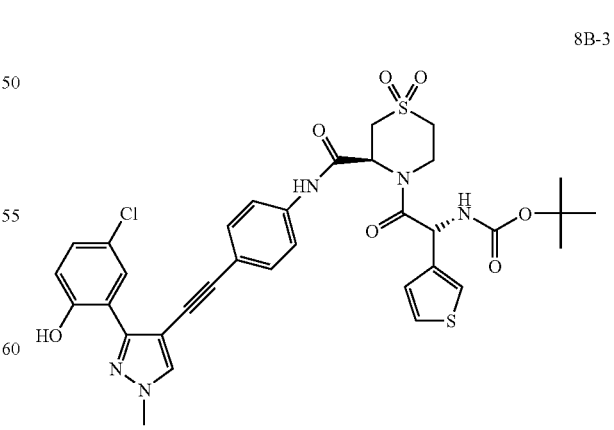

LCMS (5.35 min, [M+1]+ 724). ¹H NMR (500 MHz, d6-DMSO): δ 10.6 (s, 1H), 10.1 (s, 1H), 7.0-8.4 (m, 11H), 5.6-5.9 (m, 2H), 4.9 (m, 1H), 4.0-4.3 (m, 2H), 4.0 (s, 3H), 3.7-3.9 (m, 2H), 2.9-3.2 (m, 3H), 1.4 (s, 9H).

Example 52

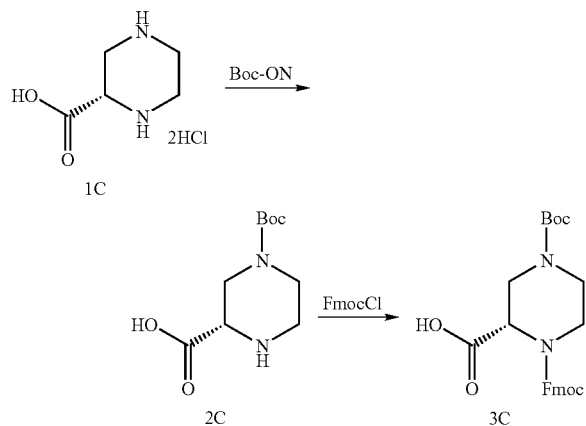

(S)-piperazine-2-carboxylic acid dihydrochloride (10.0 g, 49.23 mmol) was dissolved in 1:1 dioxane/water (320 mL). 50% aqueous sodium hydroxide was added to bring the pH to 11. 2-(Tert-butoxycarbonyloxyimino)-2-phenylacetonitrile (Boc-ON, 15.59 g, 63.32 mmol) was dissolved in dioxane (80 mL) and added dropwise while maintaining the pH at 11 with 50% NaOH. The reaction was stirred overnight at ambient temperature. The reaction mixture was then extracted with diethyl ether (200 mL×3) and the aqueous phase was acidified to pH 2 with concentrated HCl. The di-Boc product was then extracted with EtOAc (200 mL×2) and the acidic solution containing the desired mono-Boc product was then taken on in the synthesis.

The aqueous acidic solution of 4-Boc-piperazine-2-carboxylic acid prepared above was basified to pH 9 with 50% NaOH. Sodium carbonate (10.6 g, 100 mmol) was added with stirring. A solution of 9-fluorenylmethyl chloroformate (15.27 g) in dioxane (50 mL) was added with an ice bath. The reaction was stirred at 0° C. for 5 hr. and at ambient temperature overnight. The reaction mixture was acidified to pH 2 and extracted with EtOAc twice. The combined organic layer was washed with brine and dried over $Na_2SO_4$. The solution was concentrated under vacuum to about 100 mL and hexane was added. The precipitate was collected and dried under vacuum to give 17.34 g (78% for 2 steps) of product as white solid.

Example 53

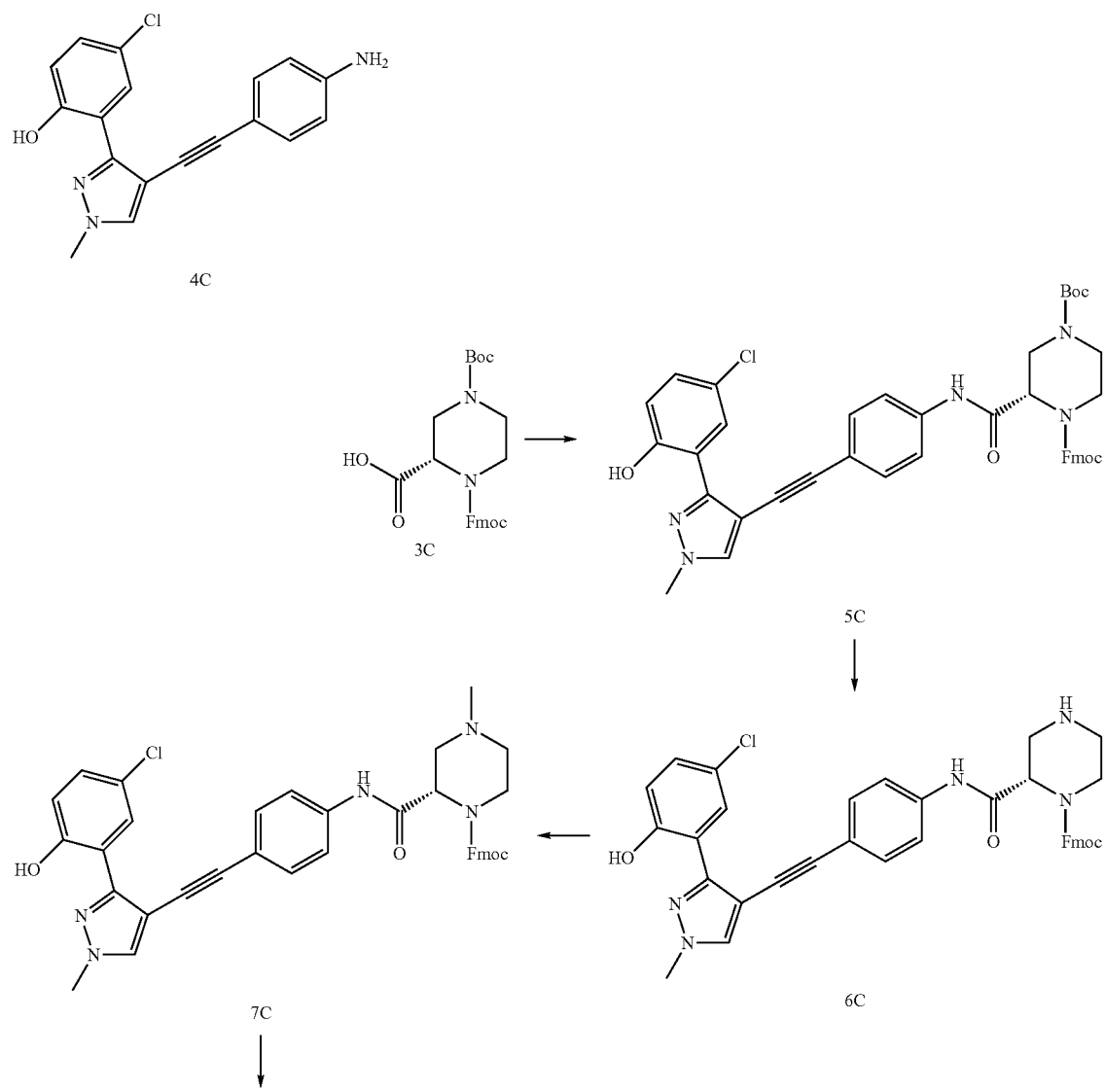

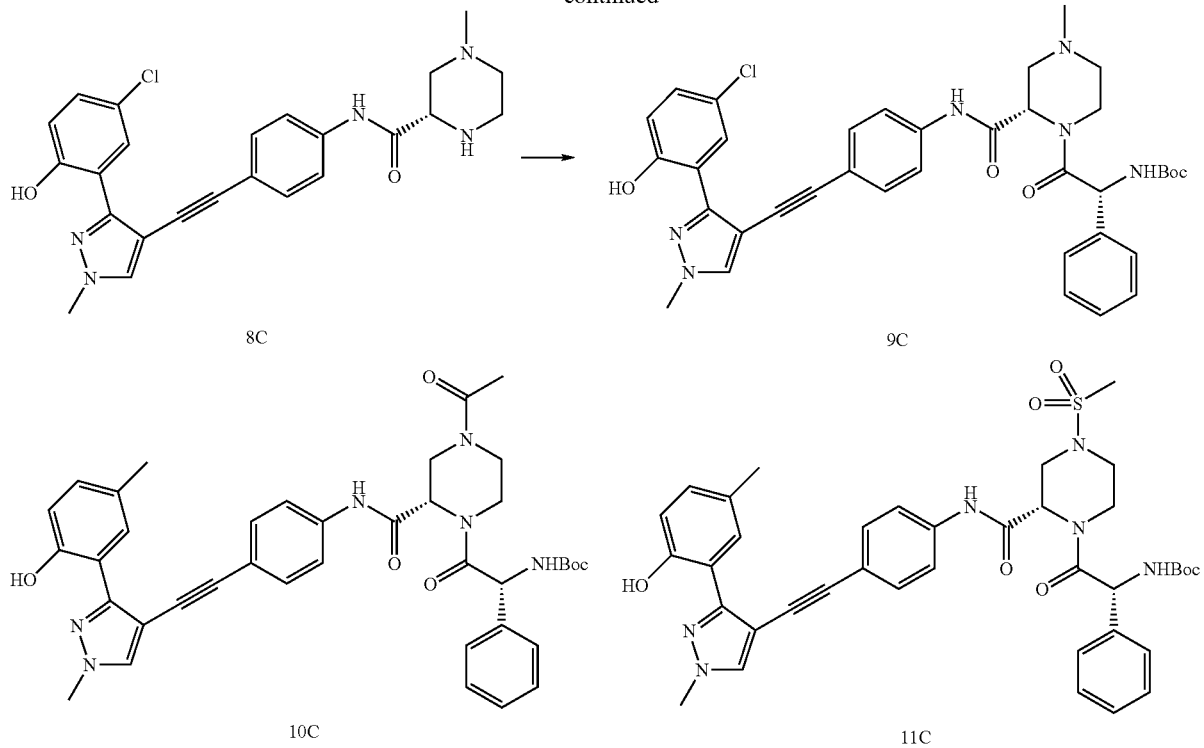

To a solution of 2-[4-(4-amino-phenylethynyl)-1-methyl-1H-pyrazol-3-yl]-4-chloro-phenol 4C (3.24 g, 10 mmol) in methylene chloride (250 mL) was added acid 3 (5.43 g, 12 mmol) and diisopropylcarbodiimide (2.3 mL, 15 mmol) at rt. The reaction was stirred at ambient temperature overnight. The solvent was removed under vacuum and the residue was purified on column to give 6.5 g of product in 86% yield.

The product from the above reaction was dissolved in methylene chloride (100 mL). 10 mL of TFA was added and stirred at rt. The reaction was complete after 3 hr. as determined by TLC monitoring. The solvents were removed under vacuum and the residue was purified on a column to yield 5.64 g of product in quantitative yield.

To a solution of 6C (1.32 g, 2 mmol) in 1,2-dichloroethane (15 mL) was added formaldehyde (37%, 0.18 mL, 6.4 mmol) and Na(OAc)$_3$BH (600 mg, 2.8 mmol). The reaction was stirred at rt overnight. Methylene chloride was added and washed with water and brine successively. The organic phase was dried over Na$_2$SO$_4$, and concentrated under vacuum.

The residue obtained above was dissolved in DMF (15 mL) and piperidine (5 mL) was added. The reaction was stirred at rt overnight. Water was added and the mixture was extracted twice with ethyl acetate. The organic layer was combined and dried over Na$_2$SO$_4$. The product was purified on a column to give 584 mg of product (65% for 2 steps) after removal of solvent under vacuum. $^1$H NMR (500 MHz, CDCl$_3$) δ 10.67 (s, 1H), 9.32 (s, 1H), 8.68 (d, J=1.5 Hz, 1H), 7.63 (s, 1H), 7.62 (d, J=8.0 Hz, 2H), 7.57 (d, J=8.0 Hz, 2H), 7.20 (dd, J=8.5, 1.5 Hz, 1H), 6.97 (d, J=8.5 Hz, 1H), 3.97 (s, 3H), 3.58 (m, 1H), 3.04 (m, 1H), 2.96 (m, 1H), 2.81 (m, 1H), 2.51 (m, 2H), 2.33 (s, 3H), 2.30 (m, 2H). LCMS m/z 450.2 (M$^+$), 452.1.

To a solution of 8C (35 mg, 0.078 mmol) in CH$_2$Cl$_2$ (2 mL) was added Boc-D-phenylglycine (29 mg, 1.5 equiv.) and DIPC (18 μL, 1.5 equiv.). After being stirred at rt overnight, the urea by-product was filtered off and the solution was loaded onto the preparative TLC for purification. Compound 9C (38.0 mg, 72%) was obtained. $^1$H NMR (500 MHz, CDCl$_3$) δ 10.68 (s, 1H), 8.71 (s, 2H), 7.89 (d, J=8.5 Hz, 2H), 7.62 (s, 1H), 7.55 (d, J=8.5 Hz, 2H), 7.42 (m, 6H), 7.19 (d, J=8.0 Hz, 1H), 6.96 (d, J=8.0 Hz, 1H), 5.54 (d, J=6.5 Hz, 1H), 5.48 (d, J=5.5 Hz, 1H), 5.43 (s, 1H), 3.96 (s, 3H), 3.77 (d, J=12.5 Hz, 1H), 3.66 (d, J=11.5 Hz, 1H), 3.53 (t, J=11.5 Hz, 1H), 2.64 (d, J=10.5 Hz, 1H), 2.24 (s, 3H), 1.95 (dd, J=11.5, 3.5 Hz, 1H), 1.55 (t, J=11.0 Hz, 1H), 1.44 (s, 9H). LCMS m/z 683.2 (M$^+$), 685.1.

Compound 10C: $^1$H NMR (500 MHz, CDCl$_3$) δ 10.48 (s, 1H), 8.65 (s, 1H), 8.43 (s, 1H), 7.81 (d, J=8.0 Hz, 2H), 7.62 (s, 1H), 7.50 (d, J=8.0 Hz, 2H), 7.44 (m, 5H), 7.06 (d, J=8.0 Hz, 1H), 6.94 (d, J=8.0 Hz, 1H), 5.51 (m, 2H), 5.44 (m, 1H), 4.72 (d, J=13.5 Hz, 1H), 4.45 (d, J=13.0 Hz, 1H), 3.95 (s, 3H), 3.82 (d, J=12.5 Hz, 1H), 3.37 (t, J=12.0 Hz, 1H), 3.11 (d, J=13.5 Hz, 1H), 2.33 (s, 3H), 2.27 (s, 3H), 2.25 (m, 1H), 1.44 (s, 9H). LCMS m/z 691.3 (M$^+$), 692.3.

Compound 11C: $^1$H NMR (500 MHz, CDCl$_3$) δ 10.48 (s, 1H), 8.62 (s, 1H), 8.43 (s, 1H), 7.85 (d, J=8.5 Hz, 2H), 7.62 (s, 1H), 7.50 (d, J=8.5 Hz, 2H), 7.44 (m, 5H), 7.07 (d, J=8.5 Hz, 1H), 6.94 (d, J=8.5 Hz, 1H), 5.59 (s, 1H), 5.50 (d, J=6.0 Hz, 1H), 5.42 (d, J=5.5 Hz, 1H), 4.50 (d, J=12.0 Hz, 1H), 3.95 (s, 3H), 3.90 (d, J=11.5 Hz, 1H), 3.66 (m, 1H), 3.49 (t, J=12.0 Hz, 1H), 3.12 (m, 1H), 2.96 (s, 3H), 2.85 (dd, J=12.5, 3.0 Hz, 1H), 2.33 (s, 3H), 1.45 (s, 9H). LCMS m/z 727.3 (M$^+$), 749.3 (M+Na$^+$).

Example 54

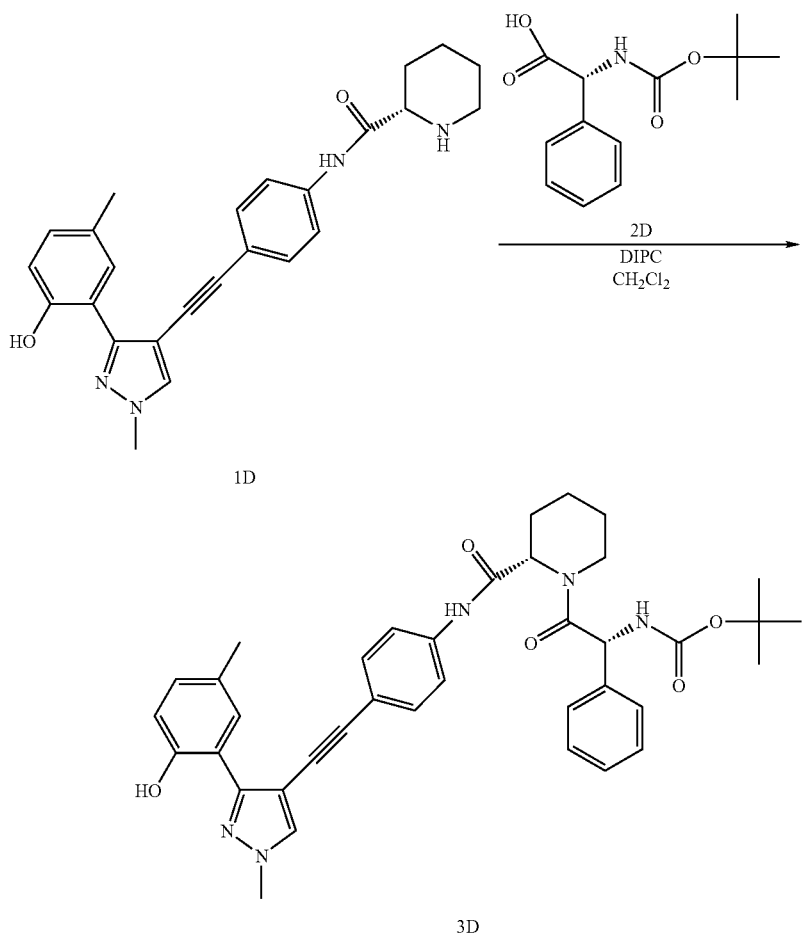

[2-(2-{4-[3-(2-Hydroxy-5-methyl-phenyl)-1-methyl-1H-pyrazol-4-ylethynyl]-phenylcarbamoyl}-piperidin-1-yl)-2-oxo-1-phenyl-ethyl]-carbamic acid tert-butyl ester (3D)

To a mixture of compound 1D (4.90 g, 11.82 mmol) and BOC-D-Phg-OH (2D, 4.46 g, 17.75 mmol) was added anhydrous CH$_2$Cl$_2$ (500 mL) and the resultant mixture was stirred at rt for 10 min. N,N'-Diisopropylcarbodiimide (DIPC, 2.75 mL, 17.75 mmol) was added slowly at rt. The final reaction mixture was stirred at rt overnight. It was then concentrated to small volume and filtered. The filtrate was loaded on silica column, eluting with hexanes-ethyl acetate (v/v 10/1, 2/1, 1/1). Recrystallized from hexanes-ethyl acetate gave the title compound (3D, 4.50 g) as white crystals in 58.9% yield. $^1$H NMR (CDCl$_3$, 500 MHz) δ 10.50 (s, 1H), 8.52 (s, 1H), 8.45 (s, 1H), 7.81 (d, 2H, J=8.0 Hz), 7.61 (s, 1H), 7.50 (d, 2H, J=8.0 Hz), 7.41 (m, 5H), 7.07 (d, 1H, J=8.5 Hz), 6.95 (d, 1H, J=8.5 Hz), 5.60 (s, 2H), 5.54 (d, 1H, J=2.5 Hz), 3.94 (s, 3H), 3.88 (d, 1H, J=13.0 Hz), 3.19 (t, 1H, J=13.0 Hz), 2.49 (d, 1H, J=13.5 Hz), 2.35 (s, 3H), 1.61 (br s, 2H), 1.56-1.22 (m, 11H), 0.90 (m, 1H). LCMS (ESI) m/z 670.42 (MNa$^+$), 648.42 (MH$^+$), 592.33 (100), 548.32, 345.23, 289.16. HPLC: t$_R$=5.85 min.

Example 55

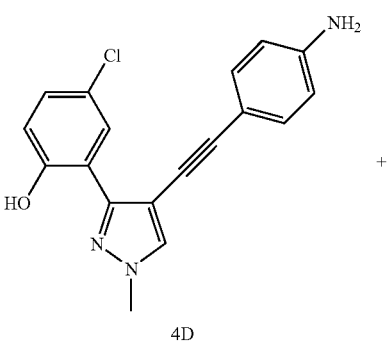

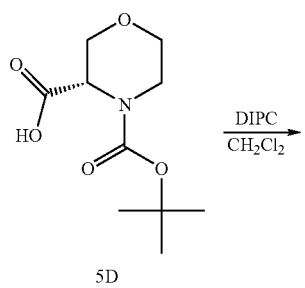

Example 56

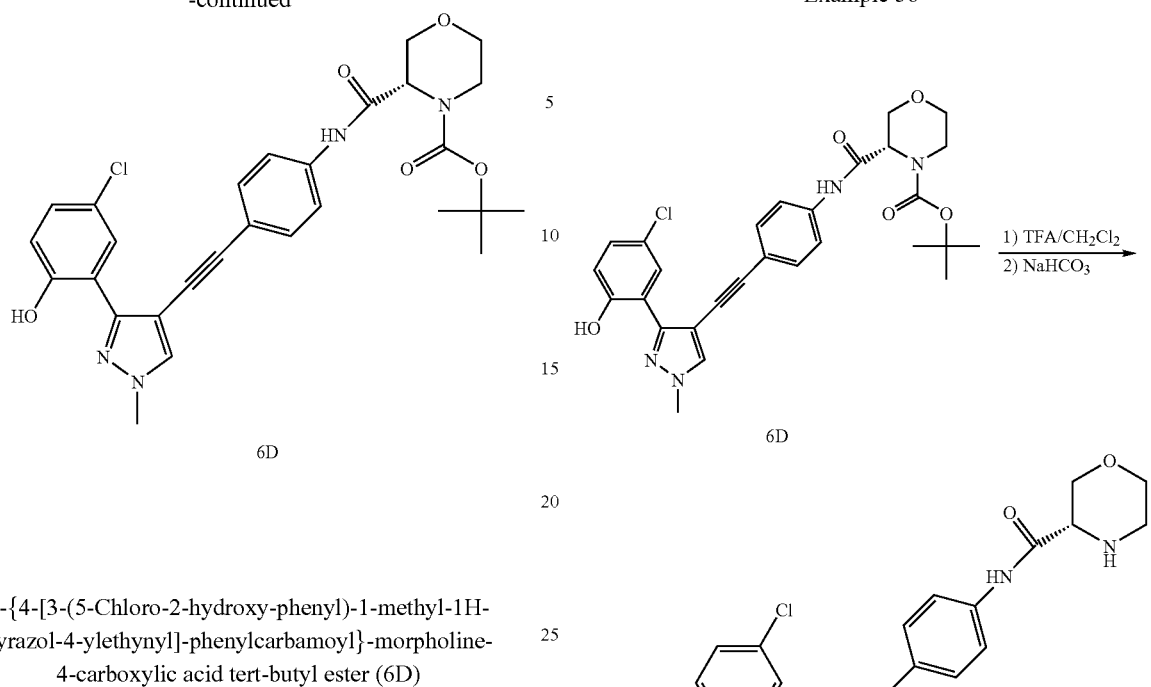

3-{4-[3-(5-Chloro-2-hydroxy-phenyl)-1-methyl-1H-pyrazol-4-ylethynyl]-phenylcarbamoyl}-morpholine-4-carboxylic acid tert-butyl ester (6D)

To a solution of compound 4D (24.4 g, 75.36 mmol) and morpholine-3,4-dicarboxylic acid 4-tert-butyl ester (5D) (21.74 g, 94.01 mmol) in anhydrous $CH_2Cl_2$ (400 mL) was added N,N'-Diisopropylcarbodiimide (DIPC, 17.8 mL, 114.95 mmol). The reaction mixture was stirred at rt overnight. It was filtered to remove diisopropylurea. The filtrate was purified with silica column chromatography, eluting with dichloromethane/EtOAc (v/v 9/1, 7/1) to provide the title compound (6D, 34.4 g) as white powder in 85% yield. $^1$H NMR (CDCl$_3$, 500 MHz) δ 10.66 (s, 1H), 8.66 (s, 1H), 8.45 (br s, 1H), 7.49 (s, 5H), 7.18 (d, 1H, J=8.0 Hz), 6.95 (d, 1H, J=8.0 Hz), 4.65 (s, 1H), 4.52 (d, 1H, J=11.5 Hz), 3.90 (m, 5H), 3.65 (d, 1H, J=11.0 Hz), 3.55 (t, 1H, J=11.5 Hz), 3.37 (br s, 1H), 1.53 (s, 9H).

Morpholine-3-carboxylic acid {4-[3-(5-chloro-2-hydroxy-phenyl)-1-methyl-1H-pyrazol-4-ylethynyl]-phenyl}-amide (7D)

Using the same procedure for the preparation of compound 5A, treatment of compound 6D with TFA in methylene chloride gives the title compound 7D as a white powder in similar yield. LCMS (ESI) m/z 437.28 (MH$^+$, 100); HPLC: $t_R$=4.15 min.

Example 57

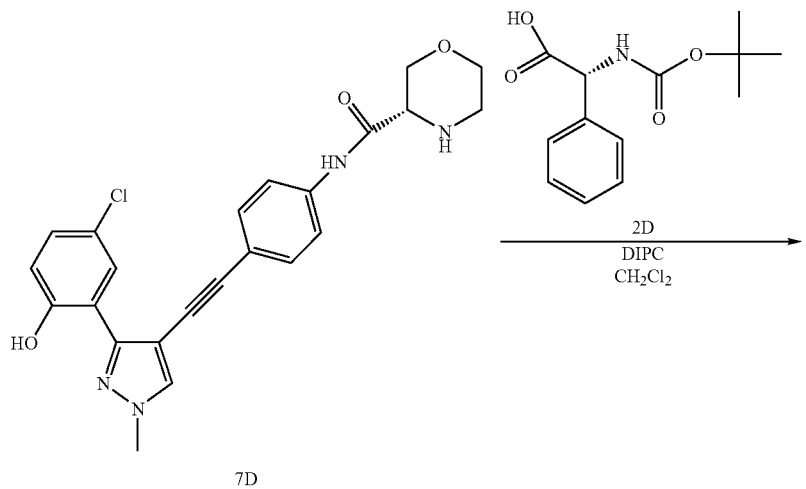

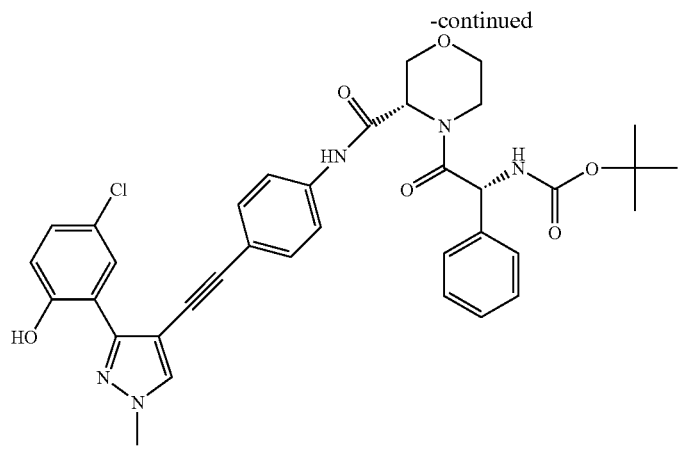

8D

[2-(3-{4-[3-(5-Chloro-2-hydroxy-phenyl)-1-methyl-1H-pyrazol-4-ylethynyl]-phenylcarbamoyl}-morpholin-4-yl)-2-oxo-1-phenyl-ethyl]-carbamic acid tert-butyl ester (8D)

Using the same procedure for the preparation of 3D, reaction of compound 7D with BOC-D-Phg-OH (2D) afforded the title compound 8D, which was purified by silica column chromatography eluting with dichloromethane/EtOAc (9/1, 8/1, 7/1) to give pure 8D as white powder in similar yield. $^1$H NMR (CDCl$_3$, 500 MHz) δ 10.68 (s, 1H), 8.72 (s, 1H), 8.61 (s, 1H), 7.92 (d, 2H, J=7.0 Hz), 7.63 (s, 1H), 7.57 (d, 2H, J=8.0 Hz), 7.43 (m, 5H), 7.20 (d, 1H, J=8.5 Hz), 6.97 (dd, 1H, J=9.0, 1.0 Hz), 5.48 (d, 1H, J=6.0 Hz), 5.40 (d, 1H, J=5.5 Hz), 5.29 (s, 1H), 4.82 (d, 1H, J=12.0 Hz), 3.96 (s, 3H), 3.78 (d, 1H, J=10.5 Hz), 3.65 (t, 1H, J=12.5 Hz), 3.60 (t, 1H, J=10.0 Hz), 3.43 (dd, 1H, J=11.5, 2.0 Hz), 3.07 (t, 1H, J=11.5 Hz), 1.45 (s, 9H). LCMS (ESI) m/z 692.34 (MNa$^+$), 670.33 (MH$^+$), 614.24 (100), 570.23. HPLC: t$_R$=5.35 min.

Example 58

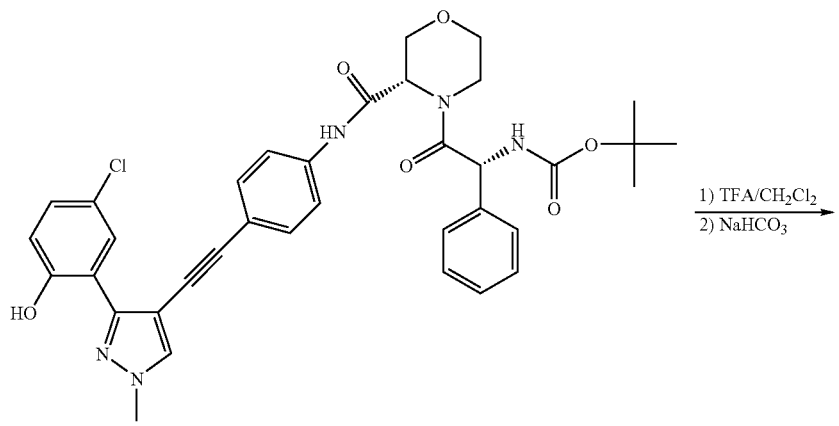

8D

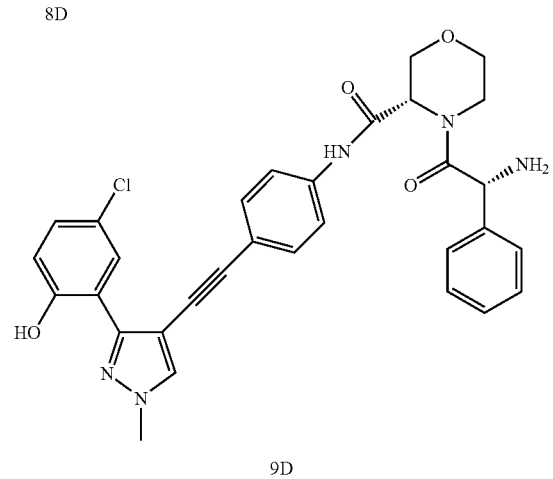

9D

4-(2-Amino-2-phenyl-acetyl)-morpholine-3-carboxylic acid {4-[3-(5-chloro-2-hydroxy-phenyl)-1-methyl-1H-pyrazol-4-ylethynyl]-phenyl}-amide (9D)

To a solution of compound 8D was slowly added TFA (20 eq). The reaction mixture was stirred at rt till all the compound 8D was reacted (4-5 h, checked with LCMS). The solvent was removed with rotavapor at 25° C. More dichloromethane was added and the solvent was removed again. The same process repeated two more times. The residua were then transferred to a separatory funnel with EtOAc and washed with saturated aqueous NaHCO₃. It was dried over sodium sulfate and filtered. Solvent was removed to give the title compound 9D in >85% yield. It was used for next step without further purification. LCMS (ESI) m/z 592.34 (MNa⁺), 570.44 (MH⁺). HPLC: $t_R$=4.27 min.

Example 59

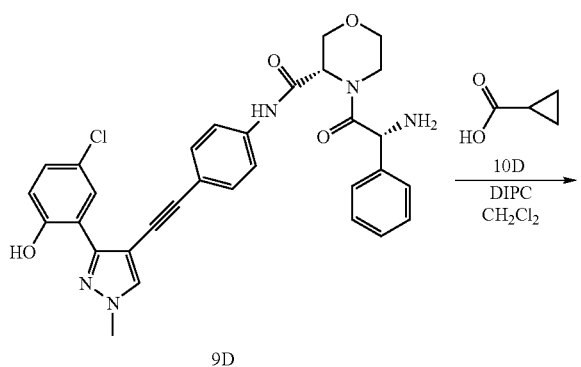

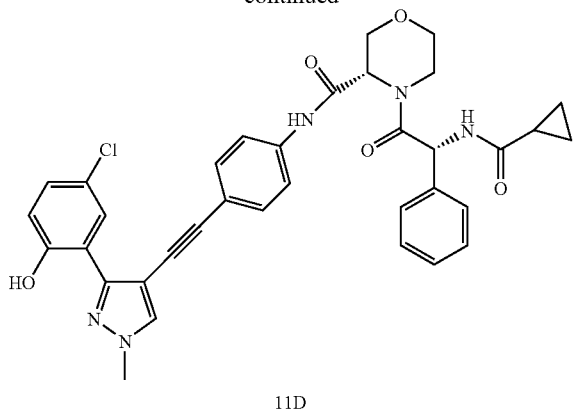

4-[2-(Cyclopropanecarbonyl-amino)-2-phenyl-acetyl]-morpholine-3-carboxylic acid {4-[3-(5-chloro-2-hydroxy-phenyl)-1-methyl-1H-pyrazol-4-ylethynyl]-phenyl}-amide (11D)

To a solution of compound 9D (4.0 g, 7.02 mmol) and cyclopropanecarboxylic acid (10D, (0.91 g, 10.53 mmol) in anhydrous CH₂Cl₂ (100 mL) was added DIPC (1.63 mL, 10.53 mmol). The reaction mixture was stirred at rt overnight. It was filtered to remove diisopropylurea. The filtrate was purified with silica column chromatography eluting with dichloromethane/EtOAc (v/v 1/1, 7/1, 4/1) to give the title compound (11D, 3.4 g, crude), which was recrystallized from hexanes/acetone to provide pure compound 11D (2.2 g) as white powder in 49% yield. ¹H NMR (CDCl₃, 500 MHz) δ 10.68 (s, 1H), 8.75 (s, 1H), 8.71 (s, 1H), 7.90 (d, 2H, J=8.5 Hz), 7.63 (s, 1H), 7.56 (d, 2H, J=9.0 Hz), 7.50 (m, 2H), 7.45 (m, 3H), 7.20 (dd, 1H, J=8.5, 2.5 Hz), 6.97 (d, 1H, J=9.0 Hz), 6.57 (s, 1H), 5.69 (d, 1H, J=5.5 Hz), 5.23 (s, 1H), 4.82 (d, 1H, J=12.0 Hz), 3.97 (s, 3H), 3.81 (d, 1H, J=11.5 Hz), 3.72 (d, 1H, J=12.5 Hz), 3.64 (t, 1H, J=12.0 Hz), 3.43 (dd, 1H, J=11.0, 3.0 Hz), 3.11 (t, 1H, J=11.5 Hz), 1.49 (m, 1H), 1.00 (m, 2H), 0.84 (m, 2H). LCMS (ESI) m/z 669.43 (MNa⁺), 638.39 (MH⁺), 437.28. HPLC: $t_R$=4.98 min.

Example 60

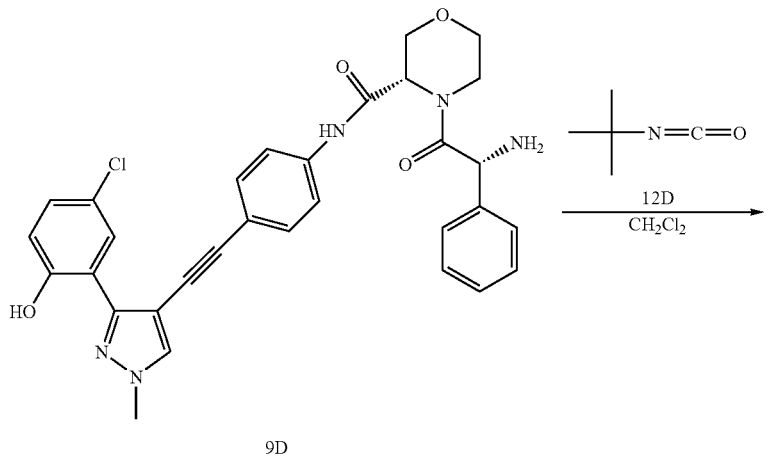

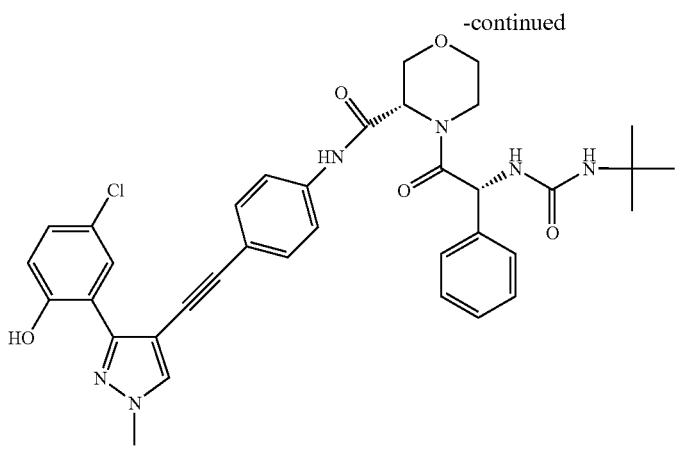

13D

4-[2-(3-tert-Butyl-ureido)-2-phenyl-acetyl]-morpholine-3-carboxylic acid {4-[3-(5-chloro-2-hydroxyphenyl)-1-methyl-1H-pyrazol-4-ylethynyl]-phenyl}-amide (13D)

To a solution of compound 9D (4.0 g, 7.02 mmol) in anhydrous $CH_2Cl_2$ (100 mL) was added tert-butyl isocyanate (12D, 3.21 mL, 28.07 mmol). The reaction mixture was stirred at rt overnight. It was concentrated to small volume and purified with silica column chromatography eluting with dichloromethane/EtOAc to give the title compound (13D) as white powder in good yield. $^1$H NMR (CDCl$_3$, 500 MHz) δ 10.68 (s, 1H), 8.92 (s, 1H), 8.72 (s, 1H), 8.02 (d, 2H, J=8.0 Hz), 7.63 (s, 1H), 7.56 (d, 2H, J=8.0 Hz), 7.38 (s, 5H), 7.19 (d, 1H, J=8.0 Hz), 6.96 (d, 1H, J=8.5 Hz), 5.58 (d, 1H, J=6.0 Hz), 5.30 (s, 1H), 5.18 (d, 1H, J=6.5 Hz), 4.85 (d, 1H, J=11.5 Hz), 4.79 (s, 1H), 3.96 (s, 3H), 3.79 (d, 1H, J=11.5 Hz), 3.62 (br s, 2H), 3.44 (d, 1H, J=10.0 Hz), 3.11 (m, 1H), 1.29 (s, 9H). LCMS (ESI) m/z 669.25 (MH$^+$), 570.23 (100). HPLC: t$_R$=5.22 min.

Example 61

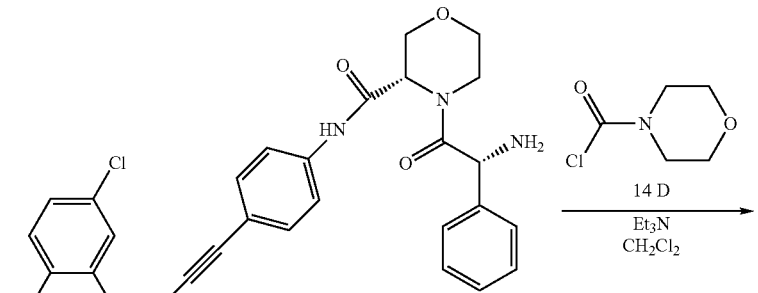

9D

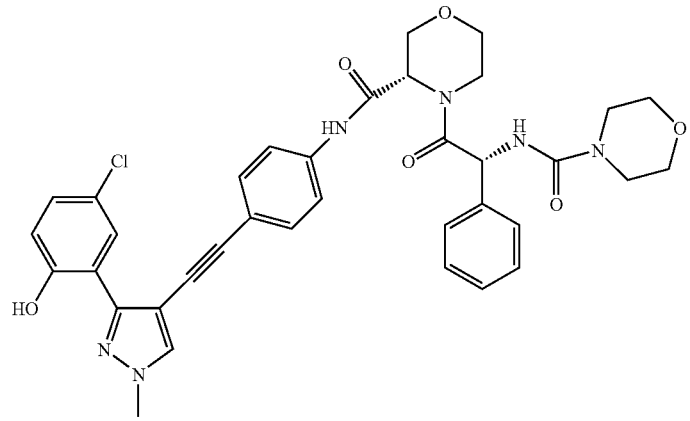

15D

4-{2-[(Morpholine-4-carbonyl)-amino]-2-phenyl-acetyl}-morpholine-3-carboxylic acid {4-[3-(5-chloro-2-hydroxy-phenyl)-1-methyl-1H-pyrazol-4-ylethynyl]-phenyl}-amide (15D)

To a solution of compound 9D in anhydrous $CH_2Cl_2$ were slowly added 4-morpholinecarbonyl chloride (14D, 1.2 eq) and triethylamine (1.5 eq), successively. The reaction mixture was stirred at rt overnight. It was concentrated to small volume and purified with silica column chromatography eluting with dichloromethane/EtOAc to give the title compound (15D) which was recrystallized from hexanes/acetone to provide compound 15D as white powder in ~60% yield. $^1$H NMR ($CDCl_3$, 500 MHz) δ 10.67 (s, 1H), 8.93 (s, 1H), 8.70 (s, 1H), 7.93 (d, 2H, J=7.5 Hz), 7.63 (s, 1H), 7.55 (d, 2H, J=7.5 Hz), 7.45 (s, 5H), 7.19 (d, 1H, J=8.0 Hz), 6.97 (d, 1H, J=8.0 Hz), 5.60 (d, 1H, J=6.5 Hz), 5.28 (s, 1H), 5.18 (d, 1H, J=6.5 Hz), 4.86 (d, 1H, J=12.0 Hz), 3.97 (s, 3H), 3.83 (m, 4H), 3.70 (br s, 4H), 3.45 (m, 2H), 3.37 (m, 2H), 3.17 (m, 1H). LCMS (ESI) m/z 705.43 ($MNa^+$), 683.39 ($MH^+$). HPLC: $t_R$=4.95 min.

Example 62

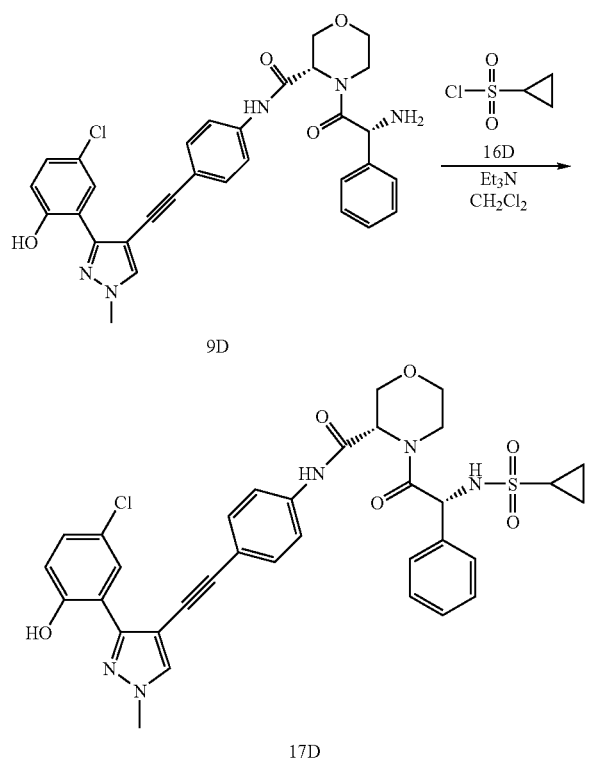

4-(2-Cyclopropanesulfonylamino-2-phenyl-acetyl)-morpholine-3-carboxylic acid {4-[3-(5-chloro-2-hydroxy-phenyl)-1-methyl-1H-pyrazol-4-ylethynyl]-phenyl}-amide (17D)

To a solution of compound 9D (4.0 g, 7.02 mmol) in anhydrous $CH_2Cl_2$ (100 mL) were added cyclopropanesulfonyl chloride (16D, (1.97 g, 14.03 mmol) and triethylamine (3.91 mL, 28.07 mmol), successively. The reaction mixture was stirred at rt overnight. It was concentrated to small volume and purified with silica column chromatography eluting with dichloromethane/EtOAc to give the title compound (17D) which was recrystallized from hexanes/acetone to provide compound 17D as white powder in ~60% yield. $^1$H NMR ($CDCl_3$, 500 MHz) δ 10.66 (s, 1H), 8.67 (s, 1H), 8.18 (s, 1H), 7.67 (d, 2H, J=8.0 Hz), 7.62 (s, 1H), 7.54 (d, 2H, J=8.0 Hz), 7.43 (s, 5H), 7.20 (d, 1H, J=8.5 Hz), 6.97 (d, 1H, J=9.0 Hz), 5.82 (d, 1H, J=8.0 Hz), 5.42 (d, 1H, J=9.0 Hz), 5.20 (s, 1H), 4.67 (d, 1H, J=11.5 Hz), 3.96 (s, 3H), 3.76 (d, 1H, J=11.5 Hz), 3.61 (br s, 2H), 3.44 (dd, 1H, J=12.0, 3.0 Hz), 2.93 (m, 1H), 2.41 (m, 1H), 1.15 (s, 2H), 0.94 (d, 2H, J=5.5 Hz). LCMS (ESI) m/z 696.19 ($MNa^+$), 674.22 ($MH^+$), 351.10 (100). HPLC: $t_R$=4.95 min.

Example 63

HCV Replicon Luciferase Assay

Huh-Luc-Neo (Genotype 1b) cells are seeded at 5000-7000/well in an opaque-walled 96 plate with Growth Medium (DMEM phenol red free+PS+2 mM glutamine; 100 μl/well). The compounds to be tested are added to the experimental wells so as to generate a dose response curve (8-9 concentrations, 10 μl/well at 10× assay concentration) and the cells are then incubated (5% $CO_2$, 37° C.) for 72 h. Inhibition of HCV replication is then measured using luciferase reporter activity as a surrogate endpoint. The luciferase assay is performed using the Bright-Glo Luciferase Assay Kit (Promega) according to the manufacturer's suggested protocol. After 72 hours of incubation with the compounds, 100 ul of Bright-Glo Luciferase Assay reagent (Bright-Glo Luciferase Assay Buffer+Bright-Glo Luciferase Assay Substrate Mixture) is added to each well. The well contents are mixed for 5 min. on an orbital shaker at room temperature to induce cell lysis and the luminescence is then measured using a luminometer. The data is analyzed and EC50s are determined using GraphPad Prism 4 software. Hits validated in the Replicon Luciferase assay have EC50s<8.0 μM and show <30% inhibition of Cell Viability at a compound concentration of 50 μM (Cell Titer Glow Assay, cell viability assay conditions identical to HCV Replicon Luciferase Assay conditions).

Example 64

HCV Replicon RNA Assay

Cell Seeding and Compound Treatment: Huh-Luc-Neo (Genotype 1b) or En5-3/Htat2ANeo (Genotype 1a) cells are seeded at 5000-7000/well in an opaque-walled 96 plate with Growth Medium (DMEM phenol red free+PS+2 mM glutamine; 100 μl/well). The compounds to be tested are added to the experimental wells so as to generate a dose response curve (8-9 concentrations, 10 μl/well at 10× assay concentration) and the cells are then incubated (5% $CO_2$, 37° C.) for 72 h.

RNA Isolation and cDNA Synthesis: After the 72 h incubation, the cells are washed once with 1× Phosphate Buffered Saline (PBS). Cells are then lysed and RNA is isolated in a 96 well format using a vacuum manifold and the RNAeasy 96 kit (Qiagen) according to the manufacturer's suggested protocol. cDNA is then synthesized from RNA isolated from each well using the Taqman Reverse Transcription Reagents kit (Applied Biosystems) according to manufacturer's suggested protocol.

Quantitative PCR Based Measurement of HCV RNA (Taqman Assay): Quantitative PCR analysis to measure HCV RNA expression from cDNA synthesized above is performed using the ABI 9700 HT Sequence Detection System (Applied Biosystems) as previously described (Lohman et al, *Science* 285, 110-113, 1999). The data is analyzed and EC50s are determined using GraphPad Prism 4 software. Hits validated in the Replicon RNA Assay have EC50s<8.0 μM and show <30% inhibition of Cell Viability at a compound concentration of 50 μM (Cell Titer Glow Assay, cell viability assay conditions identical to HCV Replicon RNA Assay conditions).

Example 65

Cell Titer-Glo Cell Viability Assay

Promega

Cell Seeding and Compound Treatment: Huh-Luc-Neo (Genotype 1b) or En5-3/Htat2ANeo (Genotype 1a) cells are seeded at 5000-7000/well in an opaque-walled 96 plate with Growth Medium (DMEM phenol red free+PS+2 mM glutamine; 100 ul/well). The compounds to be tested for inhibition of cell viability are added to the experimental wells so as to generate a dose response curve (8-9 concentrations, 10 μl/well at 10× assay concentration) and the cells are then incubated (5% $CO_2$, 37° C.) for 72 h.

Reagent Preparation and Assay: After completion of the incubation period the cell viability measurements are made using the Cell Titre Glo Assay (Promega) according to the manufacturer's recommended protocol. Briefly, the CellTiter-Glo Buffer is thawed and equilibrated to room temperature prior to use. The lyophilized CellTiter-Glo Substrate is also equilibrated to room temperature prior to use. 10 ml of CellTiter-Glo Buffer is then transferred to 1 vial of CellTiter-Glo Substrate and mixed gently with a Vortex. 100 μl of CellTiter-Glo Assay reagent (CellTiter-Glo Buffer+CellTiter-Glo Substrate Mixture) is added to each well. The well contents are mixed for 5 min. on an orbital shaker at room temperature to induce cell lysis and the luminescence is then measured using a luminometer.

The results of the Replicon Inhibition luciferase assay, the Replicon RNA (Taqman) assay, and the Cell viability assay for the HCV genotype 1b assays are reported in Table 1. As there tends to be some variability in the data for RNA-based assays, the results are reported as ranges: A, $EC_{50}$>100 μM; B, EC50=10-100 μM; C, $EC_{50}$=1-10 μM; D, $EC_{50}$<1 μM. A, $CC_{50}$>100 μM; B, $CC_{50}$=10-100 μM; C, $CC_{50}$=1-10 μM; D, $CC_{50}$<1 μM.

TABLE 1

| Compound number | Structure | HCV-1b Replicon Inhibition*, Luciferase ($EC_{50}$) | HCV-1b Replicon Inhibition*, Taqman ($EC_{50}$) | Cytotoxicity* ($CC_{50}$) |
|---|---|---|---|---|
| 1 | (structure) | C | D | A |
| 2 | (structure) | D | D | A |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
| --- | --- | --- | --- | --- |
| 3 | 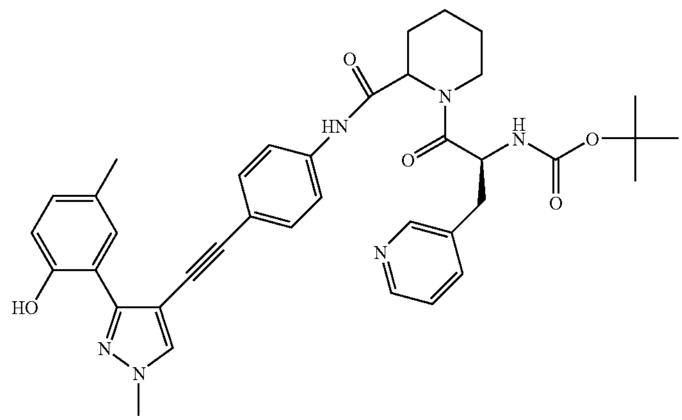 | D | D | A |
| 4 | 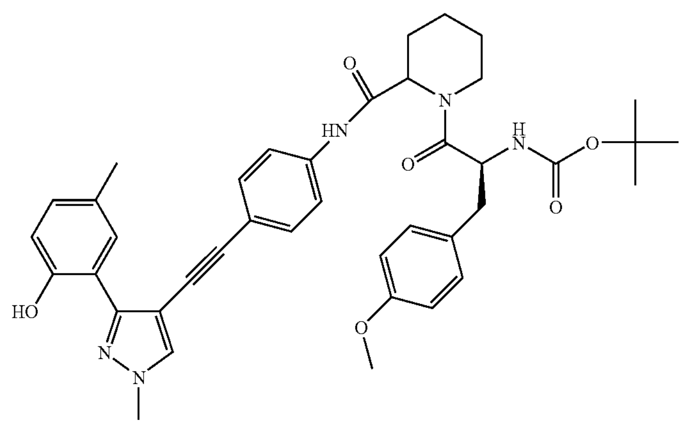 | D | D | D |
| 5 | 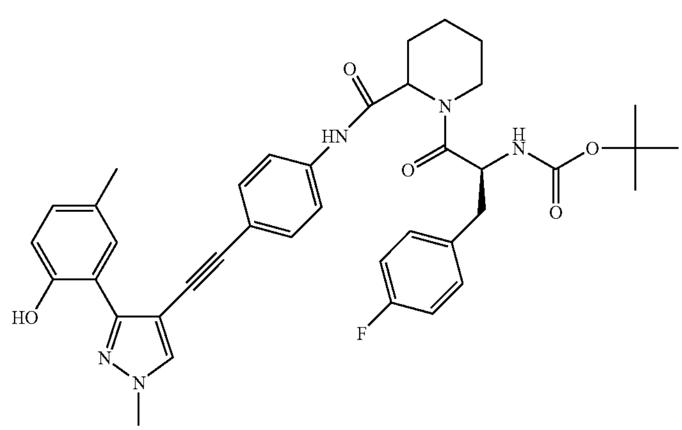 | D | D | A |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
| --- | --- | --- | --- | --- |
| 6 | 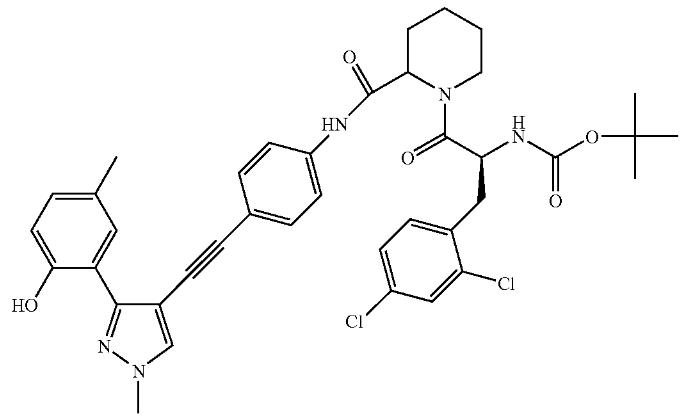 | D | D | A |
| 7 | 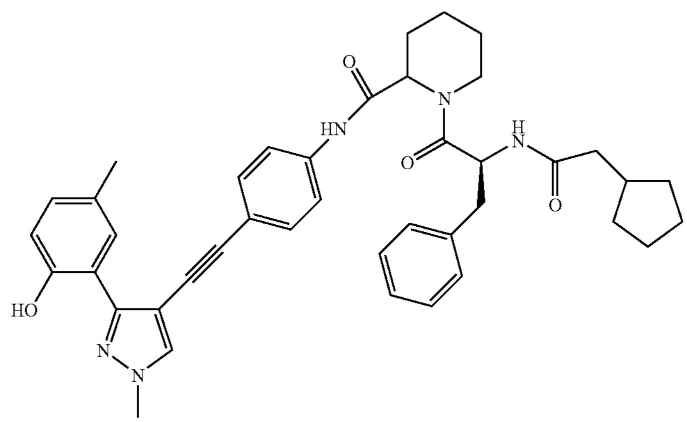 | D | D | A |
| 8 | 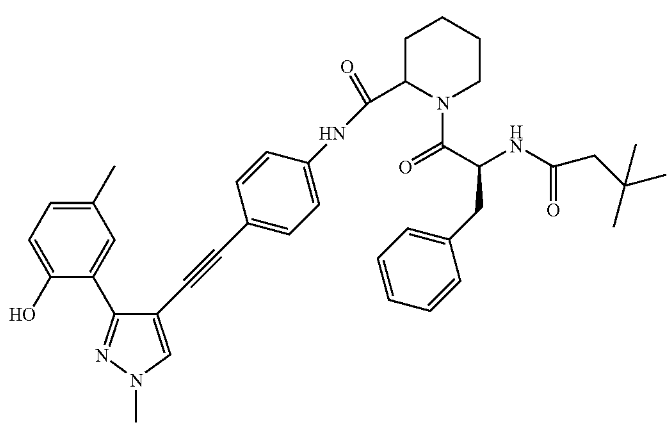 | D | D | B |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
|---|---|---|---|---|
| 9 | 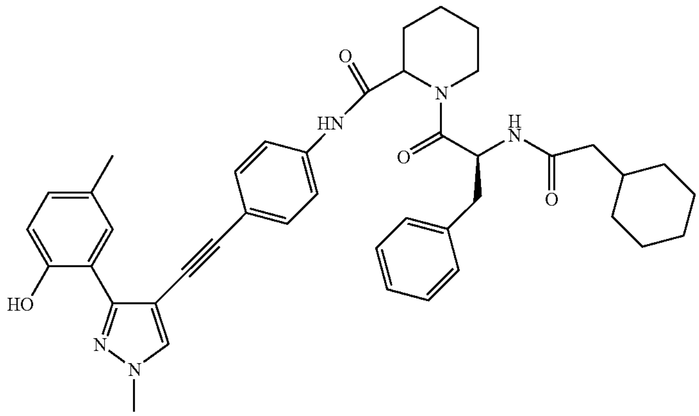 | D | D | B |
| 10 | 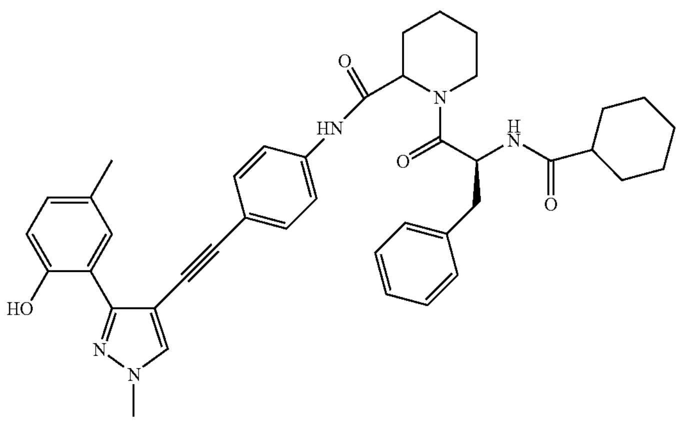 | D | D | B |
| 11 | 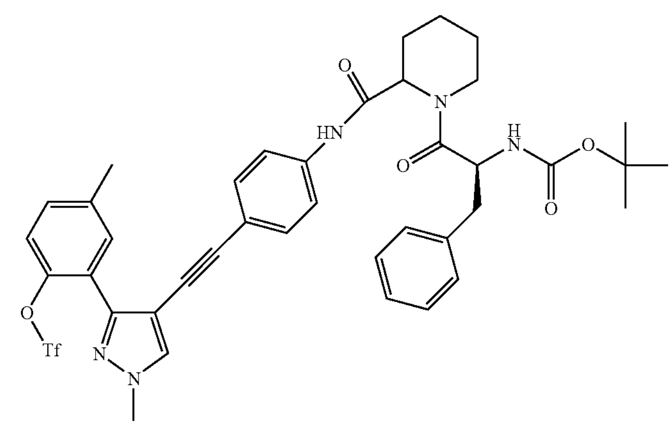 | D | D | A |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
|---|---|---|---|---|
| 12 | 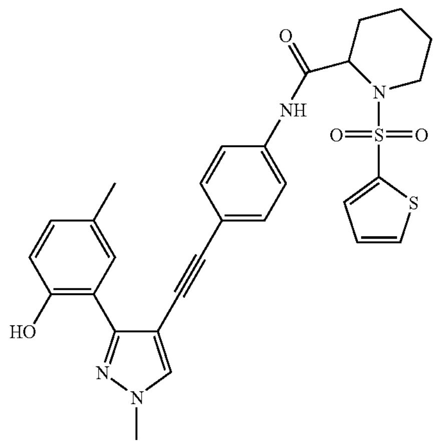 | D | D | A |
| 13 | 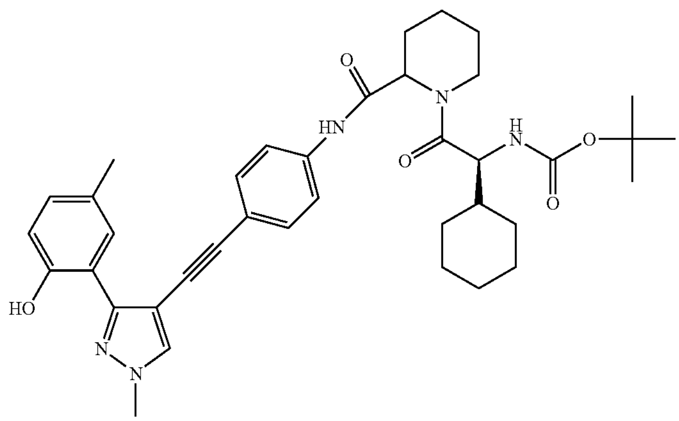 | C | D | A |
| 14 | 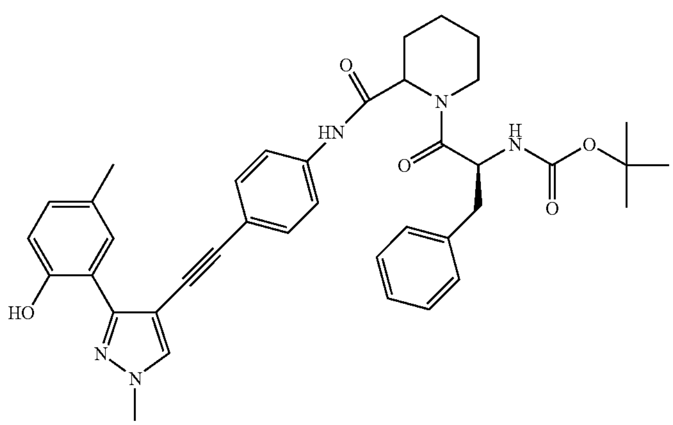 | D | D | A |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
| --- | --- | --- | --- | --- |
| 15 | 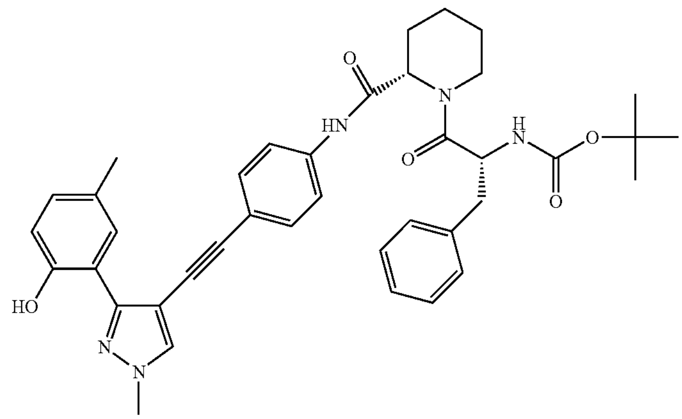 | D | D | A |
| 16 | 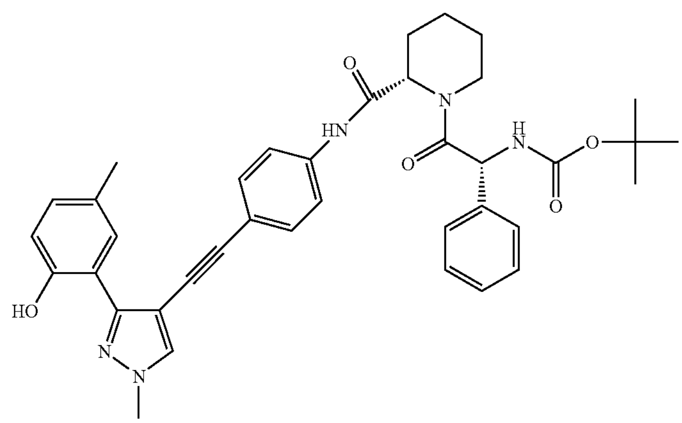 | D | D | A |
| 17 | 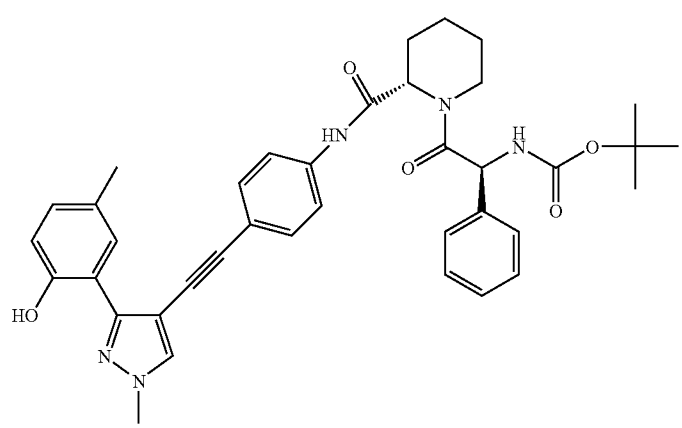 | D | D | A |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
|---|---|---|---|---|
| 18 | 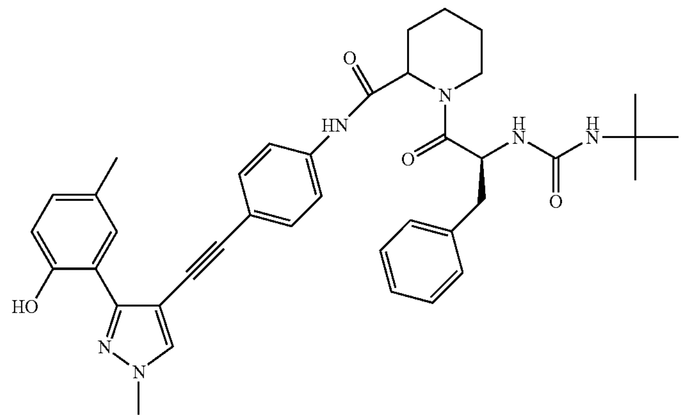 | D | D | A |
| 19 | 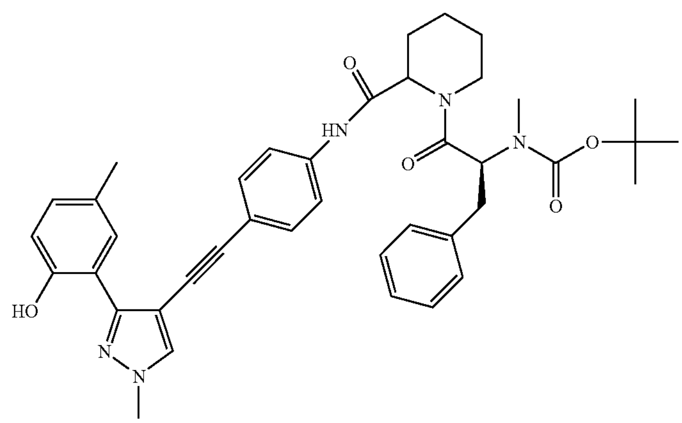 | D | D | B |
| 20 | 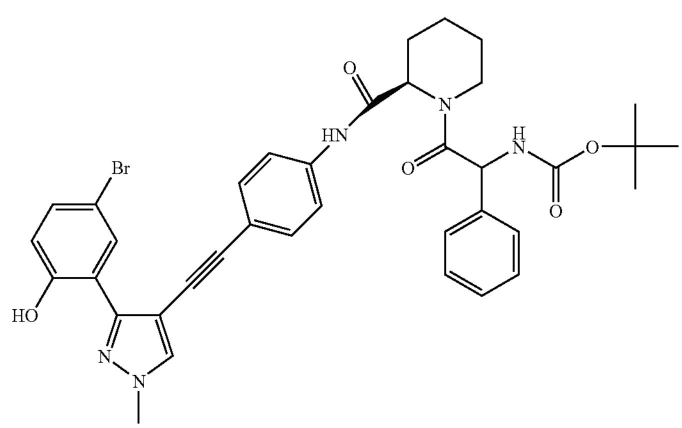 | D | D | B |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
|---|---|---|---|---|
| 21 | 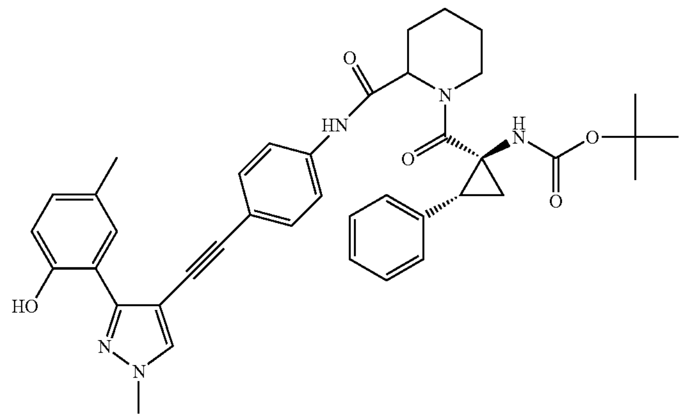 | D | D | B |
| 22 | 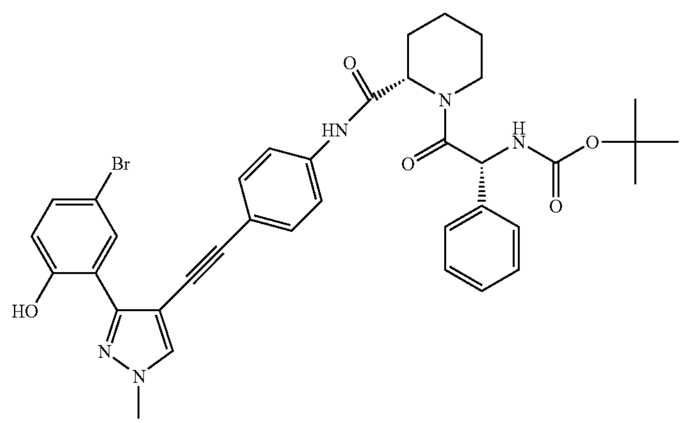 | D | D | B |
| 23 | 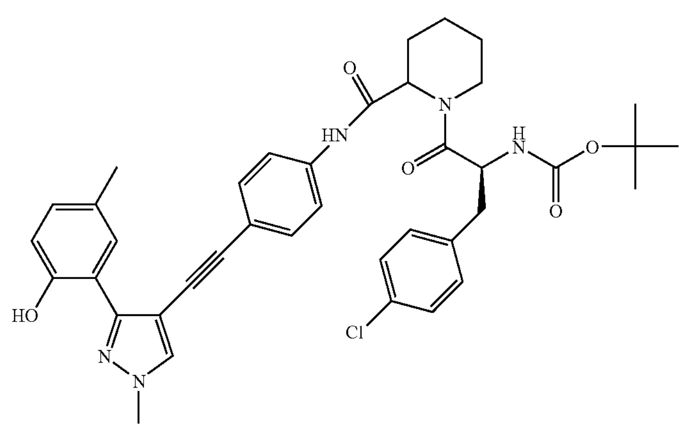 | D | D | B |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
|---|---|---|---|---|
| 24 | 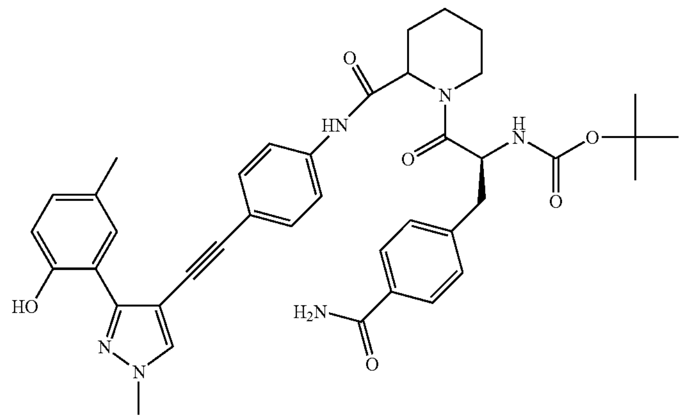 | D | D | B |
| 25 | 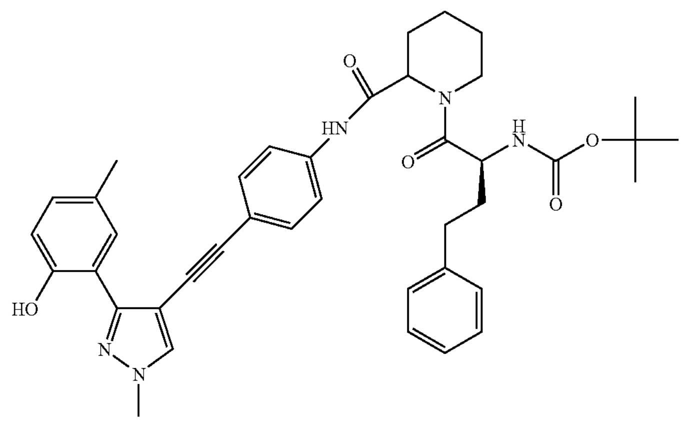 | D | D | B |
| 26 | 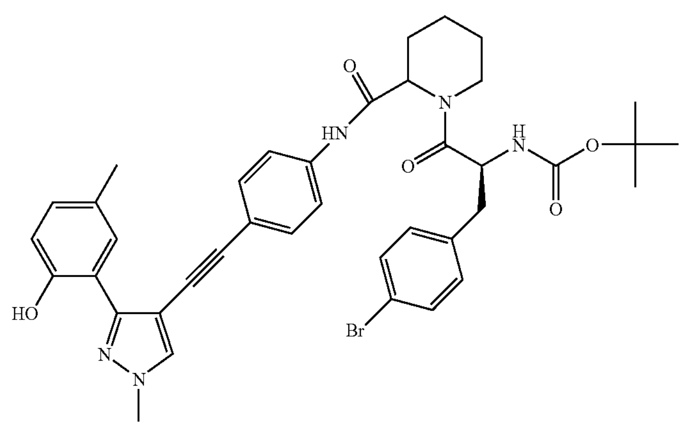 | D | D | B |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
| --- | --- | --- | --- | --- |
| 27 | 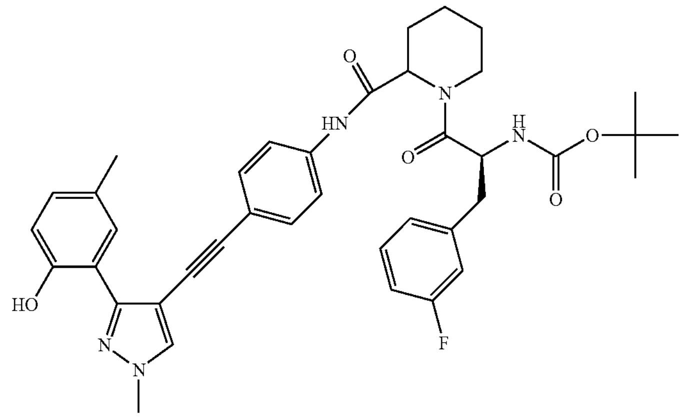 | D | D | B |
| 28 | 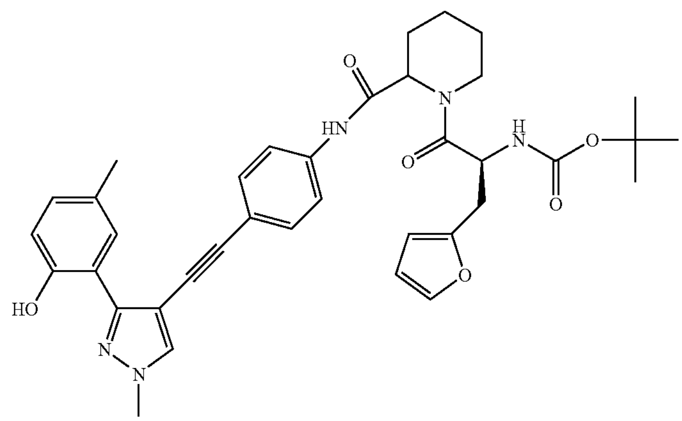 | D | D | B |
| 29 | 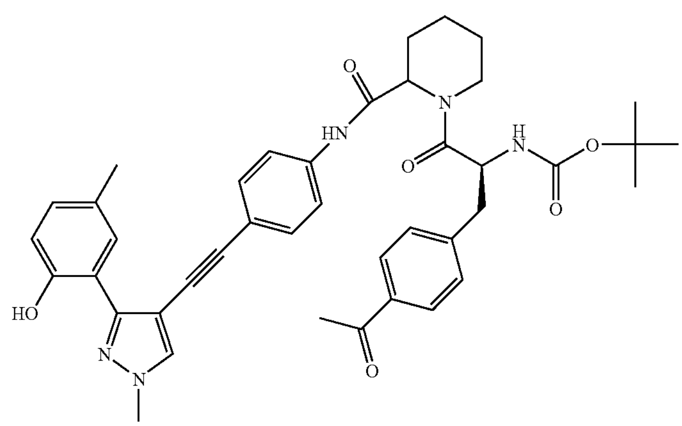 | D | D | D |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
| --- | --- | --- | --- | --- |
| 30 | 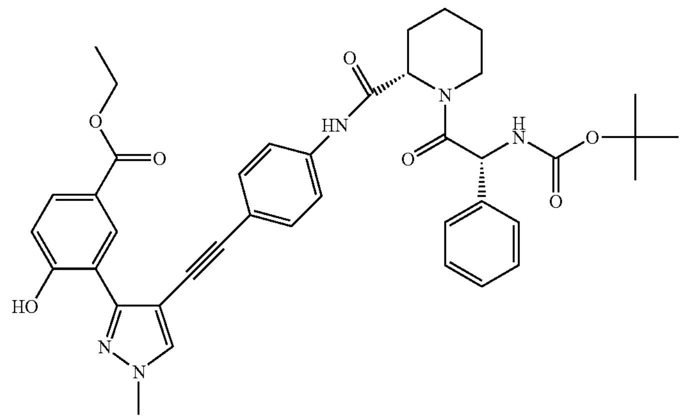 | D | D | A |
| 31 | 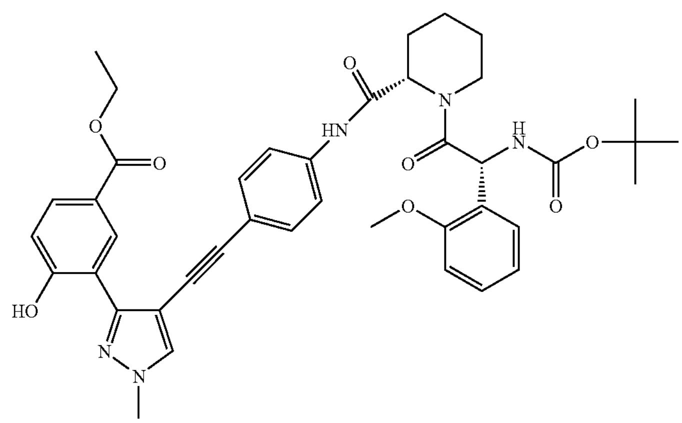 | D | D | A |
| 32 | 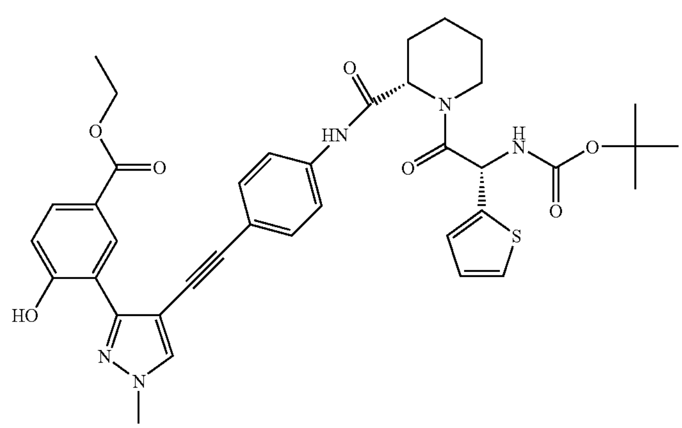 | D | D | A |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
| --- | --- | --- | --- | --- |
| 33 | 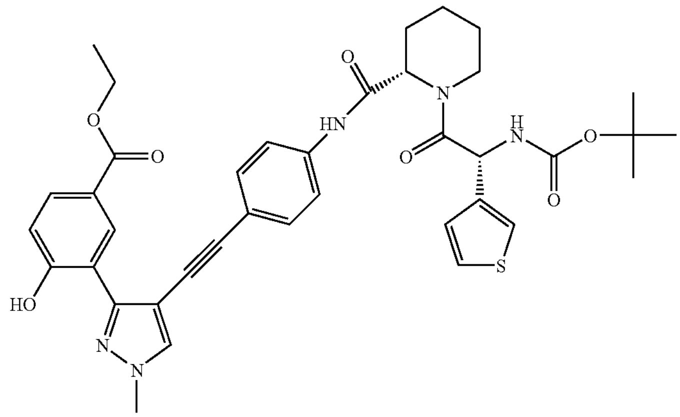 | D | D | A |
| 34 | 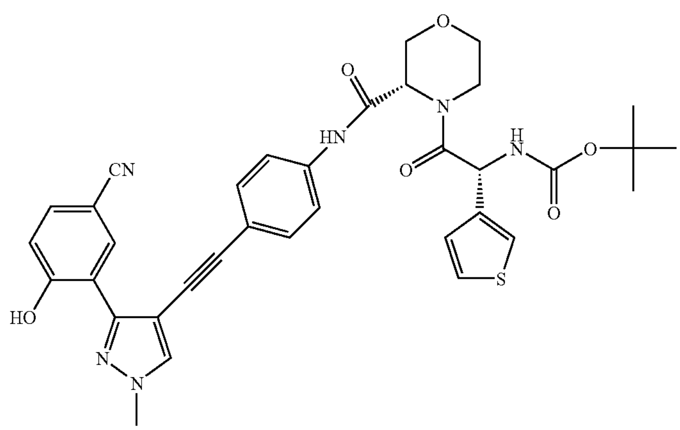 | D | D | A |
| 35 | 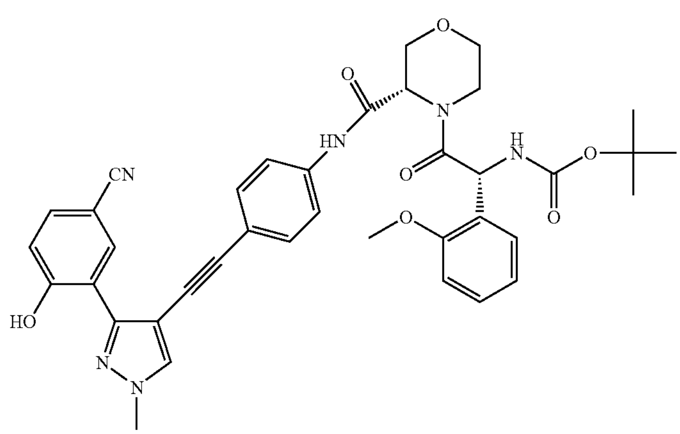 | D | D | A |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
| --- | --- | --- | --- | --- |
| 36 | 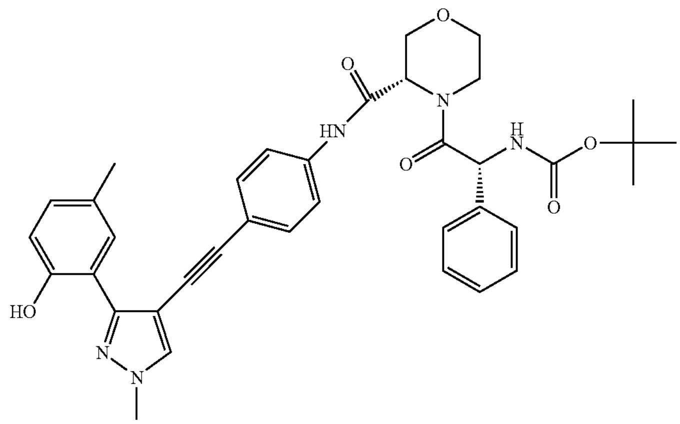 | D | D | A |
| 37 | 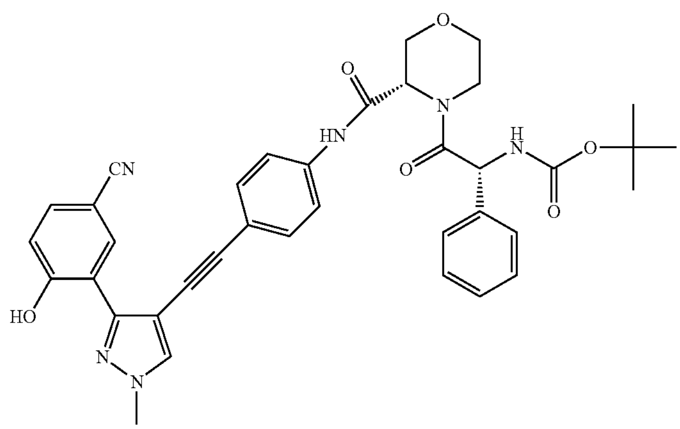 | D | D | A |
| 38 | 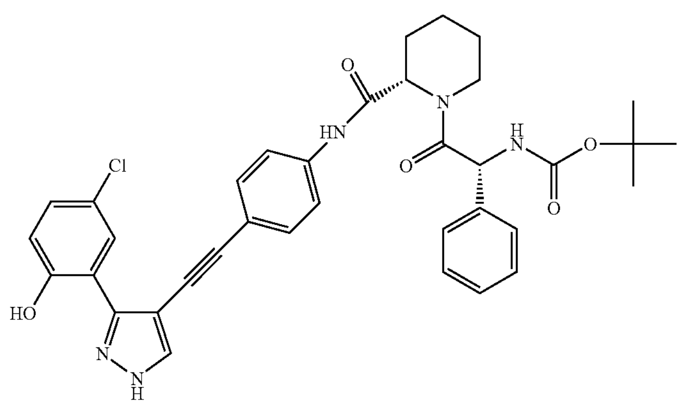 | D | D | A |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
|---|---|---|---|---|
| 39 | 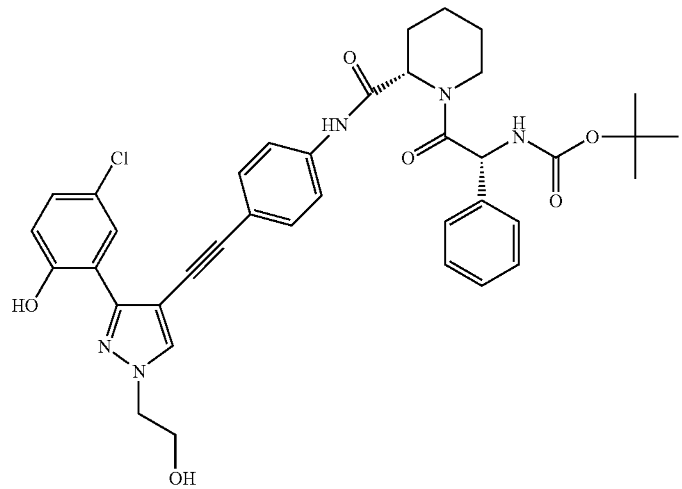 | D | D | B |
| 40 | 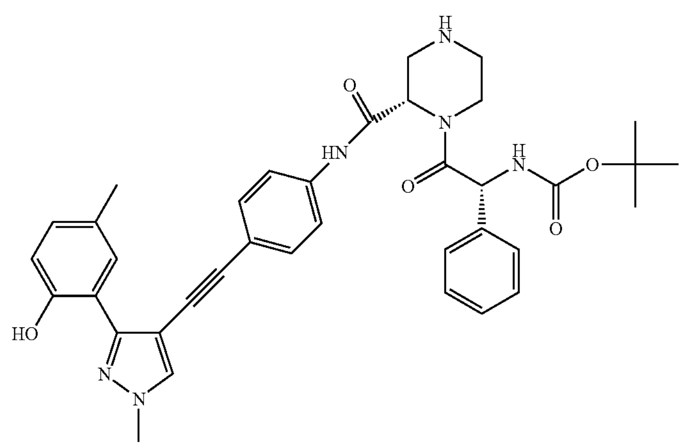 | D | D | B |
| 41 | 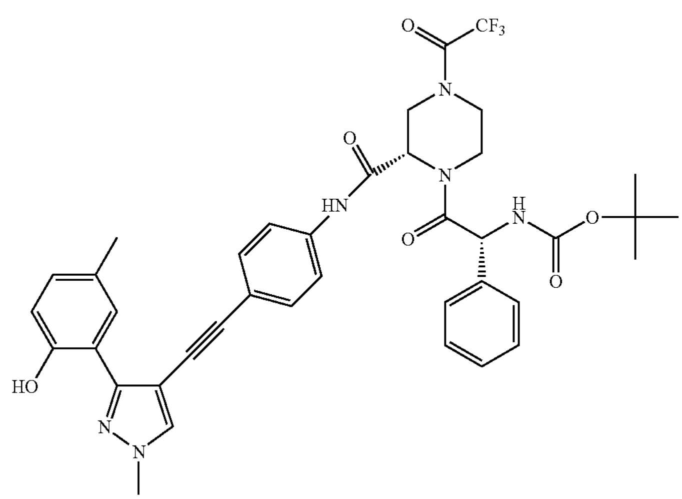 | D | D | A |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
|---|---|---|---|---|
| 42 | 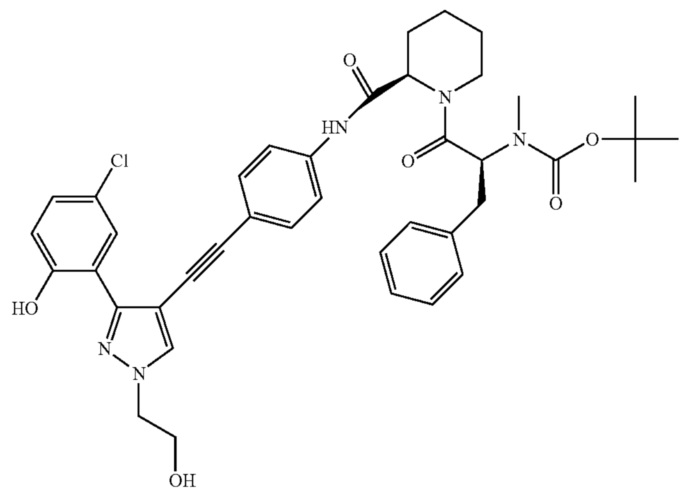 | D | D | B |
| 43 | 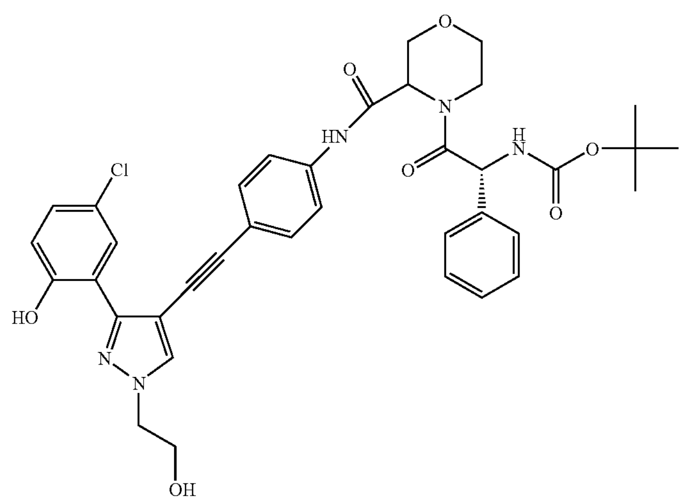 | D | D | A |
| 44 | 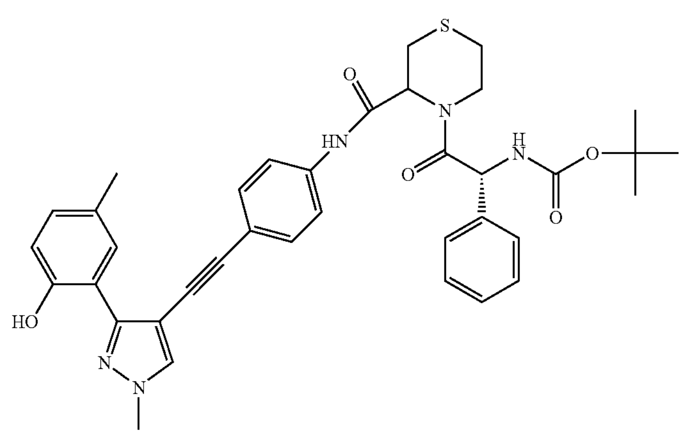 | D | D | A |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
|---|---|---|---|---|
| 45 | 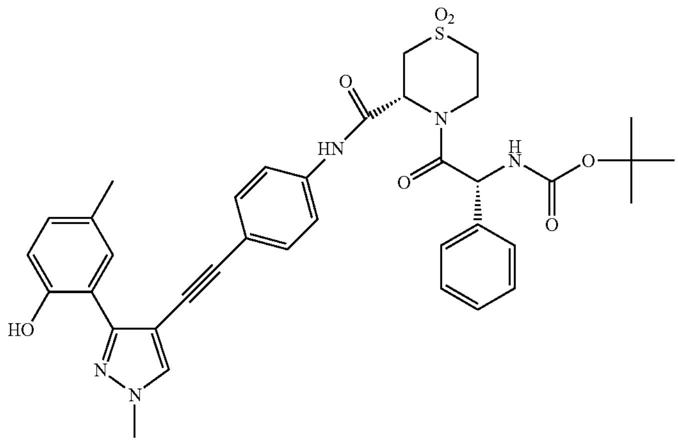 | D | D | A |
| 46 | 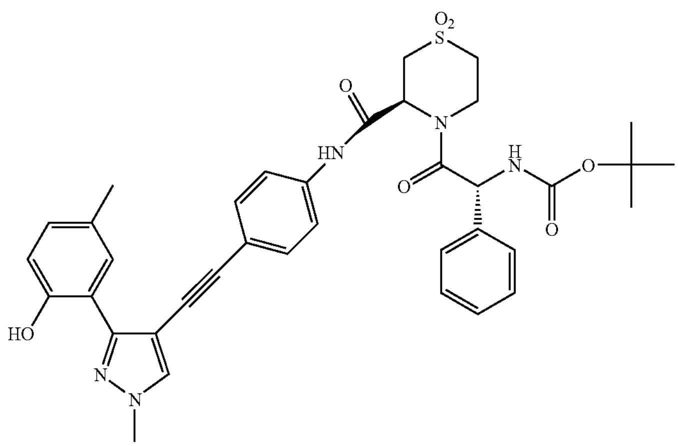 | D | D | A |
| 47 | 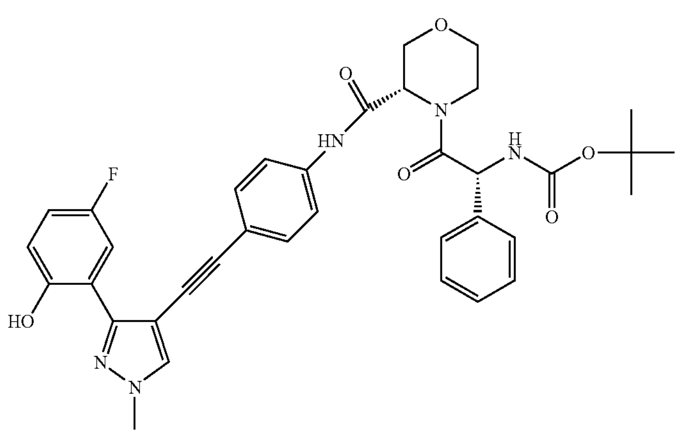 | D | D | A |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
|---|---|---|---|---|
| 48 | 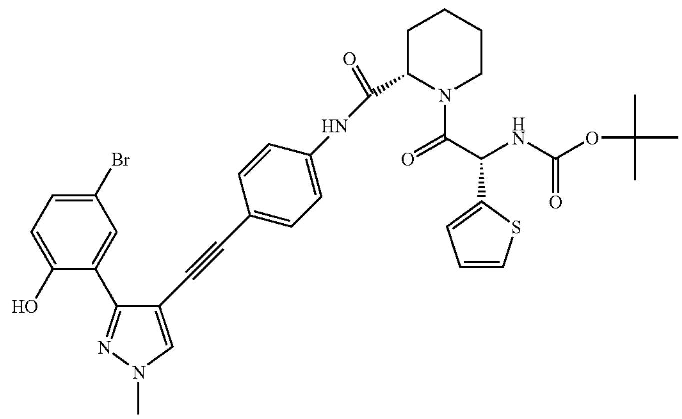 | D | D | A |
| 49 | 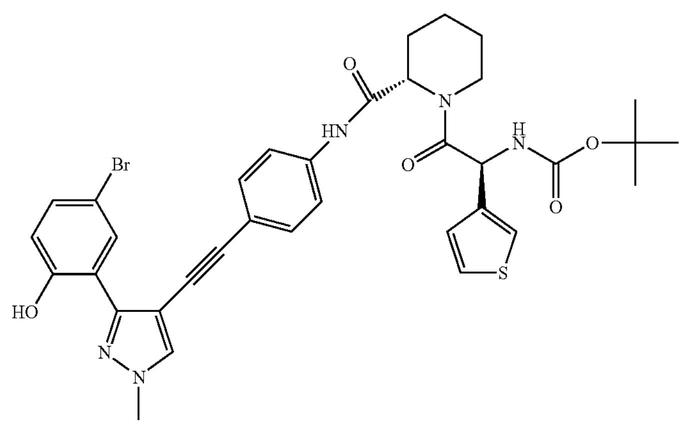 | D | D | B |
| 50 | 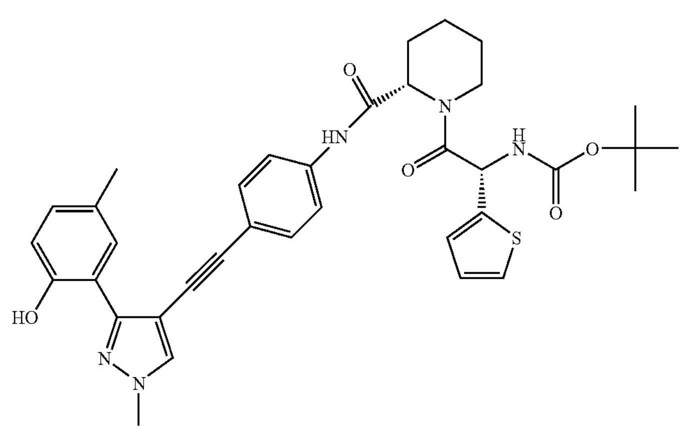 | D | D | A |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
|---|---|---|---|---|
| 51 | 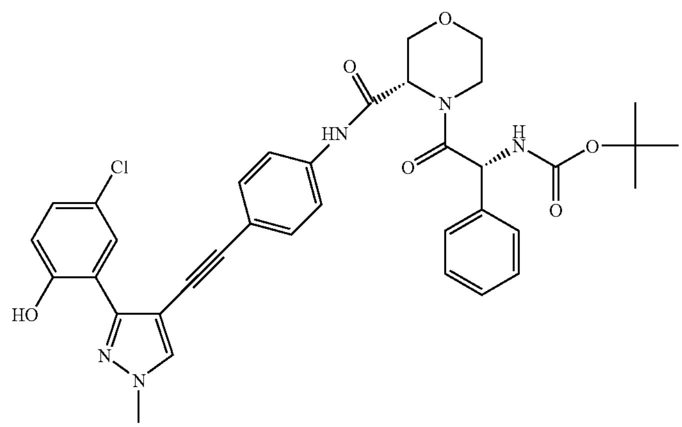 | D | D | B |
| 52 | 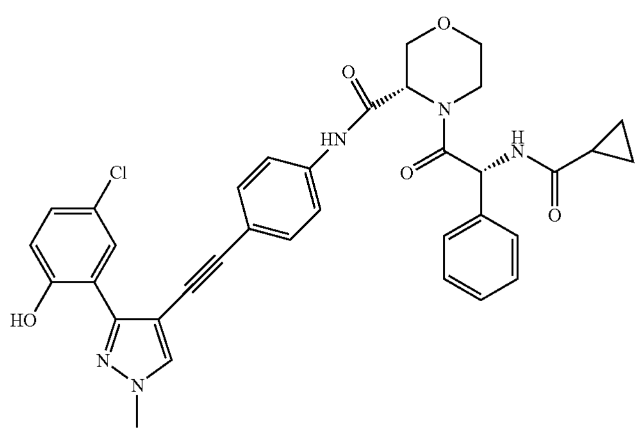 | D | D | B |
| 53 | 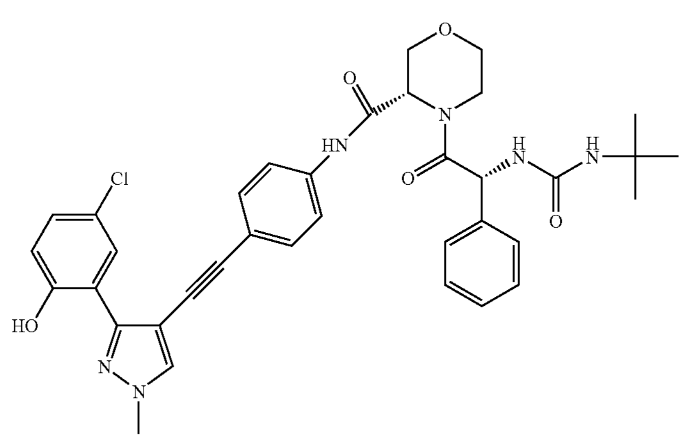 | D | D | B |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
| --- | --- | --- | --- | --- |
| 54 | 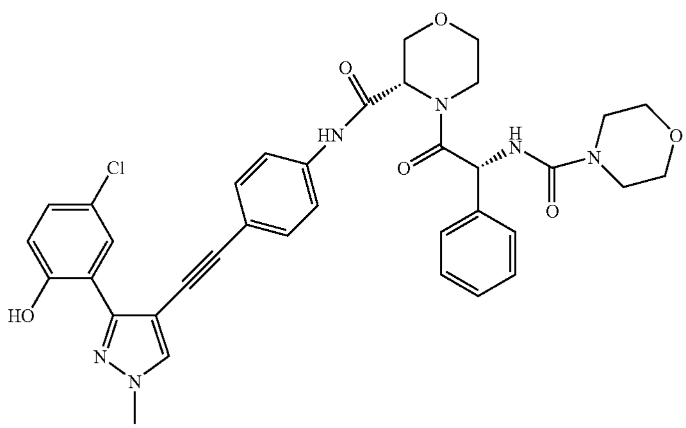 | D | D | B |
| 55 | 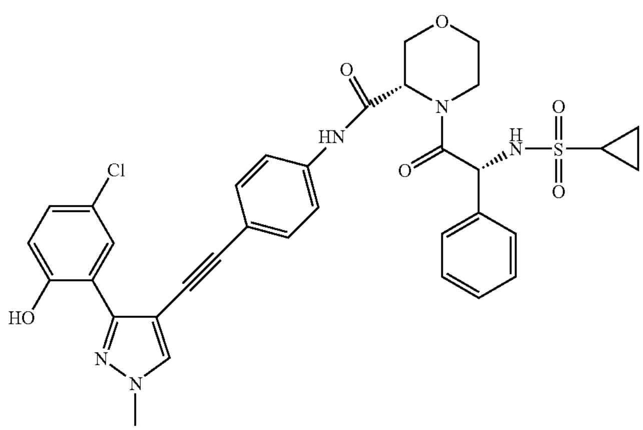 | D | D | B |
| 56 | 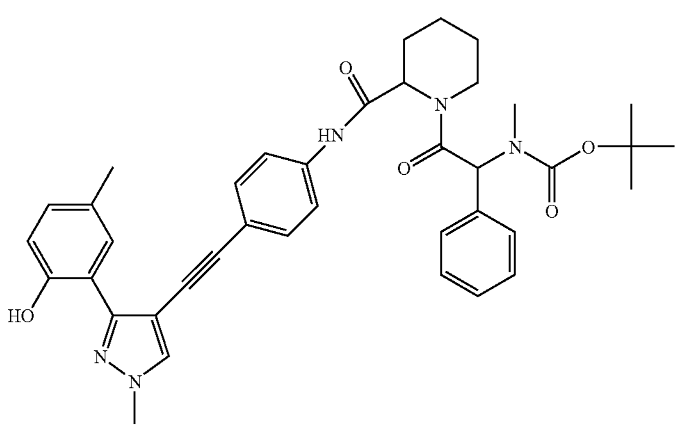 | C | C | B |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
|---|---|---|---|---|
| 57 | 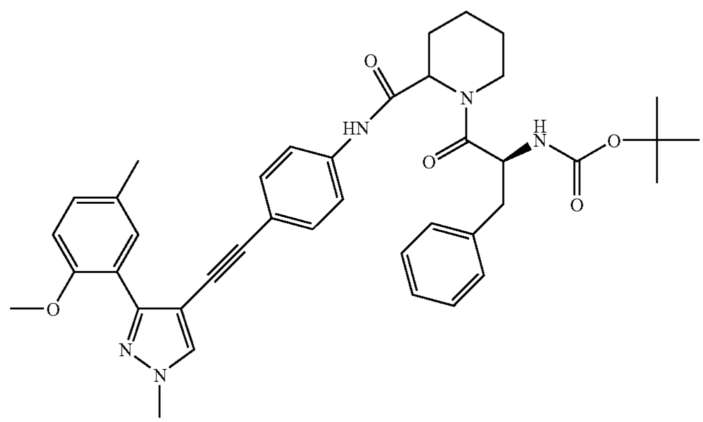 | D | A | A |
| 58 | 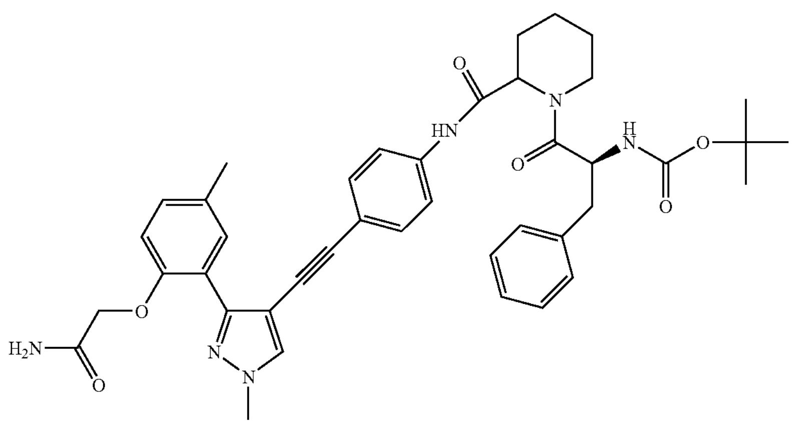 | C | A | B |
| 59 | 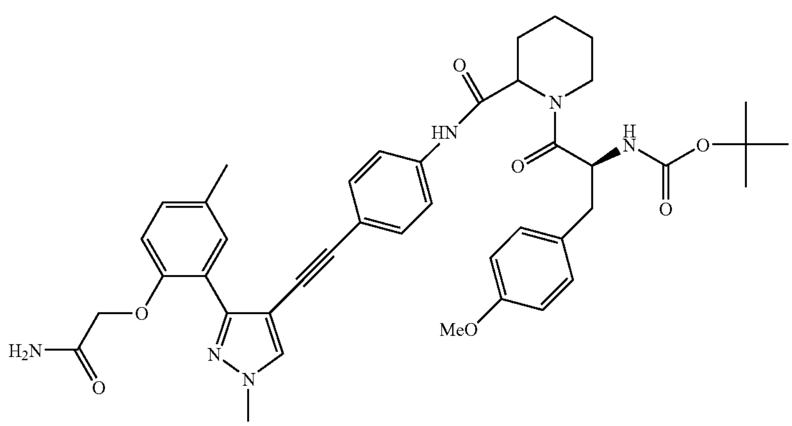 | C | C | B |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
| --- | --- | --- | --- | --- |
| 60 | 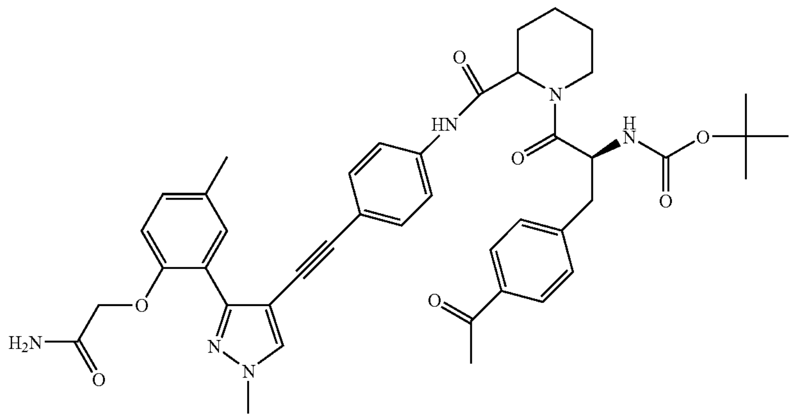 | D | D | D |
| 61 | 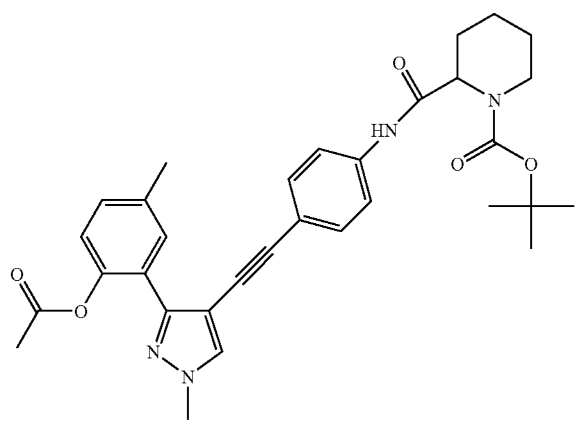 | C | C | A |
| 62 | 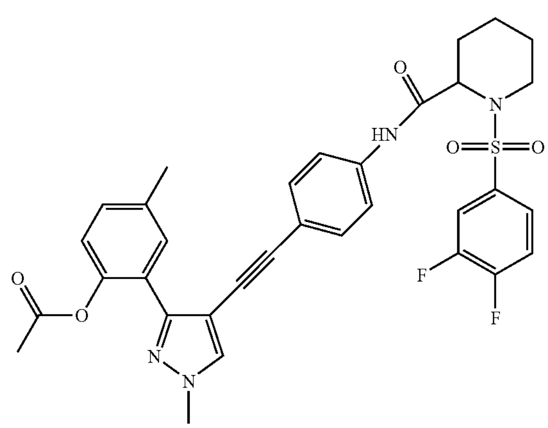 | C | C | A |

TABLE 1-continued

| Compound number | Structure | HCV-1b Replicon Inhibition*, Luciferase (EC$_{50}$) | HCV-1b Replicon Inhibition*, Taqman (EC$_{50}$) | Cytotoxicity* (CC$_{50}$) |
|---|---|---|---|---|
| 63 | 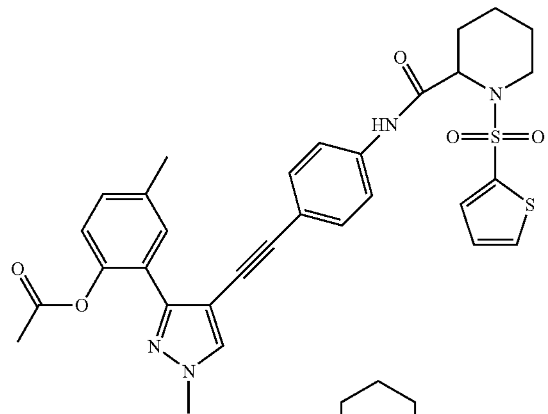 | C | C | A |
| 64 | 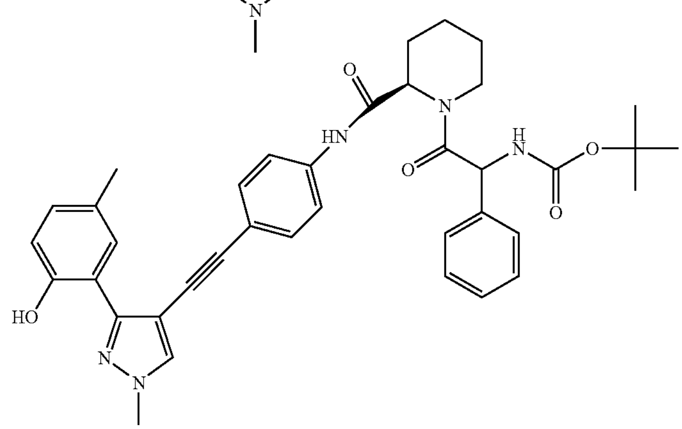 | D | D | A |

The results of the HCV-1a Replicon RNA (Taqman) inhibition assay and the Cell viability assay are reported in Table 2. As there tends to be some variability in the data for RNA-based assays, the results are reported as ranges: A, EC$_{50}$>33.3 μM; B, EC$_{50}$=10-33.3 μM; C, EC$_{50}$=1-10 μM; D, EC$_{50}$<1 μM. A, CC$_{50}$>33.3 μM; B, CC$_{50}$=10-33.3 μM; C, CC$_{50}$=1-10 μM; D, CC$_{50}$<1 μM.

TABLE 2

| Compound number | Structure | HCV-1a Replicon Inhibition*, Taqman (EC$_{50}$) | Cytotoxicity* (CC$_{50}$) |
|---|---|---|---|
| 1 | 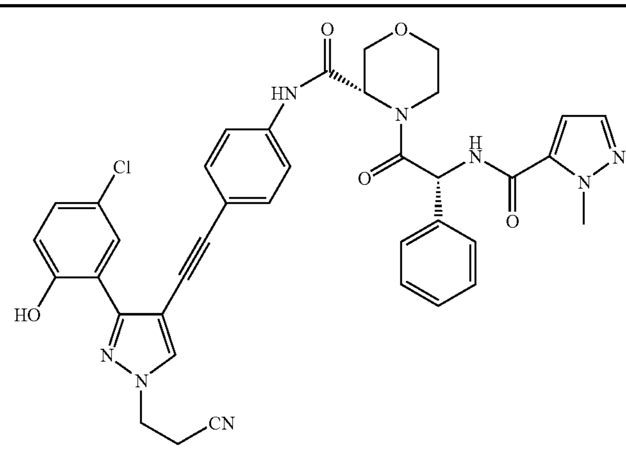 | D | A |

TABLE 2-continued

| Compound number | Structure | HCV-1a Replicon Inhibition*, Taqman (EC$_{50}$) | Cytotoxicity* (CC$_{50}$) |
| --- | --- | --- | --- |
| 2 | 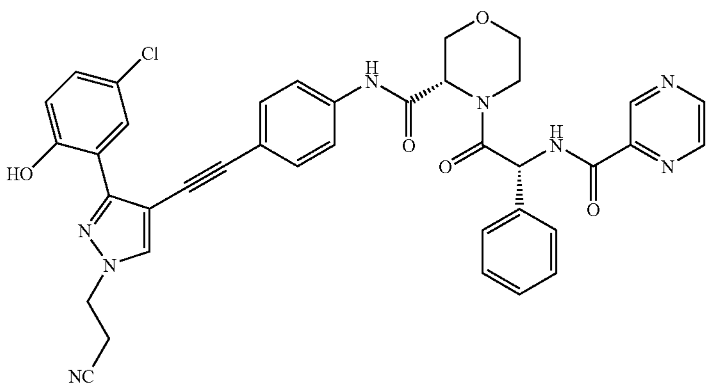 | D | A |
| 3 | 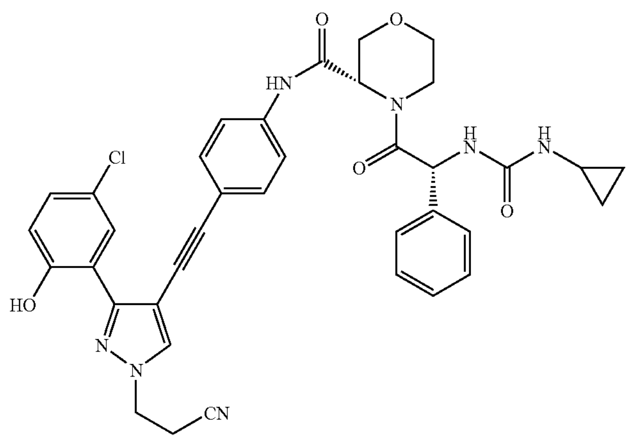 | D | A |
| 4 | 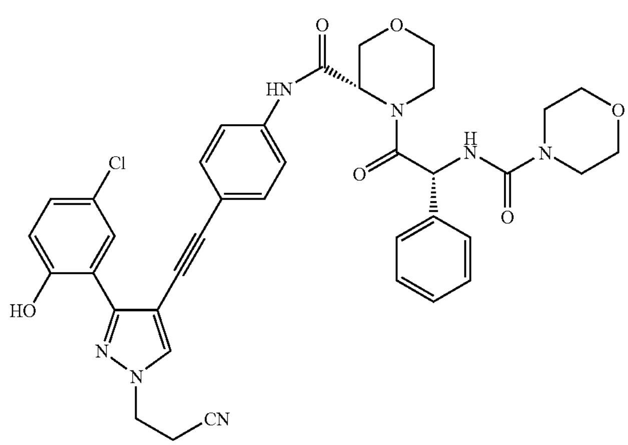 | D | A |

TABLE 2-continued

| Compound number | Structure | HCV-1a Replicon Inhibition*, Taqman (EC$_{50}$) | Cytotoxicity* (CC$_{50}$) |
| --- | --- | --- | --- |
| 5 | 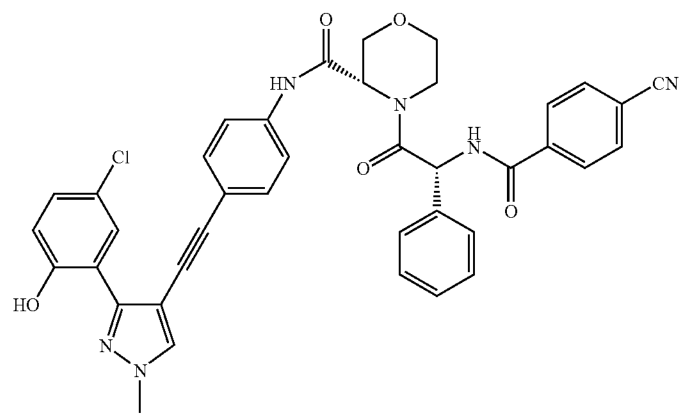 | D | A |
| 6 | 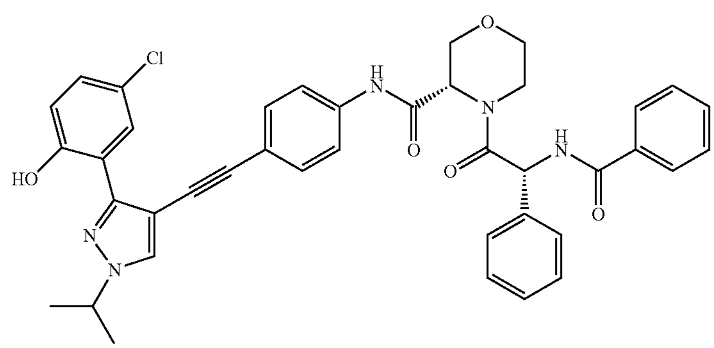 | D | A |
| 7 | 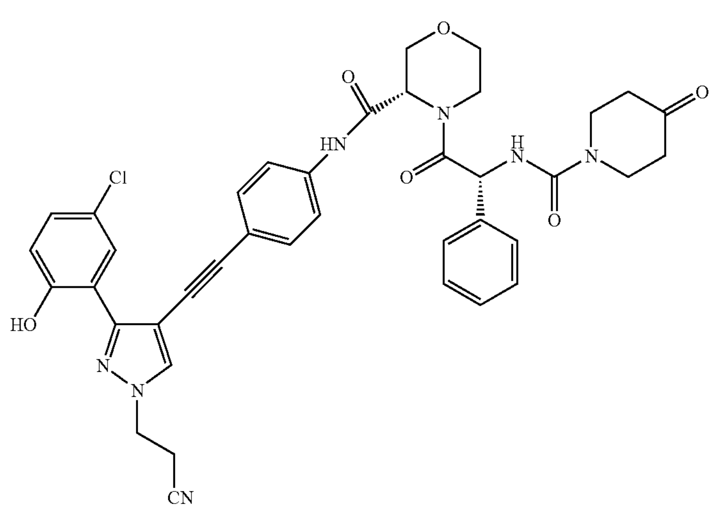 | D | A |

TABLE 2-continued

| Compound number | Structure | HCV-1a Replicon Inhibition*, Taqman (EC$_{50}$) | Cytotoxicity* (CC$_{50}$) |
| --- | --- | --- | --- |
| 8 | 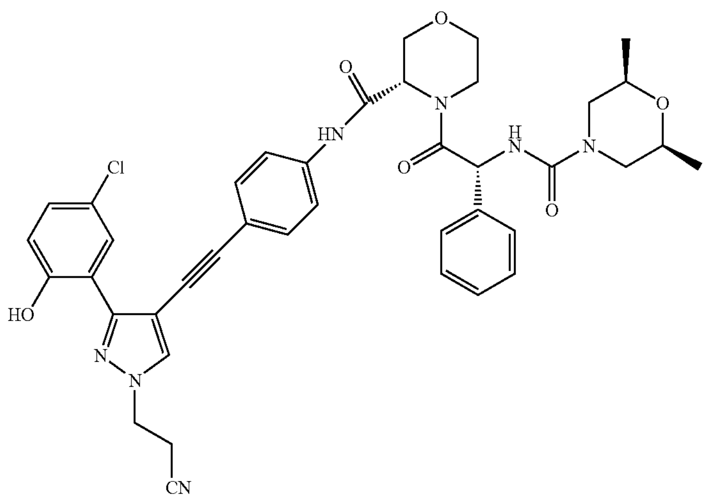 | D | A |
| 9 | 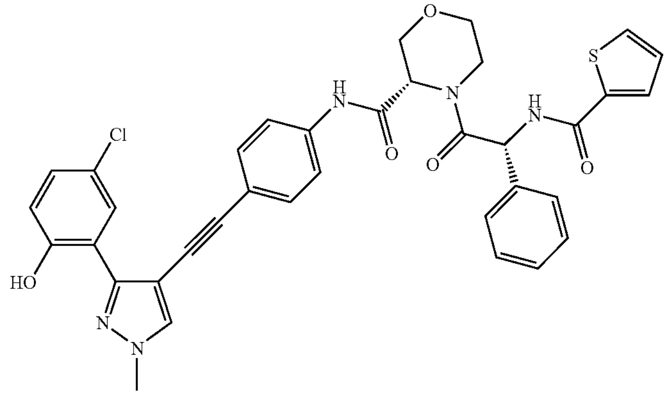 | D | A |
| 10 | 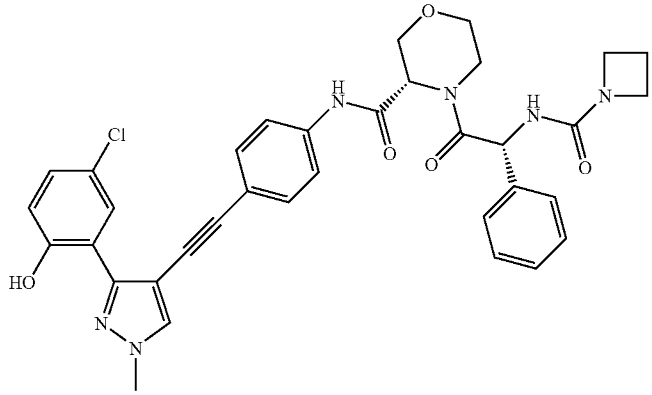 | D | A |

TABLE 2-continued

| Compound number | Structure | HCV-1a Replicon Inhibition*, Taqman (EC$_{50}$) | Cytotoxicity* (CC$_{50}$) |
|---|---|---|---|
| 11 | 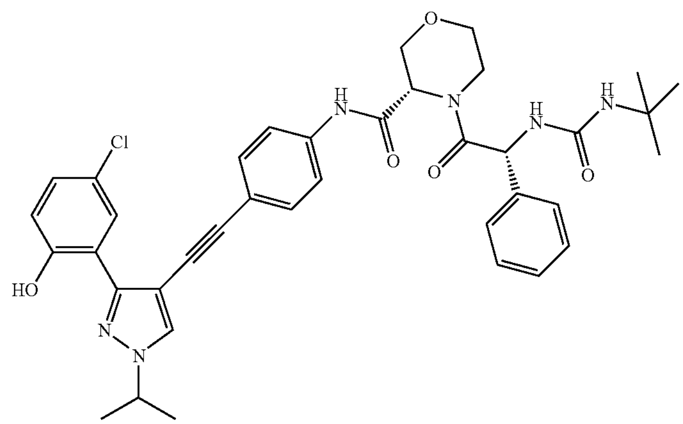 | D | A |
| 12 | 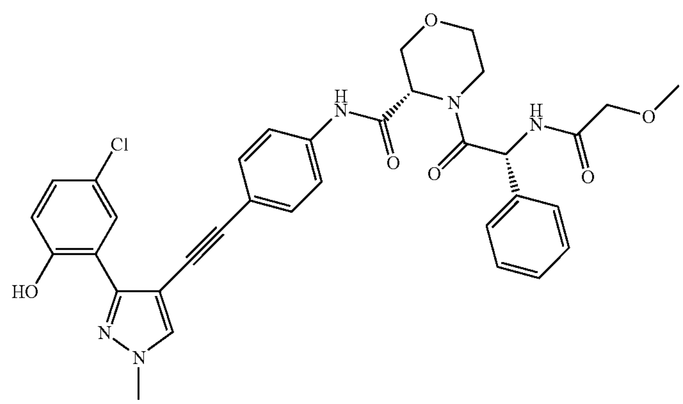 | D | A |
| 13 | 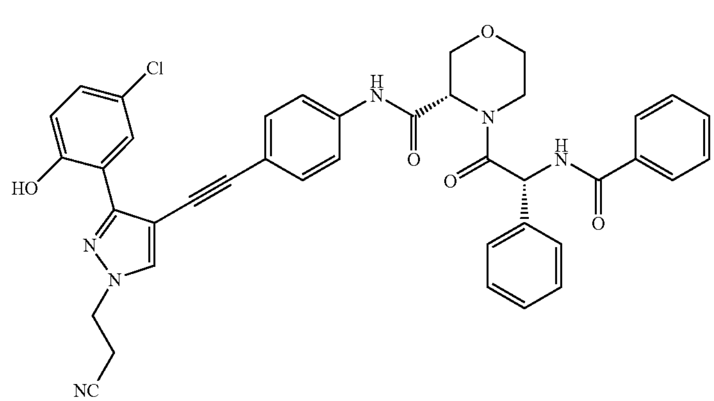 | D | A |

TABLE 2-continued

| Compound number | Structure | HCV-1a Replicon Inhibition*, Taqman (EC$_{50}$) | Cytotoxicity* (CC$_{50}$) |
| --- | --- | --- | --- |
| 14 | 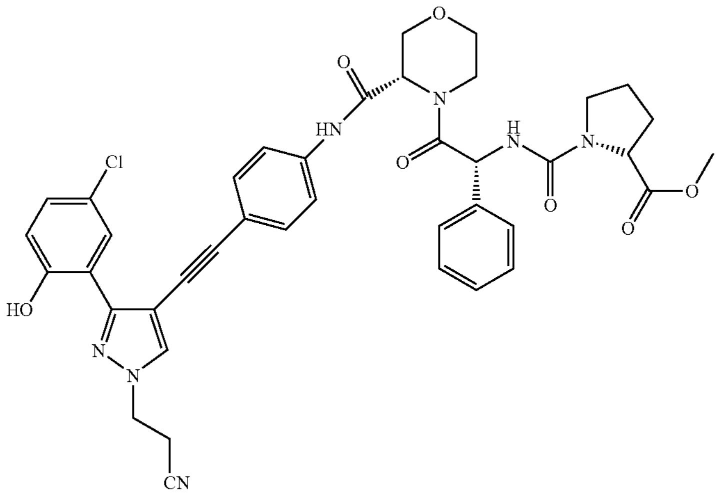 | D | A |
| 15 | 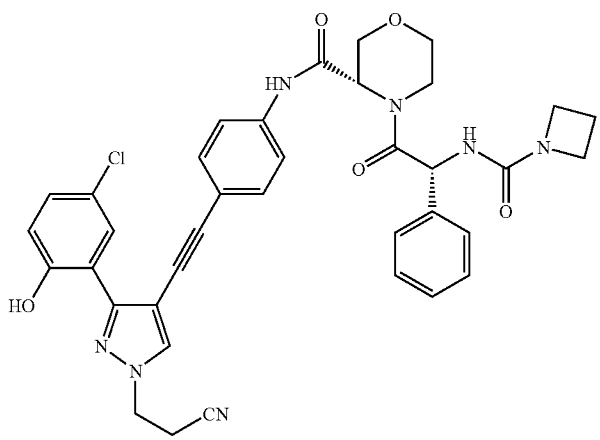 | D | A |
| 16 | 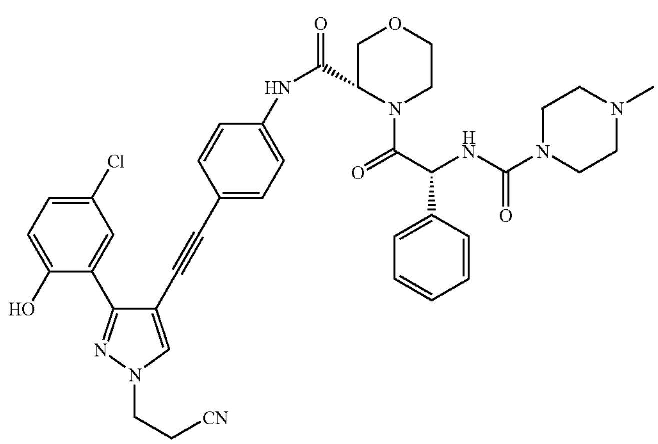 | D | C |

TABLE 2-continued

| Compound number | Structure | HCV-1a Replicon Inhibition*, Taqman (EC$_{50}$) | Cytotoxicity* (CC$_{50}$) |
|---|---|---|---|
| 17 | 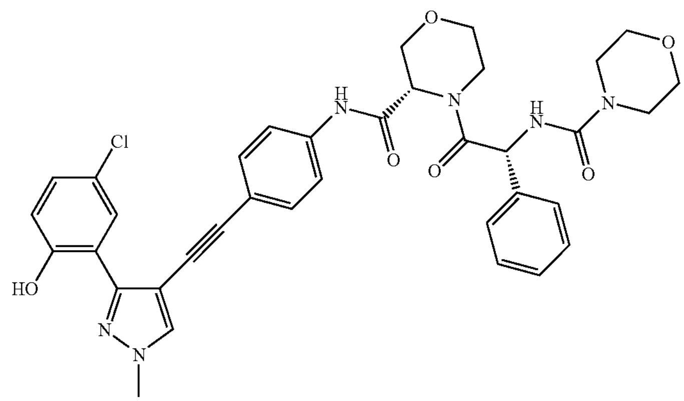 | D | A |
| 18 | 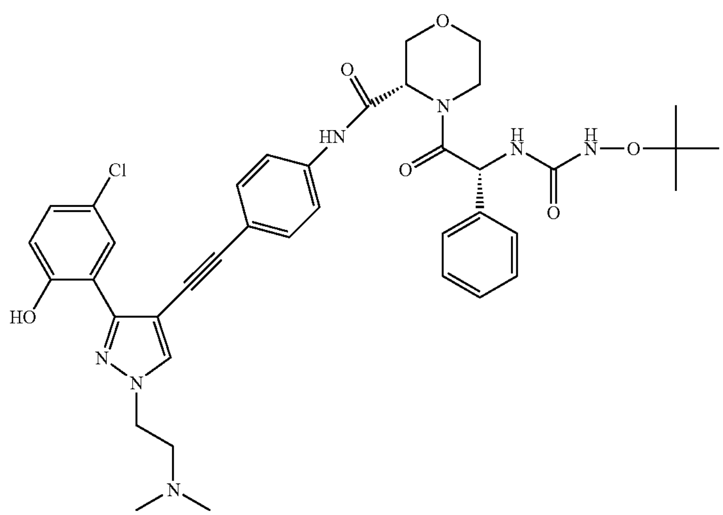 | C | C |
| 19 | 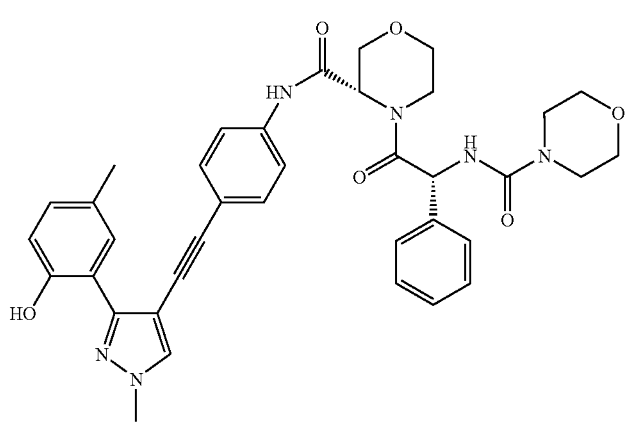 | D | A |

TABLE 2-continued

| Compound number | Structure | HCV-1a Replicon Inhibition*, Taqman (EC$_{50}$) | Cytotoxicity* (CC$_{50}$) |
| --- | --- | --- | --- |
| 20 | 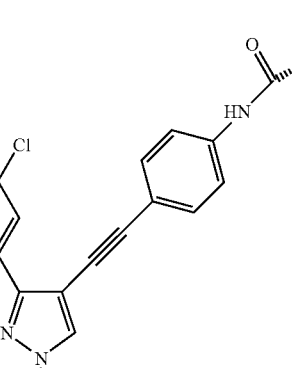 | D | A |
| 21 | 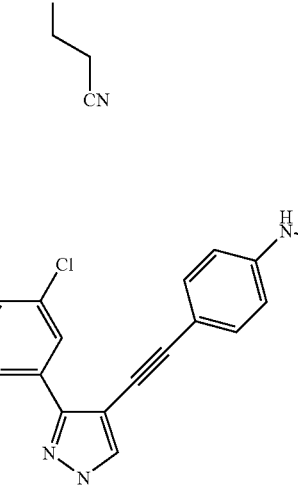 | D | A |

Example 66

Identification of Mutations in the HCV NS3 NS4A NS4B and NS5A

The identification of mutations in the HCV NS3, NS4A, NS4B, and NS5A protein is based on the selection and sequencing of HCV Replicons that are resistant to a representative compound of the present invention (Compound #64 (Table 1)). Mutations I1329V and A1630T in NS3, S1679C in NS4A, K1763R in NS4B, and A2199T in NS5A were identified in multiple (5) cellular clones from an HCV 1b Replicon (Huh-Luc-Neo, Lohman et al, Science 1999, 285, 110) selected with 2 μM Compound #64 (Table 1). A second NS5A mutation Y2065H was subsequently identified when the HCV 1b clone resistant to 2 μM Compound #64 (Table 1, .Clone Comp.64-10R4) was subjected to further selection with 10 μM Compound #64 (Table 1). Moreover, mutations I1329V and A1630T in NS3, S1679C in NS4A, K1763R in NS4B, and A2199T in NS5A were retained in the replicon selected at 10 μM Compound #64 (Table 1). The emergence of mutations in NS3, NS4A, NS4B and NS5A under selection with Compound #64 (Table 1) indicates that the compound and related pyrazoles exert their inhibitory capacity on HCV replication via NS3, NS4A, NS4B and NS5A either alone or in some combination. The occurrence of a second mutation in NS5A at increased concentrations of the replicon inhibitory compound with a resultant EC50 shift that is >75 fold indicates that the HCV NS5A protein plays particularly important role in conferring resistance to Compound #64 (Table 1) and related pyrazoles either alone or in some combination with NS3, NS4A, and NS4B.

Isolation of Resistant Replicons

An HCV Replicon cell line (luc-neo/ET) and assay (Lohman et al, Science 1999, 285, 110) was used in the present invention. Specifically the HCV 1b Replicon cell line Huh-Luc-Neo was subjected to resistance selection by growth in culture in the presence of Compound #64 (Table 1) according to methods described by Mo et al., Antimicro. Agents Chemotherapy, 49, 4305-4314, 2005. Huh-Luc-Neo cells were initially subjected to selection with 0.5 μM Compound #64 (Table 1) and selection pressure was increased gradually up to 2 µM COMPOUND #64 (TABLE 1) over a period of 7 to 9 weeks and 5 cell lines derived from individual colonies were isolated and expanded. A specific clone resistant to 2 µM Compound #64 (Table 1) (Clone Comp.64-10R4) was the subjected to further selection pressure at increasing concentrations of Compound #64 (Table 1) and a replicon resistant to 10 µM Compound #64 (Table 1) was isolated (Clone Comp.64-50R4). The wild type Huh-Luc-Neo replicon cell line was cultured in parallel with the selections and characterized in a similar fashion to the resistant clones.

Characterization of Resistant HCV Replicon Clones

EC50 determinations were performed with Compound #64 (Table 1) vs. the wild type Huh-Luc-Neo replicon cell line and the 5 resistant replicon cell lines. Resistant and wild type replicons were plated in 96 well plates (5000-7000 cells/well) and treated with compound at varying concentrations (Compound #64 (Table 1)) for 72 hours. Cells were then lysed and RNA was isolated (Qiagen RNA Easy 96 kit) according to the manufacturer's recommendations. HCV RNA levels were then measured and EC50 values were determined by cDNA synthesis and quantitative PCR using HCV specific primers and GAPDH primers as controls (Example 55, Lohman et al, Science 1999, 285, 110). The effect of the compounds on inhibition of cell viability was performed on cells treated in parallel with using the Cell Titre Glo Assay Kit (Promega) according to the manufacturer's recommendations (Example 56). CC50s for the compound vs. the wild type and resistant replicons were determined to be >50 µM. EC50s Compound #64 (Table 1) vs. the resistant replicons were from 1.5 to 75 fold greater than vs. the wild type replicon as shown in Table 3.

TABLE 3

| Resistant Clone | Resistant Conc. | EC50 Resistant Replicon/ EC50 Wild Type Replicon |
| --- | --- | --- |
| Comp. 64-10R4 | 2 µM | 3.48 |
| Comp. 64-10R3 | 2 µM | 1.5 |
| Comp. 64-10R5 | 2 µM | 2.92 |
| Comp. 64-10R6 | 2 µM | 2.18 |
| Comp. 64-10R8 | 2 µM | 3 |
| Comp. 64-50R4 | 10 µM | >75 |

Mapping of Resistance to Compound #64 (Table 1)

In order to determine the target or targets involved in mediating the inhibition of HCV replication by Compound #64 (Table 1) and related pyrazoles, sequencing was performed on the NCV non-structural protein encoding sequences from 5 cellular clones resistant to 2 µM Compound #64 (Table 1) and on the cellular clone resistant to 10 µM Compound #64 (Table 1) (Comp. 64-50R4) and a wild type replicon clone that was processed in parallel with the resistance selection. Multiple different cDNA clones were generated from the cell clones resistant to 2 and 10 µM Compound #64 (Table 1). Sequence analysis revealed 5 mutations conserved across all cDNAs in the replicon resistant to 2 µM Compound #64 (Table 1). The 5 mutations identified are as follows: I1329V and A1630T in NS3, S1679C in NS4A, K1763R in NS4B, and A2199T in NS5A. These 5 mutations were also found to be conserved in all 5 cDNAs sequenced from the replicon resistant to 10 µM Compound #64 (Table 1). However, one additional mutation in NS5A (Y2065H) was found in 4 of the 5 cDNAs sequenced from this replicon that is>75 fold more resistant to Compound #64 (Table 1) than is the wild type replicon.

Cross Resistance of Compound #64 (Table 1) Resistant Replicons to Related Pyrazoles:

In order to demonstrate that replicons resistant to Compound #64 (Table 1) are also resistant to related pyrazoles that inhibit HCV replication, EC50 determinations were performed using the replicon cell line resistant to 10 µM Compound #64 (Table 1) and a related pyrazole with potent activity in the with (Entry 36, Table 1) a related pyrazole with potent activity in the wild type Huh-7 Luc-ubi-neo/ET replicon cell line (Entry 36, Table 1). EC50s for Entry 36, Table 1, BILN 2061 (HCV protease inhibitor) vs. the replicon resistant to 10 µM Compound #64 (Table 1) and the wild type Huh-7 Luc-ubi-neo/ET replicon are tabulated below. The data indicate that Entry 36, Table 1 is cross resistant while BILN 2061 is not.

TABLE 4

| Compound | EC50 Resistant Replicon/EC50 Wild Type Replicon |
| --- | --- |
| Entry 36 (Table 1) | 7.125 |
| BILN 2061 | 0.656 |

Resistance of Compound #64 (Table 1) and Related Pyrazoles to the Parental HCV Genotype 1b luc-neo/ET Replicon Engineered to Express the Y2065H Mutation in NS5A.

In order to demonstrate that mutations in NS5A were required to confer resistance to Compound #64 (Table 1) and related pyrazoles the parental HCV Genotype 1b bi-cistronic luc-neot/ET replicon (Lohman et at, Science 285, 110-113, 1999) was engineered to contain the Y2065H mutation in NS5A via site directed mutagenesis using the Quickchange Site Directed Mutagenesis Kit (Stratagene) with mutagenesis primers: 1) ACATTCCCCATTAACGCGcACAC-CACGGGCCCCTGCA (Forward) (SEQ ID NO: 1), and, 2) TGCAGGGGCCCGTGGTGTgCGCGT-TAATGGGGAATGT (Reverse) (SEQ ID NO: 2) according to the manufacturer's suggested protocol.

Resistance of Compound #64 (Table 1) and related pyrazoles was then determined by treating Huh7-Lunet cells (Koutsoudakis et al, J. Virol. 81(2):588-98, 2007) transiently electroporated with RNAs transcribed from either the luc-neo/ET/Y2065H mutant and the parental luc-neo/ET replicons (Blight et al, J. Virol. 77(5):3181-90, 2003). Huh7-Lunet expressing the luc-neo/ET/Y2065H mutant and the parental luc-neo/ET replicons were treated with selected compounds for 72 hours. EC50 and CC50 values were determined as described in the HCV Replicon Luciferase Assay and Cell-Titer-Glo Cell Viability Assay protocols. The data tabulated in Table 5 demonstrate that the Y2065 mutation alone confers significant resistance to Compound #64 (Table 1) and related pyrazoles (i.e. a 6 to 105 fold EC50 shift). CC50s for the compound vs. the luc-neo/ETIY2065H mutant and parental luc-neo/ET replicons were determined to be>33 µM. Thus demonstrating that the Y2065H mutation is confers resistance to Compound #64 (Table 1) and related pyrazoles.

TABLE 5

| Entry # (Table1) | EC50 Luc-neo-ET-Y2065H/EC50 Luc-neo-ET |
| --- | --- |
| 64 | >65 |
| 36 | 6 |
| 52 | 79 |
| 53 | 71 |
| 54 | 105 |

We claim:

1. A compound of the formula I:

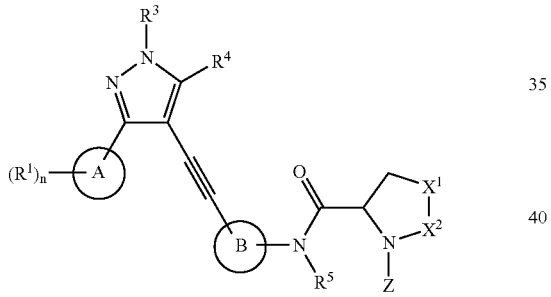

or a pharmaceutically acceptable salt thereof, wherein:
ring A is selected from a 5- or 6-membered aromatic rings which may optionally contain 0 to 3 ring heteroatoms;
each $R^1$ is independently selected from alkyl, alkenyl, alkynyl, aralkyl, —$(CH_2)_a$—O—$R^{11}$, —$(CH_2)_a$—N($R^{12}$)($R^{13}$), —$(CH_2)_a$—N($R^{11}$)—$(CH_2)_b$C(O)$R^{14}$, —$(CH_2)_a$—N($R^{11}$)SO$_2$$R^{11}$, —$(CH_2)_a$—S$R^{11}$, —$(CH_2)_a$—C(O)$R^{14}$—$(CH_2)_a$—C(O)—$(CH_2)_b$OR$^{11}$, —$(CH_2)_a$—C(O)—$(CH_2)_b$N($R^{12}$)($R^{13}$), —$(CH_2)_a$O—$(CH_2)_b$—C(O)$R^{14}$, —$(CH_2)_a$—OC(O)—$(CH_2)_b$N($R^{12}$)($R^{13}$), CN, CF$_3$, NO$_2$, SO$_2$, —SOR$^{11}$, —SO$_3$R$^{11}$, —SO$_2$N($R^{12}$)($R^{13}$), cycloalkyl, cycloalkenyl, halo, phosphate, phosphonate, aryl and a heterocyclic group;
additionally or alternatively two $R^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{11}$;
each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;
each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;
a is 0 to 6;
b is 0 to 6;
$R^3$ is selected from H, alkyl, alkenyl, alkynyl, aralkyl, —$(CH_2)_z$—O—$R^{31}$, —$(CH_2)_z$—N($R^{32}$)($R^{33}$), —$(CH_2)_w$—C(O)$R^{34}$, —$(CH_2)_w$C(O)—N($R^{32}$)($R^{33}$), —$(CH_2)_w$—SO$_2$—$R^{31}$, cycloalkyl, cycloalkenyl, aryl and a heterocyclic group;
$R^{31}$ is selected from H, alkyl, alkenyl, alkynyl, cycloalkyl, cycloalkenyl, aralkyl, aryl and a heterocyclic group;
$R^{32}$ and $R^{33}$ are independently selected from H, alkyl, alkenyl, alkynyl, cycloalkyl, cycloalkenyl, aralkyl, aryl and a heterocyclic group; or $R^{32}$ and $R^{33}$ may be taken together with the nitrogen to which they are attached form a 5- to 7-membered ring which may optionally contain a further heteroatom;
$R^{34}$ is selected from H, alkyl, —OH, —O-alkyl, —O-aryl, —O-aralkyl, alkenyl, alkynyl, cycloalkyl, cycloalkenyl, aralkyl, aryl and a heterocyclic group;
w is 0 to 6;
z is 1 to 6;
$R^4$ is independently selected from H, CN, CF$_3$, alkyl, alkenyl, alkynyl, aralkyl, cycloalkyl, cycloalkenyl, aryl and a heterocyclic group;

ring B is selected from a 5- or 6-membered aromatic rings which may optionally contain 0 to 3 ring heteroatoms;

$R^5$ is independently selected from H, alkyl, alkenyl, alkynyl, aralkyl, cycloalkyl, cycloalkenyl, aryl and a heterocyclic group;

$X^1$ is selected from $CH_2$, O, S, $SO_2$, and $-N(R^{101})-$;

$R^{101}$ is selected from H, alkyl, alkenyl, alkynyl, aralkyl, $-C(=O)-R^{102}$, cycloalkyl, cycloalkenyl, aryl and a heterocyclic group;

$R^{102}$ is selected from H, alkyl, alkenyl, alkynyl, aralkyl, $-N(R^{103})(R^{104})$, cycloalkyl, cycloalkenyl, aryl and a heterocyclic group;

$R^{103}$ and $R^{104}$ are independently selected from H, alkyl, alkenyl, alkynyl, aralkyl, cycloalkyl, cycloalkenyl, aryl and a heterocyclic group, or $R^{103}$ and $R^{104}$ may be taken together with the nitrogen to which they are attached form a 5- to 7-membered ring which may optionally contain a further heteroatom;

$X^2$ is selected from $-CH_2-$, $-CH_2CH_2-$, $-C(=O)CH_2-$, and $-C(=O)-$;

Z is selected from H, alkyl, alkenyl, alkynyl, aralkyl, cycloalkyl, cycloalkenyl, $-(CH_2)_c-O-R^{15}$, $-(CH_2)_c-N(R^{16})(R^{17})$, $-(CH_2)_c-N(R^{15})-(CH_2)_eC(O)R^{18}$, $-(CH_2)_c-SR^{15}$, $-(CH_2)_d-C(O)R^{18}$, $-(CH_2)_d-C(O)-(CH_2)_cOR^{15}$, $-(CH_2)_d-C(O)-(CH_2)_eN(R^{16})(R^{17})$, $-(CH_2)_cO-(CH_2)_e-C(O)R^{18}$, $-(CH_2)_cOC(O)-(CH_2)_eN(R^{16})(R^{17})$, $-SO_2R^{15}$, $-SO_3R^{15}$, cycloalkyl, cycloalkenyl, aryl and a heterocyclic group;

each $R^{15}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{16}$ and $R^{17}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{16}$ and $R^{17}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{18}$ is independently selected from H, alkyl, $-OH$, $-O$-alkyl, $-O$-aryl, $-O$-aralkyl, alkenyl, alkynyl, cycloalkyl, cycloalkenyl, aralkyl, aryl and a heterocyclic group;

c is 1 to 6;
d is 0 to 6;
e is 0 to 6;

or Z is a group having the formula -A-B—C—$R^8$, wherein
A is selected from $-C(=O)-$, and $-SO_2-$;
B is selected from $-(CH_2)_x-CH(R^6)-(CH_2)_y-$, and

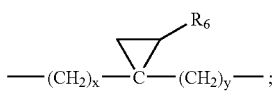

x is 0 to 4;
y is 0 to 4;
$R^6$ is independently selected from H, alkyl, alkenyl, alkynyl, aralkyl, $-(CH_2)_f-Y-(CH_2)_g-R^{61}$, $-(CH_2)_f-N(R^{62})(R^{63})$, $-(CH_2)_f-N(R^{61})-(CH_2)_gC(O)R^{64}$, $-(CH_2)_f-N(R^{61})SO_2R^{61}$, $-(CH_2)_f-SR^{61}$, $-(CH_2)_f-C(O)R^{64}$, $-(CH_2)_f-C(O)-(CH_2)_gOR^{61}$, $-(CH_2)_f-C(O)-(CH_2)_gN(R^{62})(R^{63})$, $-(CH_2)_f-Y-(CH_2)_g-C(O)R^{64}$, $-(CH_2)_f-Y-C(O)-(CH_2)_gN(R^{62})(R^{63})$, $-(CH_2)_f-Y-(CH_2)_g-C(=NOR^{61})-R^{61}$, cycloalkyl, cycloalkenyl, aryl and a heterocyclic group;

each $R^{61}$ is independently selected from H, alkyl, alkenyl, alkynyl, cycloalkyl, cycloalkenyl, aralkyl, aryl and a heterocyclic group;

each $R^{62}$ and $R^{63}$ are independently selected from H, alkyl, cycloalkyl, cycloalkenyl, alkenyl, alkynyl, aralkyl, aryl and a heterocyclic group; or $R^{62}$ and $R^{63}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{64}$ is independently selected from H, alkyl, $-OH$, $-O$-alkyl, $-O$-aryl, $-O$-aralkyl, -alkyl-O-alkyl, -alkyl-O-aryl, alkenyl, alkynyl, cycloalkyl, cycloalkenyl, aralkyl, aryl and a heterocyclic group;

Y is selected from a chemical bond, $-O-$, and aryl;

f is 1 to 6;
g is 0 to 6;

C is selected from $-N(R^7)-C(=O)-$, $-N(R^7)-S(=O)_2-$, and $-CH_2-$;

$R^7$ is independently selected from H, alkyl, alkenyl, alkynyl, aralkyl, cycloalkyl, cycloalkenyl, aryl and a heterocyclic group;

$R^8$ is independently selected from H, alkyl, alkenyl, alkynyl, aralkyl, $-(CH_2)_r-O-(CH_2)-R^{81}$, $-(CH_2)_r-N(R^{82})(R^{83})$, $-(CH_2)_r-N(R^{81})-(CH_2)_sC(O)R^{84}$, $-(CH_2)_r-N(R^{81})SO_2R^{81}$, $-(CH_2)_r-SR^{81}$, $-(CH_2)_r-C(O)R^{84}$, $-(CH_2)_r-C(O)-(CH_2)_sOR^{81}$, $-(CH_2)_r-R^{81}$, $-(CH_2)_r-C(O)(CH_2)_sN(R^{82})(R^{83})$, $-(CH_2)_rO-(CH_2)_s-C(O)R^{84}$, $-(CH_2)_rOC(O)-(CH_2)_sN(R^{82})(R^{83})$, cycloalkyl, cycloalkenyl, aryl and a heterocyclic group;

each $R^{81}$ is independently selected from H, alkyl, alkenyl, alkynyl, cycloalkyl, cycloalkenyl, aralkyl, aryl and a heterocyclic group;

each $R^{82}$ and $R^{83}$ are independently selected from H, alkyl, cycloalkyl, cycloalkenyl, alkenyl, alkynyl, aralkyl, aryl and a heterocyclic group; or $R^{82}$ and $R^{83}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

each $R^{84}$ is independently selected from H, alkyl, $-OH$, $-O$-alkyl, $-O$-aryl, $-O$-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;
s is 0 to 6; and
n is 0 to 5.

2. The compound of claim 1, having the formula II

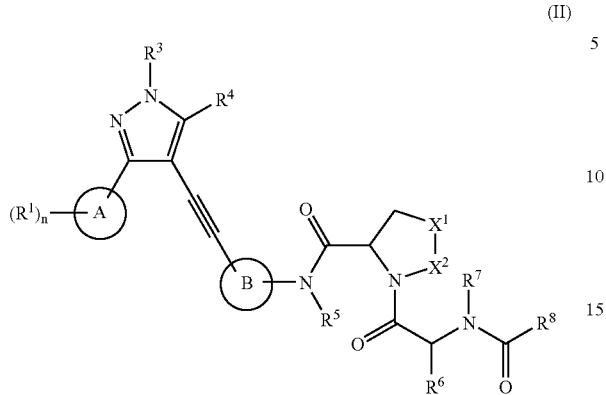

(II)

or a pharmaceutically acceptable salt thereof, wherein:
ring A is selected from a 5- or 6-membered aromatic rings which may optionally contain 0 to 3 ring heteroatoms;
each $R^1$ is independently selected from alkyl, alkenyl, alkynyl, aralkyl, $-(CH_2)_a-O-R^{11}$, $-(CH_2)_a-N(R^{12})(R^{13})$, $-(CH_2)_a-N(R^{11})-(CH_2)_bC(O)R^{14}$, $-(CH_2)_a-N(R^{11})SO_2R^{11}$, $-(CH_2)_a-SR^{11}$, $-(CH_2)_a-C(O)R^{14}$, $-(CH_2)_a-C(O)-(CH_2)_bOR^{11}$, $-(CH_2)_a-C(O)-(CH_2)_bN(R^{12})(R^{13})$, $-(CH_2)_aO-(CH_2)_b-C(O)R^{14}$, $-(CH_2)_aOC(O)-(CH_2)_bN(R^{12})(R^{13})$, CN, $CF_3$, $NO_2$, $SO_2$, $-SOR^{11}$, $-SO_3R^{11}$, $-SO_2N(R^{12})(R^{13})$, cycloalkyl, cycloalkenyl, halo, phosphate, phosphonate, aryl and a heterocyclic group;
additionally or alternatively two $R^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{11}$;
each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;
each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;
each $R^{14}$ is independently selected from H, alkyl, $-OH$, $-O$-alkyl, $-O$-aryl, $-O$-aralkyl, -alkyl-O-alkyl, -alkyl-O-aryl, alkenyl, alkynyl, cycloalkyl, cycloalkenyl, aralkyl, aryl and a heterocyclic group;
a is 0 to 6;
b is 0 to 6;
$R^3$ is selected from H, alkyl, alkenyl, alkynyl, aralkyl, $-(CH_2)_z-O-R^{31}$, $-(CH_2)_z-N(R^{32})(R^{33})$, $-(CH_2)_w-C(O)R^{34}$, $-(CH_2)_wC(O)-N(R^{32})(R^{33})$, $-(CH_2)_w-SO_2-R^{31}$, cycloalkyl, cycloalkenyl, aryl and a heterocyclic group;

$R^{31}$ is selected from H, alkyl, alkenyl, alkynyl, cycloalkyl, cycloalkenyl, aralkyl, aryl and a heterocyclic group;
$R^{32}$ and $R^{33}$ are independently selected from H, alkyl, alkenyl, alkynyl, cycloalkyl, cycloalkenyl, aralkyl, aryl and a heterocyclic group; or $R^{32}$ and $R^{33}$ may be taken together with the nitrogen to which they are attached form a 5- to 7-membered ring which may optionally contain a further heteroatom;
$R^{34}$ is selected from H, alkyl, $-OH$, $-O$-alkyl, $-O$-aryl, $-O$-aralkyl, alkenyl, alkynyl, cycloalkyl, cycloalkenyl, aralkyl, aryl and a heterocyclic group;
w is 0 to 6;
z is 1 to 6;
$R^4$ is independently selected from H, CN, $CF_3$, alkyl, alkenyl, alkynyl, aralkyl, cycloalkyl, cycloalkenyl, aryl and a heterocyclic group;
ring B is selected from a 5- or 6-membered aromatic rings which may optionally contain 0 to 3 ring heteroatoms;
$R^5$ is independently selected from H, alkyl, alkenyl, alkynyl, aralkyl, cycloalkyl, cycloalkenyl, aryl and a heterocyclic group;
$X^1$ is selected from $CH_2$, O, S, $SO_2$, and $-N(R^{101})-$;
$R^{101}$ is selected from H, alkyl, alkenyl, alkynyl, aralkyl, $-C(=O)-R^{102}$, cycloalkyl, cycloalkenyl, aryl and a heterocyclic group;
$R^{102}$ is selected from H, alkyl, alkenyl, alkynyl, aralkyl, $-N(R^{103})(R^{104})$, cycloalkyl, cycloalkenyl, aryl and a heterocyclic group;
$R^{103}$ and $R^{104}$ are independently selected from H, alkyl, alkenyl, alkynyl, aralkyl, cycloalkyl, cycloalkenyl, aryl and a heterocyclic group, or $R^{103}$ and $R^{104}$ may be taken together with the nitrogen to which they are attached form a 5- to 7-membered ring which may optionally contain a further heteroatom;
$X^2$ is selected from $-CH_2-$, $-CH_2CH_2-$, $-C(=O)CH_2-$, and $-C(=O)-$;
$R^6$ is independently selected from H, alkyl, alkenyl, alkynyl, aralkyl, $-(CH_2)_f-Y-(CH_2)_g-R^{61}$, $-(CH_2)_f-N(R^{62})(R^{63})$, $-(CH_2)_f-N(R^{61})-(CH_2)_gC(O)R^{64}$, $-(CH_2)_f-N(R^{61})SO_2R^{61}$, $-(CH_2)_f-SR^{61}$, $-(CH_2)_f-C(O)R^{64}$, $-(CH_2)_f-C(O)-(CH_2)_gOR^{61}$, $-(CH_2)_f-C(O)-(CH_2)_gN(R^{62})(R^{63})$, $-(CH_2)_f-Y-(CH_2)_g-C(O)R^{64}$, $-(CH_2)_f-Y-C(O)-(CH_2)_gN(R^{62})(R^{63})$, $-(CH_2)_r-Y-(CH_2)_g-C(=NOR^{61})-R^{61}$, cycloalkyl, cycloalkenyl, aryl and a heterocyclic group;
each $R^{61}$ is independently selected from H, alkyl, alkenyl, alkynyl, cycloalkyl, cycloalkenyl, aralkyl, aryl and a heterocyclic group;
each $R^{62}$ and $R^{63}$ are independently selected from H, alkyl, cycloalkyl, cycloalkenyl, alkenyl, alkynyl, aralkyl, aryl and a heterocyclic group; or $R^{62}$ and $R^{63}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;
each $R^{64}$ is independently selected from H, alkyl, $-OH$, $-O$-alkyl, $-O$-aryl, $-O$-aralkyl, -alkyl-O-alkyl, -alkyl-O-aryl, alkenyl, alkynyl, cycloalkyl, cycloalkenyl, aralkyl, aryl and a heterocyclic group;
Y is selected from a chemical bond, $-O-$, and aryl;
f is 1 to 6;
g is 0 to 6;

$R^7$ is independently selected from H, alkyl, alkenyl, alkynyl, aralkyl, cycloalkyl, cycloalkenyl, aryl and a heterocyclic group;

$R^8$ is independently selected from H, alkyl, alkenyl, alkynyl, aralkyl, $-(CH_2)_r-O-(CH_2)_s-R^{81}$, $-(CH_2)_r-N(R^{82})(R^{83})$, $-(CH_2)_r-N(R^{81})-(CH_2)_sC(O)R^{84}$, $-(CH_2)_r-N(R^{81})SO_2R^{81}$, $-(CH_2)_r-SR^{81}$, $-(CH_2)_r-C(O)R^{84}$, $-(CH_2)_r-C(O)-(CH_2)_sOR^{81}$, $-(CH_2)_r-R^{81}$, $-(CH_2)_r-C(O)-(CH_2)_sN(R^{82})(R^{83})$, $-(CH_2)_s-C(O)R^{84}$, $-(CH_2)_sOC(O)-(CH_2)_sN(R^{82})(R^{83})$, cycloalkyl, cycloalkenyl, aryl and a heterocyclic group;

each $R^{81}$ is independently selected from H, alkyl, alkenyl, alkynyl, cycloalkyl, cycloalkenyl, aralkyl, aryl and a heterocyclic group;

each $R^{82}$ and $R^{83}$ are independently selected from H, alkyl, cycloalkyl, cycloalkenyl, alkenyl, alkynyl, aralkyl, aryl and a heterocyclic group; or $R^{82}$ and $R^{83}$ may be taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group;

each $R^{84}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;

s is 0 to 6; and n is 0 to 5.

3. The compound of claim 1, having the formula III:

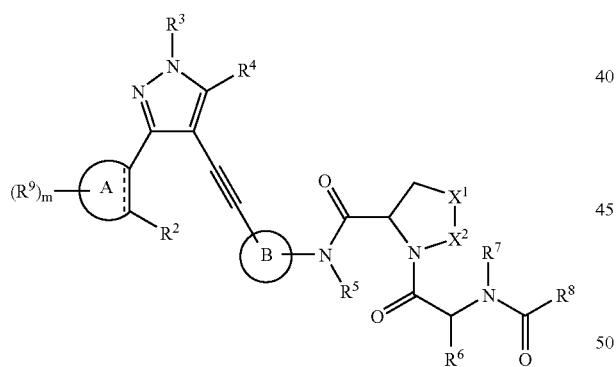

(III)

or a pharmaceutically acceptable salt thereof, wherein:

ring A is selected from a 5- or 6-membered aromatic rings which may optionally contain 0 to 3 ring heteroatoms;

each $R^9$ is independently selected from alkyl, alkenyl, alkynyl, aralkyl, $-(CH_2)-O-R^{91}$, $-(CH_2)_a-N(R^{92})(R^{93})$, $-(CH_2)_a-N(R^{91})-(CH_2)_bC(O)R^{94}$, $-(CH_2)_a-N(R^{91})SO_2R^{91}$, $-(CH_2)_a-SR^{91}$, $-(CH_2)_a-C(O)R^{94}$, $-(CH_2)_a-C(O)-(CH_2)_bOR^{91}$, $-(CH_2)_a-C(O)-(CH_2)_bN(R^{92})(R^{93})$, $-(CH_2)_aO-(CH_2)_b-C(O)R^{94}$, $-(CH_2)_aOC(O)-(CH_2)_bN(R^{92})(R^{93})$, CN, CF₃, NO₂, SO₂, $-SOR^{91}$, $-SO_3R^{91}$, $-SO_2N(R^{92})(R^{93})$, cycloalkyl, cycloalkenyl, halo, phosphate, phosphonate, aryl and a heterocyclic group; additionally or alternatively two $R^9$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{91}$;

each $R^{91}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{92}$ and $R^{93}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{92}$ and $R^{93}$ may be taken together with the nitrogen to which they are attached form a 5- to 7-membered ring which may optionally contain a further heteroatom and may be optionally substituted with up to three substituents selected from halo, CN, NO₂, alkyl, cycloalkyl, alkenyl, alkynyl, aralkyl, aryl, and a heterocyclic group;

each $R^{94}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

a is 0 to 6;

b is 0 to 6;

$R^2$ is selected from OH, SH, and NH₂;

$R^3$ is selected from H, alkyl, alkenyl, alkynyl, aralkyl, $-(CH_2)_z-O-R^{31}$, $-(CH_2)_z-N(R^{32})(R^{33})$, $-(CH_2)_w-C(O)R^{34}$, $-(CH_2)_wC(O)-N(R^{32})(R^{33})$, $-(CH_2)_w-SO_2-R^{31}$, cycloalkyl, cycloalkenyl, aryl and a heterocyclic group;

$R^{31}$ is selected from H, alkyl, alkenyl, alkynyl, cycloalkyl, cycloalkenyl, aralkyl, aryl and a heterocyclic group;

$R^{32}$ and $R^{33}$ are independently selected from H, alkyl, alkenyl, alkynyl, cycloalkyl, cycloalkenyl, aralkyl, aryl and a heterocyclic group; or $R^{32}$ and $R^{33}$ may be taken together with the nitrogen to which they are attached form a 5- to 7-membered ring which may optionally contain a further heteroatom;

$R^{34}$ is selected from H, alkyl, —OH, —O-alkyl, —O-aryl, —O-aralkyl, alkenyl, alkynyl, cycloalkyl, cycloalkenyl, aralkyl, aryl and a heterocyclic group;

w is 0 to 6;

z is 1 to 6;

$R^4$ is independently selected from H, CN, CF₃, alkyl, alkenyl, alkynyl, aralkyl, cycloalkyl, cycloalkenyl, aryl and a heterocyclic group;

ring B is selected from a 5- or 6-membered aromatic rings which may optionally contain 0 to 3 ring heteroatoms;

$R^5$ is independently selected from H, alkyl, alkenyl, alkynyl, aralkyl, cycloalkyl, cycloalkenyl, aryl and a heterocyclic group;

$X^1$ is selected from CH₂, O, S, SO₂, and —N($R^{101}$)—;

$R^{101}$ is selected from H, alkyl, alkenyl, alkynyl, aralkyl, —C(=O)—$R^{102}$, cycloalkyl, cycloalkenyl, aryl and a heterocyclic group;

$R^{102}$ is selected from H, alkyl, alkenyl, alkynyl, aralkyl, —N($R^{103}$)($R^{104}$), cycloalkyl, cycloalkenyl, aryl and a heterocyclic group;

$R^{103}$ and $R^{104}$ are independently selected from H, alkyl, alkenyl, alkynyl, aralkyl, cycloalkyl, cycloalkenyl, aryl and a heterocyclic group, or $R^{103}$ and $R^{104}$ may be taken together with the nitrogen to which they are attached form a 5- to 7-membered ring which may optionally contain a further heteroatom;

$X^2$ is selected from —$CH_2$—, —$CH_2CH_2$—, —C(=O)$CH_2$—, and —C(=O)—;

$R^6$ is independently selected from H, alkyl, alkenyl, alkynyl, aralkyl, —$(CH_2)_f$—Y—$(CH_2)_g$—$R^{61}$, —$(CH_2)_f$—$N(R^{62})(R^{63})$, —$(CH_2)_f$—$N(R^{61})$—$(CH_2)_g C(O)R^{64}$, —$(CH_2)_f$—$N(R^{61})SO_2 R^{61}$, —$(CH_2)_f$—$SR^{61}$, —$(CH_2)_f$—$C(O)R^{64}$, —$(CH_2)_f$—C(O)—$(CH_2)_g OR^{61}$, —$(CH_2)_f$—C(O)—$(CH_2)_g N(R^{62})(R^{63})$, —$(CH_2)_f$—Y—$(CH_2)_g$—$C(O)R^{64}$, —$(CH_2)_f$—Y—C(O)—$(CH_2)_g N(R^{62})(R^{63})$, —$(CH_2)_f$—Y—$(CH_2)_g$—C(=$NOR^{61}$)—$R^{61}$, cycloalkyl, cycloalkenyl, aryl and a heterocyclic group;

each $R^{61}$ is independently selected from H, alkyl, alkenyl, alkynyl, cycloalkyl, cycloalkenyl, aralkyl, aryl and a heterocyclic group;

each $R^{62}$ and $R^{63}$ are independently selected from H, alkyl, cycloalkyl, cycloalkenyl, alkenyl, alkynyl, aralkyl, aryl and a heterocyclic group; or $R^{62}$ and $R^{63}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{64}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

Y is selected from a chemical bond, —O—, and aryl;

f is 1 to 6;

g is 0 to 6;

$R^7$ is independently selected from H, alkyl, alkenyl, alkynyl, aralkyl, cycloalkyl, cycloalkenyl, aryl and a heterocyclic group;

$R^8$ is independently selected from H, alkyl, alkenyl, alkynyl, aralkyl, —$(CH_2)_r$—O—$(CH_2)_s$—$R^{81}$, —$(CH_2)_r$—$N(R^{82})(R^{83})$, —$(CH_2)_r$—$N(R^{81})$—$(CH_2)_s C(O)R^{84}$, —$(CH_2)_r$—$N(R^{81})SO_2 R^{81}$, —$(CH_2)_r$—$SR^{81}$, —$(CH_2)_r$—$C(O)R^{84}$, —$(CH_2)_r$—C(O)—$(CH_2)_s OR^{81}$, —$(CH_2)_r$—$R^{81}$, —$(CH_2)_r$—C(O)—$(CH_2)_s N(R^{82})(R^{83})$, —$(CH_2)_r O$—$(CH_2)_s$—$C(O)R^{84}$, —$(CH_2)_r OC(O)$—$(CH_2)_s N(R^{82})(R^{83})$, cycloalkyl, cycloalkenyl, aryl and a heterocyclic group;

each $R^{81}$ is independently selected from H, alkyl, alkenyl, alkynyl, cycloalkyl, cycloalkenyl, aralkyl, aryl and a heterocyclic group;

each $R^{82}$ and $R^{83}$ are independently selected from H, alkyl, cycloalkyl, cycloalkenyl, alkenyl, alkynyl, aralkyl, aryl and a heterocyclic group; or $R^{82}$ and $R^{83}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

each $R^{84}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;

s is 0 to 6; and m is 0 to 4.

4. The compound of claim 1, having the formula IV:

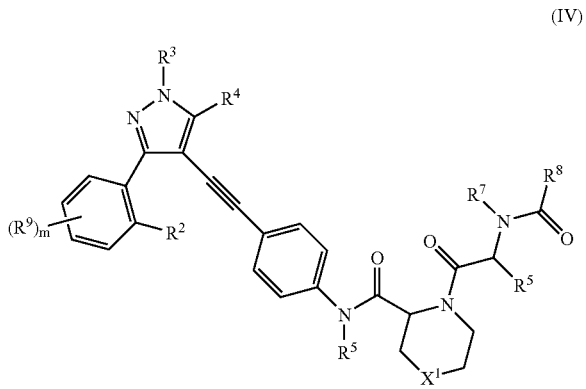

(IV)

or a pharmaceutically acceptable salt thereof, wherein:

each $R^9$ is independently selected from alkyl, alkenyl, alkynyl, aralkyl, —$(CH_2)_a$—O—$R^{91}$, —$(CH_2)_a$—$N(R^{92})(R^{93})$, —$(CH_2)_a$—$N(R^{91})$—$(CH_2)_b C(O)R^{94}$, —$(CH_2)_a$—$N(R^{91})SO_2 R^{91}$, —$(CH_2)_a$—$SR^{91}$, —$(CH_2)_a$—$C(O)R^{94}$, —$(CH_2)_a$—C(O)—$(CH_2)_b OR^{91}$, —$(CH_2)_a$—C(O)—$(CH_2)_b N(R^{92})(R^{93})$, —$(CH_2)_a O$—$(CH_2)_b$—$C(O)R^{94}$, —$(CH_2)_a OC(O)$—$(CH_2)_b N(R^{92})(R^{93})$, CN, $CF_3$, $NO_2$, $SO_2$, —$SOR^{91}$, —$SO_3 R^{91}$, —$SO_2 N(R^{92})(R^{93})$, cycloalkyl, cycloalkenyl, halo, phosphate, phosphonate, aryl and a heterocyclic group;

additionally or alternatively two $R^9$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{91}$;

each $R^{91}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{92}$ and $R^{93}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{92}$ and $R^{93}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{94}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

a is 0 to 6;

b is 0 to 6;

$R^2$ is selected from OH, SH, and $NH_2$;

$R^3$ is selected from H, alkyl, alkenyl, alkynyl, aralkyl, —$(CH_2)_z$—O—$R^{31}$, —$(CH_2)_z$—$N(R^{32})(R^{33})$, —$(CH_2)_w$—$C(O)R^{34}$, —$(CH_2)_w C(O)$—$N(R^{32})(R^{33})$, —$(CH_2)_w$—$SO_2$—$R^{31}$, cycloalkyl, cycloalkenyl, aryl and a heterocyclic group;

$R^{31}$ is selected from H, alkyl, alkenyl, alkynyl, cycloalkyl, cycloalkenyl, aralkyl, aryl and a heterocyclic group;

R³² and R³³ are independently selected from H, alkyl, alkenyl, alkynyl, cycloalkyl, cycloalkenyl, aralkyl, aryl and a heterocyclic group; or R³² and R³³ may be taken together with the nitrogen to which they are attached form a 5- to 7-membered ring which may optionally contain a further heteroatom;

R³⁴ is selected from H, alkyl, —OH, —O-alkyl, —O-aryl, —O-aralkyl, alkenyl, alkynyl, cycloalkyl, cycloalkenyl, aralkyl, aryl and a heterocyclic group;

w is 0 to 6;

z is 1 to 6;

R⁴ is independently selected from H, CN, CF₃, alkyl, alkenyl, alkynyl, aralkyl, cycloalkyl, cycloalkenyl, aryl and a heterocyclic group;

R⁵ is independently selected from H, alkyl, alkenyl, alkynyl, aralkyl, cycloalkyl, cycloalkenyl, aryl and a heterocyclic group;

X¹ is selected from CH₂, O, S, SO₂, and —N(R¹⁰¹)—;

R¹⁰¹ is selected from H, alkyl, alkenyl, alkynyl, aralkyl, —C(=O)—R¹⁰², cycloalkyl, cycloalkenyl, aryl and a heterocyclic group;

R¹⁰² is selected from H, alkyl, alkenyl, alkynyl, aralkyl, —N(R¹⁰³)(R¹⁰⁴), cycloalkyl, cycloalkenyl, aryl and a heterocyclic group;

R¹⁰³ and R¹⁰⁴ are independently selected from H, alkyl, alkenyl, alkynyl, aralkyl, cycloalkyl, cycloalkenyl, aryl and a heterocyclic group, or R¹⁰³ and R¹⁰⁴ may be taken together with the nitrogen to which they are attached form a 5- to 7-membered ring which may optionally contain a further heteroatom;

R⁶ is independently selected from H, alkyl, alkenyl, alkynyl, aralkyl, —(CH₂)f—Y—(CH₂)g R⁶¹, —(CH₂)f—N (R⁶²)(R⁶³), —(CH₂)fN(R⁶¹)—(CH₂)gC(O)R⁶⁴, —(CH₂)f—N(R⁶¹)SO₂R⁶¹, —(CH₂)f—SR⁶¹, —(CH₂)f—C(O)R⁶⁴, —(CH₂)f—C(O)—(CH₂)gOR⁶¹, —(CH₂)f—C(O)—(CH₂)gN(R⁶²)(R⁶³), —(CH₂)f—Y—(CH₂)g—C(O)R⁶⁴, —(CH₂)f—Y—C(O)—(CH₂)gN (R⁶²)(R⁶³), —(CH₂)f—Y—(CH₂)g—C(=NOR⁶¹)—R⁶¹, cycloalkyl, cycloalkenyl, aryl and a heterocyclic group;

each R⁶¹ is independently selected from H, alkyl, alkenyl, alkynyl, cycloalkyl, cycloalkenyl, aralkyl, aryl and a heterocyclic group;

each R⁶² and R⁶³ are independently selected from H, alkyl, cycloalkyl, cycloalkenyl, alkenyl, alkynyl, aralkyl, aryl and a heterocyclic group; or R⁶² and R⁶³ may be taken together with the nitrogen to which they are attached form a 5- to 7-membered ring which may optionally contain a further heteroatom and may be optionally substituted with up to three substituents selected from halo, CN, NO₂, alkyl, cycloalkyl, alkenyl, alkynyl, aralkyl, aryl, and a heterocyclic group;

each R⁶⁴ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

Y is selected from a chemical bond, —O—, and aryl;

f is 1 to 6;

g is 0 to 6;

R⁷ is independently selected from H, alkyl, alkenyl, alkynyl, aralkyl, cycloalkyl, cycloalkenyl, aryl and a heterocyclic group;

R⁸ is independently selected from H, alkyl, alkenyl, alkynyl, aralkyl, —(CH₂)r—O—(CH₂)s—R⁸¹, —(CH₂)r—N(R⁸²)(R⁸³), —(CH₂)r—N(R⁸¹)—(CH₂)sC(O)R⁸⁴, —(CH₂)r—N(R⁸¹)SO₂R⁸¹, —(CH₂)r—SR⁸¹, —(CH₂)r—C(O)R⁸⁴, —(CH₂)r—C(O)—(CH₂)sOR⁸¹, —(CH₂)r—R⁸¹, —(CH₂)r—C(O)—(CH₂)sN(R⁸²)(R⁸³), —(CH₂)rO—(CH₂)s—C(O)R⁸⁴, —(CH₂)rOC(O)—(CH₂)sN(R⁸²)(R⁸³), cycloalkyl, cycloalkenyl, aryl and a heterocyclic group;

each R⁸¹ is independently selected from H, alkyl, alkenyl, alkynyl, cycloalkyl, cycloalkenyl, aralkyl, aryl and a heterocyclic group;

each R⁸² and R⁸³ are independently selected from H, alkyl, cycloalkyl, cycloalkenyl, alkenyl, alkynyl, aralkyl, aryl and a heterocyclic group; or R⁸² and R⁸³ may be taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group;

each R⁸⁴ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;

s is 0 to 6; and m is 0 to 4.

5. The compound of claim 1, having the formula V:

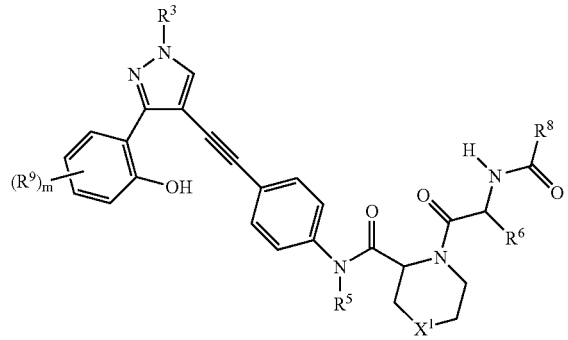

(V)

or a pharmaceutically acceptable salt thereof, wherein:

each R⁹ is independently selected from alkyl, alkenyl, alkynyl, aralkyl, —(CH₂)a—O—R⁹¹, —(CH₂)a—N(R⁹²)(R⁹³), —(CH₂)a—N(R⁹¹)—(CH₂)bC(O)R⁹⁴, —(CH₂)a—N(R⁹¹)SO₂R⁹¹, —(CH₂)a—SR⁹¹, —(CH₂)a—C(O)R⁹⁴, —(CH₂)a—C(O)—(CH₂)bOR⁹¹, —(CH₂)a—C(O)—(CH₂)bN(R⁹²)(R⁹³), —(CH₂)aO—(CH₂)b—C(O)R⁹⁴, —(CH₂)aOC(O)—(CH₂)bN(R⁹²)(R⁹³), CN, CF₃, NO₂, SO₂, —SOR⁹¹, —SO₃R⁹¹, —SO₂N(R⁹²)(R⁹³), cycloalkyl, cycloalkenyl, halo, phosphate, phosphonate, aryl and a heterocyclic group;

additionally or alternatively two R⁹ substituents on adjacent ring atoms may be combined to form a fused 5 or 6-membered ring, wherein the fused 5- or 6-membered ring may contain from 0 to 3 ring heteroatoms and may be further substituted with one or more substituents selected from R⁹¹;

each R⁹¹ is independently selected from H, alkyl, alkyl-O-alkyl, alkyl-O-aryl, alkenyl, alkynyl, cycloalkyl, cycloalkenyl, aralkyl, aryl and a heterocyclic group;

each R⁹² and R⁹³ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{92}$ and $R^{93}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{94}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

a is 0 to 6;
b is 0 to 6;

$R^3$ is selected from H, alkyl, alkenyl, alkynyl, aralkyl, —$(CH_2)_z$—O—$R^{31}$, —$(CH_2)_z$—$N(R^{32})(R^{33})$, —$(CH_2)_w$—$C(O)R^{34}$, —$(CH_2)_w C(O)$—$N(R^{32})(R^{33})$, —$(CH_2)_w$—$SO_2$—$R^{31}$ cycloalkyl, cycloalkenyl, aryl and a heterocyclic group;

$R^{31}$ is selected from H, alkyl, alkenyl, alkynyl, cycloalkyl, cycloalkenyl, aralkyl, aryl and a heterocyclic group;

$R^{32}$ and $R^{33}$ are independently selected from H, alkyl, alkenyl, alkynyl, cycloalkyl, cycloalkenyl, aralkyl, aryl and a heterocyclic group; or $R^{32}$ and $R^{33}$ may be taken together with the nitrogen to which they are attached form a 5- to 7-membered ring which may optionally contain a further heteroatom;

$R^{34}$ is selected from H, alkyl, —OH, —O-alkyl, —O-aryl, —O-aralkyl, alkenyl, alkynyl, cycloalkyl, cycloalkenyl, aralkyl, aryl and a heterocyclic group;

w is 0 to 6;
z is 1 to 6;

$R^6$ is independently selected from H, alkyl, alkenyl, alkynyl, aralkyl, —$(CH_2)_f$—Y—$(CH_2)_g$—$R^{61}$, —$(CH_2)_f$—$N(R^{62})(R^{63})$, —$(CH_2)_f$—$N(R^{61})$—$(CH_2)_g C(O)R^{64}$, —$(CH_2)_f$—$N(R^{61})SO_2R^{61}$, —$(CH_2)_f$—$SR^{61}$, —$(CH_2)_f$—$C(O)R^{64}$, —$(CH_2)_f$—$C(O)$—$(CH_2)_g OR^{61}$, —$(CH_2)_f$—$C(O)$—$(CH_2)_g N(R^{62})(R^{63})$, —$(CH_2)_f$—Y—$(CH_2)_g$—$C(O)R^{64}$, —$(CH_2)_g$—Y—$C(O)$—$(CH_2)_g N(R^{62})(R^{63})$, —$(CH_2)_g$—Y—$(CH_2)_g$—$C(=NOR^{61})$—$R^{61}$, cycloalkyl, cycloalkenyl, aryl and a heterocyclic group;

each $R^{61}$ is independently selected from H, alkyl, alkenyl, alkynyl, cycloalkyl, cycloalkenyl, aralkyl, aryl and a heterocyclic group;

each $R^{62}$ and $R^{63}$ are independently selected from H, alkyl, cycloalkyl, cycloalkenyl, alkenyl, alkynyl, aralkyl, aryl and a heterocyclic group; or $R^{62}$ and $R^{63}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{64}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

Y is selected from a chemical bond, —O—, and aryl;
f is 1 to 6;
g is 0 to 6;

$X^1$ is selected from $CH_2$, O, S, $SO_2$, and —$N(R^{101})$—;

$R^{101}$ is selected from H, alkyl, alkenyl, alkynyl, aralkyl, —C(=O)—$R^{102}$, cycloalkyl, cycloalkenyl, aryl and a heterocyclic group;

$R^{102}$ is selected from H, alkyl, alkenyl, alkynyl, aralkyl, —$N(R^{103})(R^{104})$, cycloalkyl, cycloalkenyl, aryl and a heterocyclic group;

$R^{103}$ and $R^{104}$ are independently selected from H, alkyl, alkenyl, alkynyl, aralkyl, cycloalkyl, cycloalkenyl, aryl and a heterocyclic group, or $R^{103}$ and $R^{104}$ may be taken together with the nitrogen to which they are attached form a 5- to 7-membered ring which may optionally contain a further heteroatom;

$R^8$ is independently selected from H, alkyl, alkenyl, alkynyl, aralkyl, —$(CH_2)_r$—O—$(CH_2)_s R^{81}$, —$(CH_2)_r$—$N(R^{82})(R^{83})$, —$(CH_2)_r$—$N(R^{81})$—$(CH_2)_s C(O)R^{84}$, —$(CH_2)_r$—$N(R^{81})SO_2R^{81}$, —$(CH_2)_r$—$SR^{81}$, —$(CH_2)_r$—$C(O)R^{84}$, —$(CH_2)_r$—$C(O)$—$(CH_2)_s OR^{81}$, —$(CH_2)_r$—$R^{81}$, —$(CH_2)_r$—$C(O)$—$(CH_2)_s N(R^{82})(R^{83})$, —$(CH_2)_r O(CH_2)_s$—$C(O)R^{84}$, —$(CH_2)_r OC(O)$—$(CH_2)_s N(R^{82})(R^{83})$, cycloalkyl, cycloalkenyl, aryl and a heterocyclic group;

each $R^{81}$ is independently selected from H, alkyl, alkenyl, alkynyl, cycloalkyl, cycloalkenyl, aralkyl, aryl and a heterocyclic group;

each $R^{82}$ and $R^{83}$ are independently selected from H, alkyl, cycloalkyl, cycloalkenyl, alkenyl, alkynyl, aralkyl, aryl and a heterocyclic group; or $R^{82}$ and $R^{83}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

each $R^{84}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;
s is 0 to 6; and
m is 0 to 4.

6. The compound of claim 1, having the formula VI:

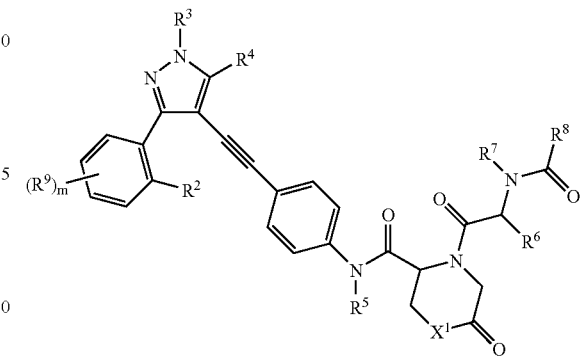

(VI)

or a pharmaceutically acceptable salt thereof, wherein:
each $R^9$ is independently selected from alkyl, alkenyl, alkynyl, aralkyl, —$(CH_2)_a$—O—$R^{91}$, —$(CH_2)_a$—$N(R^{92})(R^{93})$, —$(CH_2)_a$—$N(R^{91})$—$(CH_2)_b C(O)R^{94}$, —$(CH_2)_a$ —N($R^{91}$)$SO_2$$R^{91}$, —$(CH_2)_a$—$SR^{91}$, —$(CH_2)_a$—C(O)$R^{94}$, —$(CH_2)_a$—C(O)—$(CH_2)_b$$OR^{91}$, —$(CH_2)_a$—C(O)—$(CH_2)_b$N($R^{92}$)($R^{93}$), —$(CH_2)_a$O—$(CH_2)_b$—C(O)$R^{94}$, —$(CH_2)_a$OC(O)—$(CH_2)_b$N($R^{92}$)($R^{93}$), CN, $CF_3$, $NO_2$, $SO_2$, —$SOR^{91}$, —$SO_3R^{91}$, —$SO_2$N($R^{92}$)($R^{93}$), cycloalkyl, cycloalkenyl, halo, phosphate, phosphonate, aryl and a heterocyclic group;

additionally or alternatively two $R^9$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{91}$;

each $R^{91}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{92}$ and $R^{93}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{92}$ and $R^{93}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{94}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

a is 0 to 6;
b is 0 to 6;

$R^2$ is selected from OH, SH, and $NH_2$;

$R^3$ is selected from H, alkyl, alkenyl, alkynyl, aralkyl, —$(CH_2)_z$—O—$R^{31}$, —$(CH_2)_z$—N($R^{32}$)($R^{33}$), —$(CH_2)_w$—C(O)$R^{34}$, —$(CH_2)_w$C(O)—N($R^{32}$)($R^{33}$), —$(CH_2)_w$—$SO_2$—$R^{31}$, cycloalkyl, cycloalkenyl, aryl and a heterocyclic group;

$R^{31}$ is selected from H, alkyl, alkenyl, alkynyl, cycloalkyl, cycloalkenyl, aralkyl, aryl and a heterocyclic group;

$R^{32}$ and $R^{33}$ are independently selected from H, alkyl, alkenyl, alkynyl, cycloalkyl, cycloalkenyl, aralkyl, aryl and a heterocyclic group; or $R^{32}$ and $R^{33}$ may be taken together with the nitrogen to which they are attached form a 5- to 7-membered ring which may optionally contain a further heteroatom;

$R^{34}$ is selected from H, alkyl, —OH, —O-alkyl, —O-aryl, —O-aralkyl, alkenyl, alkynyl, cycloalkyl, cycloalkenyl, aralkyl, aryl and a heterocyclic group;

w is 0 to 6;
z is 1 to 6;

$R^4$ is independently selected from H, CN, $CF_3$, alkyl, alkenyl, alkynyl, aralkyl, cycloalkyl, cycloalkenyl, aryl and a heterocyclic group;

$R^5$ is independently selected from H, alkyl, alkenyl, alkynyl, aralkyl, cycloalkyl, cycloalkenyl, aryl and a heterocyclic group;

$X^1$ is selected from $CH_2$, O, S, $SO_2$, and —N($R^{101}$)—;

$R^{101}$ is selected from H, alkyl, alkenyl, alkynyl, aralkyl, —C(=O)—$R^{102}$, cycloalkyl, cycloalkenyl, aryl and a heterocyclic group;

$R^{102}$ is selected from H, alkyl, alkenyl, alkynyl, aralkyl, —N($R^{103}$)($R^{104}$), cycloalkyl, cycloalkenyl, aryl and a heterocyclic group;

$R^{103}$ and $R^{104}$ are independently selected from H, alkyl, alkenyl, alkynyl, aralkyl, cycloalkyl, cycloalkenyl, aryl and a heterocyclic group, or $R^{103}$ and $R^{104}$ may be taken together with the nitrogen to which they are attached form a 5- to 7-membered ring which may optionally contain a further heteroatom;

$R^6$ is independently selected from H, alkyl, alkenyl, alkynyl, aralkyl, —$(CH_2)_f$—Y—$(CH_2)_g$—$R^{61}$, —$(CH_2)_f$—N($R^{62}$)($R^{63}$), —$(CH_2)_f$—N($R^{61}$)—$(CH_2)_g$C(O)$R^{64}$, —$(CH_2)_f$—N($R^{61}$)$SO_2R^{61}$, —$(CH_2)_f$—$SR^{61}$, —$(CH_2)_f$—C(O)$R^{64}$, —$(CH_2)_f$—C(O)—$(CH_2)_g$$OR^{61}$, —$(CH_2)_f$—C(O)—$(CH_2)_g$N($R^{62}$)($R^{63}$), —$(CH_2)_f$—Y—$(CH_2)_g$—C(O)$R^{64}$, —$(CH_2)_f$—Y—C(O)—$(CH_2)_g$N($R^{62}$)($R^{63}$), —$(CH_2)_f$—Y—$(CH_2)_g$—C(=NO$R^{61}$)—$R^{61}$, cycloalkyl, cycloalkenyl, aryl and a heterocyclic group;

each $R^{61}$ is independently selected from H, alkyl, alkenyl, alkynyl, cycloalkyl, cycloalkenyl, aralkyl, aryl and a heterocyclic group;

each $R^{62}$ and $R^{63}$ are independently selected from H, alkyl, cycloalkyl, cycloalkenyl, alkenyl, alkynyl, aralkyl, aryl and a heterocyclic group; or $R^{62}$ and $R^{63}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{64}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

Y is selected from a chemical bond, —O—, and aryl;
f is 1 to 6;
g is 0 to 6;

$R^7$ is independently selected from H, alkyl, alkenyl, alkynyl, aralkyl, cycloalkyl, cycloalkenyl, aryl and a heterocyclic group;

$R^8$ is independently selected from H, alkyl, alkenyl, alkynyl, aralkyl, —$(CH_2)_r$—O—$(CH_2)_s$—$R^{81}$, —$(CH_2)_r$—N($R^{82}$)($R^{83}$), —$(CH_2)_r$—N($R^{81}$)—$(CH_2)_s$C(O)$R^{84}$, —$(CH_2)_r$—N($R^{81}$)$SO_2R^{81}$, —$(CH_2)_r$—$SR^{81}$, —$(CH_2)_r$—C(O)$R^{84}$, —$(CH_2)_r$—C(O)—$(CH_2)_s$$OR^{81}$, —$(CH_2)_r$—$R^{81}$, —$(CH_2)_r$—C(O)—$(CH_2)_s$N($R^{82}$)($R^{83}$), —$(CH_2)_r$O—$(CH_2)_s$—C(O)$R^{84}$, —$(CH_2)_r$OC(O)—$(CH_2)_s$N($R^{82}$)($R^{83}$), cycloalkyl, cycloalkenyl, aryl and a heterocyclic group;

each $R^{81}$ is independently selected from H, alkyl, alkenyl, alkynyl, cycloalkyl, cycloalkenyl, aralkyl, aryl and a heterocyclic group;

each $R^{82}$ and $R^{83}$ are independently selected from H, alkyl, cycloalkyl, cycloalkenyl, alkenyl, alkynyl, aralkyl, aryl and a heterocyclic group; or $R^{82}$ and $R^{83}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

each $R^{84}$ is independently selected from H, alkyl, —OH, —O-alkyl, —O-aryl, —O-aralkyl, -alkyl-O- alkyl, -alkyl-O-aryl, alkenyl, alkynyl, cycloalkyl, cycloalkenyl, aralkyl, aryl and a heterocyclic group;
r is 0 to 6;
s is 0 to 6; and
m is 0 to 4.

7. The compound of claim 1, having the VII:

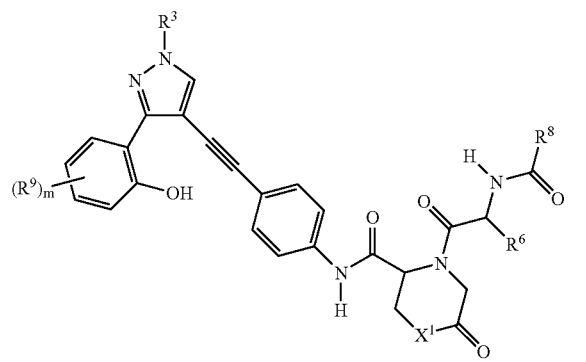

(VII)

or a pharmaceutically acceptable salt thereof, wherein:
each $R^9$ is independently selected from alkyl, alkenyl, alkynyl, aralkyl, $-(CH_2)_a-O-R^{91}$, $-(CH_2)_a-N(R^{92})(R^{93})$, $-(CH_2)_a-N(R^{91})-(CH_2)_bC(O)R^{94}$, $-(CH_2)_a-N(R^{91})SO_2R^{91}$, $-(CH_2)_a-SR^{91}$, $-(CH_2)_a-C(O)R^{94}$, $-(CH_2)_a-C(O)-(CH_2)_bOR^{91}$, $-(CH_2)_a-C(O)-(CH_2)_bN(R^{92})(R^{93})$, $-(CH_2)_aO-(CH_2)_b-C(O)R^{94}$, $-(CH_2)_aOC(O)-(CH_2)_bN(R^{92})(R^{93})$, CN, $CF_3$, $NO_2$, $SO_2$, $-SOR^{91}$, $-SO_3R^{91}$, $-SO_2N(R^{92})(R^{93})$, cycloalkyl, cycloalkenyl, halo, phosphate, phosphonate, aryl and a heterocyclic group;
additionally or alternatively two $R^9$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{91}$;
each $R^{91}$ is independently selected from H, alkyl, alkyl-O-alkyl, alkyl-O-aryl, alkenyl, alkynyl, cycloalkyl, cycloalkenyl, aralkyl, aryl and a heterocyclic group;
each $R^{92}$ and $R^{93}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{92}$ and $R^{93}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;
each $R^{94}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;
a is 0 to 6;
b is 0 to 6;
$R^3$ is selected from H, alkyl, alkenyl, alkynyl, aralkyl, $-(CH_2)_z-O-R^{31}$, $-(CH_2)_z-N(R^{32})(R^{33})$, $-(CH_2)_w-C(O)R^{34}$, $-(CH_2)_wC(O)-N(R^{32})(R^{33})$, $-(CH_2)_w-SO_2-R^{31}$ cycloalkyl, cycloalkenyl, aryl and a heterocyclic group;
$R^{31}$ is selected from H, alkyl, alkenyl, alkynyl, cycloalkyl, cycloalkenyl, aralkyl, aryl and a heterocyclic group;
$R^{32}$ and $R^{33}$ are independently selected from H, alkyl, alkenyl, alkynyl, cycloalkyl, cycloalkenyl, aralkyl, aryl and a heterocyclic group; or $R^{32}$ and $R^{33}$ may be taken together with the nitrogen to which they are attached form a 5- to 7-membered ring which may optionally contain a further heteroatom;
$R^{34}$ is selected from H, alkyl, —OH, —O-alkyl, —O-aryl, —O-aralkyl, alkenyl, alkynyl, cycloalkyl, cycloalkenyl, aralkyl, aryl and a heterocyclic group;
w is 0 to 6;
z is 1 to 6;
$R^6$ is independently selected from H, alkyl, alkenyl, alkynyl, aralkyl, $-(CH_2)_f-Y-(CH_2)_g-R^{61}$, $-(CH_2)_f-N(R^{62})(R^{63})$, $-(CH_2)_f-N(R^{61})-(CH_2)_gC(O)R^{64}$, $-(CH_2)_f-N(R^{61})SO_2R^{61}$, $-(CH_2)_f-SR^{61}$, $-(CH_2)_fC(O)R^{64}$, $-(CH_2)_f-C(O)-(CH_2)_gOR^{61}$, $-(CH_2)_f-C(O)-(CH_2)_gN(R^{62})(R^{63})$, $-(CH_2)_f-Y-(CH_2)_g-C(O)R^{64}$, $-(CH_2)_f-Y-C(O)-(CH_2)_gN(R^{62})(R^{63})$, $-(CH_2)_f-Y-(CH_2)_g-C(=NOR^{61})-R^{61}$, cycloalkyl, cycloalkenyl, aryl and a heterocyclic group;
each $R^{61}$ is independently selected from H, alkyl, alkenyl, alkynyl, cycloalkyl, cycloalkenyl, aralkyl, aryl and a heterocyclic group;
each $R^{62}$ and $R^{63}$ are independently selected from H, alkyl, cycloalkyl, cycloalkenyl, alkenyl, alkynyl, aralkyl, aryl and a heterocyclic group; or $R^{62}$ and $R^{63}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;
each $R^{64}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;
Y is selected from a chemical bond, —O—, and aryl;
f is 1 to 6;
g is 0 to 6;
$X^1$ is selected from $CH_2$, O, S, $SO_2$, and $-N(R^{101})-$;
$R^{101}$ is selected from H, alkyl, alkenyl, alkynyl, aralkyl, $-C(=O)-R^{102}$, cycloalkyl, cycloalkenyl, aryl and a heterocyclic group;
$R^{102}$ is selected from H, alkyl, alkenyl, alkynyl, aralkyl, $-N(R^{103})(R^{104})$, cycloalkyl, cycloalkenyl, aryl and a heterocyclic group;
$R^{103}$ and $R^{104}$ are independently selected from H, alkyl, alkenyl, alkynyl, aralkyl, cycloalkyl, cycloalkenyl, aryl and a heterocyclic group, or $R^{103}$ and $R^{104}$ may be taken together with the nitrogen to which they are attached form a 5- to 7-membered ring which may optionally contain a further heteroatom;
$R^8$ is independently selected from H, alkyl, alkenyl, alkynyl, aralkyl, $-(CH_2)_r-O-(CH_2)_s-R^{81}$, $-(CH_2)_r-N(R^{82})(R^{83})$, $-(CH_2)_r-N(R^{81})-(CH_2)_sC(O)R^{84}$, $-(CH_2)_r-N(R^{81})SO_2R^{81}$, $-(CH_2)_r-SR^{81}$, $-(CH_2)_r-C(O)R^{84}$, $-(CH_2)_r-C(O)-(CH_2)_sOR^{81}$, $-(CH_2)_r-R^{81}$, $-(CH_2)_rC(O)-(CH_2)_sN(R^{82})(R^{83})$, —(CH$_2$)$_r$O—(CH$_2$)$_s$—C(O)R$^{84}$, —(CH$_2$)$_r$OC(O)—(CH$_2$)$_s$N(R$^{82}$)(R$^{83}$), cycloalkyl, cycloalkenyl, aryl and a heterocyclic group;

each R$^{81}$ is independently selected from H, alkyl, alkenyl, alkynyl, cycloalkyl, cycloalkenyl, aralkyl, aryl and a heterocyclic group;

each R$^{82}$ and R$^{83}$ are independently selected from H, alkyl, cycloalkyl, cycloalkenyl, alkenyl, alkynyl, aralkyl, aryl and a heterocyclic group; or R$^{82}$ and R$^{83}$ may be taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group;

each R$^{84}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;
s is 0 to 6; and
m is 0 to 4.

8. The compound of claim 1, having the structure selected from:

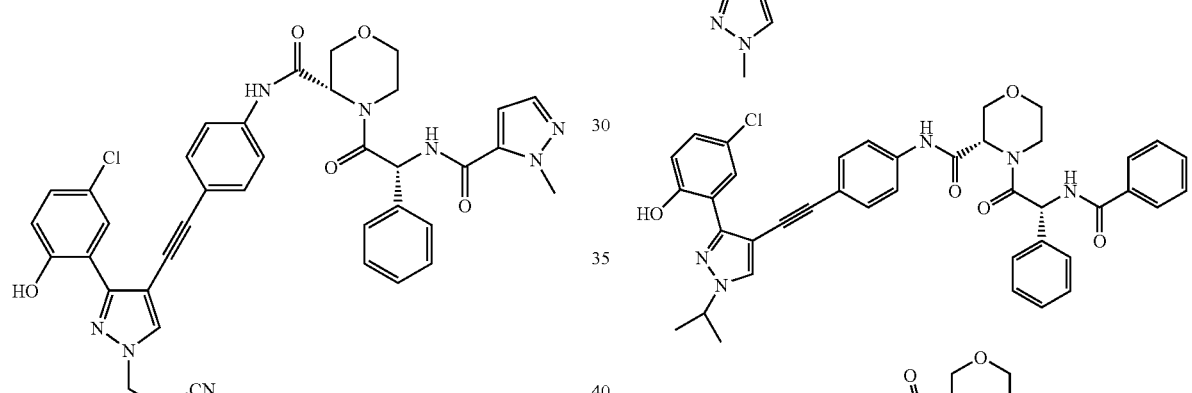

-continued

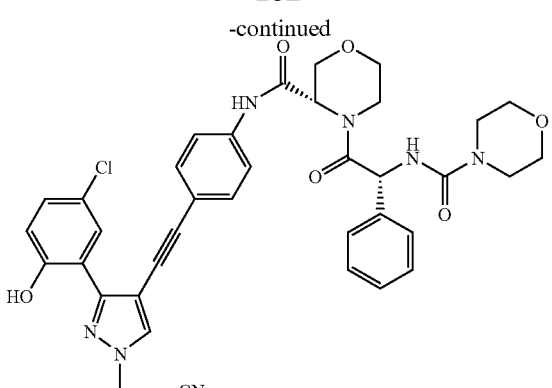

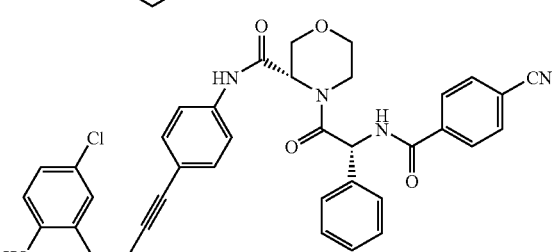

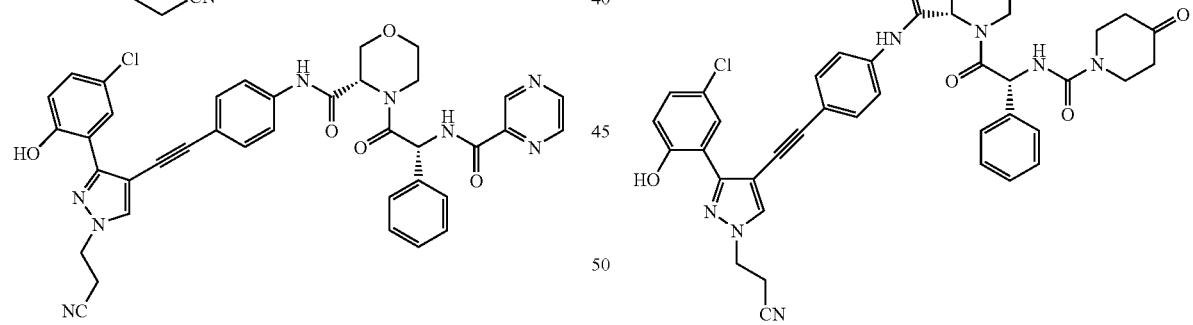

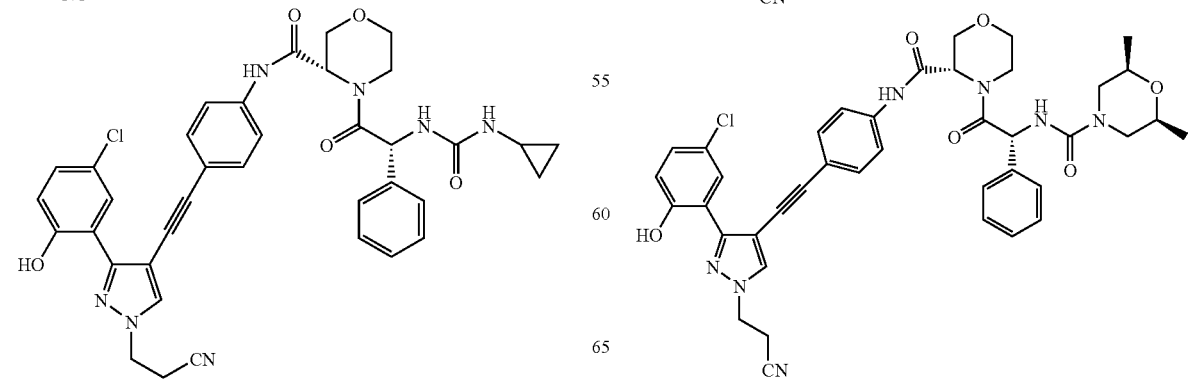

183
-continued
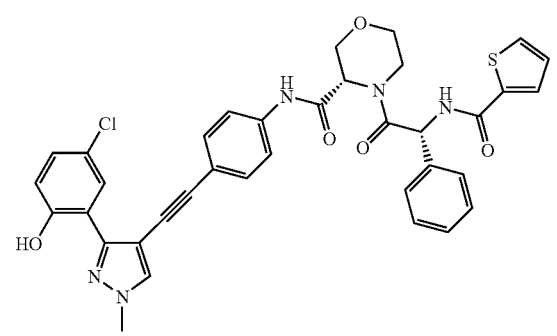
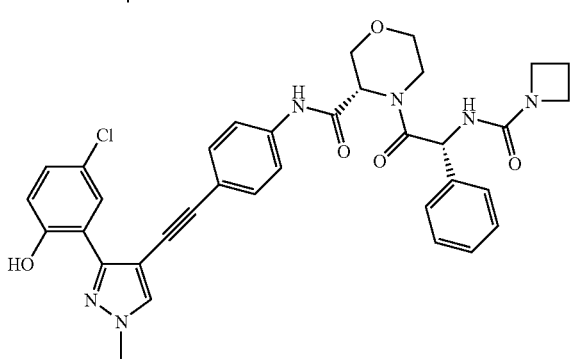
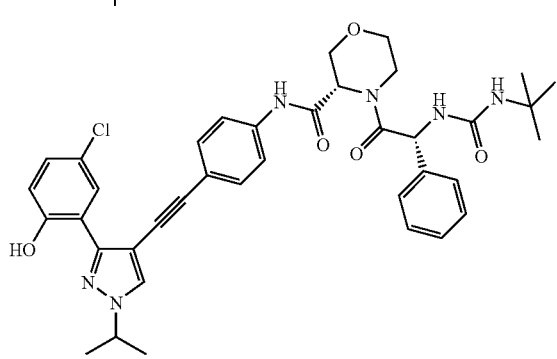
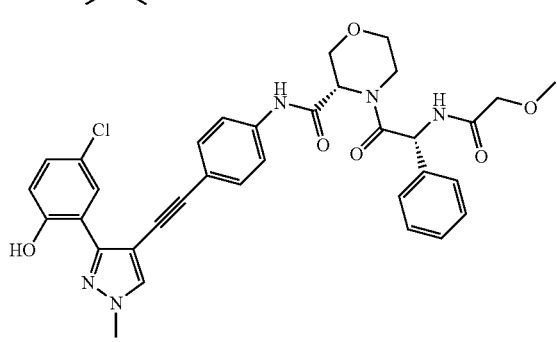
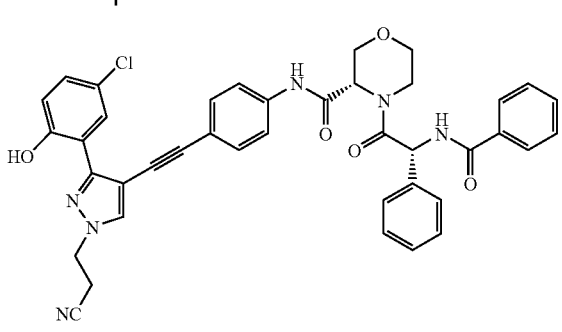
184
-continued
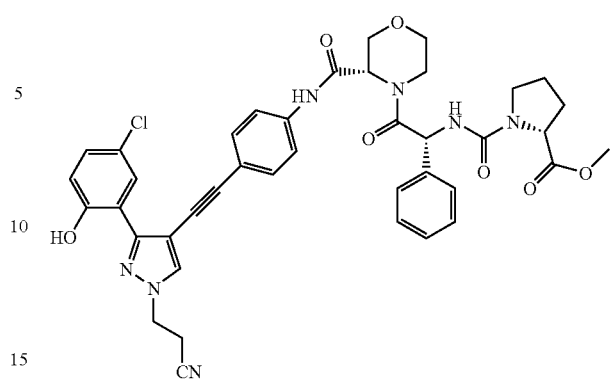
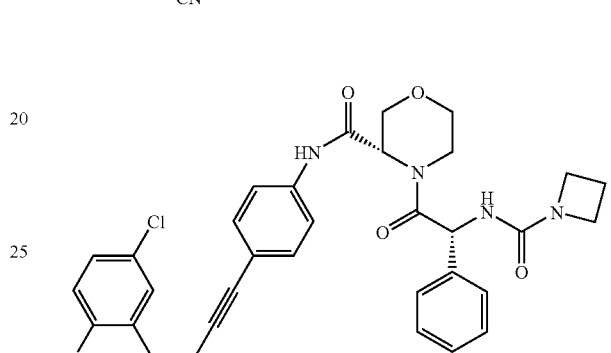
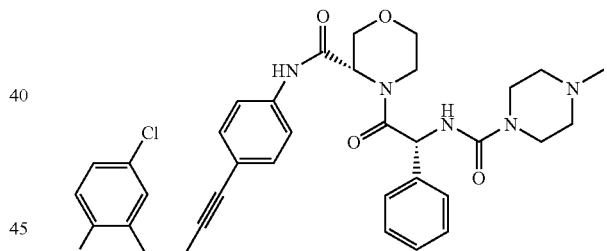
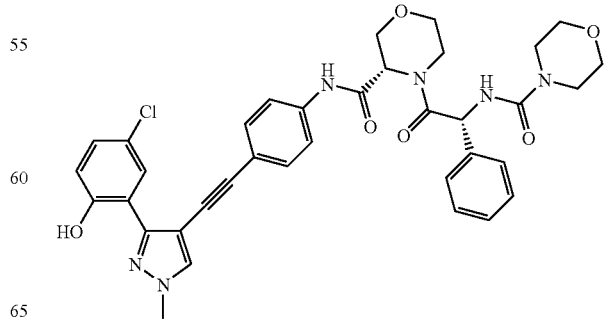

185
-continued
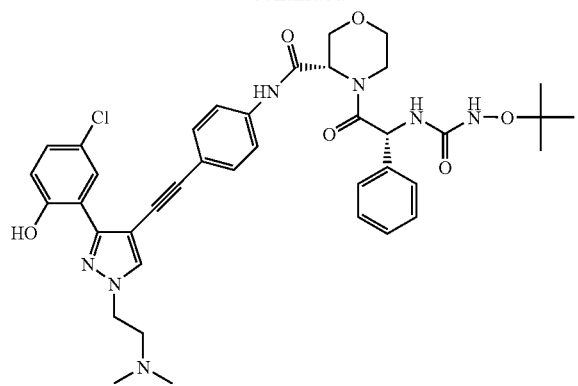
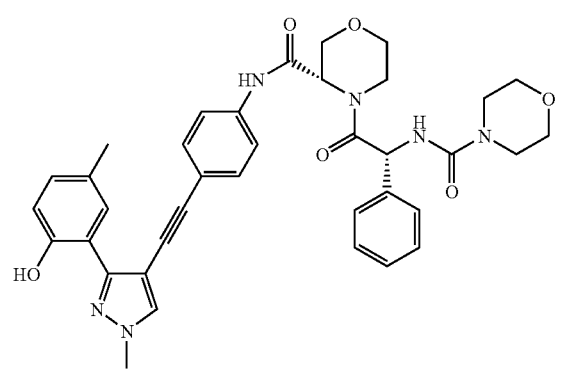
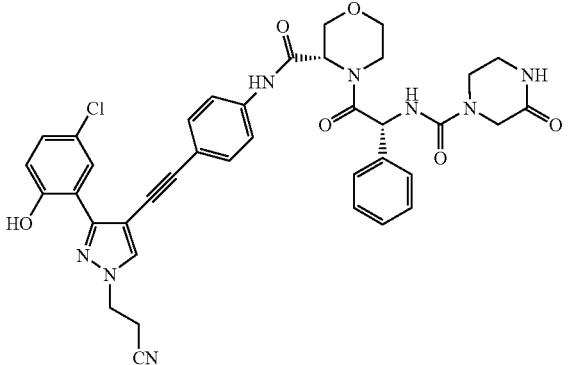
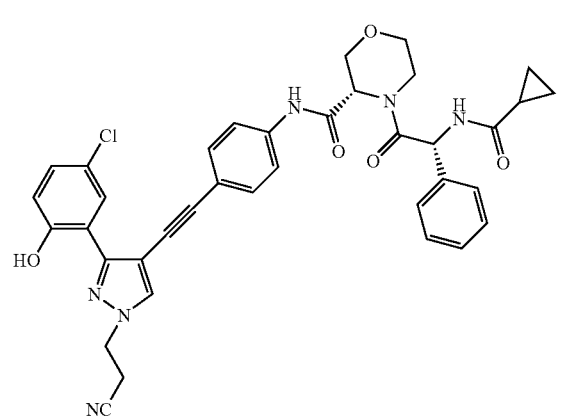
186
-continued
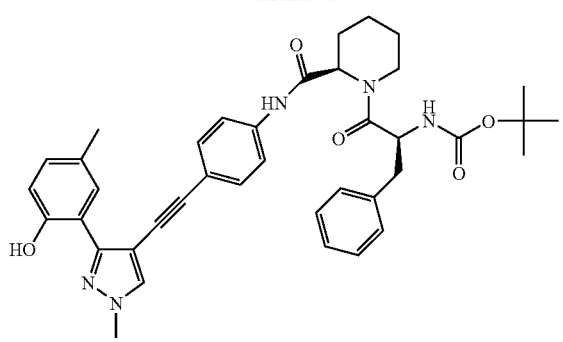
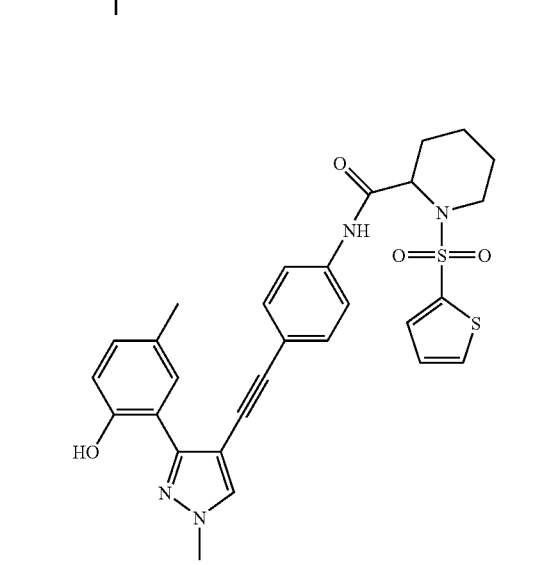
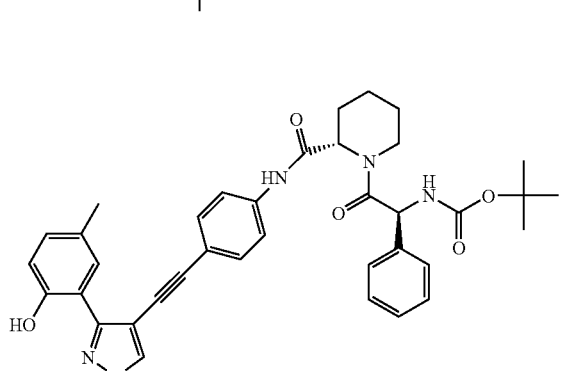
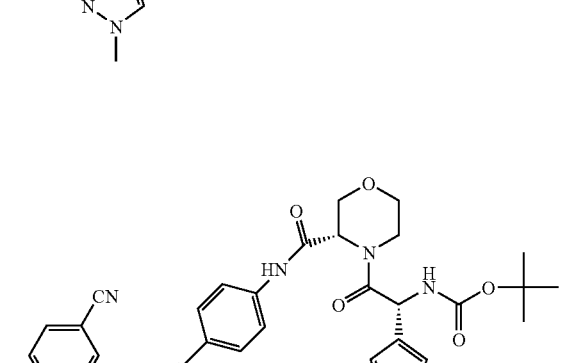

187
-continued
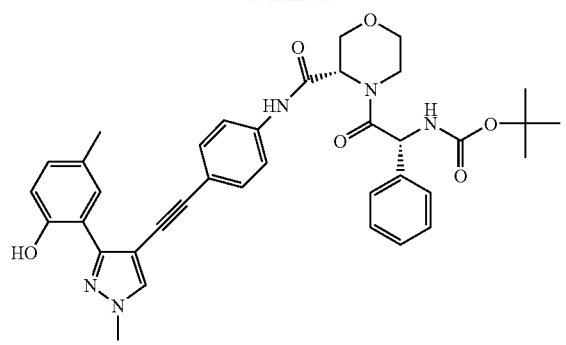
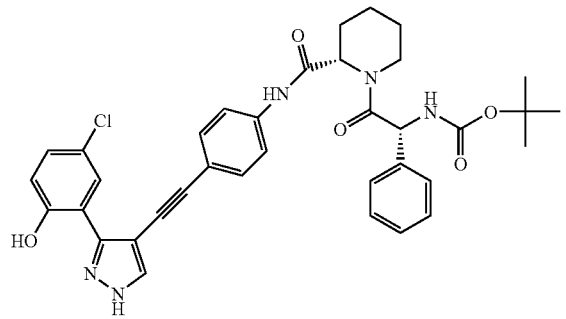
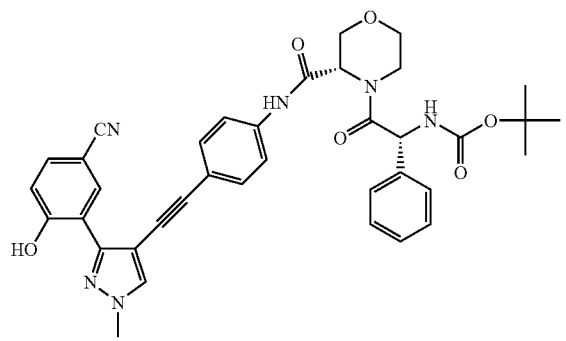
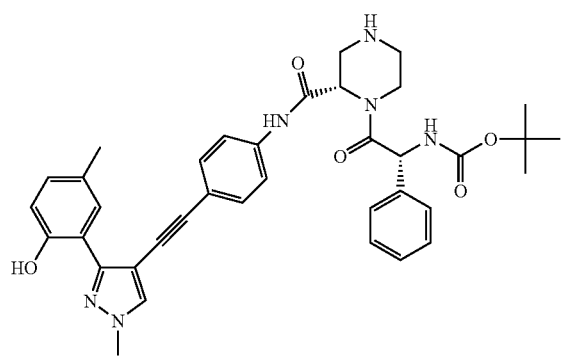
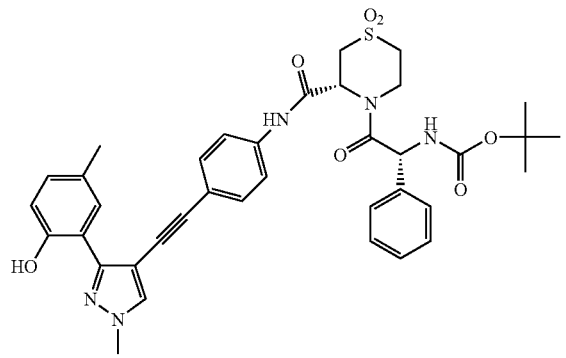
188
-continued
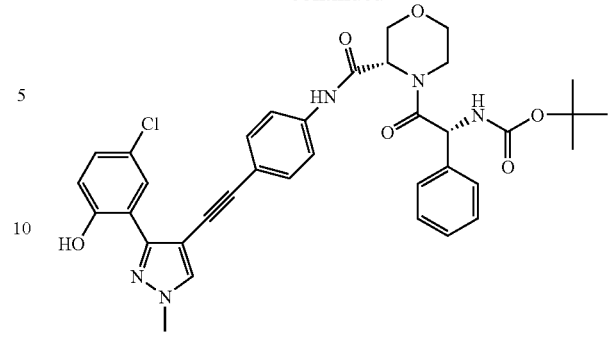
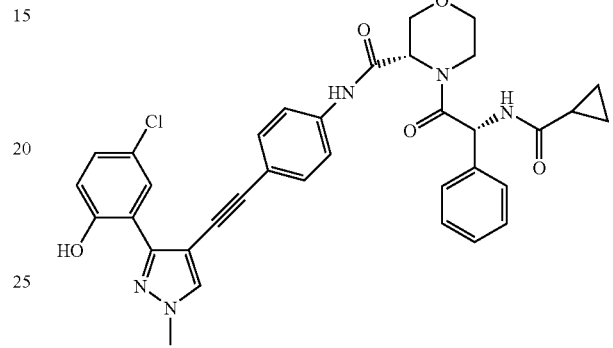
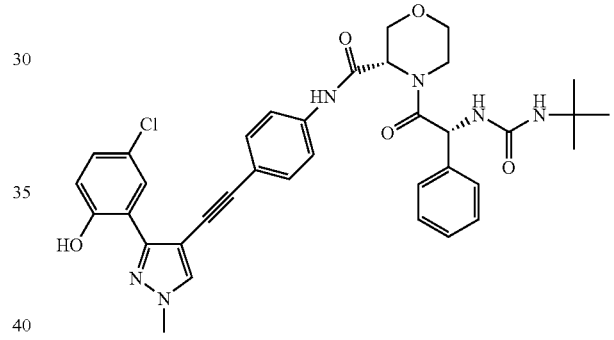
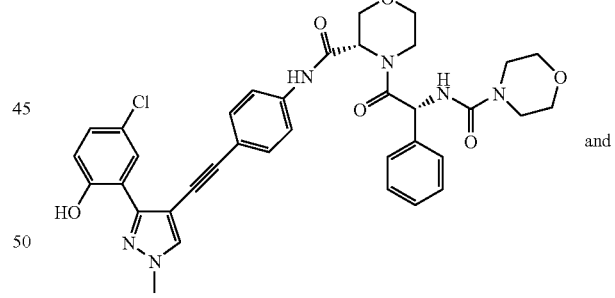
and
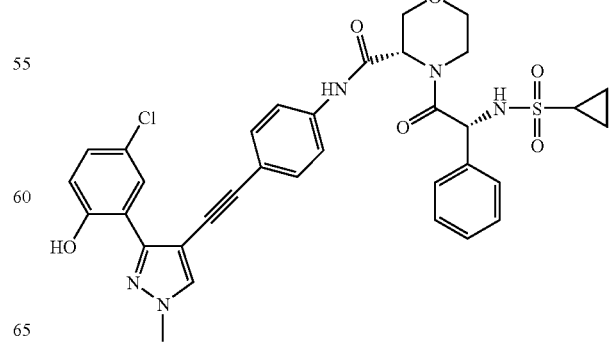

9. The compound of claim 1, having the structure selected from:

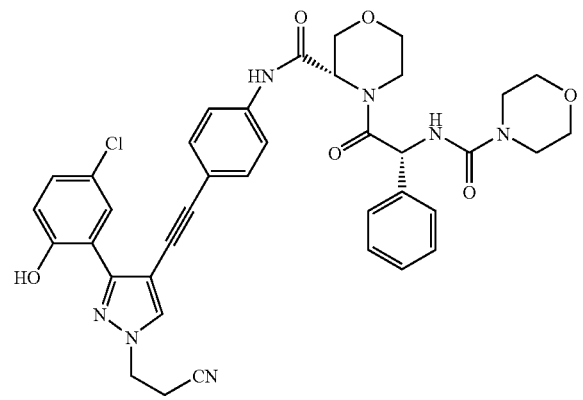

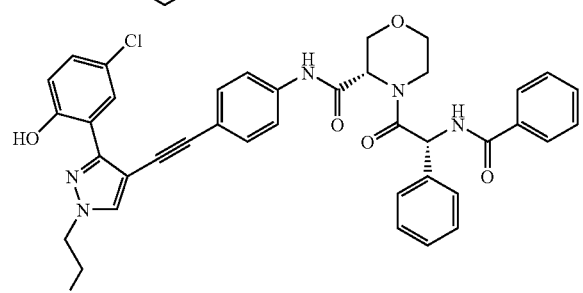

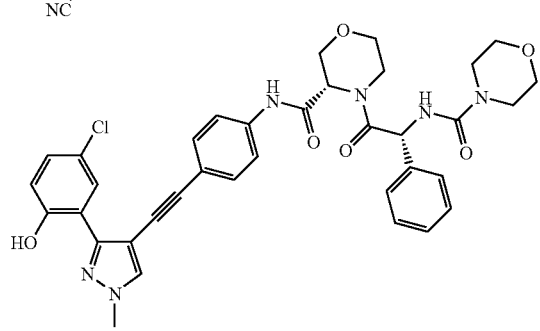

and

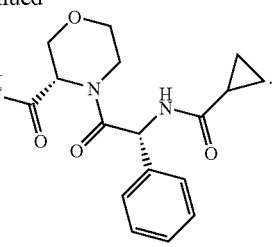

10. A method of treating HCV infection in a human comprising administering a therapeutically effective amount of a compound according to claim 1, or a pharmaceutically acceptable salt thereof.

11. A method of treating HCV infection in a human comprising administering a therapeutically effective amount of a combination of the compound according to claim 1, or a pharmaceutically acceptable salt thereof, and at least one additional agent selected from an interferon, ribavirin, an HCV protease inhibitor, an HCV polymerase inhibitor, an HCV IRES inhibitor, an HCV Helicase, an HCV ATPase inhibitor, an NS5A modulator, or an HCV NS2 inhibitor.

12. The method of claim 11, wherein the at least one additional agent is an interferon.

13. The method of claim 12, wherein the at least one additional agent is α-interferon.

* * * * *

UNITED STATES PATENT AND TRADEMARK OFFICE
CERTIFICATE OF CORRECTION

PATENT NO. : 7,923,004 B2  
APPLICATION NO. : 11/974744  
DATED : April 12, 2011  
INVENTOR(S) : Guolin Li et al.

Page 1 of 1

It is certified that error appears in the above-identified patent and that said Letters Patent is hereby corrected as shown below:

Claim 5:

Column 174, line 54, delete "$(R^3)$" and insert --$(R^{93})$--.

Signed and Sealed this

Sixth Day of September, 2011

David J. Kappos  
*Director of the United States Patent and Trademark Office*

SEQUENCE LISTING

<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
acattcccca ttaacgcgca caccacgggc ccctgca     37

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
tgcaggggcc cgtggtgtgc gcgttaatgg ggaatgt     37